US012678508B2

(12) United States Patent
Gray et al.

(10) Patent No.: US 12,678,508 B2
(45) Date of Patent: Jul. 14, 2026

(54) COMPOUNDS FOR TARGETED DEGRADATION OF INTERLEUKIN-2-INDUCIBLE T-CELL KINASE AND METHODS OF USE

(71) Applicant: DANA-FARBER CANCER INSTITUTE, INC., Boston, MA (US)

(72) Inventors: Nathanael S. Gray, Stanford, CA (US); Baishan Jiang, Watertown, MA (US); David Weinstock, Jamaica Plain, MA (US); Wenchao Wu, Brookline, MA (US)

(73) Assignee: DANA-FARBER CANCER INSTITUTE, INC., Boston, MA (US)

(*) Notice: Subject to any disclaimer, the term of this patent is extended or adjusted under 35 U.S.C. 154(b) by 687 days.

(21) Appl. No.: 18/010,699

(22) PCT Filed: Jun. 22, 2021

(86) PCT No.: PCT/US2021/038354
§ 371 (c)(1),
(2) Date: Dec. 15, 2022

(87) PCT Pub. No.: WO2021/262636
PCT Pub. Date: Dec. 30, 2021

(65) Prior Publication Data

US 2023/0226196 A1 Jul. 20, 2023

Related U.S. Application Data

(60) Provisional application No. 63/042,739, filed on Jun. 23, 2020.

(51) Int. Cl.

| | |
|---|---|
| ***A61K 47/54*** | (2017.01) |
| ***A61K 39/00*** | (2006.01) |
| ***A61K 40/31*** | (2025.01) |
| ***A61P 35/00*** | (2006.01) |

(52) U.S. Cl.
CPC ............ *A61K 47/545* (2017.08); *A61K 39/00* (2013.01); *A61K 40/31* (2025.01); *A61P 35/00* (2018.01)

(58) Field of Classification Search
CPC ...... A61K 47/54; A61K 47/545; A61K 45/06; A61K 47/55; A61K 40/31; A61P 35/00
USPC ........................................................ 514/235.2
See application file for complete search history.

(56) References Cited

U.S. PATENT DOCUMENTS

| | | | |
|---|---|---|---|
| 2004/0067989 | A1 | 4/2004 | Barish et al. |
| 2019/0375743 | A1 | 12/2019 | Hudson et al. |

FOREIGN PATENT DOCUMENTS

| | | | |
|---|---|---|---|
| WO | 2017079267 | A1 | 5/2017 |

OTHER PUBLICATIONS

Golub et al., Science, vol. 286, Oct. 15, 1999, pp. 531-537. (Year: 1999).*
Antunes et al., Bioengineering (Basel), Apr. 7, 2022;9(4):166, pp. 1-15. (Year: 2022).*
Weeks et al., "Targeting ITK signaling for T-cell mediated diseases", IScience 24, 102842, Aug. 20, 2021. (Year: 2021).*
Kamailyan et al., "Zinc Finger proteins: guardians of genome stability", Frontiers in Cell and Development Biology, Jul. 25, 2024. (Year: 2024).*
Hatcher et al., "Development of Highly Potent and Selective Steroidal Inhibitors and Degraders of CDK8," ACS Med. Chem. Lett., 2018, vol. 9, pp. 540-545.
Lopachin et al., "Molecular Mechanism of Acrylamide Neurotoxicity: Lessons Learned from Organic Chemistry," Environmental Health Perspectives, 2012, vol. 120, No. 12, pp. 1650-1657.
Huang et al., "A Chemoproteomic Approach to Query the Degradable Kinome Using a Multi-kinase Degrader," Cell Chemical Biology, 2018, vol. 25, pp. 88-99.

* cited by examiner

*Primary Examiner* — Brian-Yong S Kwon
(74) *Attorney, Agent, or Firm* — ArentFox Schiff LLP; Daniel W. Clarke; Shawn P. Foley

(57) ABSTRACT

Disclosed are bispecific compounds (degraders) that target ITK or a zinc finger (ZnF) protein for degradation. Also disclosed are pharmaceutical compositions containing the degraders and methods of using the compounds to treat diseases and disorders characterized or mediated by ITK or ZnF protein activity.

27 Claims, 10 Drawing Sheets

COMPOUNDS FOR TARGETED DEGRADATION OF INTERLEUKIN-2-INDUCIBLE T-CELL KINASE AND METHODS OF USE

RELATED APPLICATIONS

This application is a national stage application, filed under 35 U.S.C. § 371, of International Application No. PCT/US2021/038354, filed Jun. 22, 2021, which claims the benefit of priority under 35 U.S.C. § 119(e) to U.S. Provisional Application No. 63/042,739, filed Jun. 23, 2020, each of which is incorporated herein by reference in its entirety.

GOVERNMENT LICENSE RIGHTS

This invention was made with government support under grant number R01 CA218278 awarded by the National Institutes of Health. The government has certain rights in the invention.

BACKGROUND OF THE INVENTION

Interleukin-2-inducible t-cell kinase (ITK) is one of the Tec family of non-receptor tyrosine kinases. It has been primarily associated with the regulation of T-helper 2 (Th2)-cell driven immunological diseases as well as development of Th17 cells and their production of the pro-inflammatory cytokine interleukin 17A (IL17A). Both knockout and gene expression studies suggest that ITK has a dominant role in mediating T cell receptor (TCR) signaling, and there is potential therapeutic benefit to its inhibition in T cell malignancies, autoimmune and inflammatory diseases (August et al., In. Rev. Immunol. 31:155-165 (2012)). ITK can phosphorylate phosphoinositide phospholipase C-gamma-1 ($PLC_{\gamma}1$). Phosphorylated $PLC_{\gamma}1$ (p-$PLC_{\gamma}1$) then hydrolyzes phosphatidylinositol 4,5-biphosphate (PIP2) to the second messengers inositol triphosphate (IP3) and diacylglycerol (DAG), which will lead to calcium mobilization and flux, protein kinase C (PKC) and mitogen-activated protein kinase/extracellular signal-regulated kinase (MEK/ERK) pathway activation, and transcriptional activation via activator protein 1 (AP1), nuclear factor of activated T cells (NFAT) and nuclear factor kappa-light-chain-enhancer of activated B cells (NF-$_{\kappa}$B) (Bryan et al., J. Med. Chem. 61:9030-9058 (2018)). These in turn lead to cytokine production and T cell proliferation and differentiation in T cells, natural killer (NK) cells, and mast cells where ITK is predominantly expressed. ITK also has some kinase independent activity through its src homology 2 (SH2) domain to regulate serum response factor (SRF) activation (Hao et al., FEBS Lett. 580:2691-2697 (2006)). Activating mutations and copy number alternations involving ITK, $PCL_{\gamma}1$ and other factors in that signaling pathways are found in T-cell lymphomas and indicate that ITK represents a possible therapeutic target (Vaque et al., Blood 123:2034-2043 (2014); Liang et al., Int. J. Clin. Exp. Pathol. 7:6097-6107 (2014)).

Current reported ITK inhibitors are mainly either covalent or reversible adenosine triphosphate (ATP) competitive inhibitors, many of which target other kinases as well. Ibrutinib, an FDA-approved BTK/ITK inhibitor, has demonstrated efficacy in enhancing the action of CAR-T cells (Fraietta et al., Blood 127:1117-1127 (2016)), checkpoint blockade and anti-tumor vaccines (Sagiv-Barfi et al., Proc. Natl. Acad. Sci. USA 112:E966-972 (2015)), as well as for patients with chronic graft-versus-host disease (Miklos et al., Blood 130:2243-2250 (2017)). The primary mechanism of action in these settings appears to be inhibition of ITK which affects the polarization of Th2 cells. Fundamentally new approaches are still needed to achieve further understanding of ITK kinase independent functions.

SUMMARY OF THE INVENTION

A first aspect of the present invention is directed to a bispecific compound of formula (I), (I)

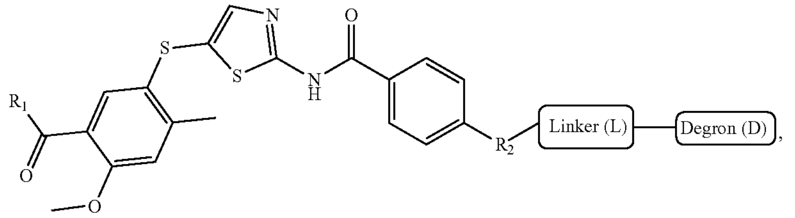

wherein $R_1$ and $R_2$ are as defined herein, the degron represents a ligand that binds an E3 ubiquitin ligase, and the linker represents a moiety that covalently connects $R_2$ to the degron, or a pharmaceutically acceptable salt or stereoisomer thereof.

Another aspect of the present invention is directed to a pharmaceutical composition containing a therapeutically effective amount of a bispecific compound of formula (I) or a pharmaceutically acceptable salt or stereoisomer thereof, and a pharmaceutically acceptable carrier.

In another aspect of the present invention, methods of making the bispecific compounds are provided.

A further aspect of the present invention is directed to a method of treating a disease or disorder involving interleukin-2-inducible T-cell kinase (ITK) and/or zinc finger (ZnF) protein activity, that includes administering a therapeutically effective amount of a bispecific compound of formula (I) or a pharmaceutically acceptable salt or stereoisomer thereof, to a subject in need thereof.

In some embodiments, the ZnF protein that is targeted is IKZF1, IKZF3, ZFP91, RNF166, ZNF653, or ZNF692.

BRIEF DESCRIPTION OF THE DRAWINGS

FIG. 4A shows DERL-2 cells supplemented in culture with IL-2 and treated with compound 1 or DMSO. FIG. 4B shows DERL-2 cells in culture without IL-2 and after treatment with compound 1 or DMSO. FIG. 4C shows Hut78 cells treated with compound 1 or DMSO.

DETAILED DESCRIPTION OF THE INVENTION

Figure 1A:
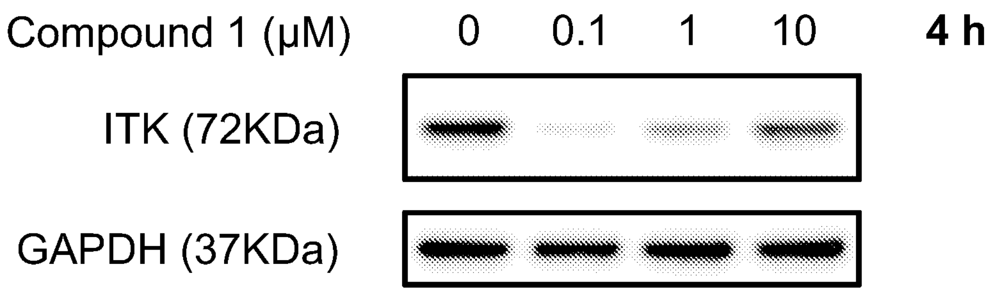
FIG. 1A-FIG. 1B are immunoblots that show ITK degradation in DERL-2 cells after the treatment of inventive compound 1 at the indicated concentrations after 4 h and 18 h.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms “a”, “an”, and “the” include plural referents unless the context clearly dictates otherwise. Therefore, for example, reference to “a composition” includes mixtures of two or more such compositions, reference to “an inhibitor” includes mixtures of two or more such inhibitors, and the like.

Unless stated otherwise, the term “about” means within 10% (e.g., within 5%, 2%, or 1%) of the particular value modified by the term “about.”

The transitional term “comprising,” which is synonymous with “including,” “containing,” or “characterized by,” is inclusive or open-ended and does not exclude additional, unrecited elements or method steps. When used in the context of the number of heteroatoms in a heterocyclic structure, it means that the heterocyclic group that that minimum number of heteroatoms. By contrast, the transitional phrase “consisting of” excludes any element, step, or ingredient not specified in the claim. The transitional phrase “consisting essentially of” limits the scope of a claim to the specified materials or steps “and those that do not materially affect the basic and novel characteristic(s)” of the claimed invention.

With respect to compounds of the present invention, and to the extent the following terms are used herein to further describe them, the following definitions apply.

As used herein, the term “alkyl” refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group, or a methyl group.

As used herein, the term “alkylene” refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term “alkenyl” refers to a linear or branched-chain monovalent hydrocarbon radical with at least one carbon-carbon double bond. An alkenyl includes radicals having “cis” and “trans” orientations, or alternatively, “E” and “Z” orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term “alkynyl” refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

The terms “alkoxyl” or “alkoxy” as used herein refer to an alkyl group, as defined above, having an oxygen radical attached thereto, and which is the point of attachment. Representative alkoxyl groups include methoxy, ethoxy, propyloxy, tert-butoxy and the like. An “ether” is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term “halogen” (or “halo” or “halide”) refers to fluorine, chlorine, bromine, or iodine.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Therefore, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Therefore, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Therefore, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom or heteroatom-containing group (e.g., O, N, N(O), S, S(O), or $S(O)_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur and oxygen. In some embodiments, heterocyclyl includes 4- to 6-membered monocycles having one or more heteroatoms selected from nitrogen, sulfur and oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Therefore, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tricyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Therefore, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Unless stated otherwise, and to the extent not further defined for any particular group(s), any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

targeting ligand and the target protein, but nonetheless wherein the affinity is sufficient to achieve recruitment of the ligase to the targeted degradation and the selective degradation of the targeted protein.

Broadly, the bispecific compounds of the present invention have a structure represented by formula I:

(I)

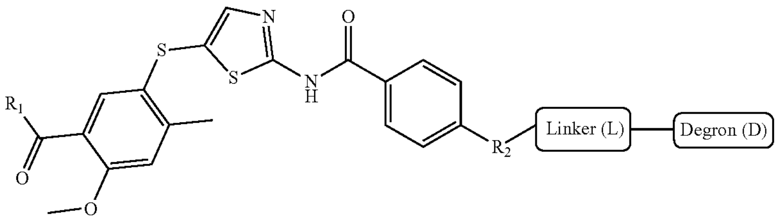

To the extent not disclosed otherwise for any particular group(s), representative examples of substituents may include alkyl, substituted alkyl (e.g., $C_1$-$C_6$, $C_1$-$C_5$, $C_1$-$C_4$, $C_1$-$C_3$, $C_1$-$C_2$, $C_1$), alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, $C_1$), haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

As used herein, the phrase "optionally substituted with one or more halogen(s)" or "optionally substituted with $C_6$-$C_{10}$ aryl group(s)", means at least one or more of said functional group provided that such substitution is in accordance with permitted valence of the substituted atom and the substituent.

The term "binding" as it relates to interaction between the targeting ligand and the targeted proteins, which are ITK and ZnF protein, refers to inter-molecular interactions that are substantially specific in that binding of the targeting ligand with other kinases and non-kinase proteinaceous entities present in the cell may be functionally insignificant. Present bispecific compounds preferentially bind and recruit ITK and ZnF protein for targeted degradation.

The term "binding" as it relates to interaction between the degron and the E3 ubiquitin ligase, typically refers to an inter-molecular interaction that may or may not exhibit an affinity level that equals or exceeds that affinity between the wherein the degron represents a ligand that binds an E3 ubiquitin ligase, and the linker represents a moiety that covalently connects $R_2$ to the degron, or a pharmaceutically acceptable salt or stereoisomer thereof.

Targeting Ligands

The targeting ligand moiety of the bispecific compounds, which binds ITK and ZnF, is represented by formula TL-1:

(TL-1)

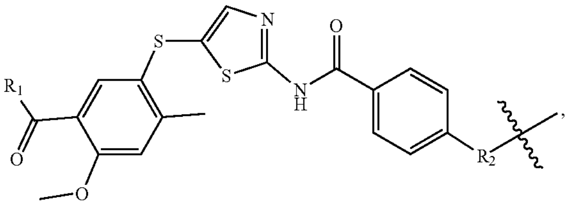

wherein $R_1$ represents

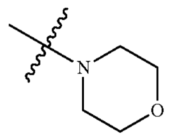

or

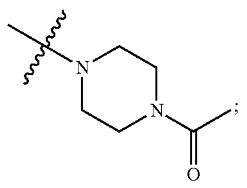

and $R_2$ represents O or

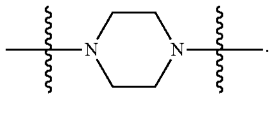 [SMILES: *N1CCN(*)CC1]

In some embodiments, $R_1$ represents

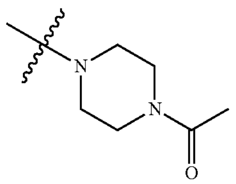 [SMILES: *N1CCN(C(C)=O)CC1]

and the targeting ligand is represented by formula TL-1a:

(TL-1a)

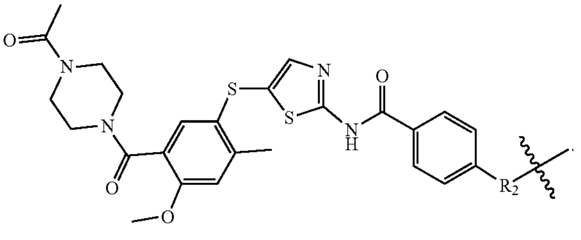

Thus, in some embodiments, the bispecific compound is represented by formula Ia:

(Ia)

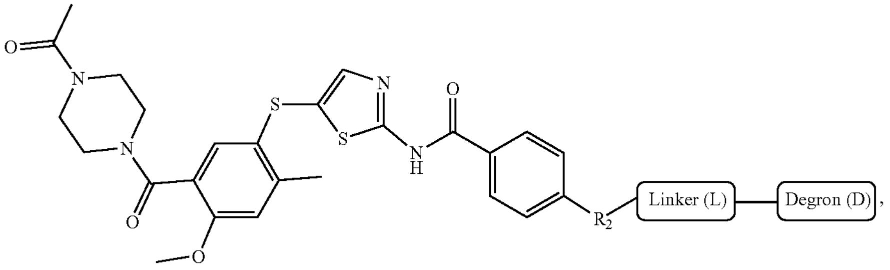

or a pharmaceutically acceptable salt or stereoisomer thereof.

In some embodiments, $R_2$ represents O and the targeting ligand is represented by formula TL-1a1:

(TL-1a1)

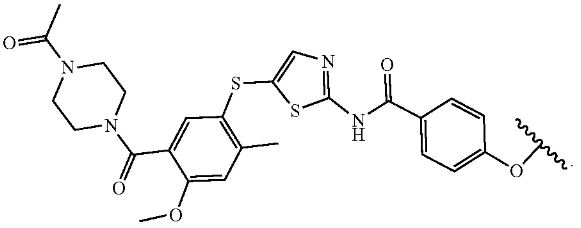

Thus, in some embodiments, the bispecific compound is represented by formula Ia1:

(Ia1)

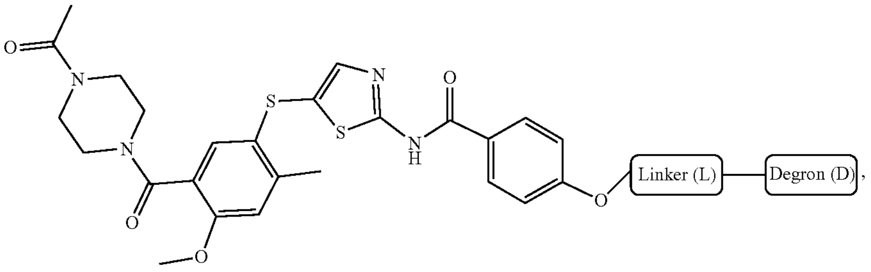

or a pharmaceutically acceptable salt or stereoisomer thereof.

In some embodiments, $R_2$ represents

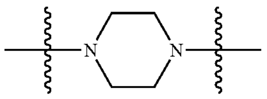 [SMILES: *N1CCN(*)CC1]

and the targeting ligand is represented by formula TL-1a2:

(TL-1a2)

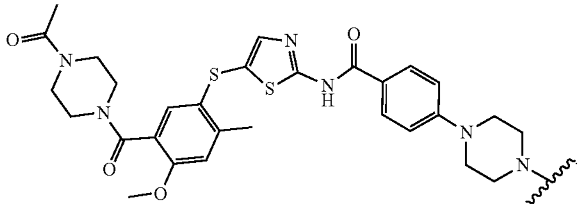

Thus, in some embodiments, the bispecific compound is represented by formula Ia2:

(Ia2)

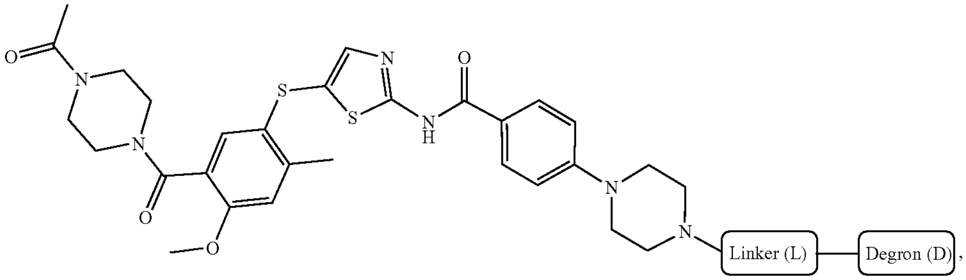, or a pharmaceutically acceptable salt or stereoisomer thereof.

In some embodiments, $R_1$ represents

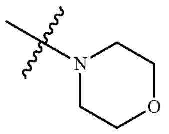 [SMILES: *N1CCOCC1]

and the targeting ligand is represented by formula TL-1b:

(TL-1b)

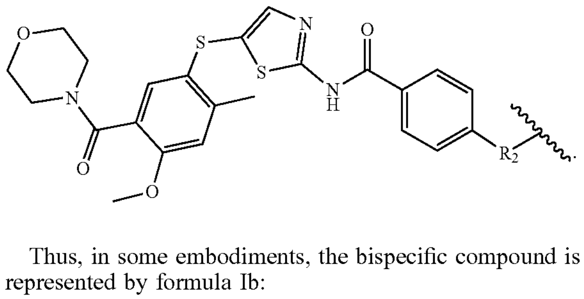.

Thus, in some embodiments, the bispecific compound is represented by formula Ib:

(Ib)

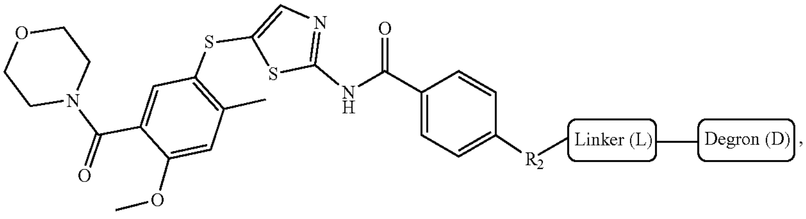, or a pharmaceutically acceptable salt or stereoisomer thereof.

In some embodiments, $R_2$ represents O and the targeting ligand is represented by formula TL-Ib1:

(TL-1b1)

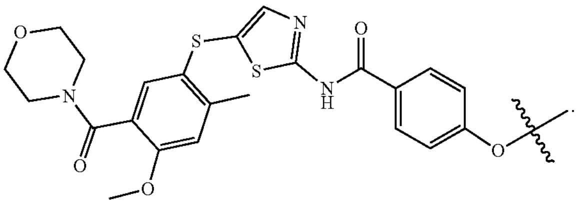

Thus, in some embodiments, the bispecific compound is represented by formula Ib1:

or a pharmaceutically acceptable salt or stereoisomer thereof.

Linkers

The linker ("L") provides a covalent attachment between the targeting ligand and the degron. The structure of linker may not be critical, provided it is substantially non-interfering with the activity of the ITK or ZnF targeting ligand or the degron. In some embodiments, the linker includes an alkylene chain (e.g., having 2-20 alkylene units). In other embodiments, the linker may include an alkylene chain or a bivalent alkylene chain, either of which may be interrupted by, and/or terminate (at either or both termini) at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, (Ib1)

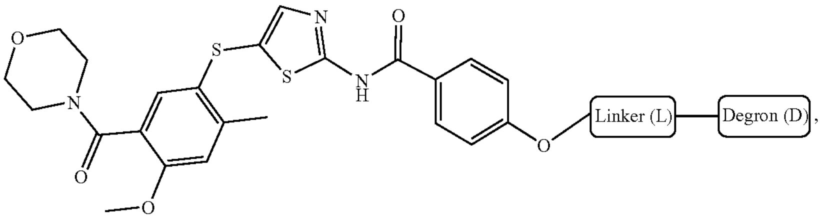

or a pharmaceutically acceptable salt or stereoisomer thereof.

In some embodiments, $R_2$ represents

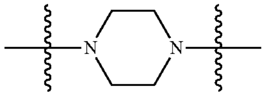

and the targeting ligand is represented by formula TL-1b2:

(TL-1b2)

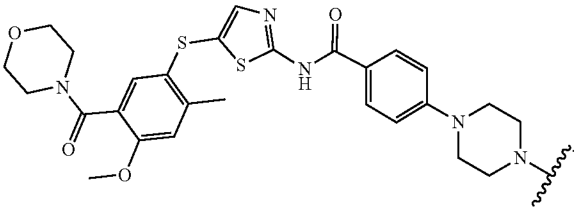

Thus, in some embodiments, the bispecific compound is represented by formula Ib2:

—$S(O)_2$—, —OS(O)—, —S(O)O—, —S(O)—, —$OS(O)_2$—, —$S(O)_2O$—, —N(R')$S(O)_2$—, —$S(O)_2$N(R')—, —N(R')S(O)—, —S(O)N(R')—, —N(R')$S(O)_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker includes an alkylene chain having 2-20 alkylene units. In some embodiments, the linker includes an alkylene chain having 3-12 alkylene units.

In some embodiments, the linker includes an alkylene chain having 1-10 alkylene units and interrupted by or terminating in

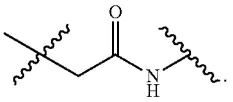 [SMILES: *CC(=O)N*]

(Ib2)

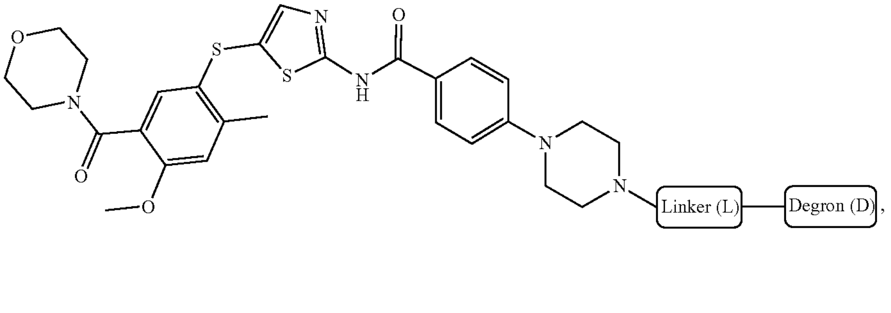

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chains:

(L1)

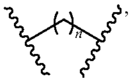

wherein n is an integer of 1-12 ("of" meaning inclusive), e.g., 1-12, 1-11, 1-10, 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

(L1-a)

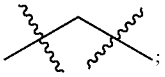

(L1-b)

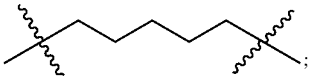

(L1-c)

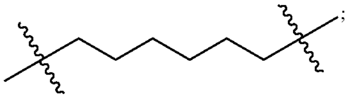

(L1-d)

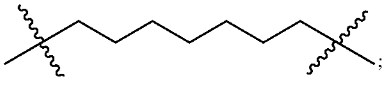

and (L1-e)

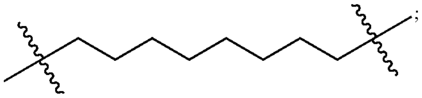

alkylene chains terminating in various functional groups (as described above), examples of which are as follows:

(L2-a)

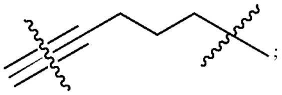

(L2-b)

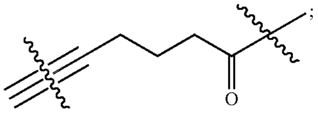

-continued (L2-c)

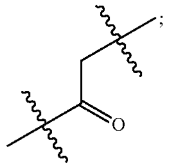

(L2-d)

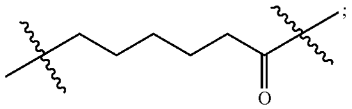

(L2-e)

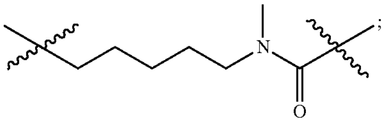

(L2-f)

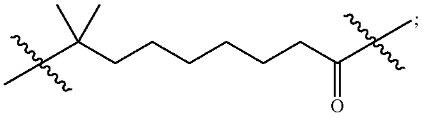

and (L2-g)

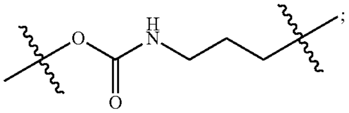

alkylene chains interrupted by various functional groups (as described above), examples of which are as follows:

(L3-a)

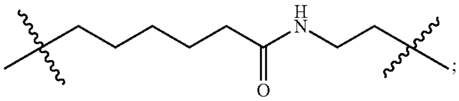

(L3-b)

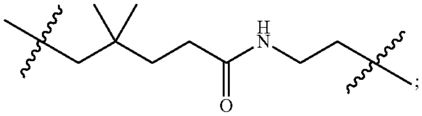

(L3-c)

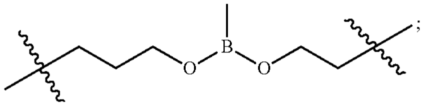

and (L3-d)

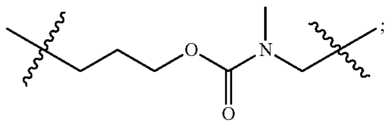

alkylene chains interrupted by or terminating with heterocyclene groups, e.g., (L4)

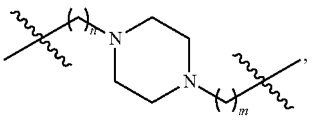

wherein m and n are independently integers of 0-10, examples of which include:

(L4-a)

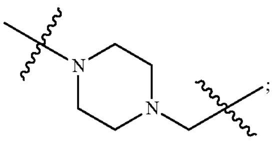

;

(L4-b)

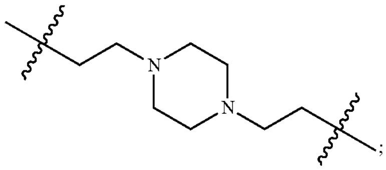

;

(L4-c)

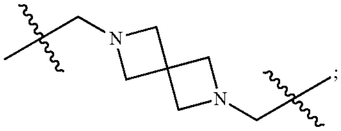

;

(L4-d)

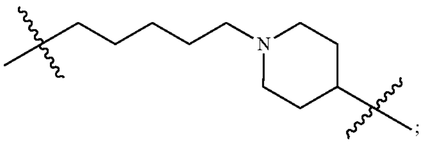

; and (L4-e)

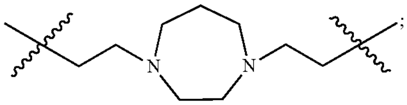

;

alkylene chains interrupted by amide, heterocyclene and/or aryl groups, examples of which include:

(L5-a)

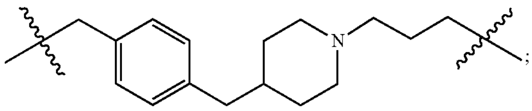

; and (L5-b)

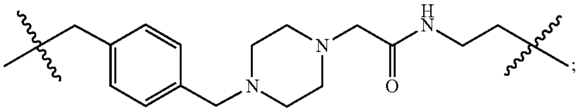

;

alkylene chains interrupted by heterocyclene and aryl groups, and a heteroatom, examples of which include:

(L6-a)

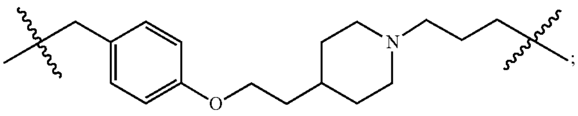

;

(L6-b)

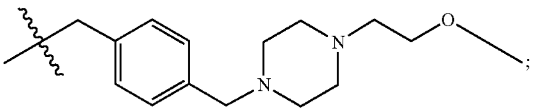

; and (L6-c)

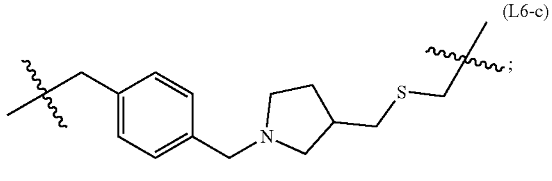

;

and alkylene chains interrupted by and/or terminating in a heteroatom such as N, O or B, e.g., (L7)

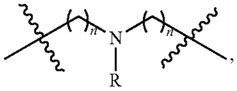

wherein each n is independently an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H or C1 to C4 alkyl, an example of which is (L7-a)

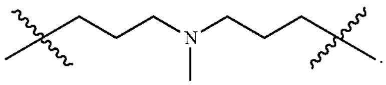

In some embodiments, the linker may include a polyethylene glycol (PEG) chain which may terminate at either or both termini with at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —R'C(O)N(R')R'—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

In some embodiments, the linker includes a polyethylene glycol chain having 1-10 PEG units. In some embodiments, the linker includes a polyethylene glycol chain having 1-6 PEG units. In some embodiments, the linker includes a polyethylene glycol chain having 1-2 PEG units.

In some embodiments, the linker includes a polyethylene glycol chain having 2-8 PEG units and terminating in

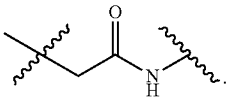 [SMILES: *CC(=O)N*]

Examples of linkers that include a polyethylene glycol chain include:

(L8)

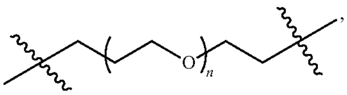

wherein n is an integer of 2-10, examples of which include:

(L8-a)

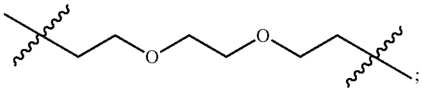

(L8-b)

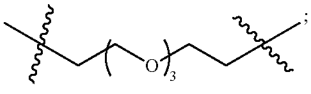

(L8-c)

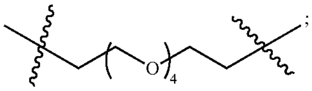

and (L8-d)

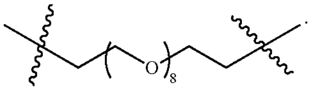

In some embodiments, the polyethylene glycol chain may terminate in a functional group, examples of which are as follows:

(L9-a)

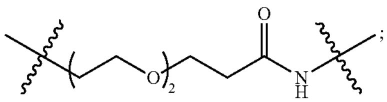

(L9-b)

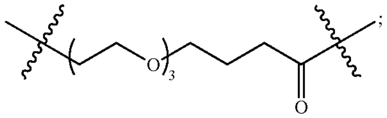

(L9-c)

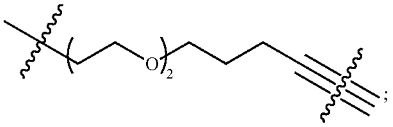

(L9-d)

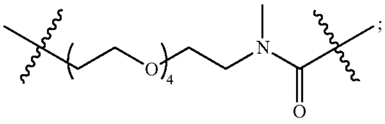

and

-continued (L9-e)

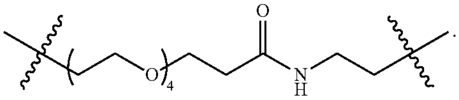

In some embodiments, the bispecific compound of formula (I) includes a linker that is represented by any one of the following structures:

(L10-a)

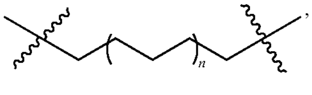

n = 0 - 6

(L10-b)

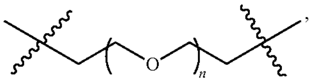

n = 1 - 6

(L10-c)

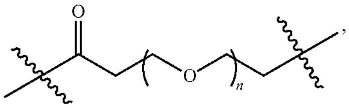

n = 1 - 6

(L10-d)

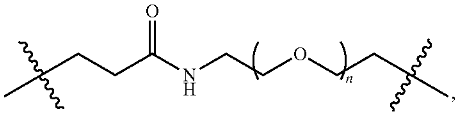

and n = 1 - 6

(L10-e)

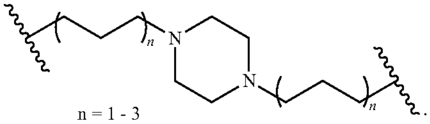

n = 1 - 3 n = 1 - 3

In some embodiments, the bispecific compound of formula (I) includes a linker that is represented by any one of the following structures:

(L11-a)

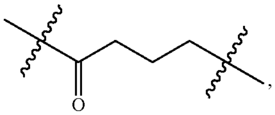

(L11-b)

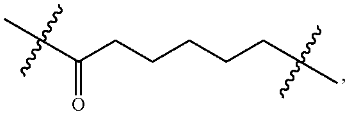

(L11-c)

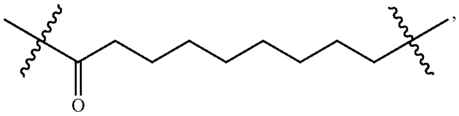

-continued
(L11-d)
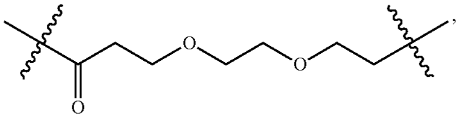
(L11-e)
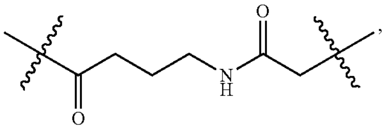
(L11-f)
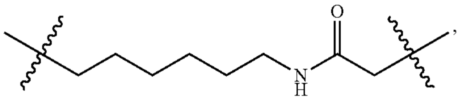
(L11-g)
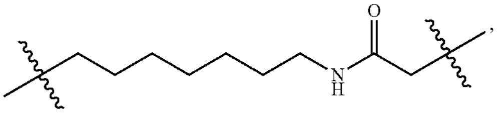
(L11-h)
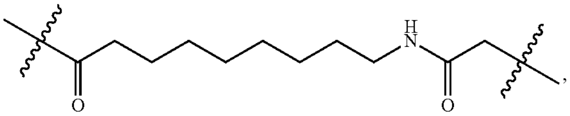
(L11-i)
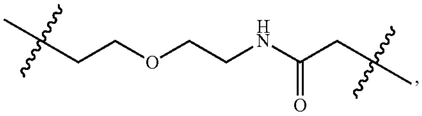
(L11-j)
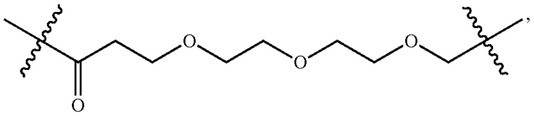
(L11-k)
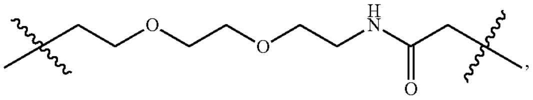
(L11-l)
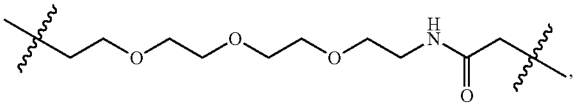
(L11-m)
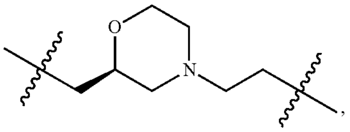
-continued
(L11-n)
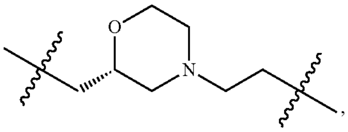
(L11-o)
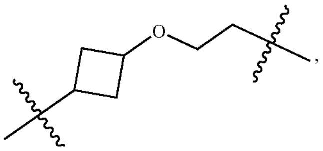
(L11-p)
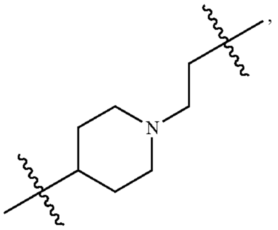
(L11-q)
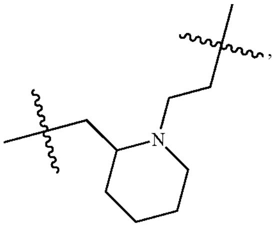
(L11-r)
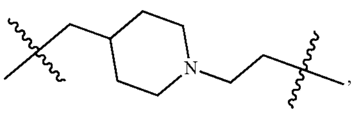
(L11-s)
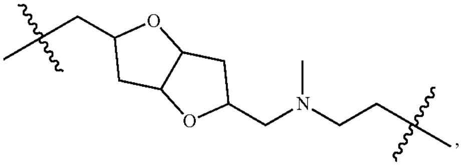
and
(L11-t)
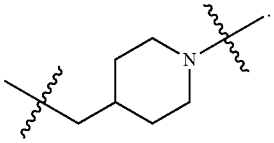
Thus, in some embodiments, the bispecific compounds of the present invention may be represented by any one of the following structures:

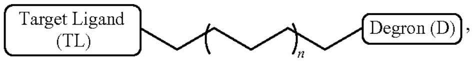,
n=0-6
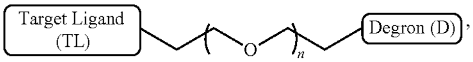,
n=1-6
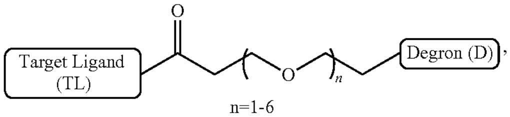,
n=1-6
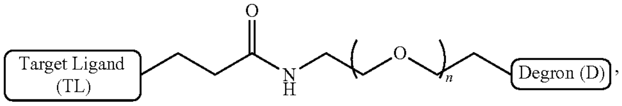,
n=1-6
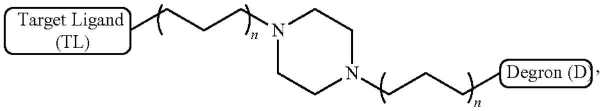,
n=1-3
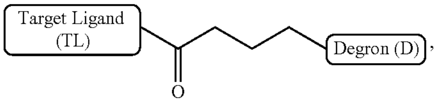,
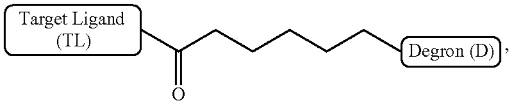,
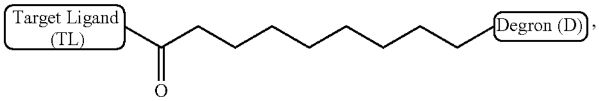,
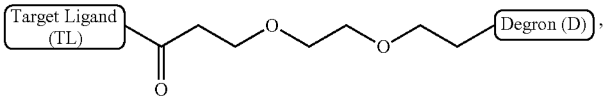,
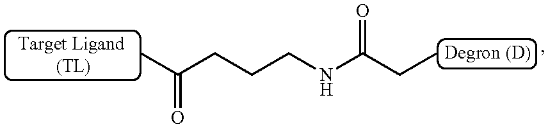,
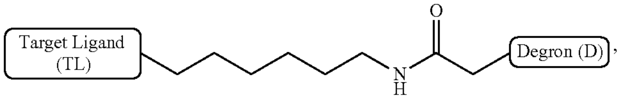,
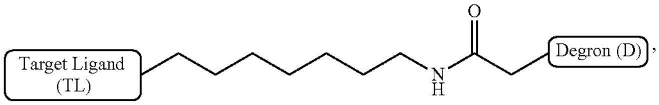,
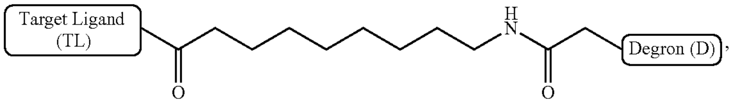,
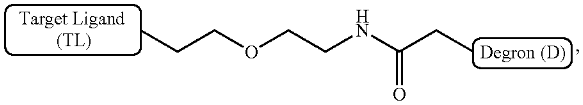,
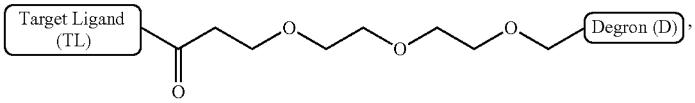,
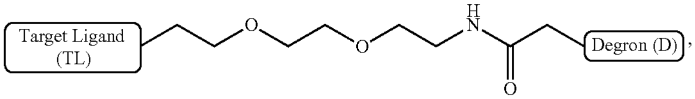,
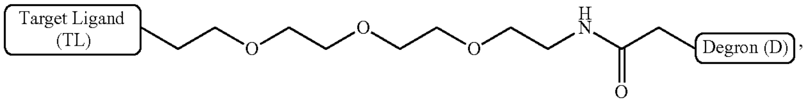,
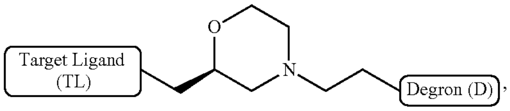,
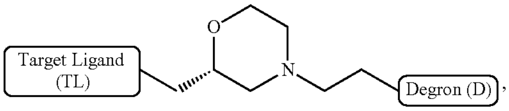,
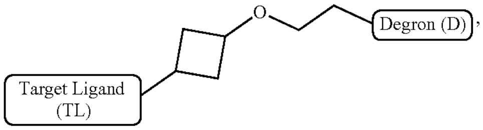,
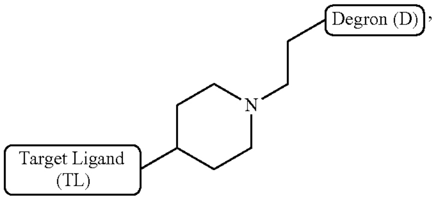, -continued
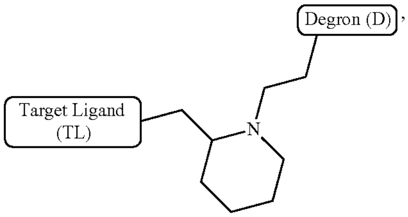
,
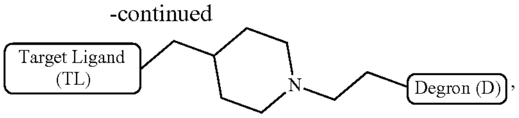
,
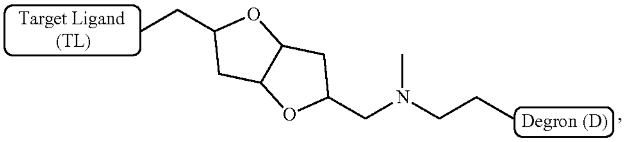
, and
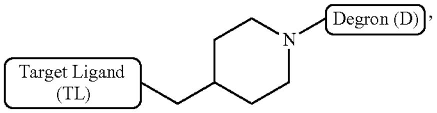
,
or a pharmaceutically acceptable salt or stereoisomer thereof.
In some embodiments, the bispecific compounds of the present invention are represented by any one of the following structures:
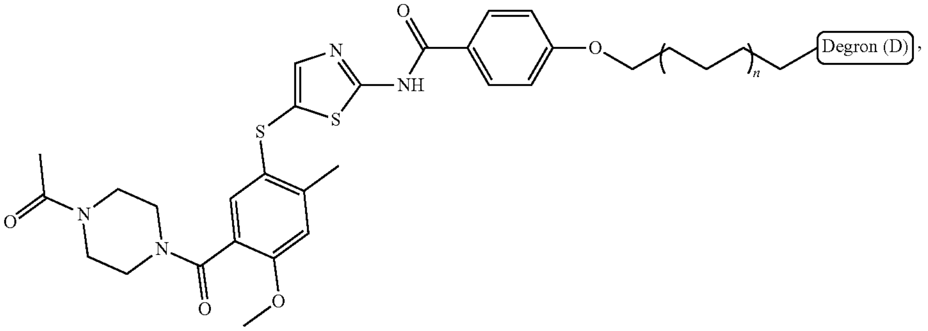
,
n=0-6
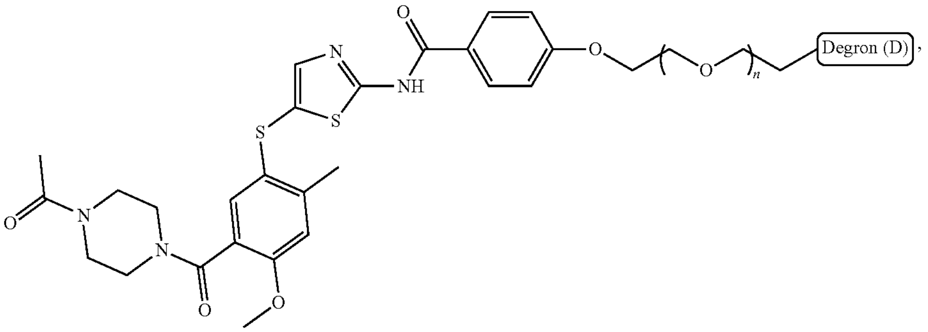
,
n=1-6

-continued
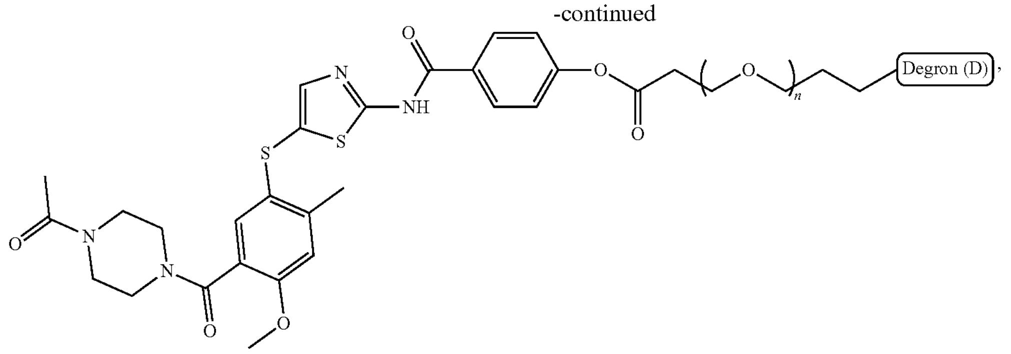
n=1-6
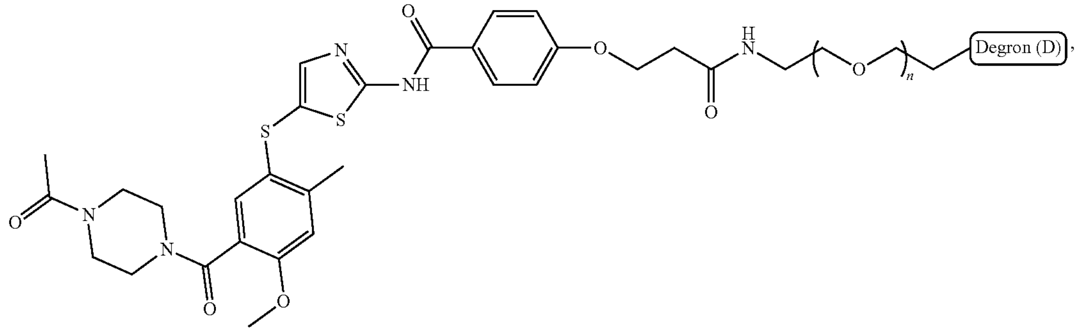
n=1-6
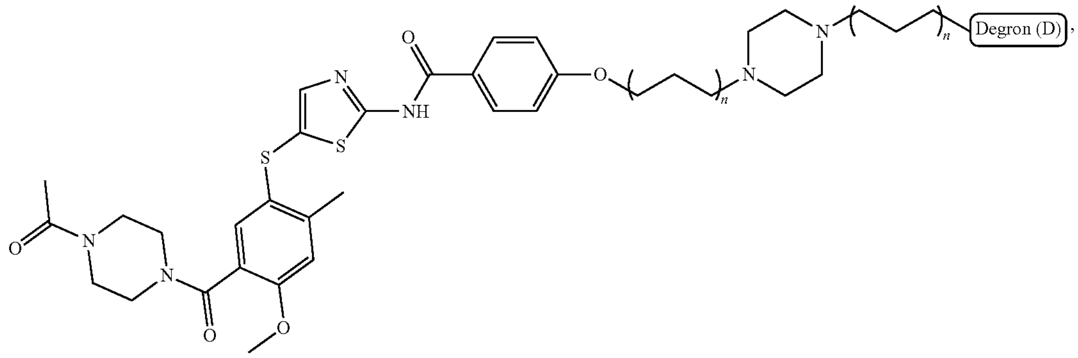
n=1-3
n=1-3
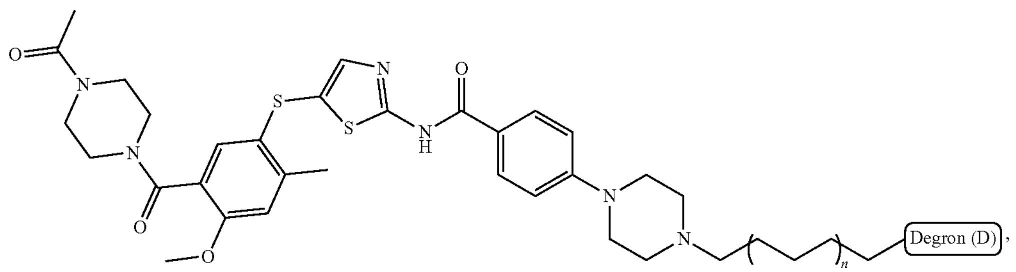
n=0-6

-continued
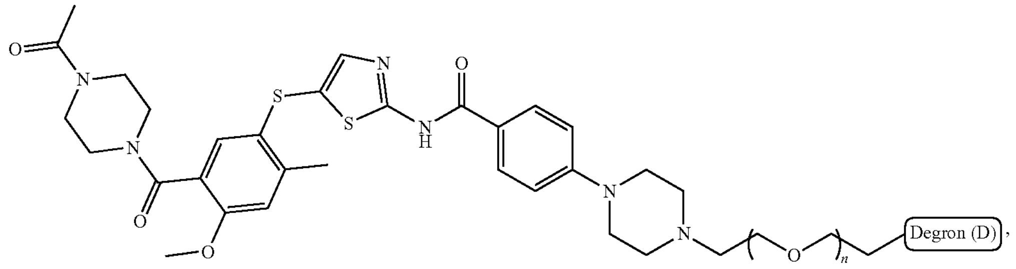
n=1-6
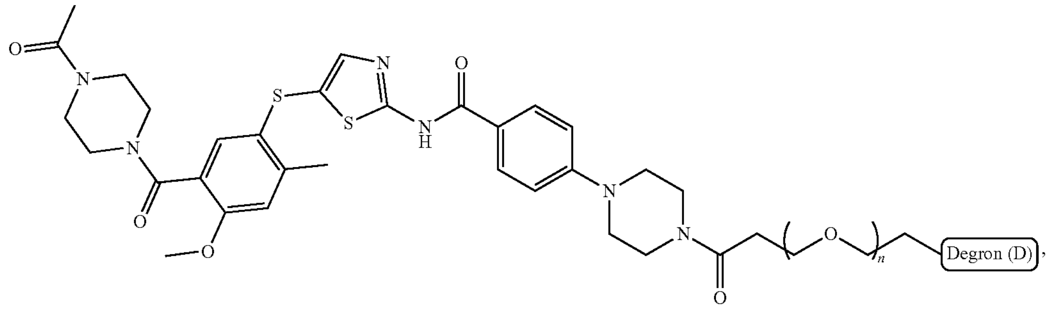
n=1-6
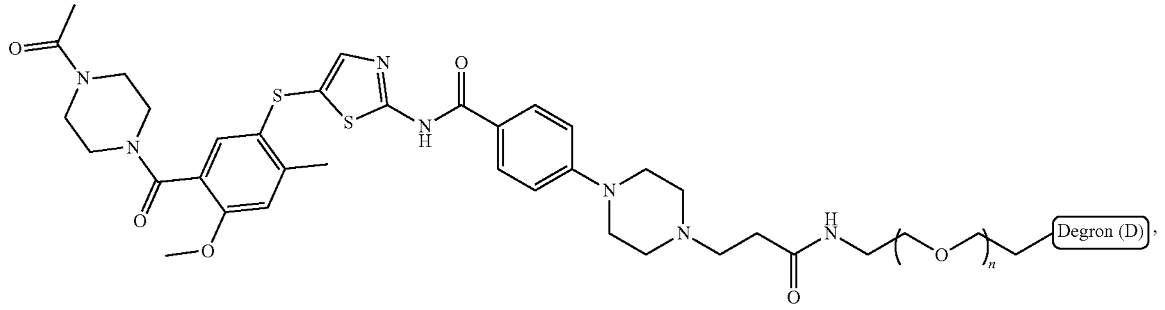
n=1-6
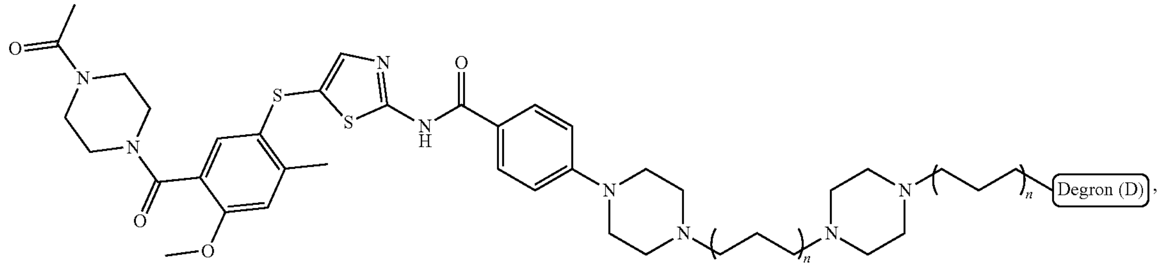
n=1-3
n=1-3
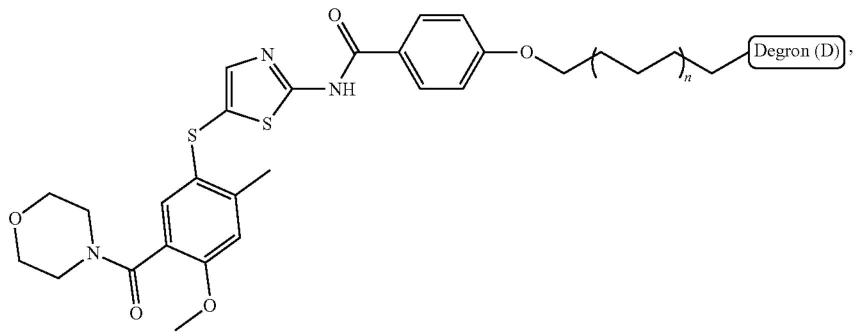
n=0-6

-continued
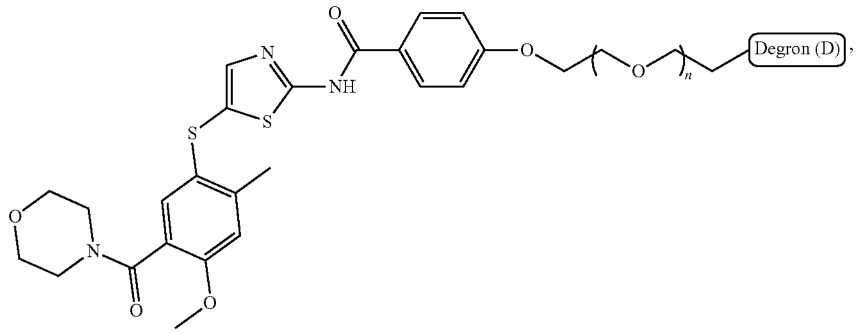
n=1-6
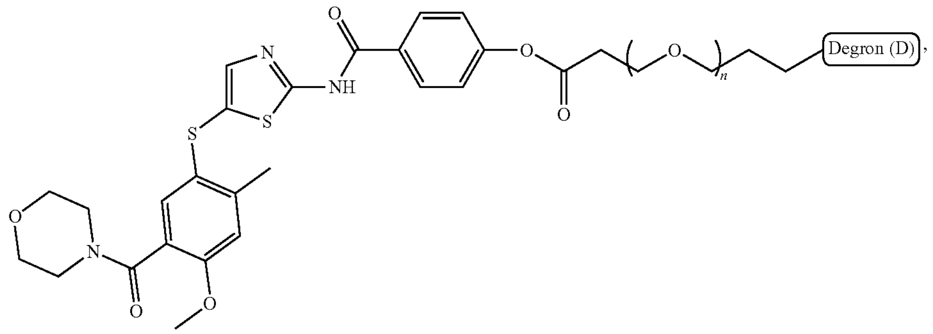
n=1-6
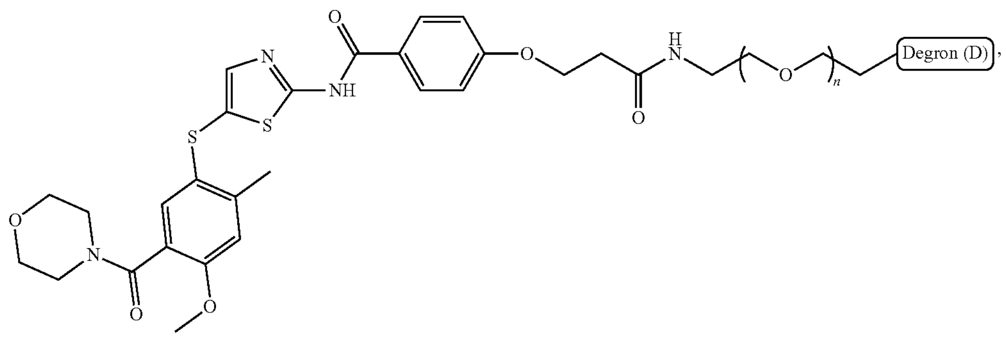
n=1-6
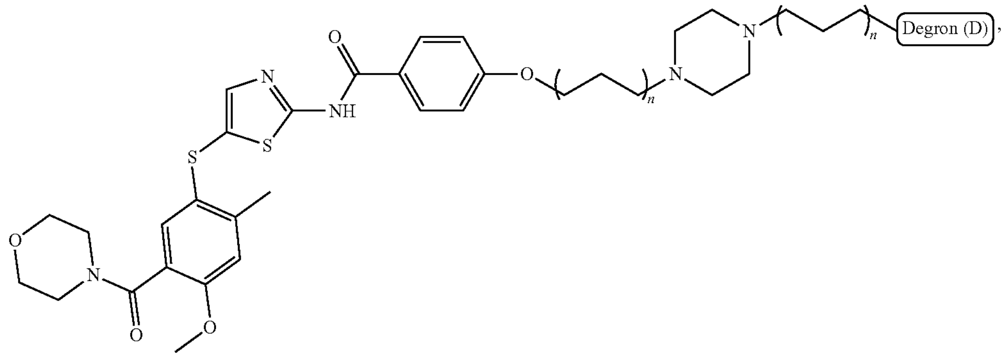
n=1-3
n=1-3

-continued
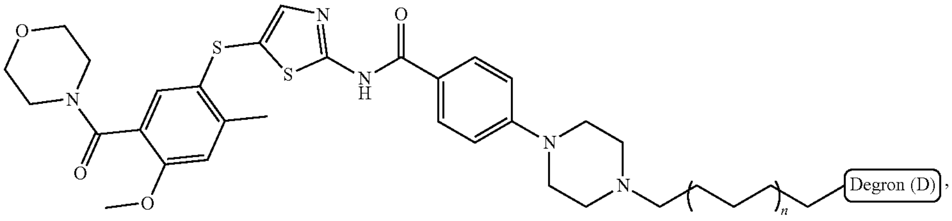
,
n=0-6
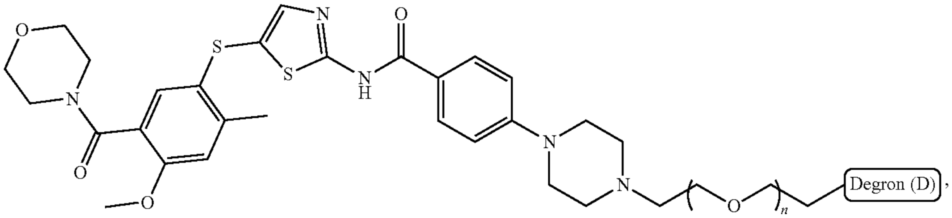
,
n=1-6
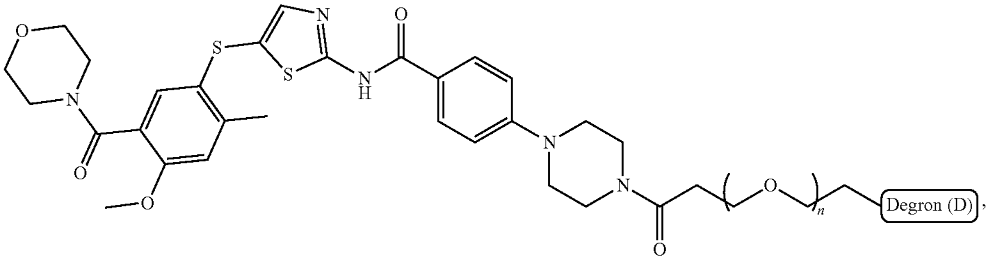
,
n=1-6
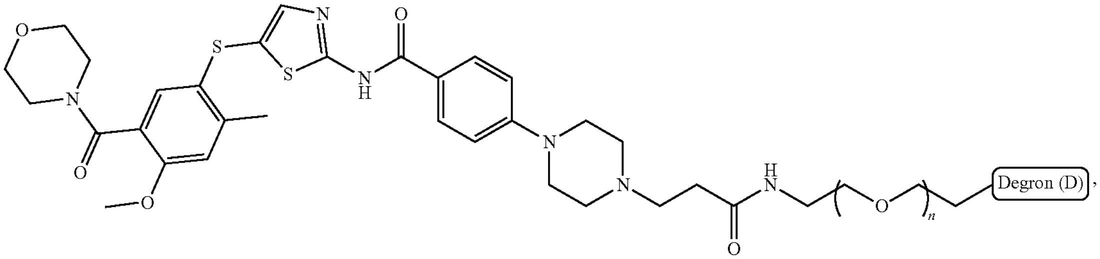
,
n=1-6
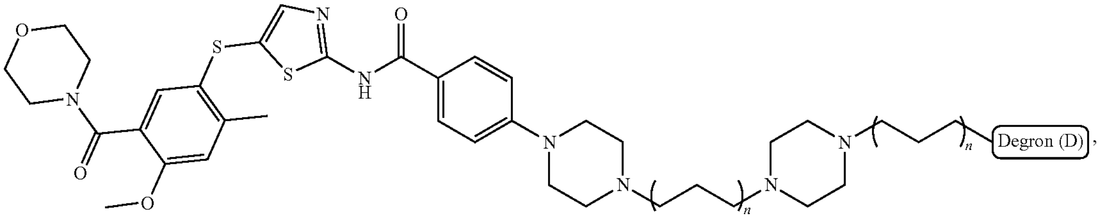
,
n=1-3
n=1-3
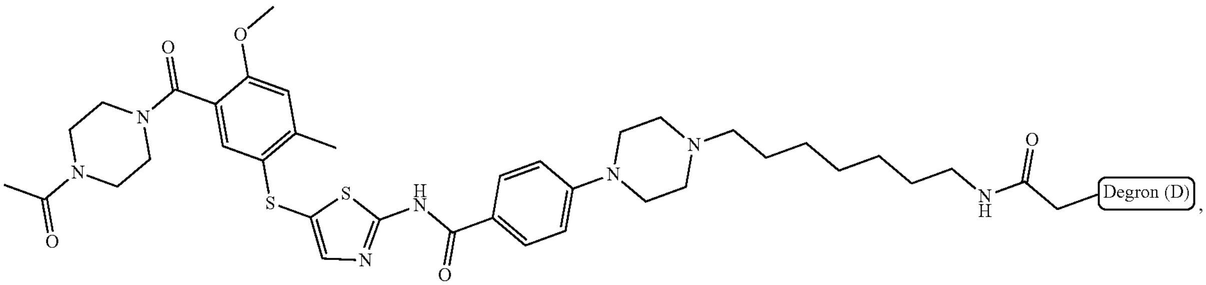
, -continued

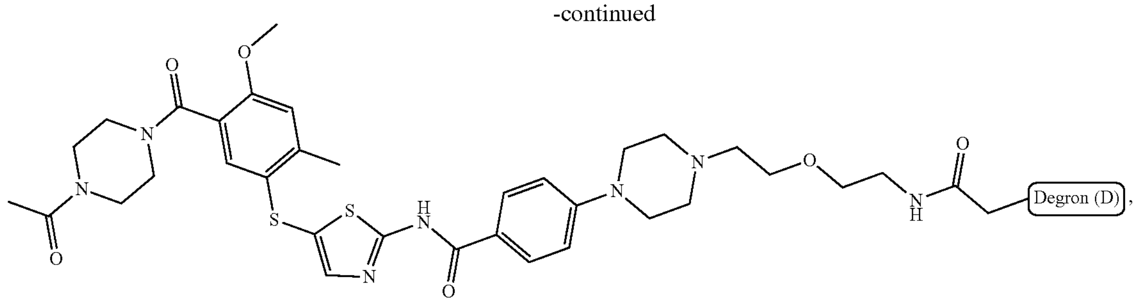

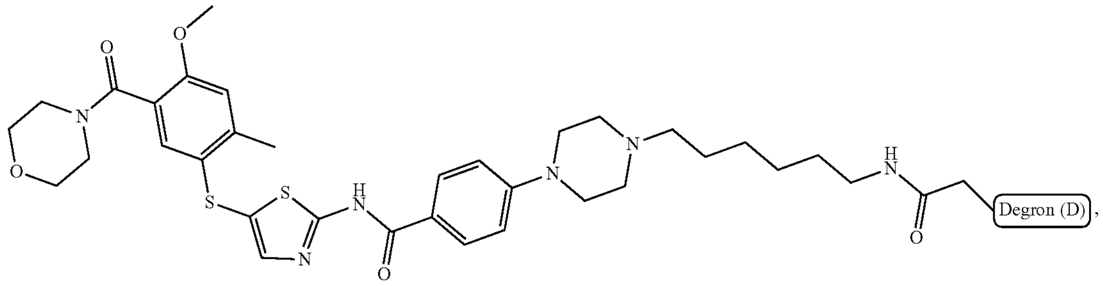

and

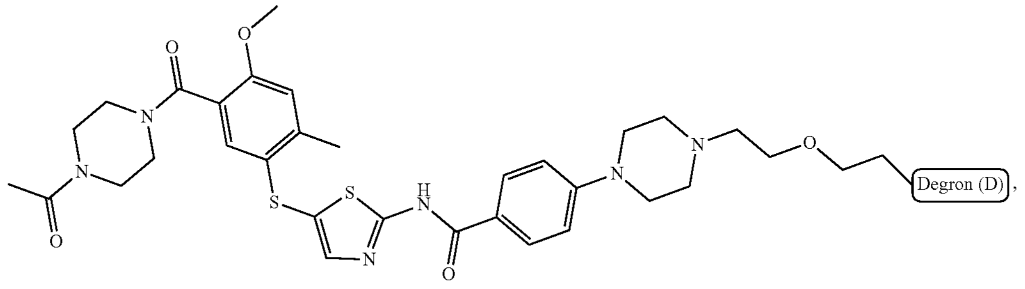 [SMILES: CCCOCCN1CCN(c2ccc(C(=O)Nc3ncc(Sc4cc(C(=O)N5CCN(C(C)=O)CC5)c(OC)cc4C)s3)cc2)CC1]

or a pharmaceutically acceptable salt or stereoisomer thereof, wherein in any of the bispecific compounds disclosed above, any two occurrences of "n" in the same compound may be the same or different.

Degrons

The Ubiquitin-Proteasome Pathway (UPP) is a critical cellular pathway that regulates key regulator proteins and degrades misfolded or abnormal proteins. UPP is central to multiple cellular processes. The covalent attachment of ubiquitin to specific protein substrates is achieved through the action of E3 ubiquitin ligases. These ligases include over 500 different proteins and are categorized into multiple classes defined by the structural element of their E3 functional activity.

In some embodiments, the degron binds the E3 ubiquitin ligase which is cereblon (CRBN), and is represented by any one of the following structures:

(D1-a)

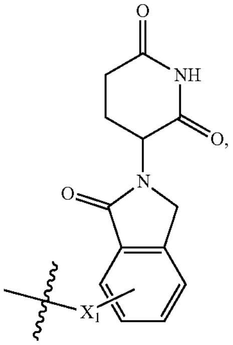

-continued
(D1-b)
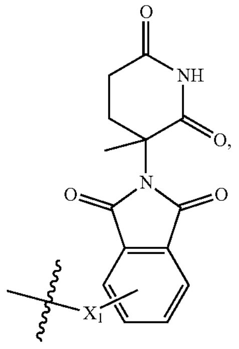
(D1-c)
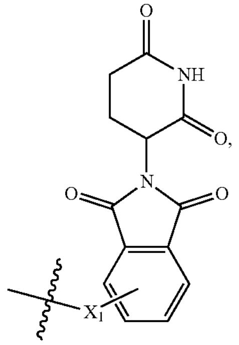
(D1-d)
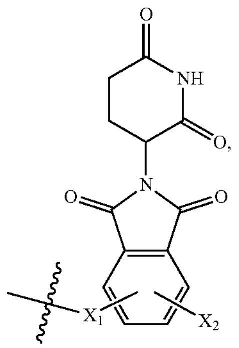
(D1-e)
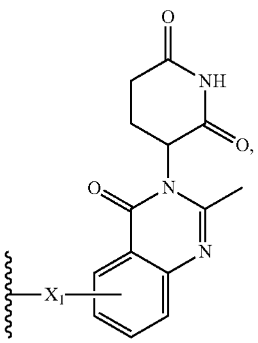
-continued
(D1-f)
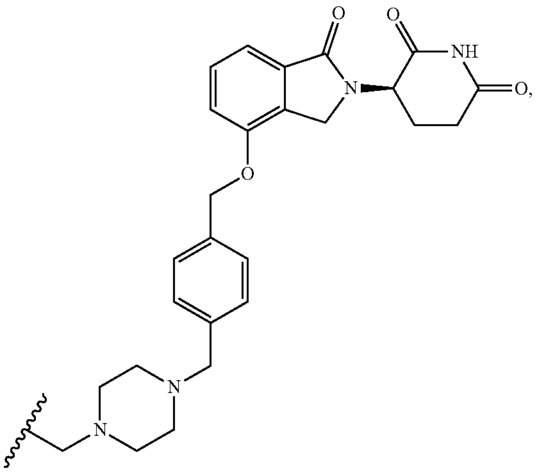
(D1-g)
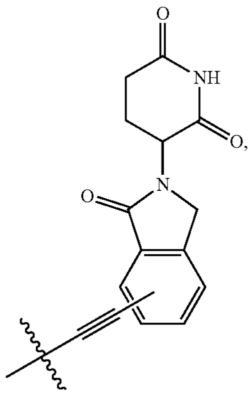
(D1-h)
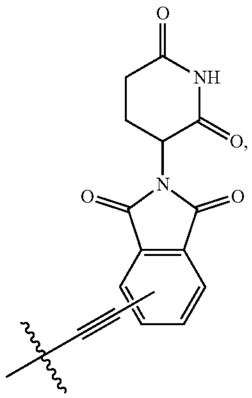

-continued
(D1-i)
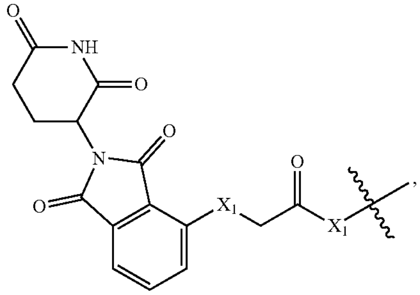
(D1-j)
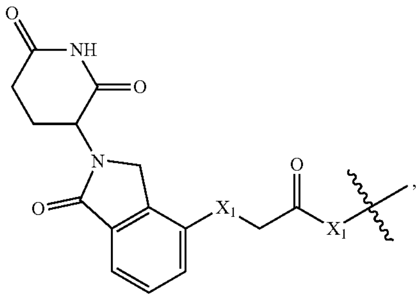
and
-continued
(D1-k)
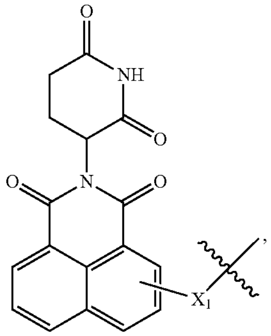
wherein $X_1$ is independently absent, $CH_2$, NH, or O; and $X_2$ is alkyl, halo, CN, $CF_3$, $OCHF_2$ or $OCF_3$.
Thus, in some embodiments, the bispecific compounds of the present invention may be represented by any one of the following structures:
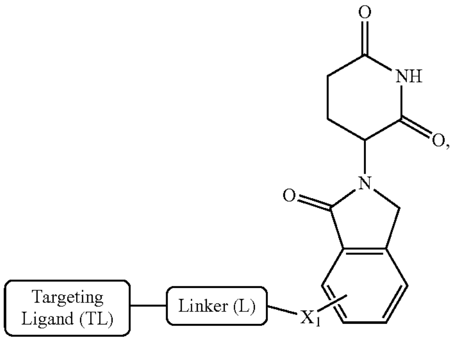
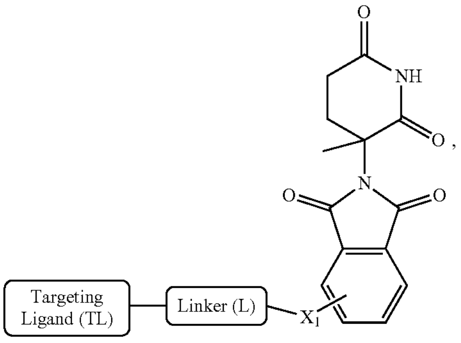
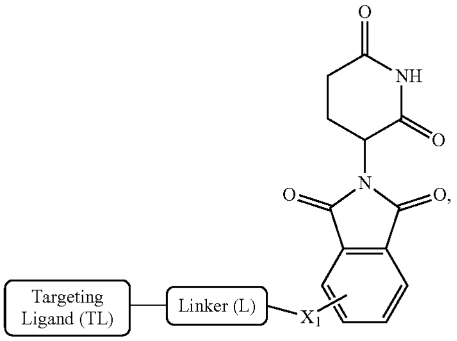
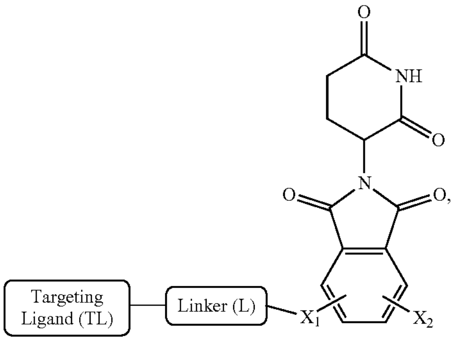

-continued
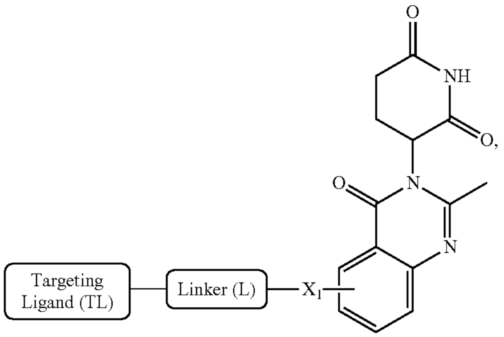
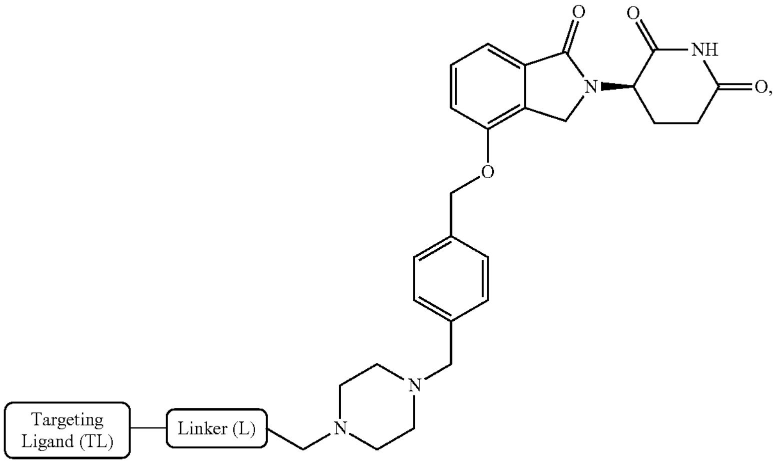
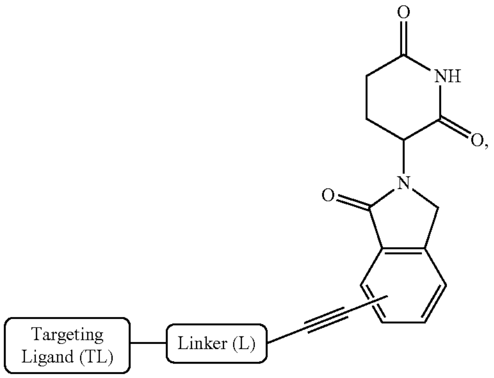
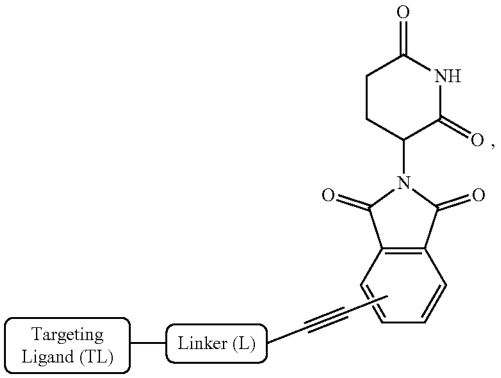
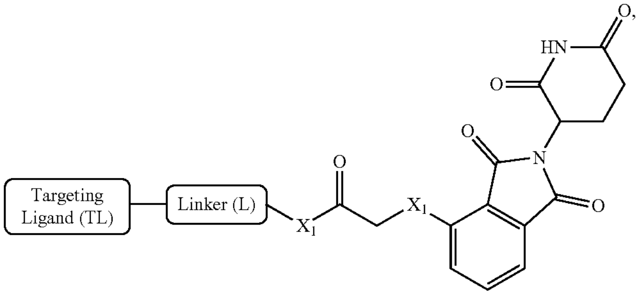

-continued
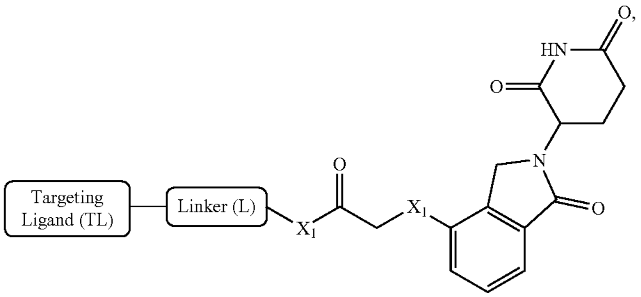
and
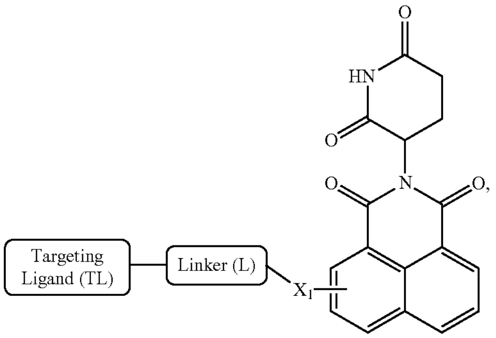
or a pharmaceutically acceptable salt or stereoisomer thereof.
In some embodiments, the bispecific compounds of the present invention are represented by any one of the following structures:
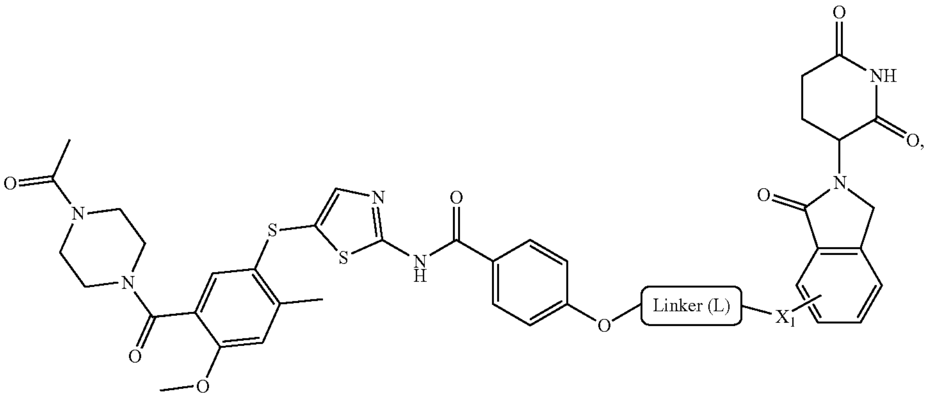
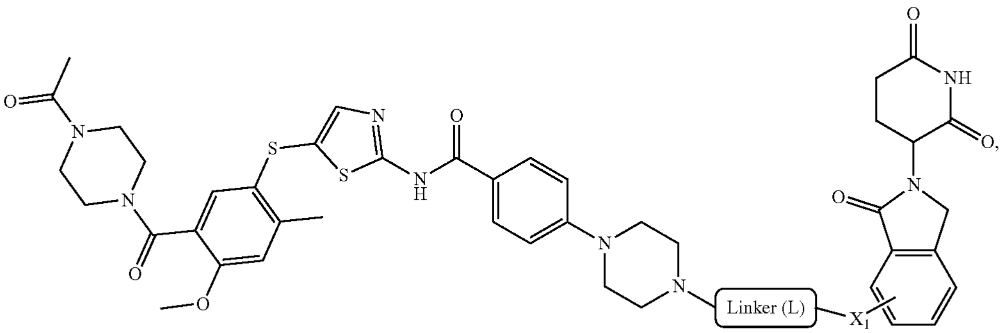

-continued
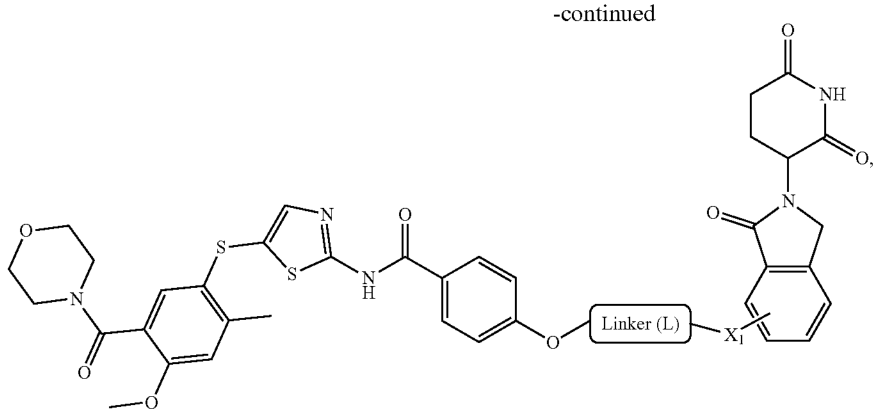
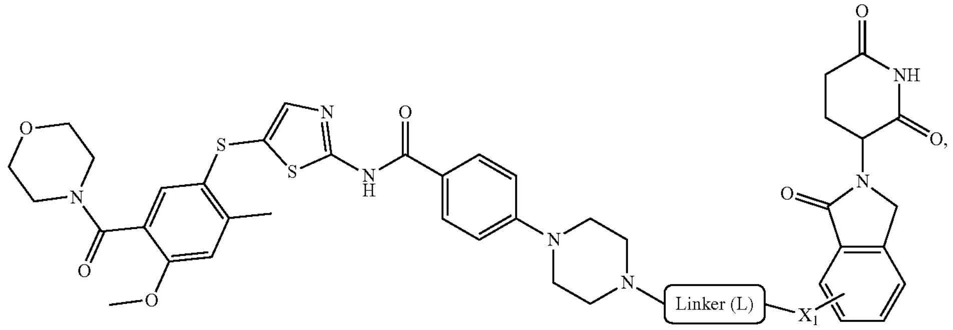
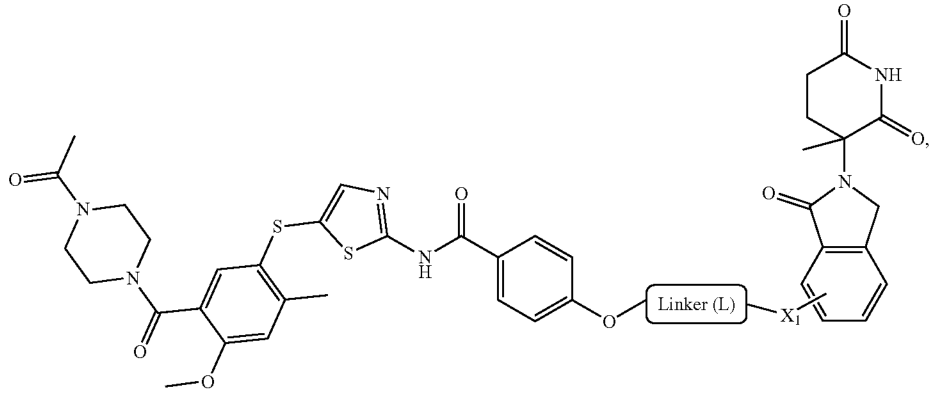
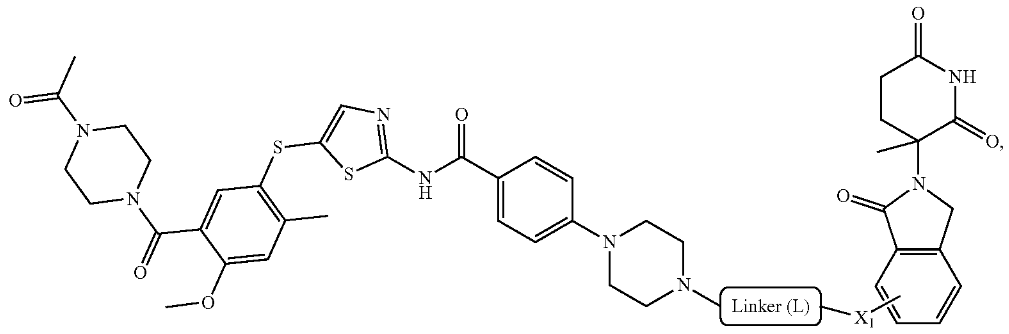

-continued
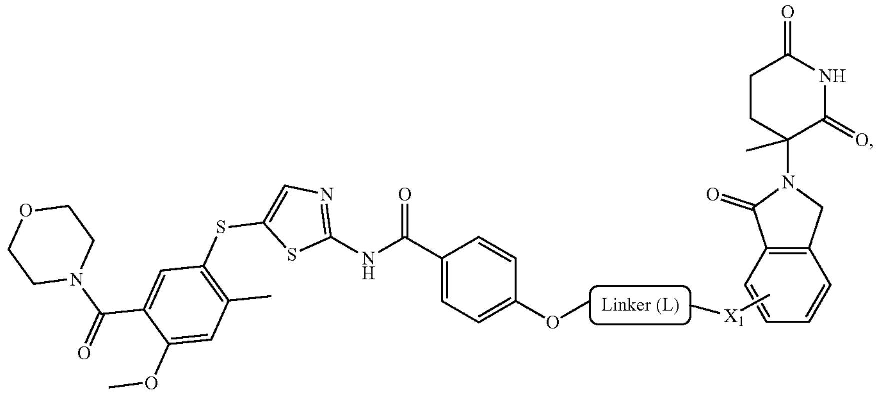
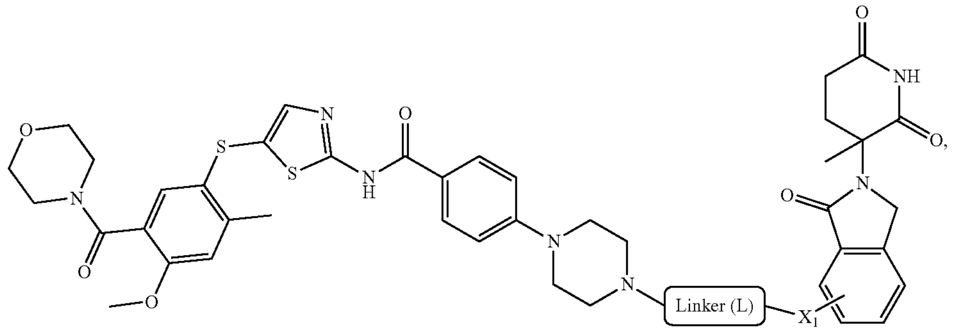
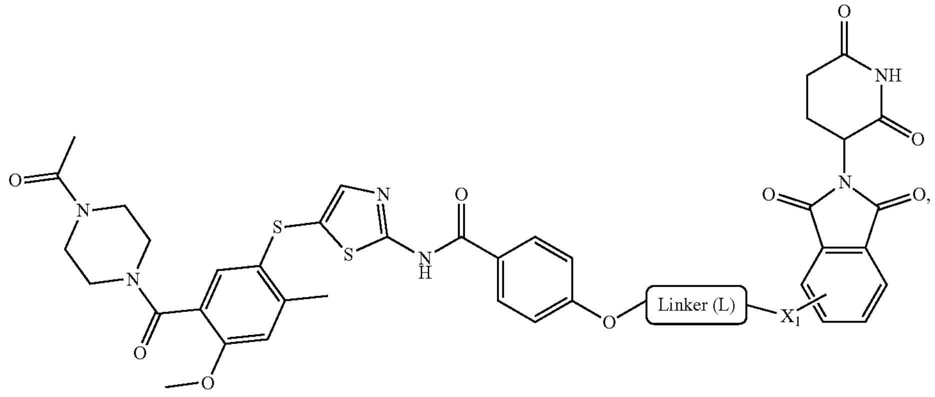
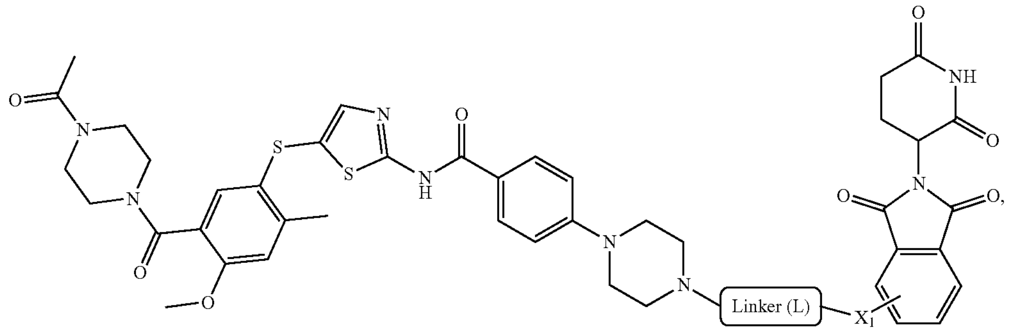

-continued
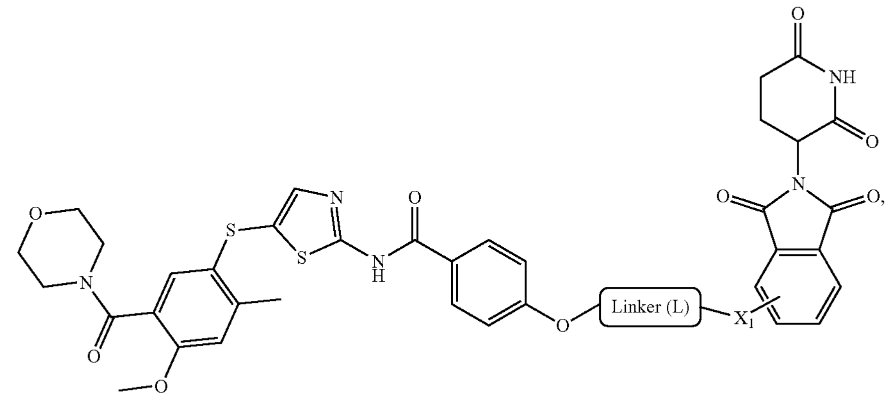
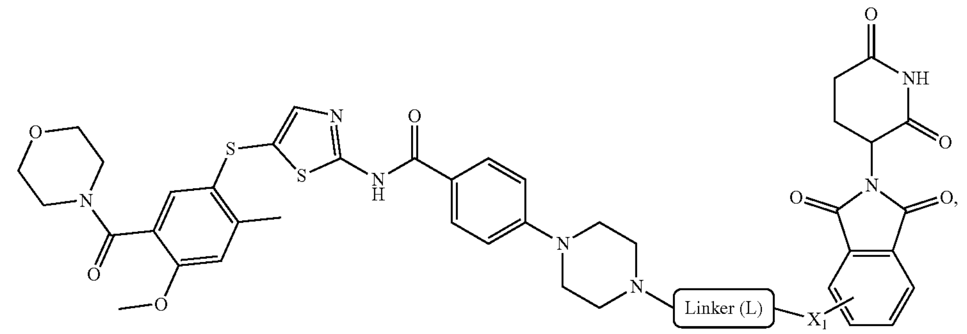
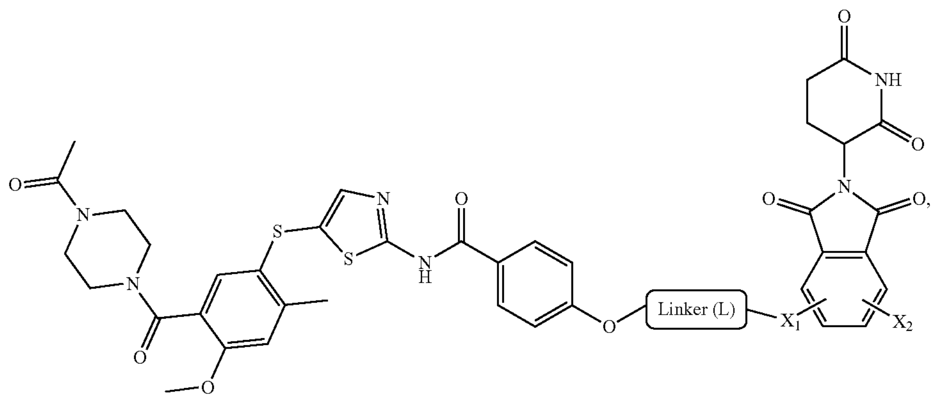
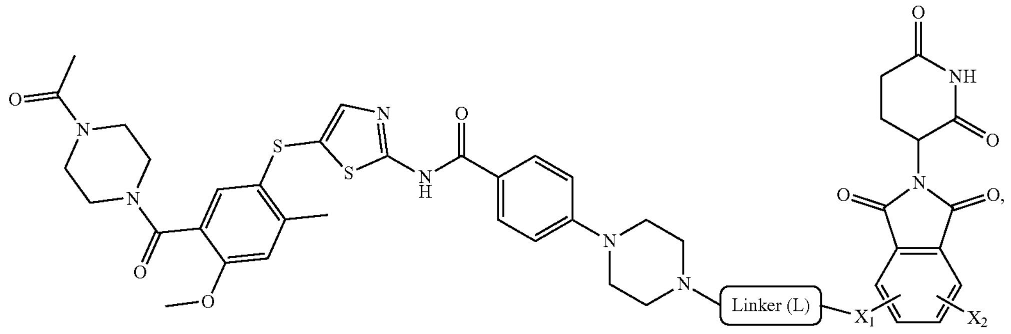

-continued
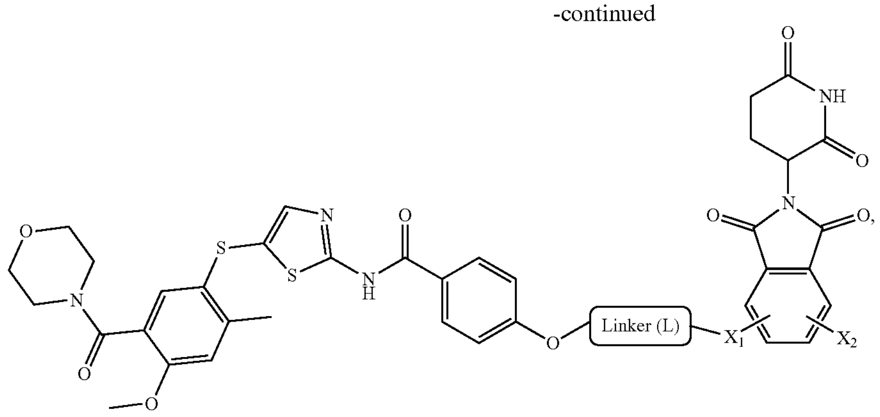
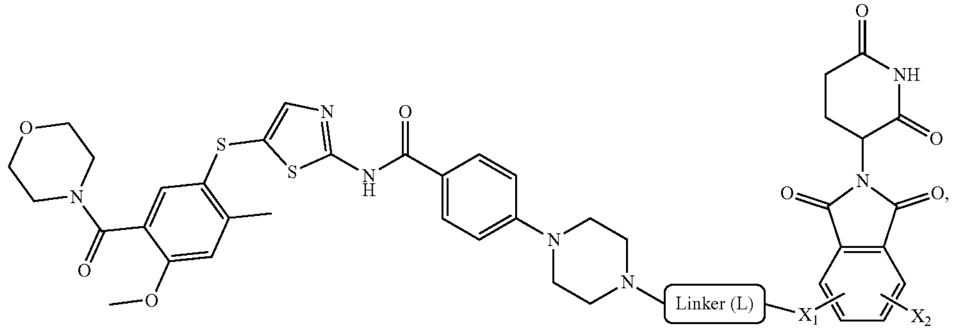
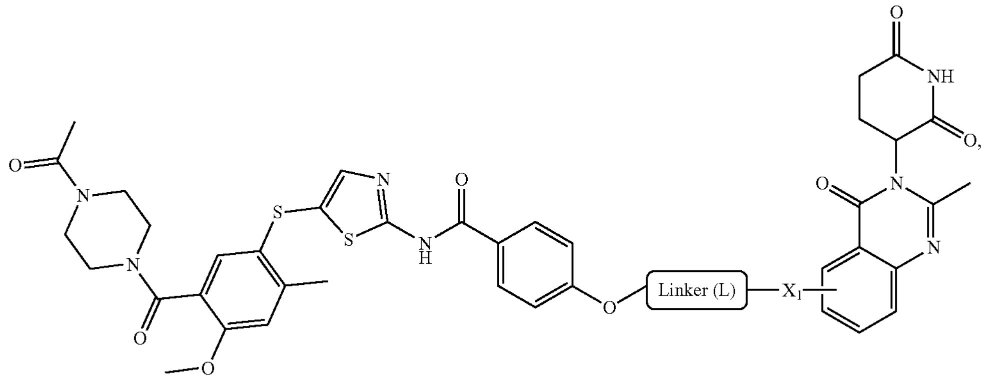
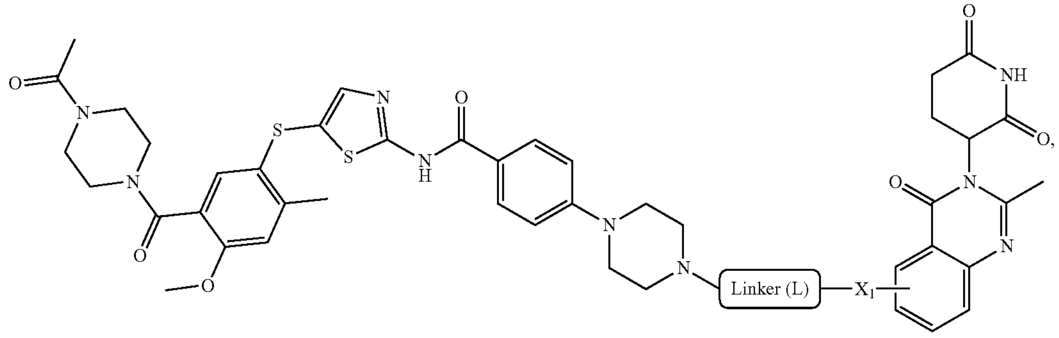

-continued
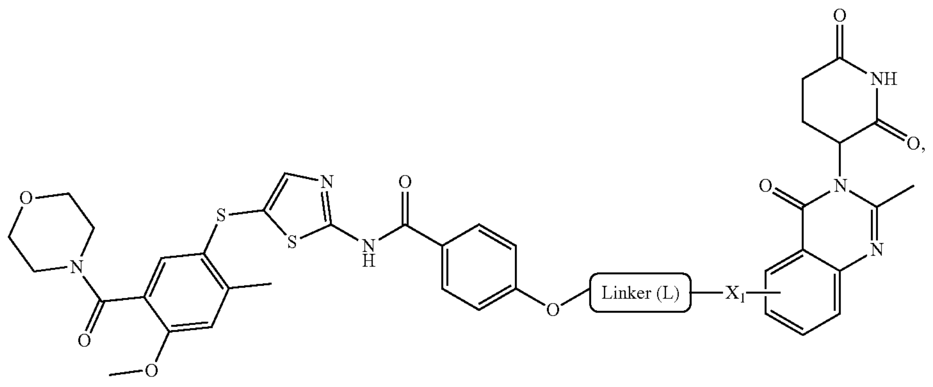
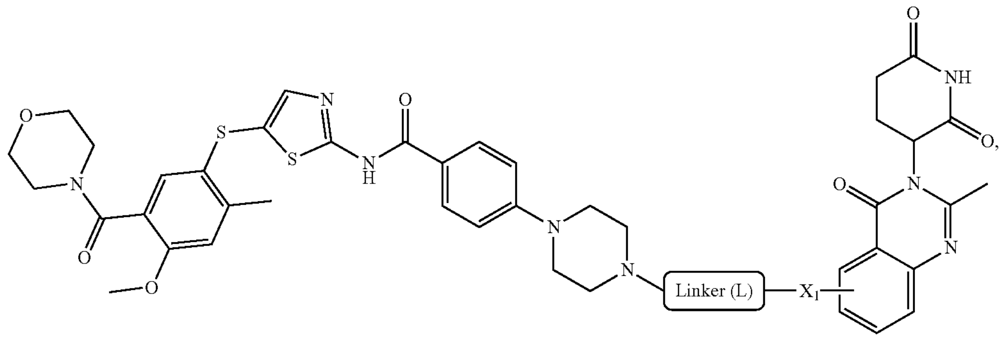
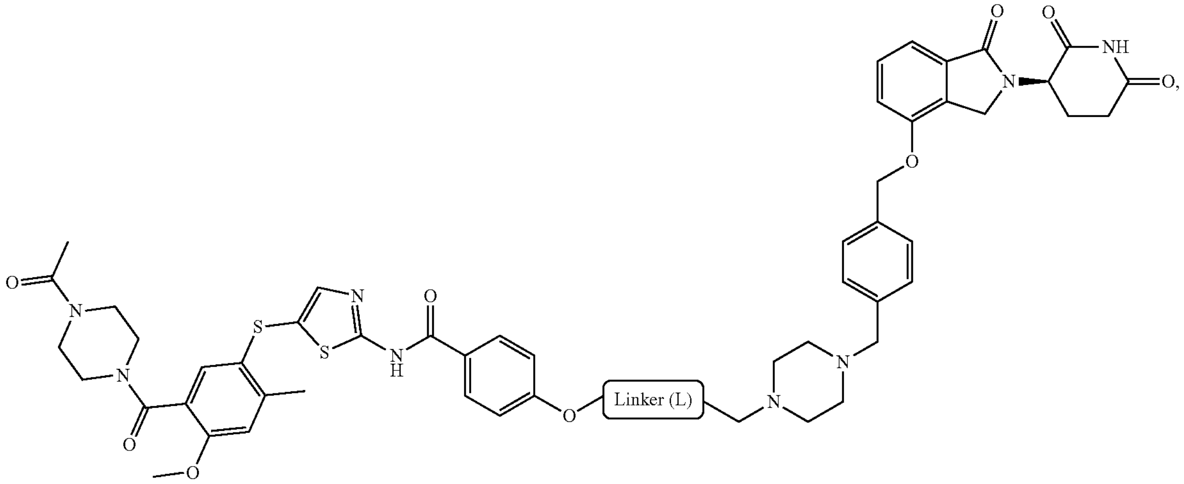
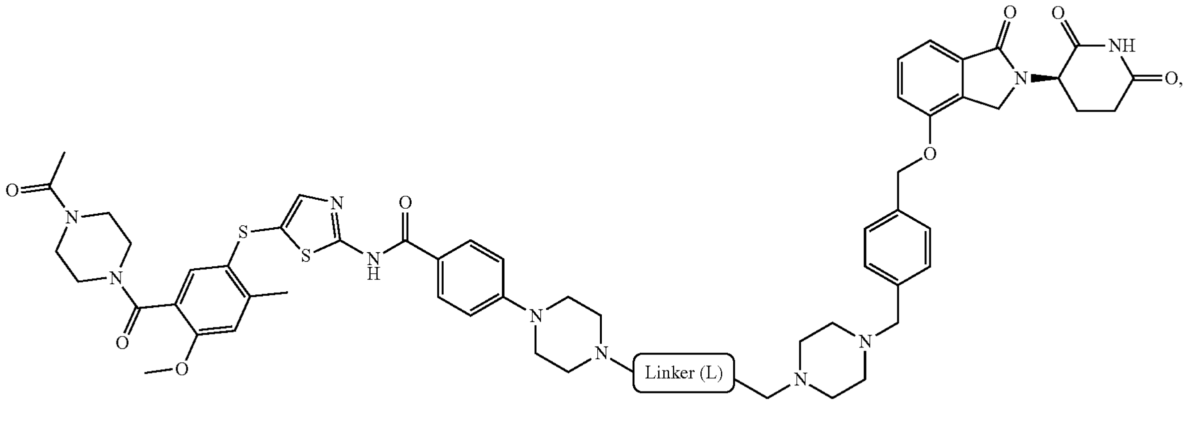

-continued
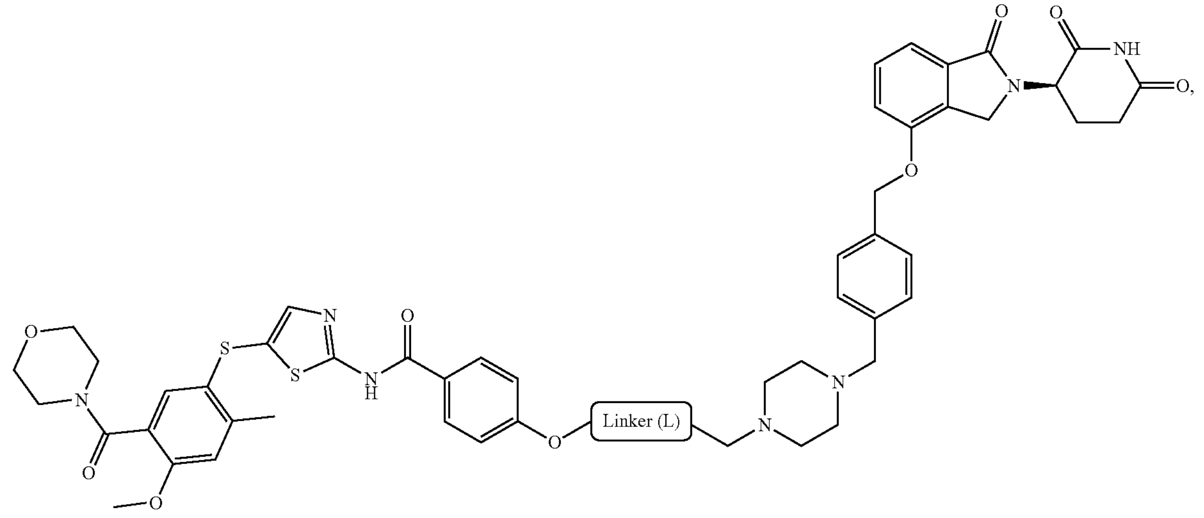
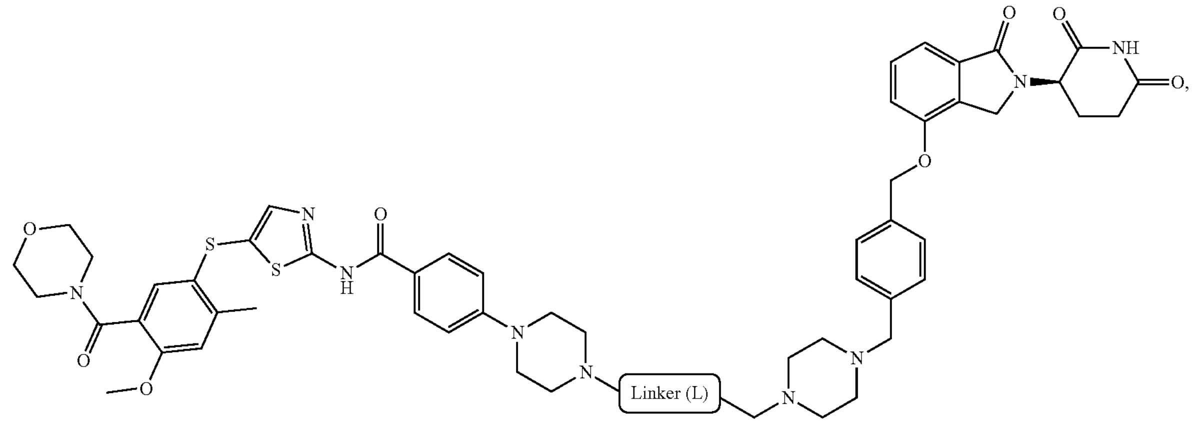
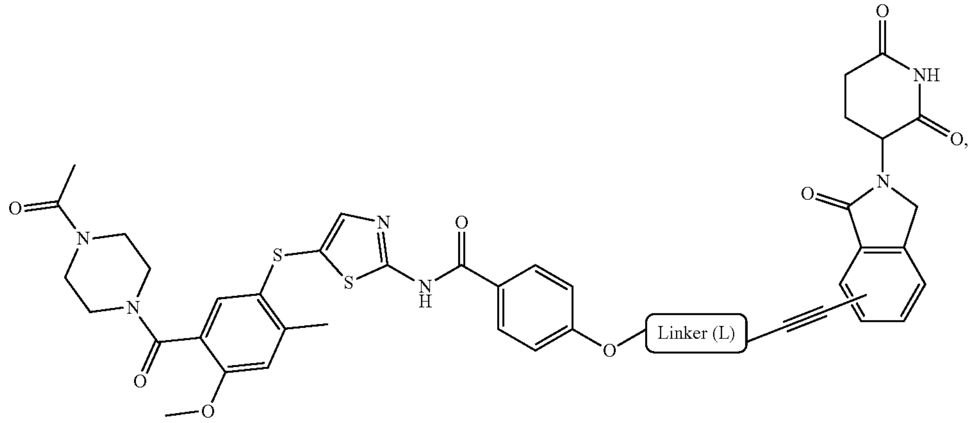
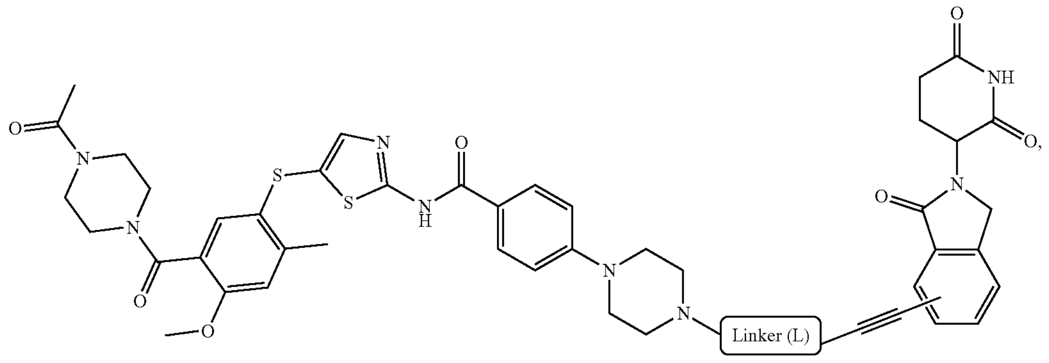

-continued
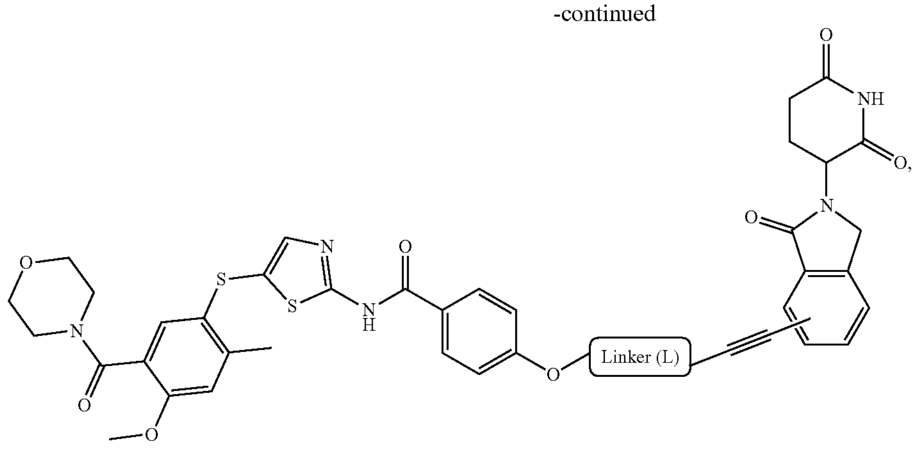
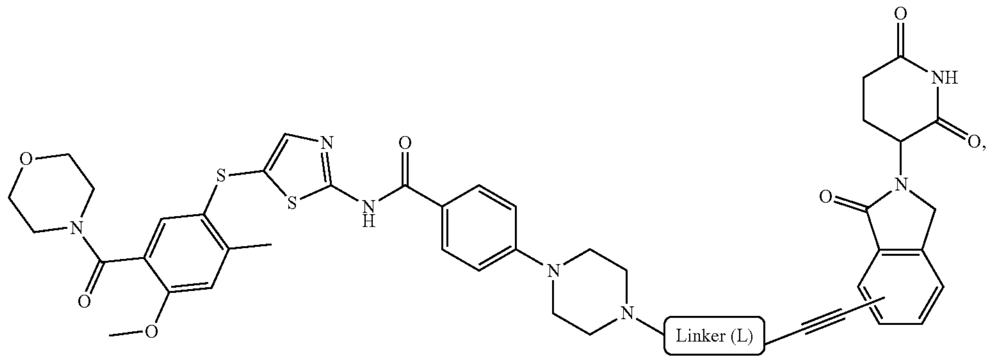
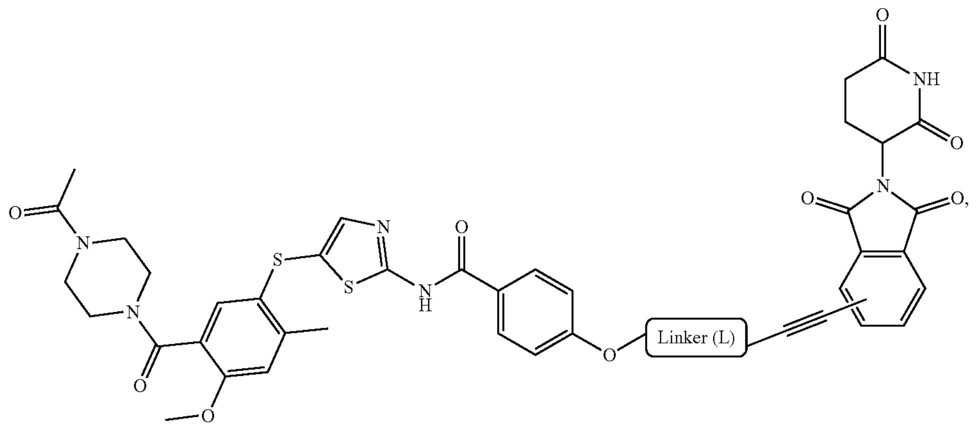
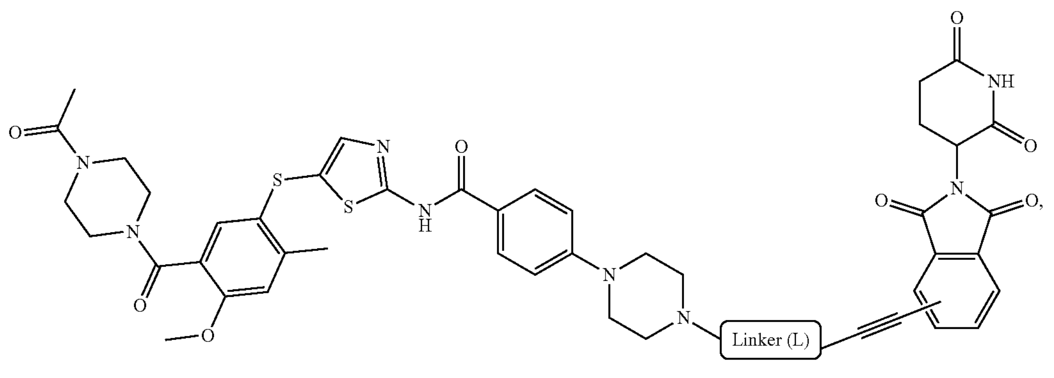

-continued
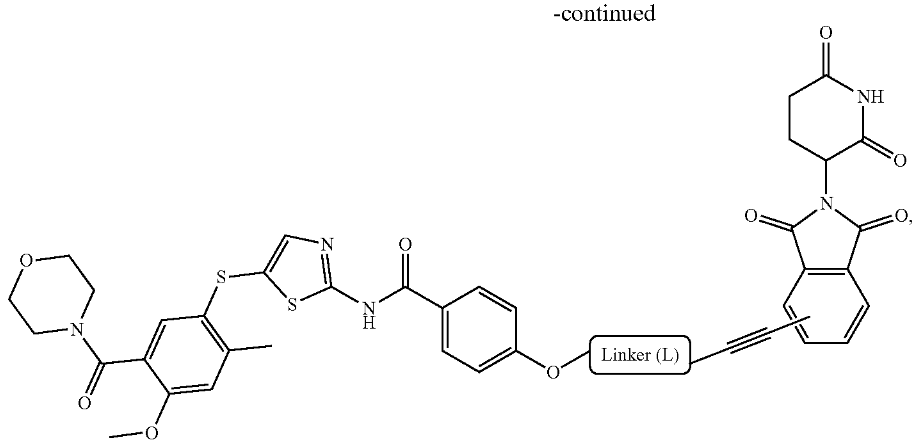
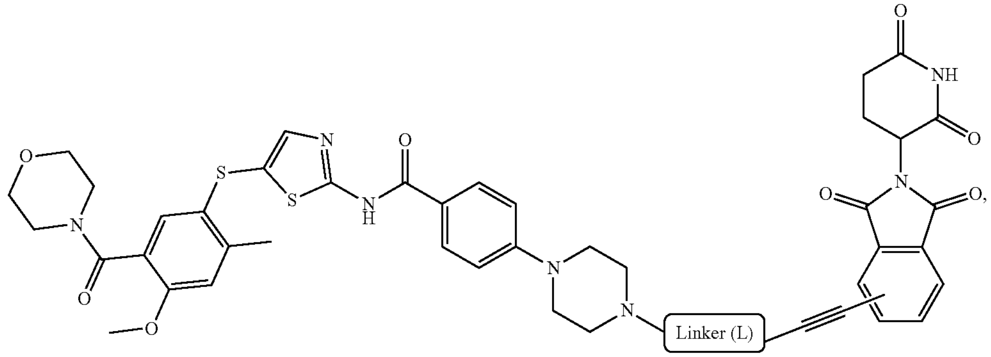
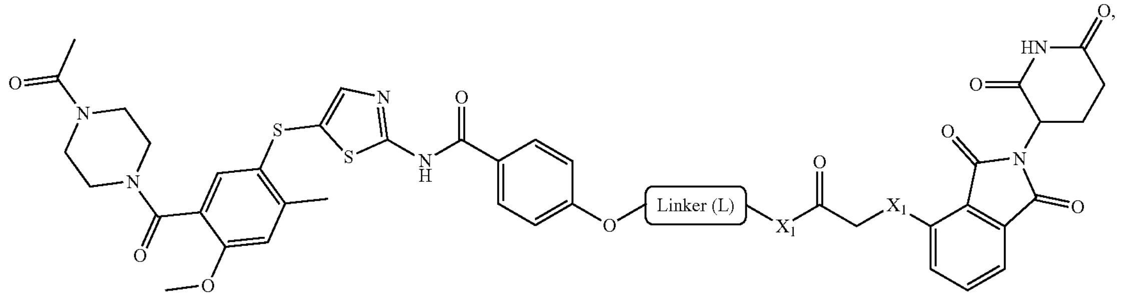
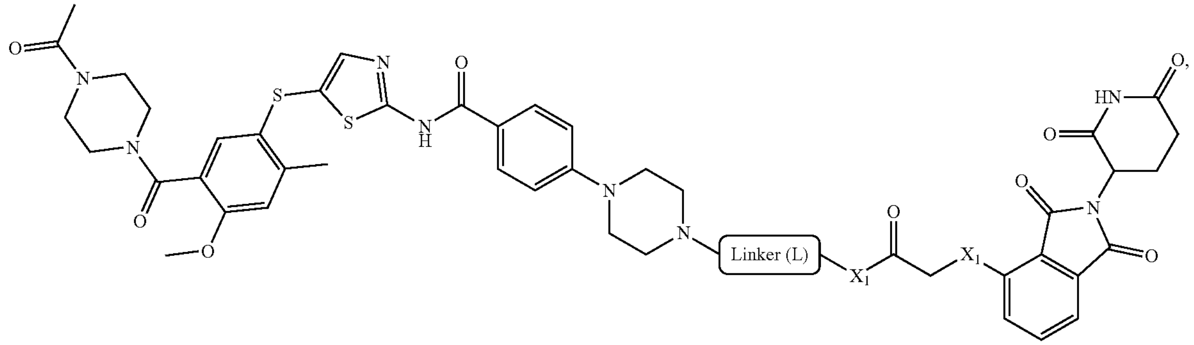
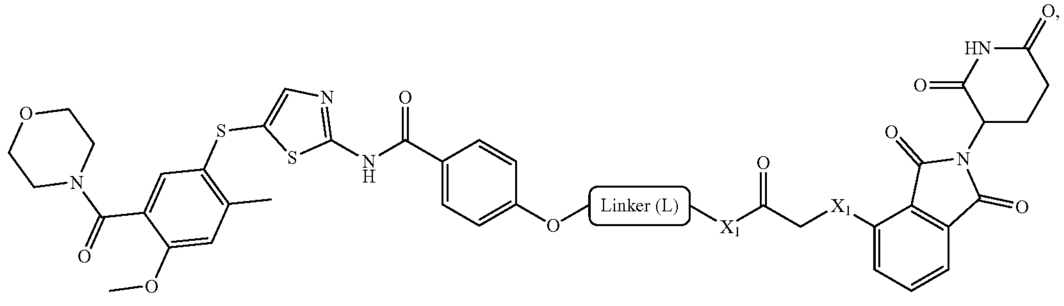

-continued
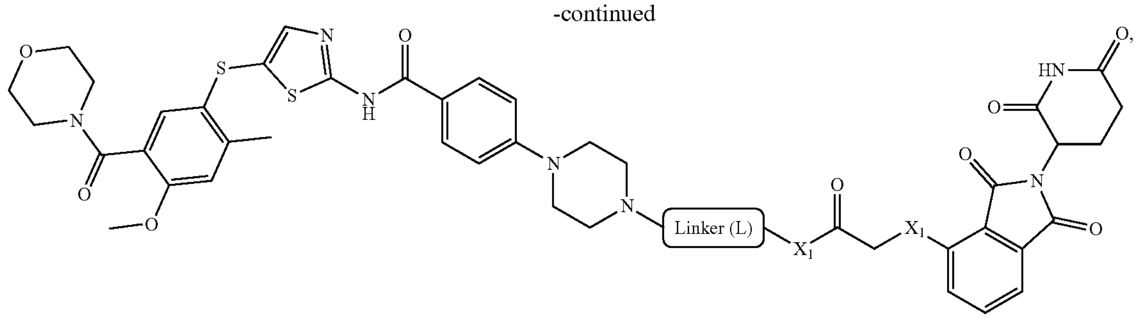
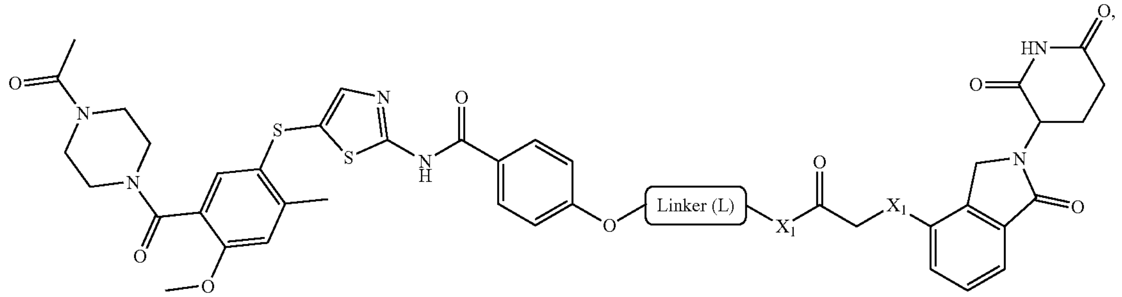
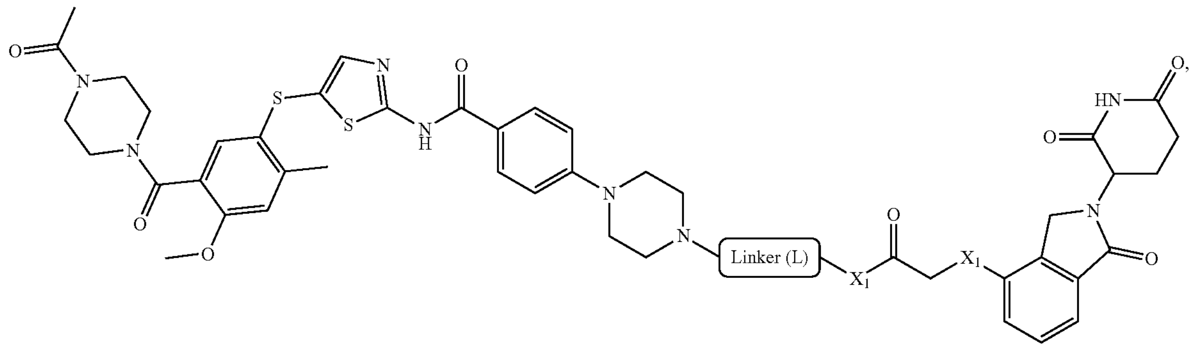
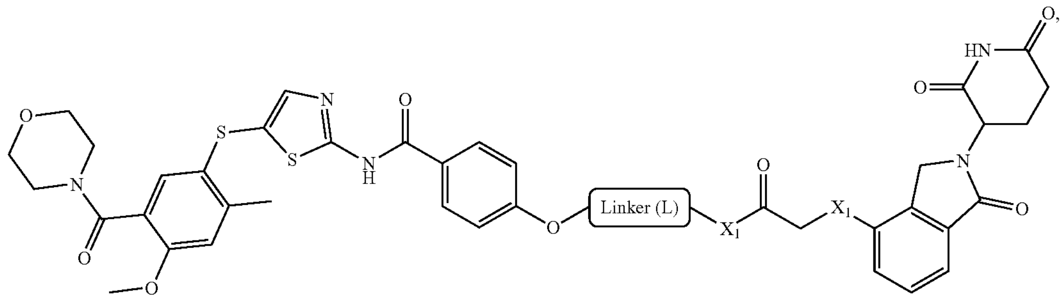
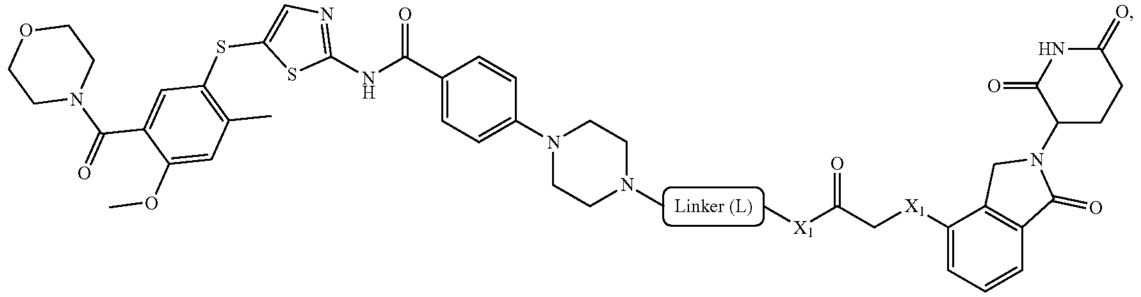

-continued

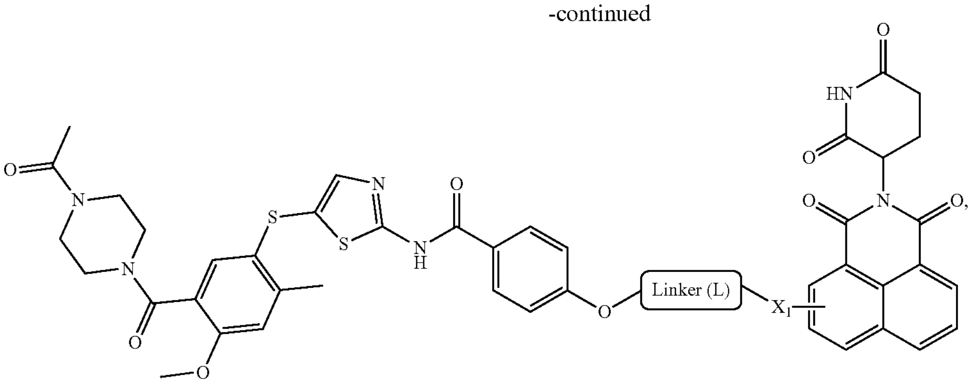

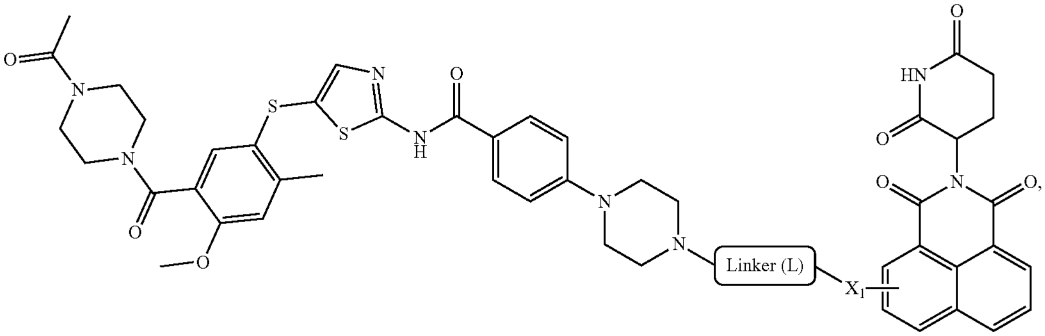

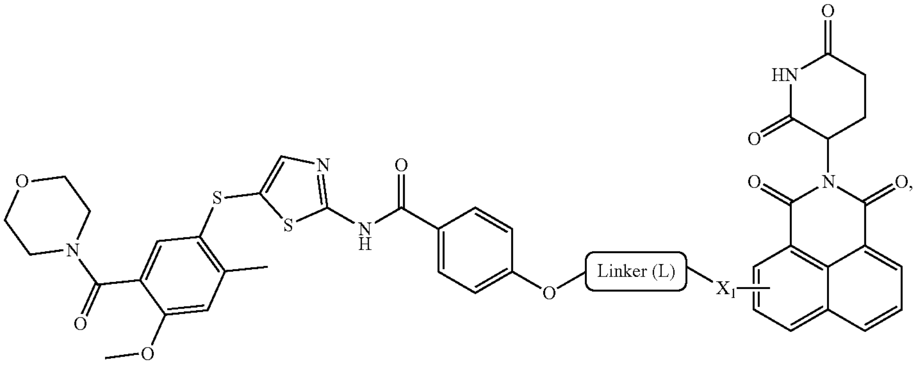

and

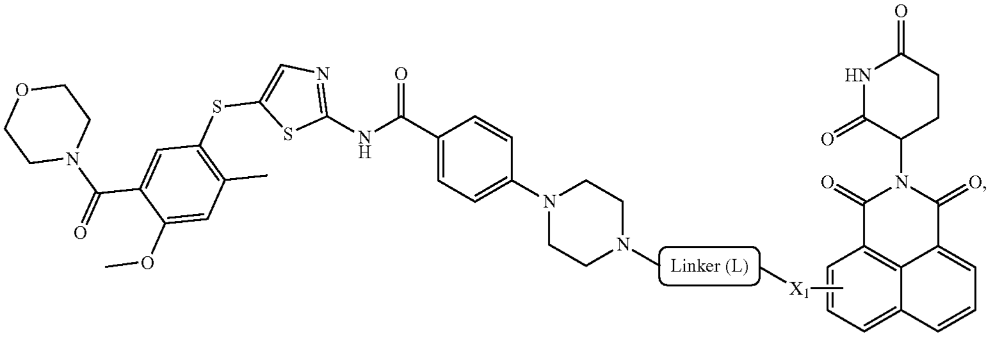

or a pharmaceutically acceptable salt or stereoisomer thereof.

Yet other degrons that bind cereblon and which may be suitable for use in the present invention are disclosed in U.S. Patent Application Publication 2018/0015085 A1 (e.g., the indolinones such as isoindolinones and isoindoline-1,3-diones embraced by formulae IA ad IA' therein, and the bridged cycloalkyl compounds embraced by formulae IB and IB' therein).

In some embodiments, the E3 ubiquitin ligase that is bound by the degron is the von Hippel-Lindau (VHL) tumor suppressor. See, Iwai et al., Proc. Nat'l. Acad. Sci. USA 96:12436-41 (1999).

Representative examples of degrons that bind VHL are as follows:

(D2-a)

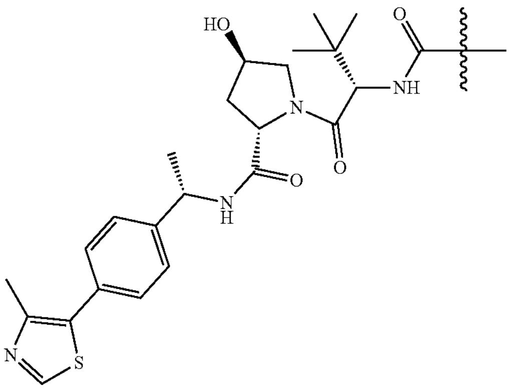

;

(D2-b)

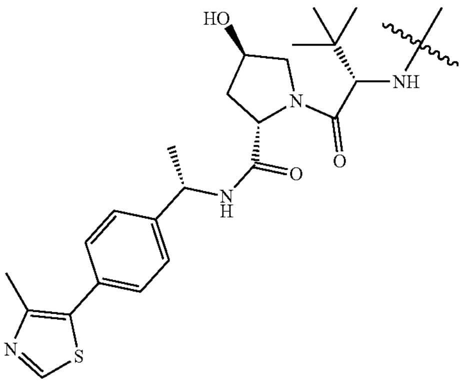

;

(D2-c)

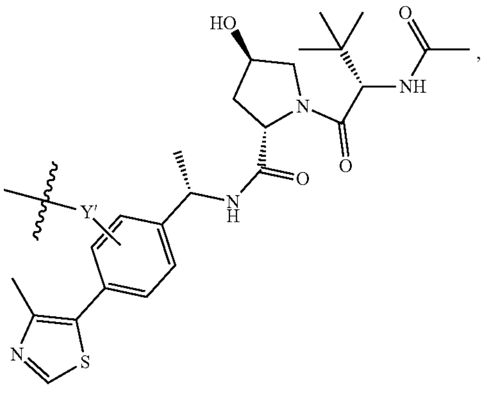

, wherein Y' is a bond, NH, O or $CH_2$;

(D2-d)

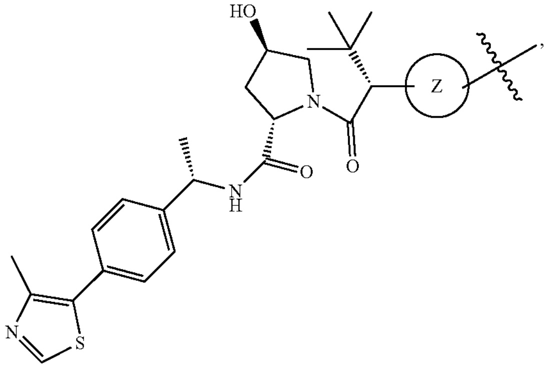

, wherein Z is a $C_5$-$C_6$ carbocyclic or a 5-6 membered heterocyclic group;

(D2-e)

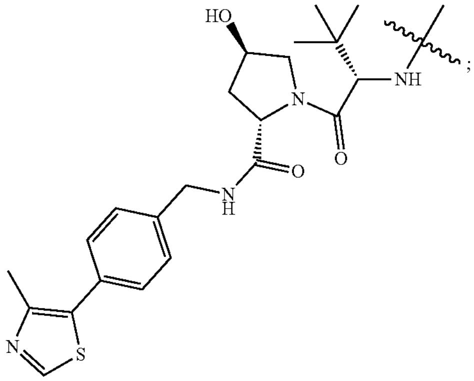

; and (D2-f)

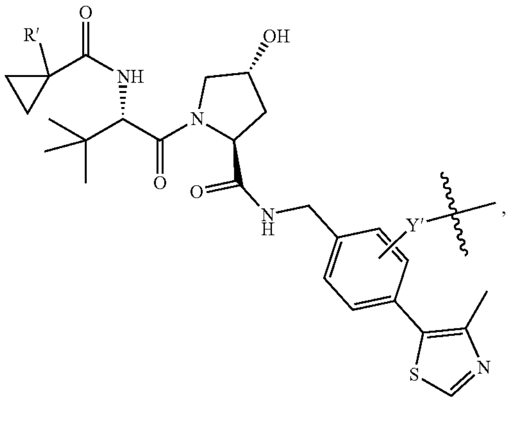

, wherein R' is H, F or CN, and Y' is a bond, NH, O or $CH_2$, or a stereoisomer thereof.

In certain embodiments, Z is a 5-6 membered cyclic or a 5-6 membered heterocyclic group. In some embodiments, Z is phenyl, pyrrolyl, furanyl, thiophenyl, pyrazolyl, imidazolyl, oxazolyl, thiazolyl, pyridinyl, pyridazinyl, or pyrimidinyl. In some embodiments, Z is

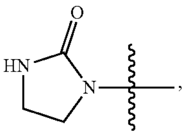
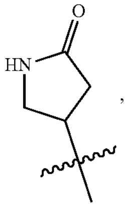
, or
-continued
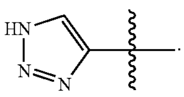
Thus, in some embodiments, the bispecific compounds of the present invention are represented by any one of the following structures:
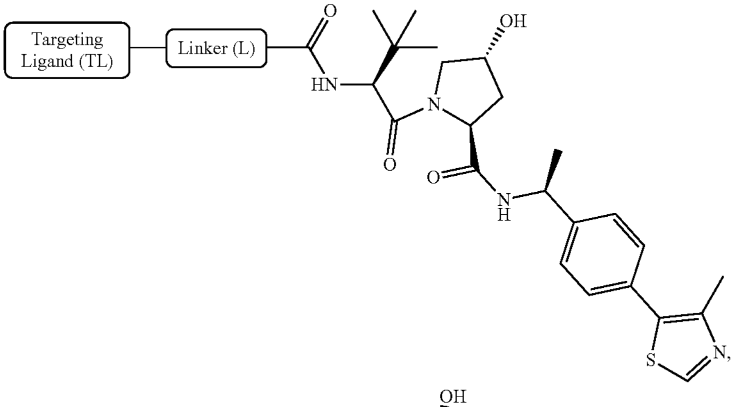
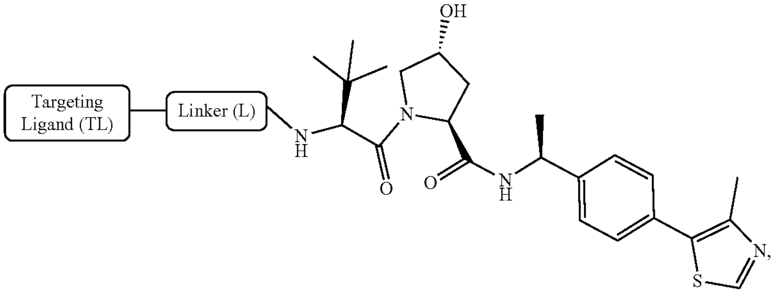
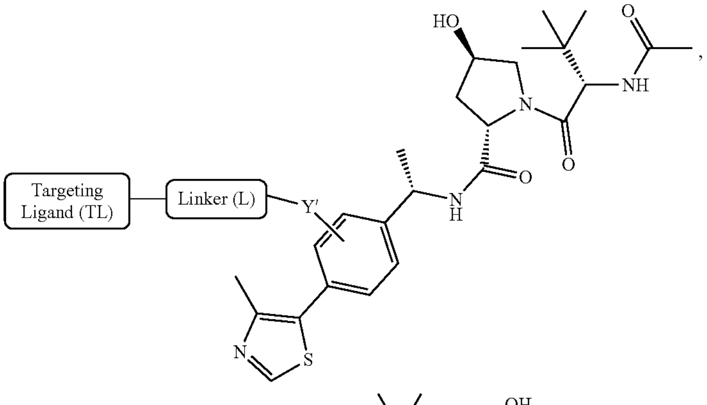
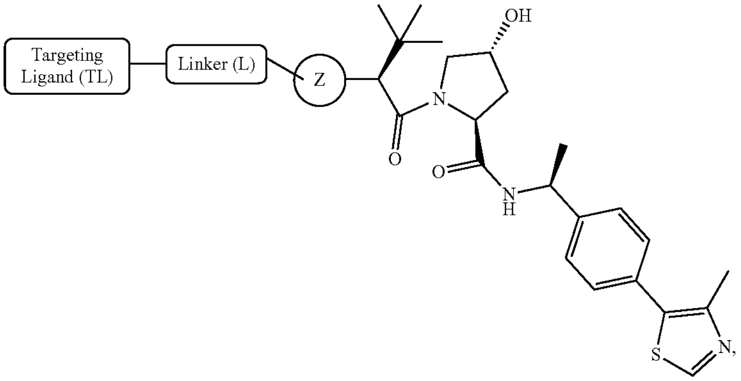

-continued
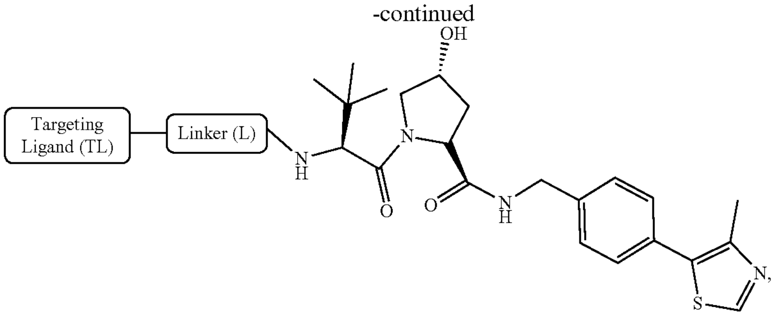
and
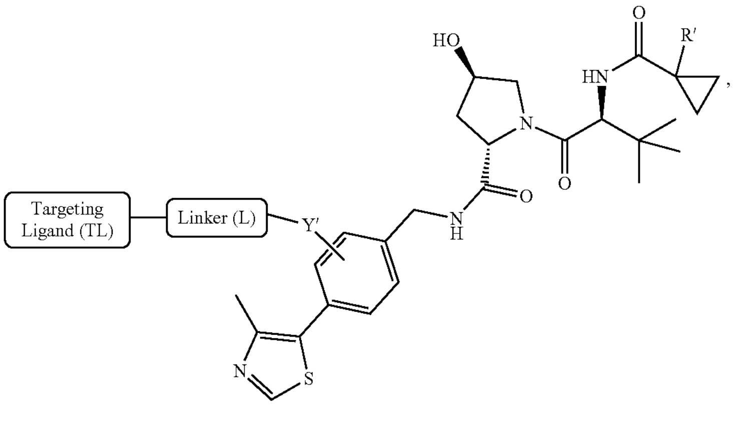
or a pharmaceutically acceptable salt or stereoisomer thereof.
In some embodiments, the bispecific compounds of the present invention are represented by any one of the following structures:
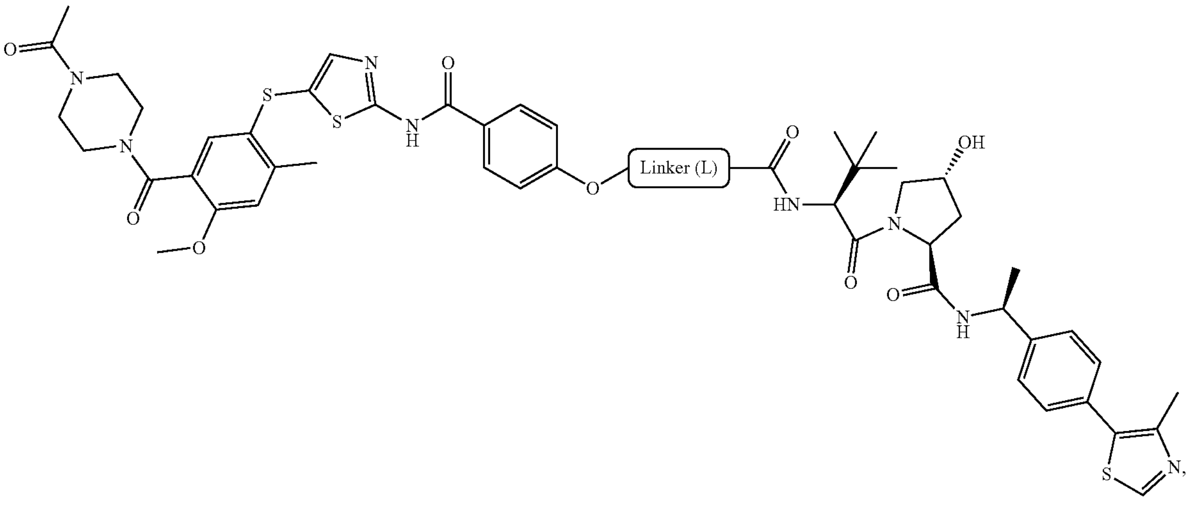

-continued
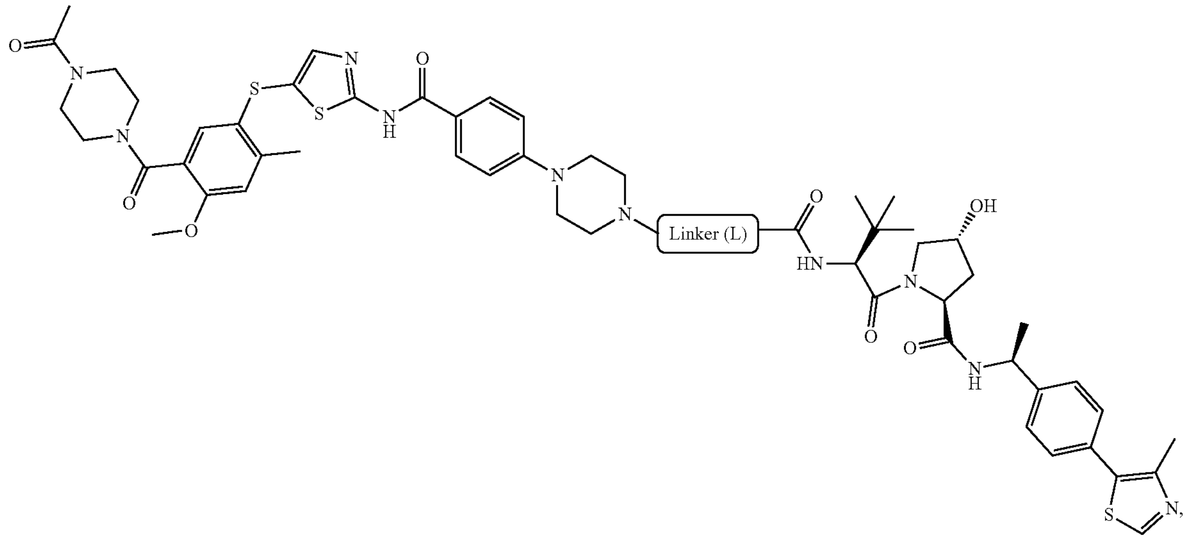
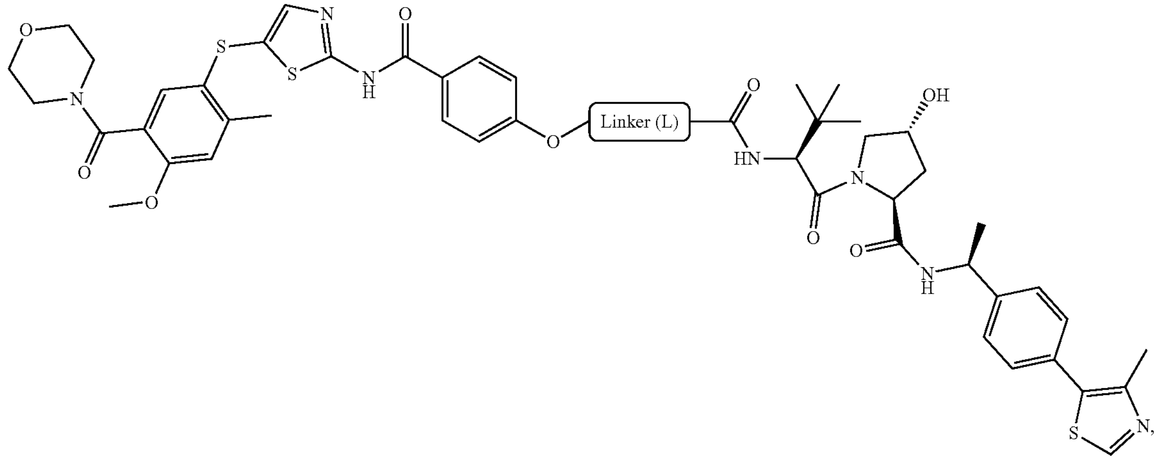
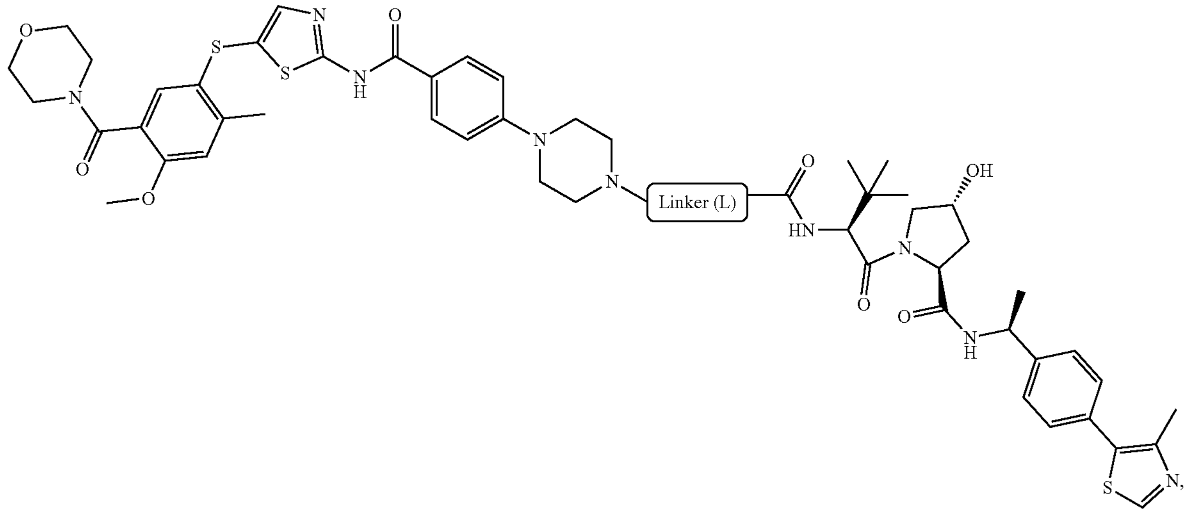

-continued
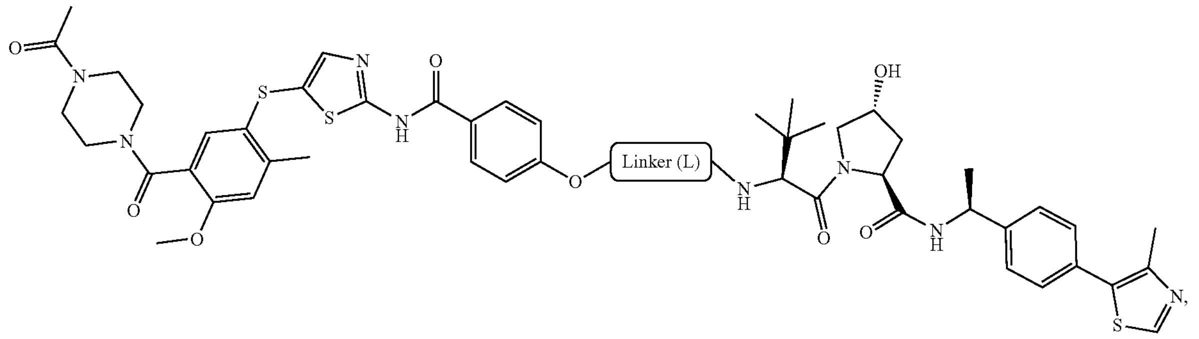
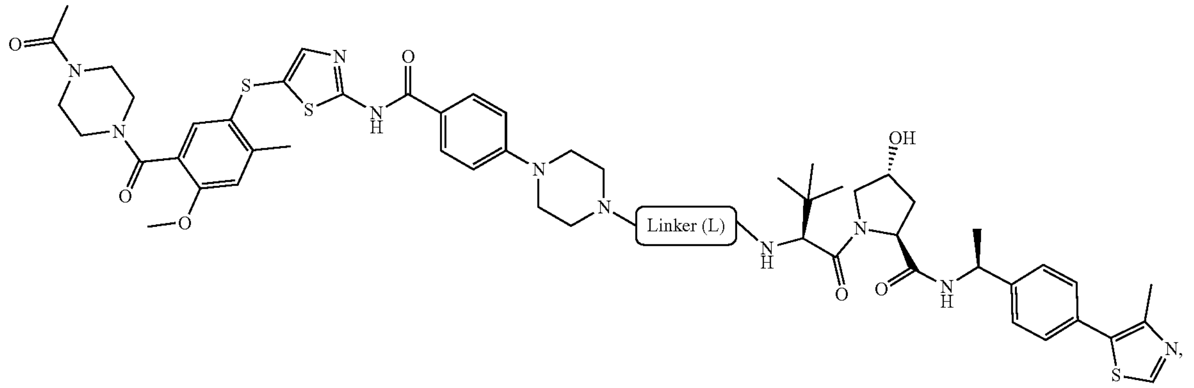
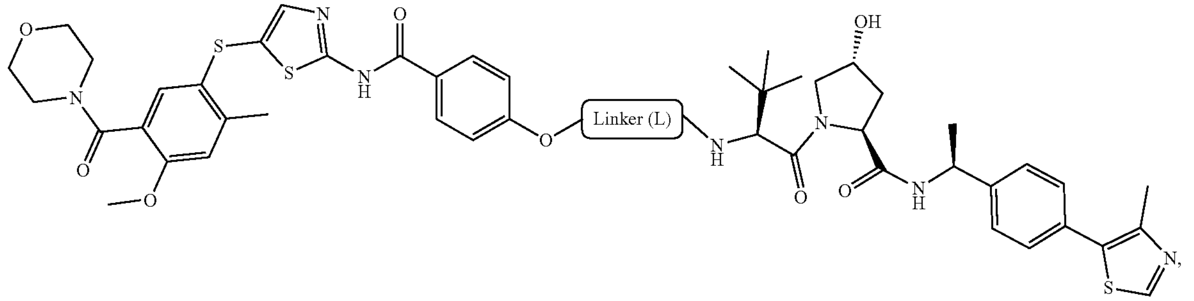
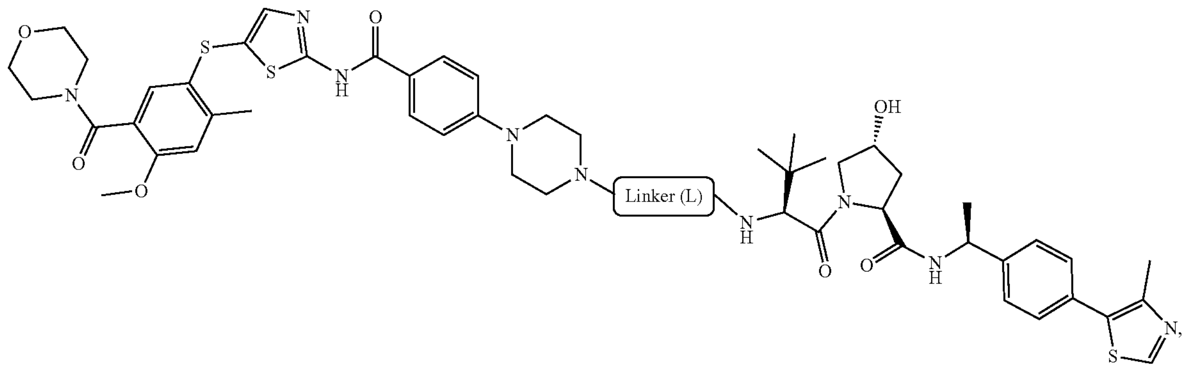

-continued
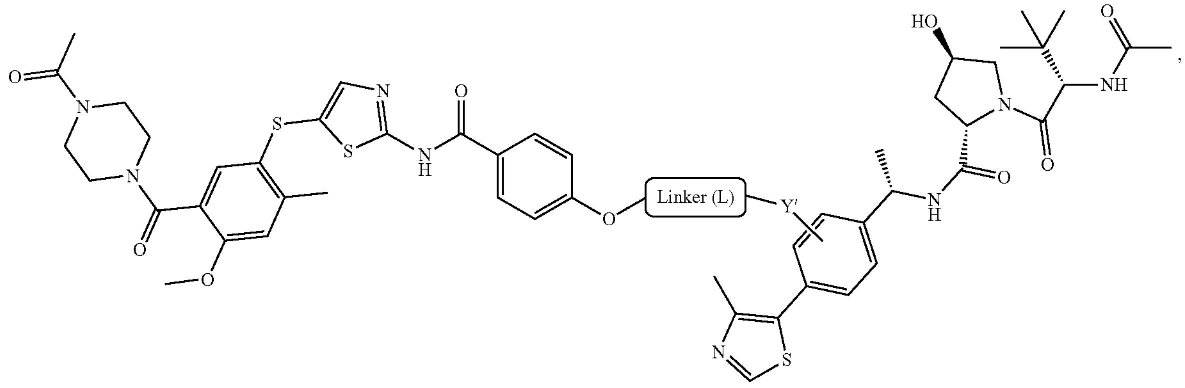
,
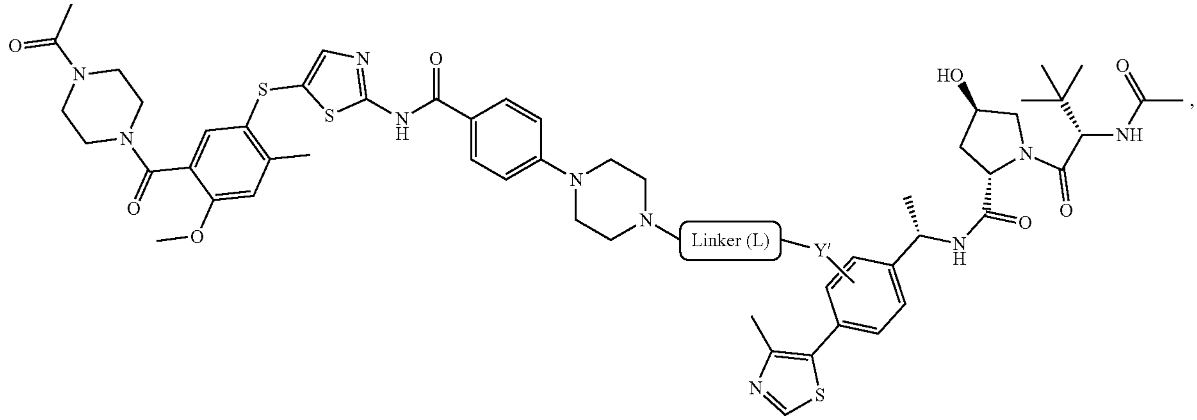
,
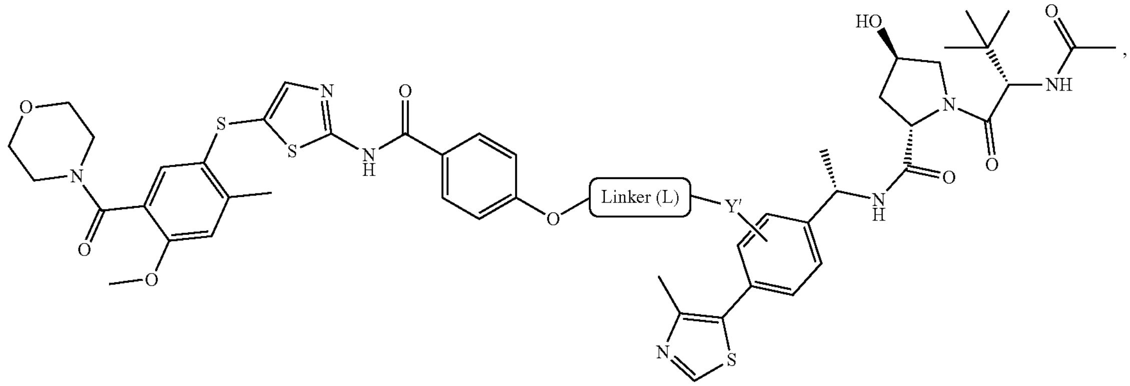
,
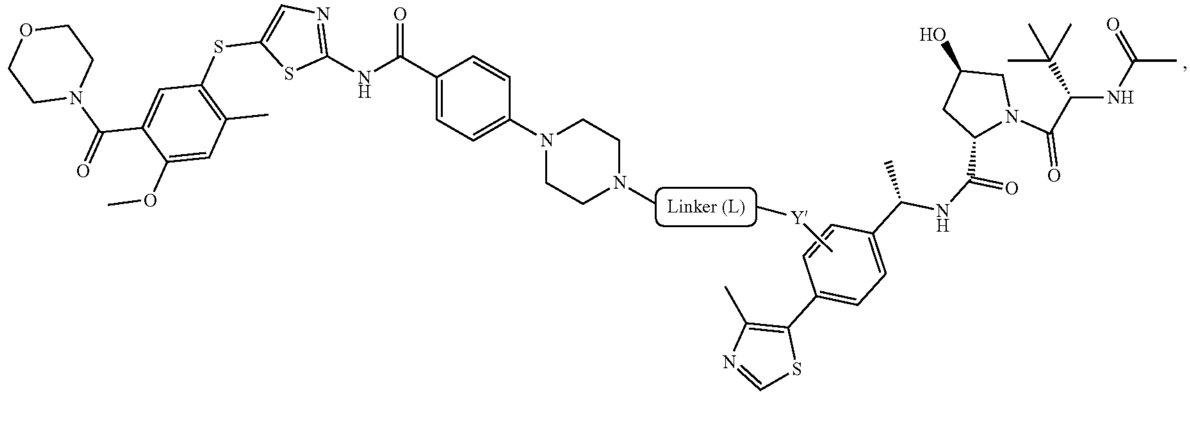
,

-continued
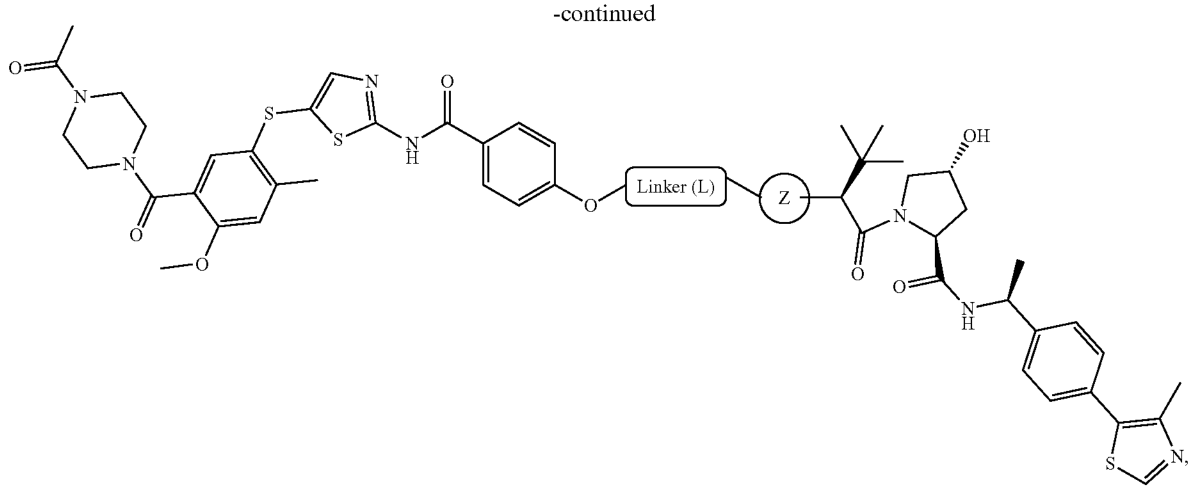
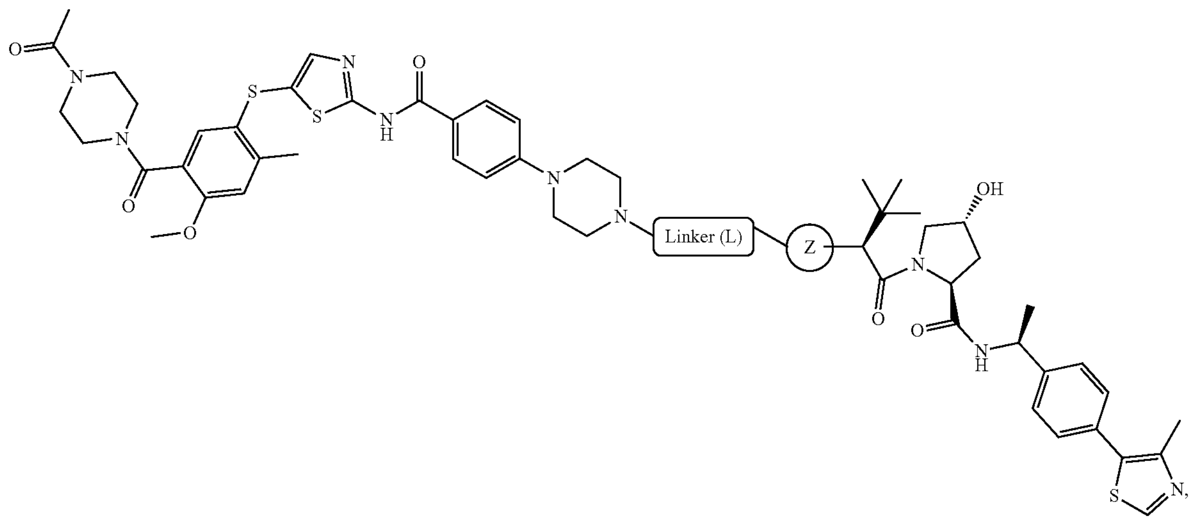
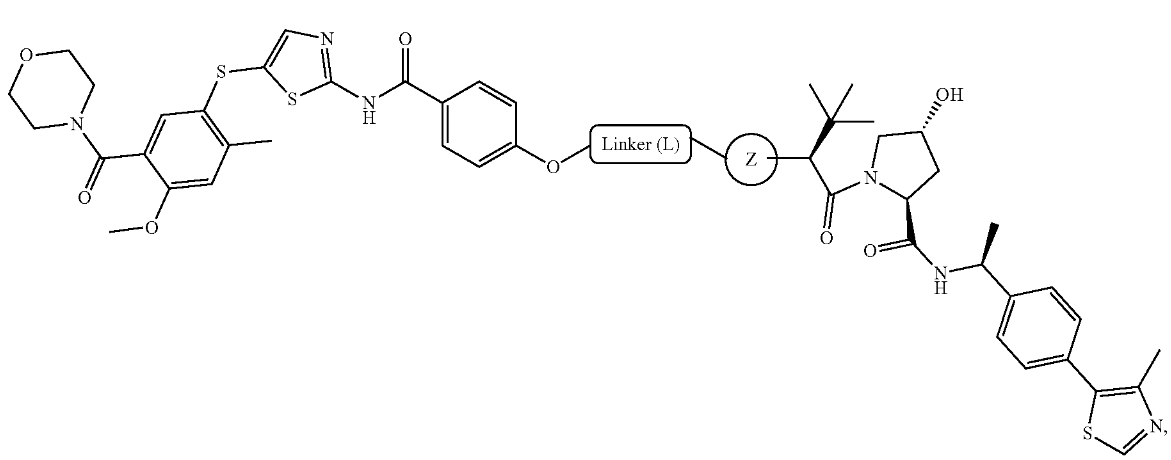

-continued
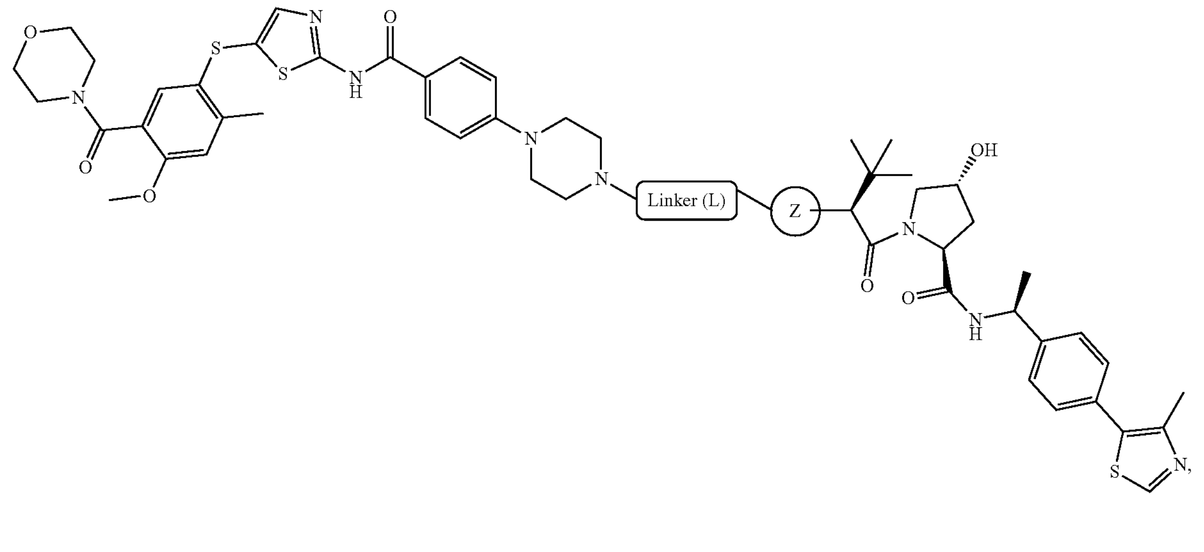
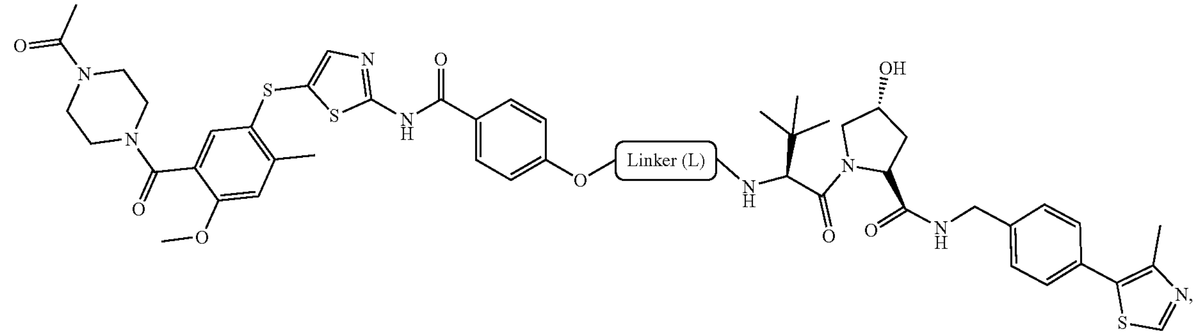
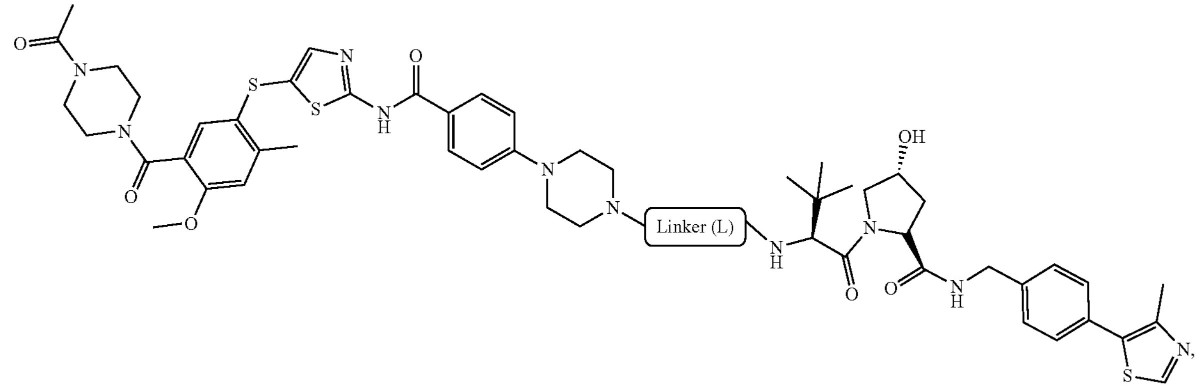
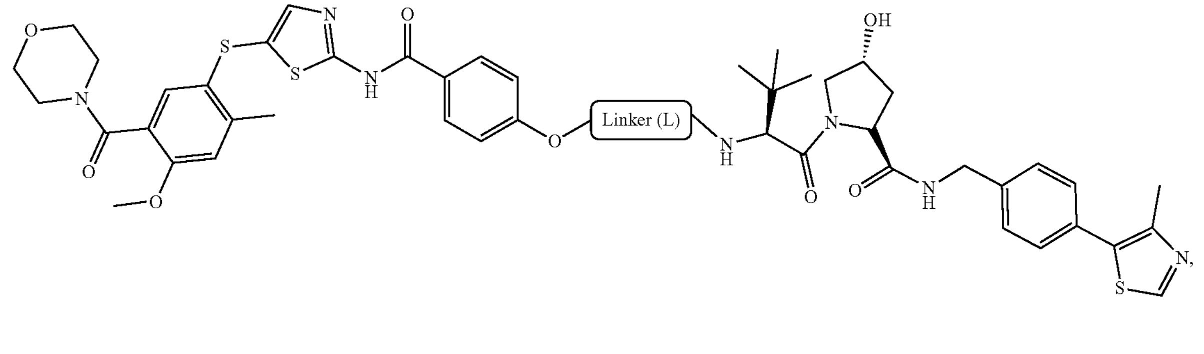

-continued
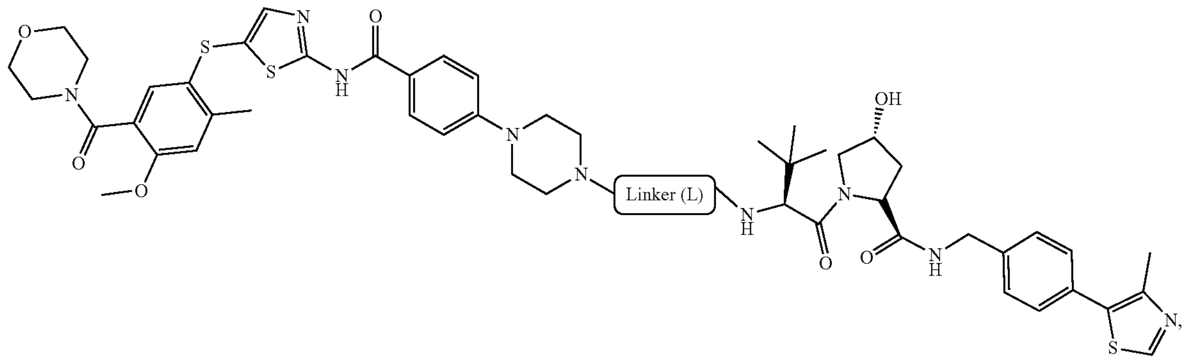
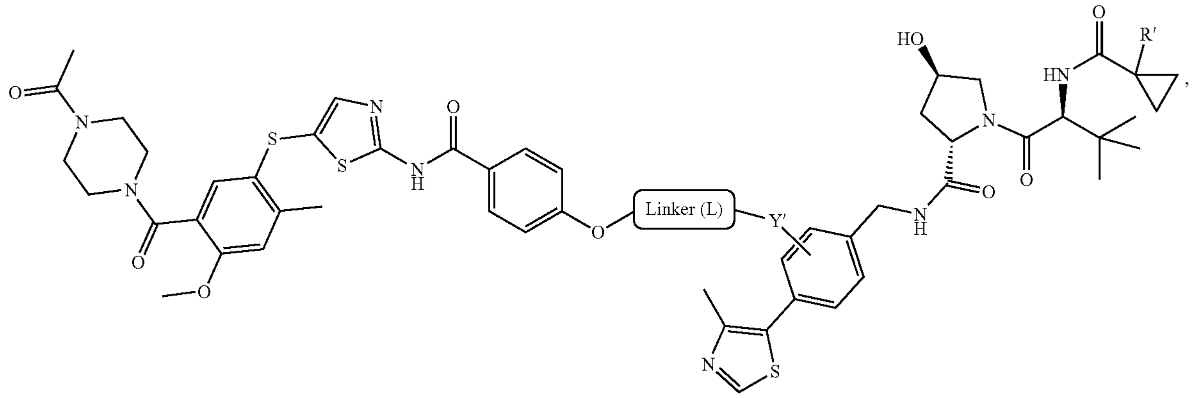
,
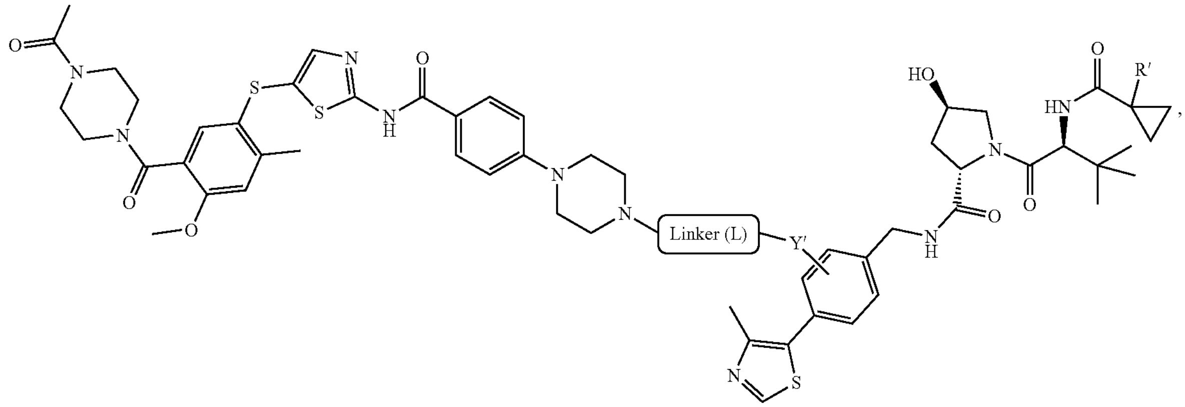
,
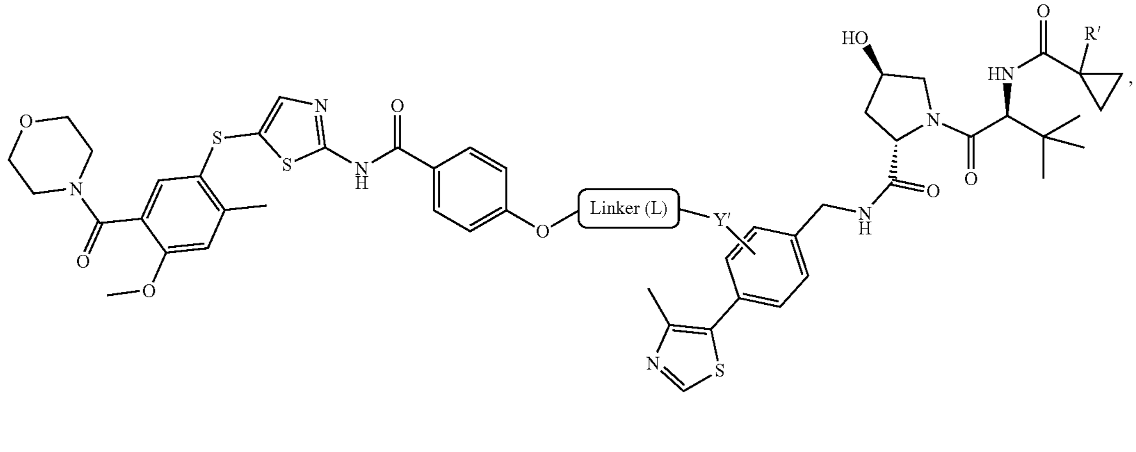
, and

-continued

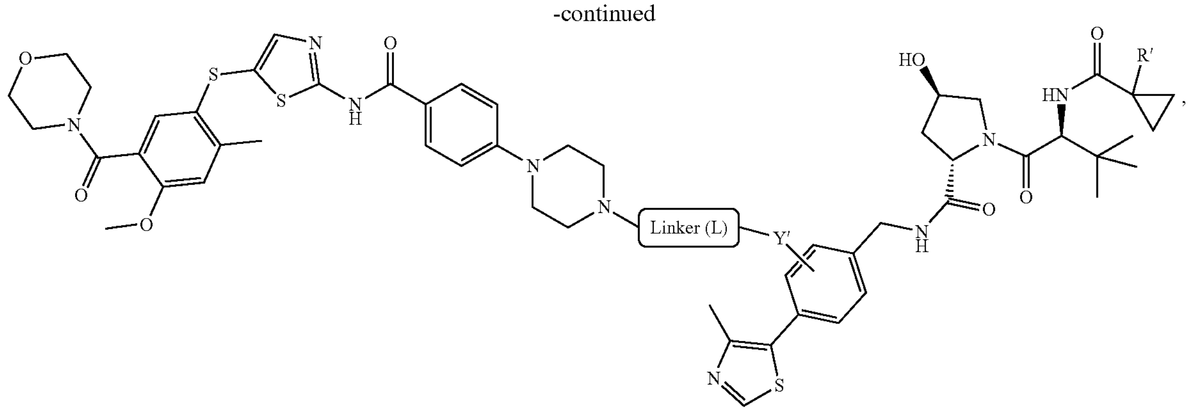

or a pharmaceutically acceptable salt or stereoisomer thereof.

Yet other degrons that bind VHL and which may be suitable for use in the present invention are disclosed in U.S. Patent Application Publication 2017/0121321 A1.

In some embodiments, the E3 ubiquitin ligase that is bound by the degron is an inhibitor of apoptosis protein (IAP). Representative examples of degrons that bind IAP and may be suitable for use in the present invention are represented by any one of the following structures:

(D3-a)

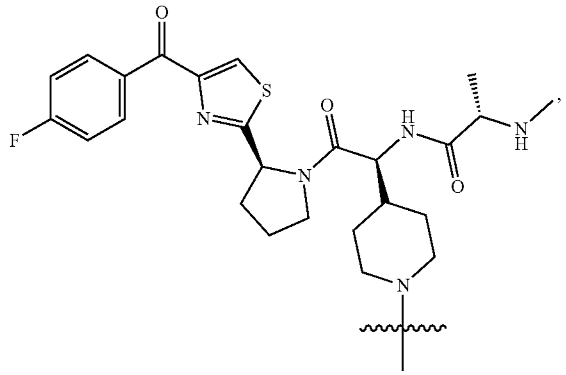

(D3-b)

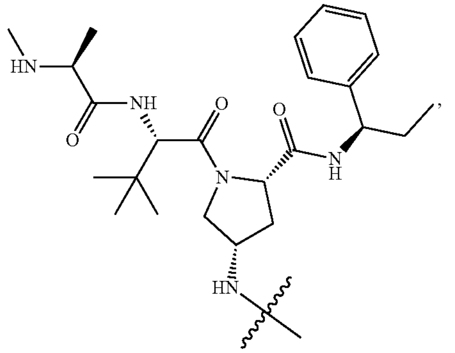

and

-continued (D3-c)

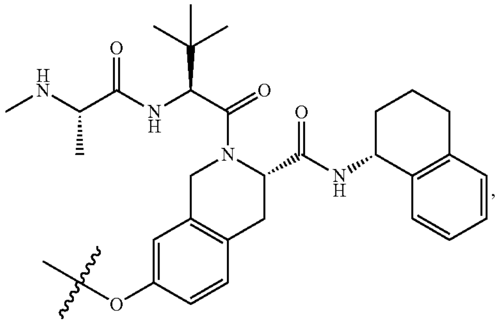

or a stereoisomer thereof.

Thus, in some embodiments, the bispecific compounds of the present invention are represented by any one of the following structures:

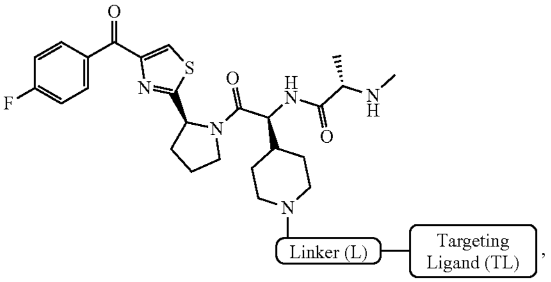

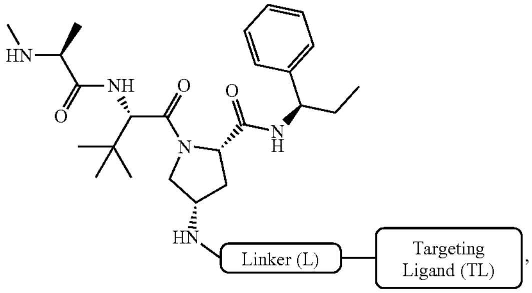

and

-continued
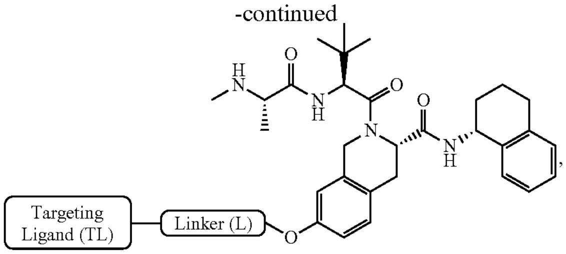
or a pharmaceutically acceptable salt or stereoisomer thereof.
In some embodiments, the bispecific compounds of the present invention are represented by any one of the following structures:
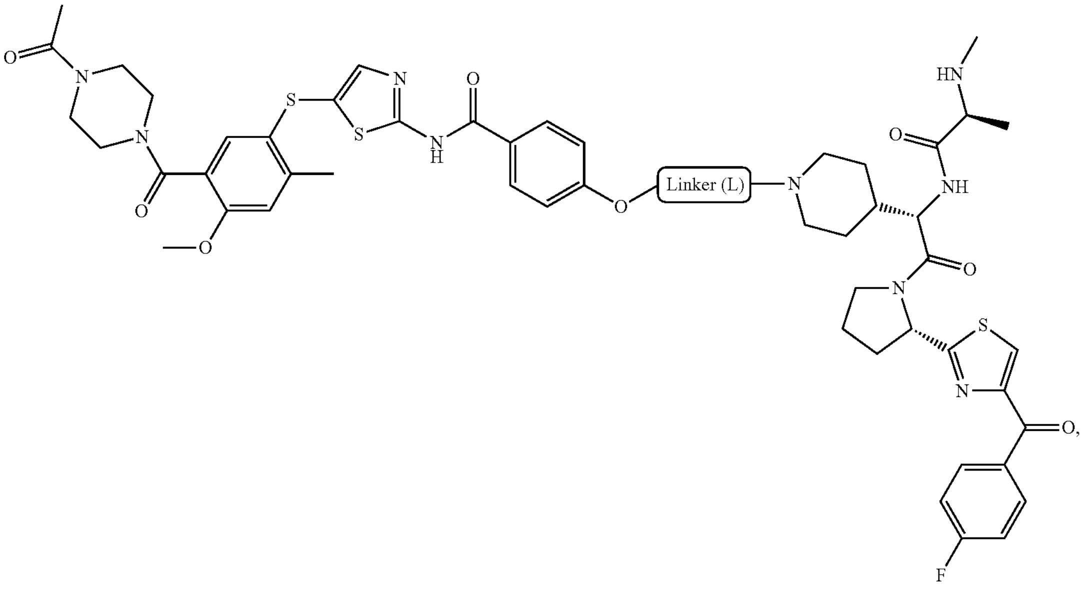
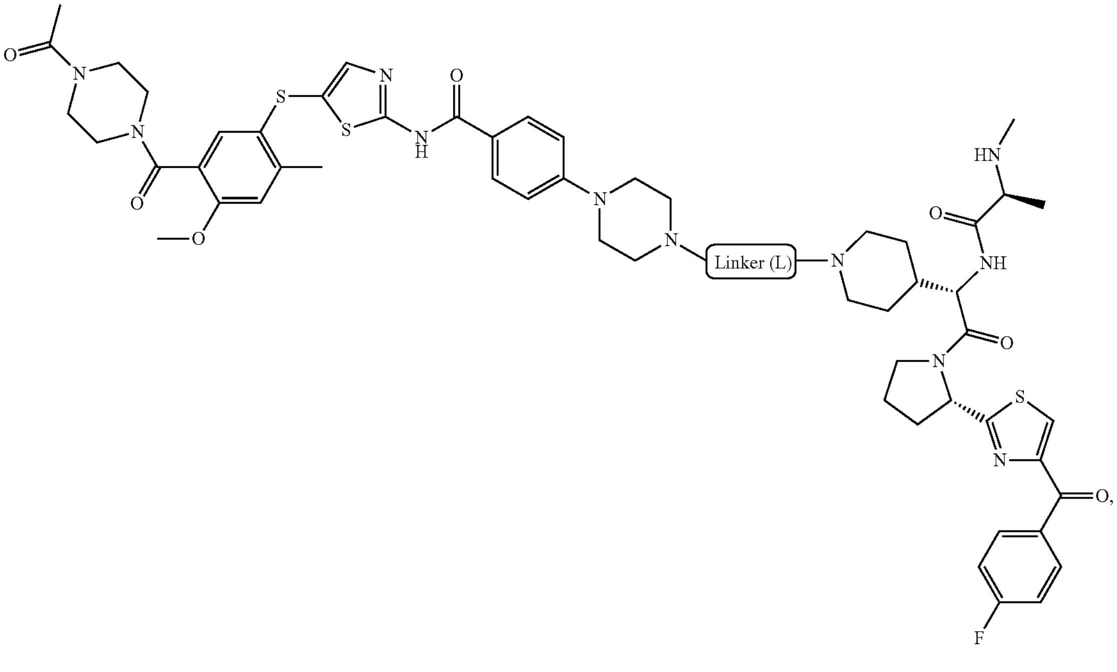

-continued
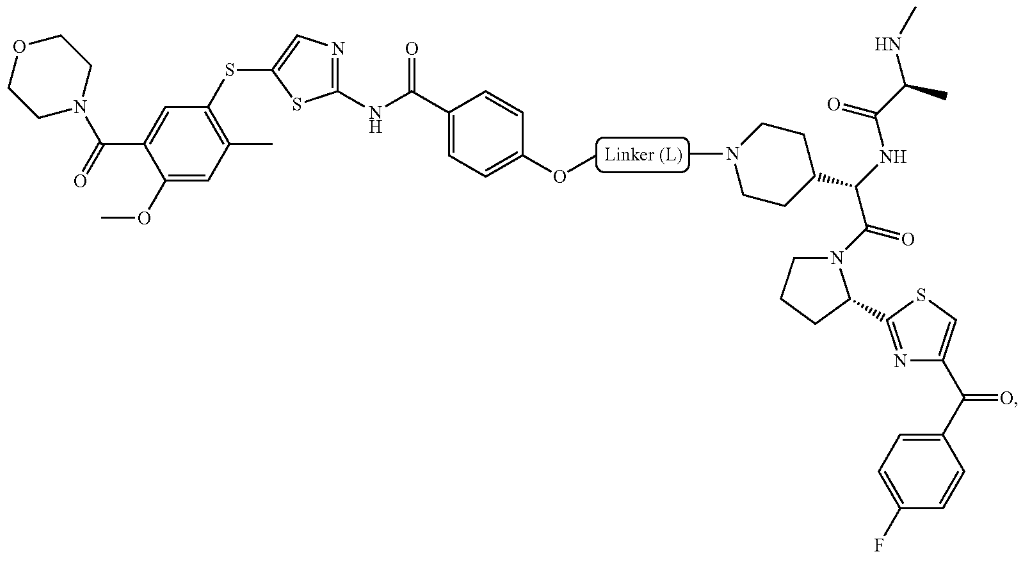
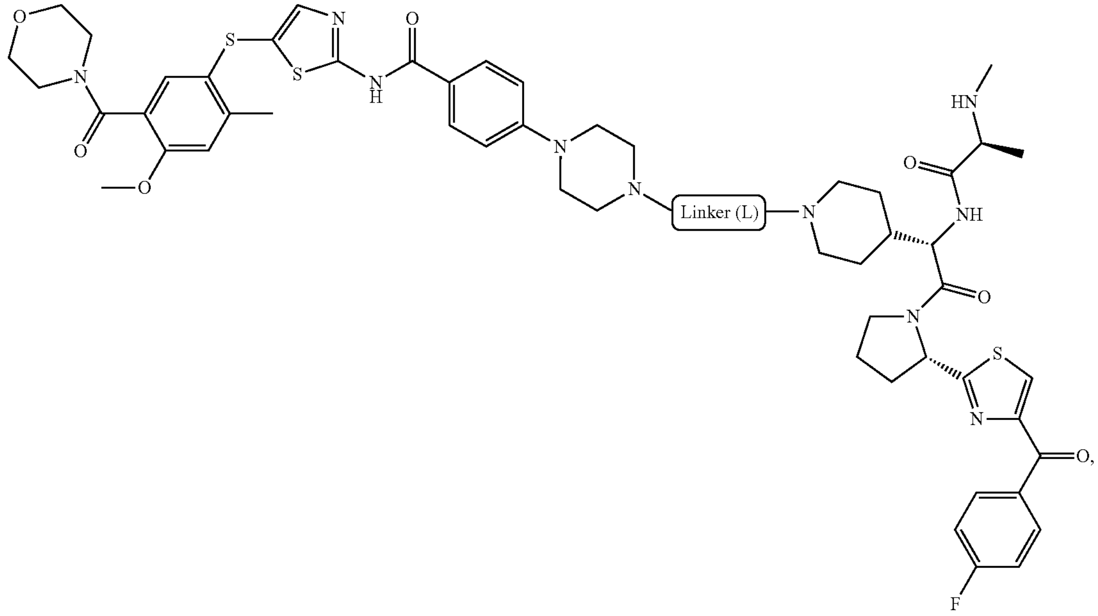
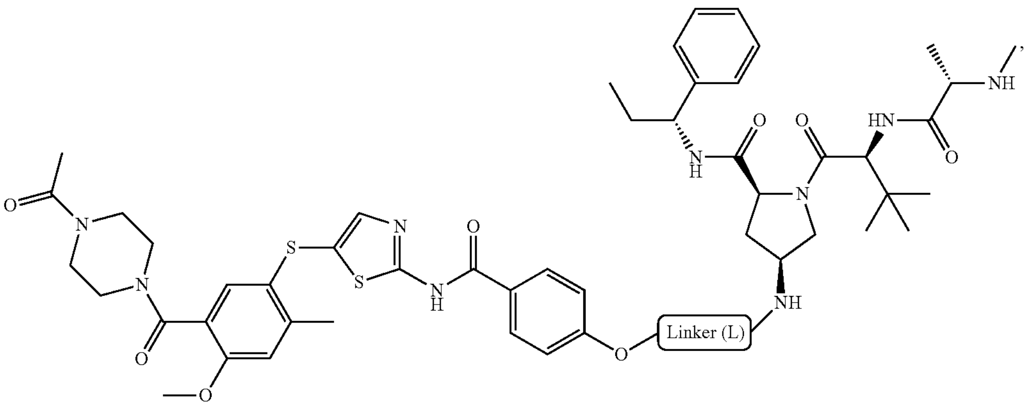

-continued
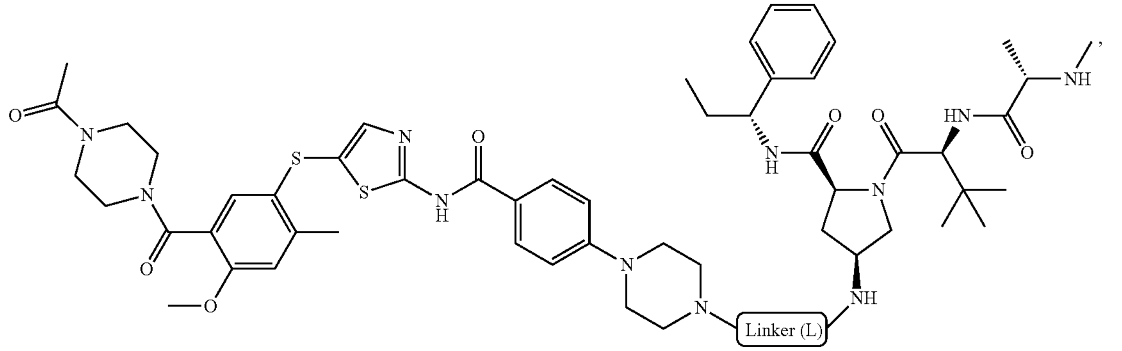
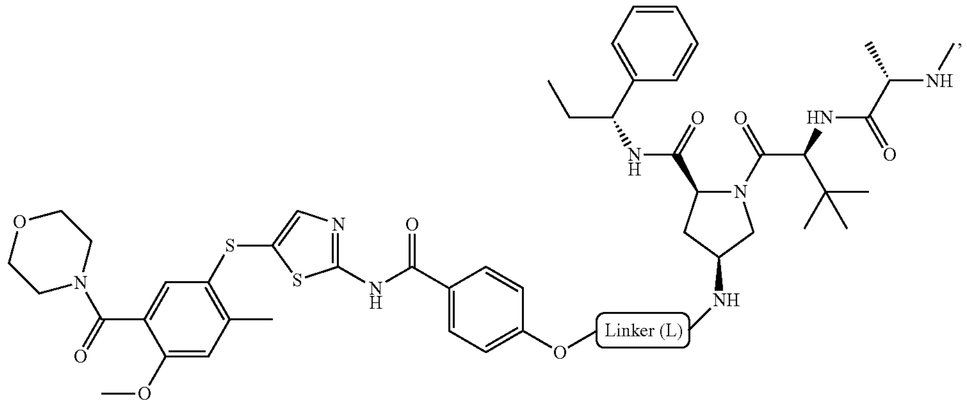
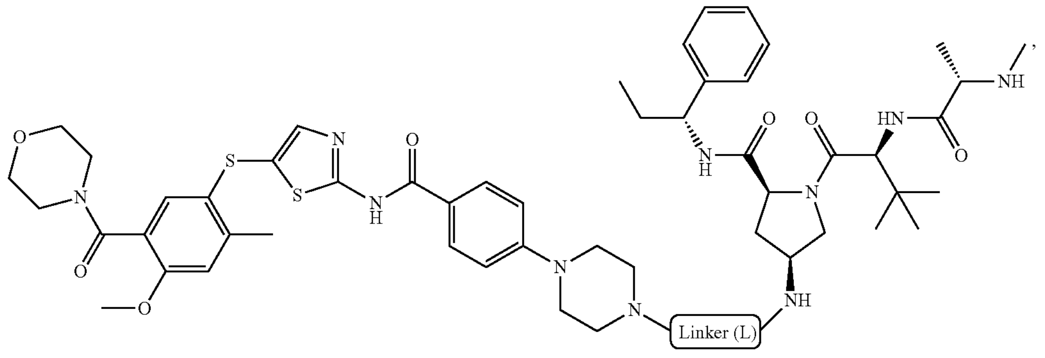
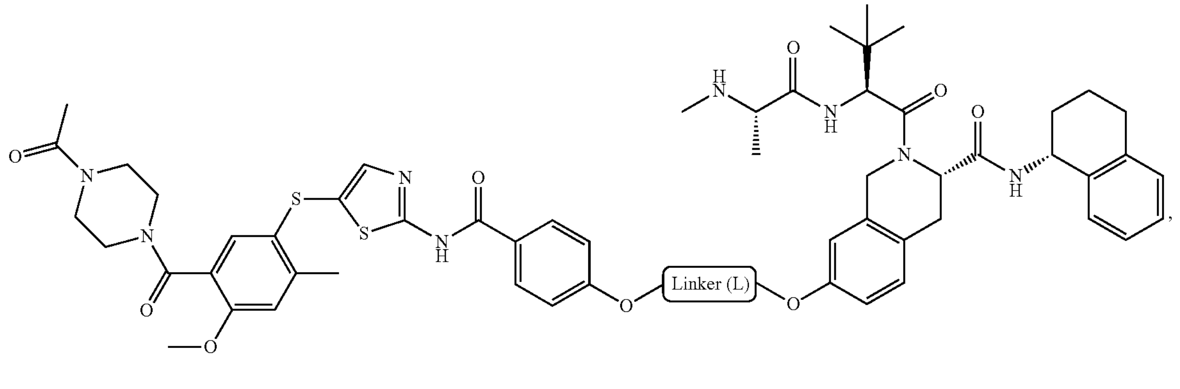

-continued

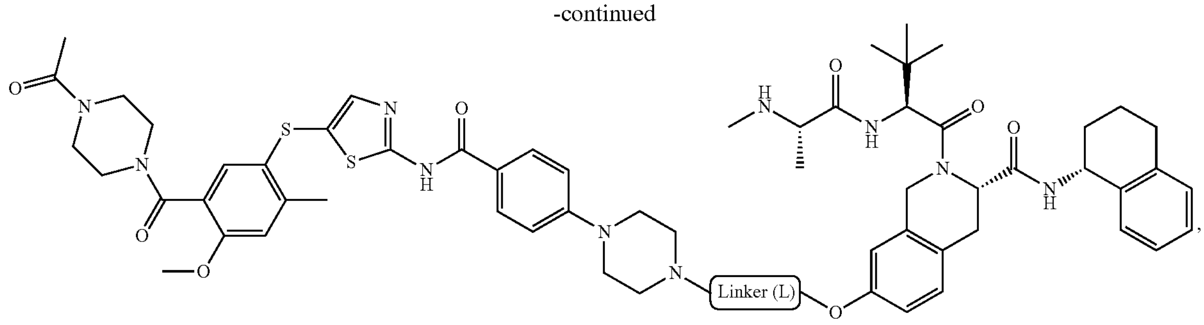

,

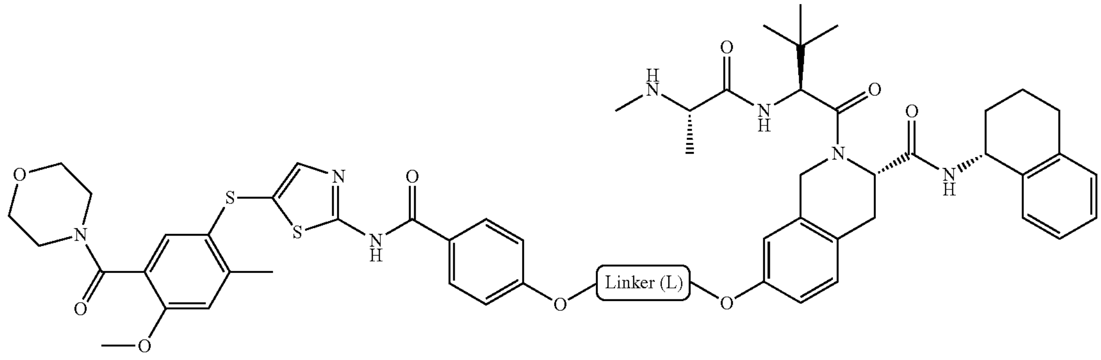

, and

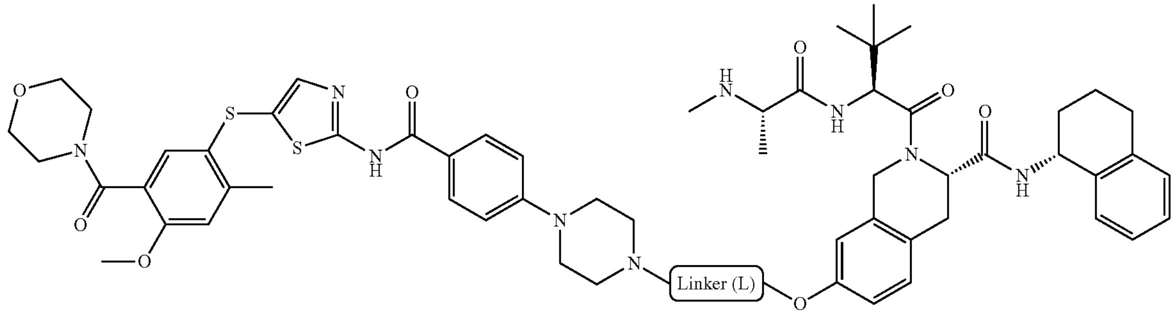

, or a pharmaceutically acceptable salt or stereoisomer thereof.

Yet other degrons that bind IAPs and which may be suitable for use as degrons in the present invention are disclosed in International Patent Application Publications WO 2008128171, WO 2008/016893, WO 2014/060768, WO 2014/060767, and WO 15092420.

In some embodiments, the E3 ubiquitin ligase that is bound by the degron is murine double minute 2 (MDM2). MDM2 is known in the art as an ubiquitin-E3 ligase. Representative examples of degrons that bind IAP and may be suitable for use in the present invention are represented by any one of the following structures:

(D4-a)

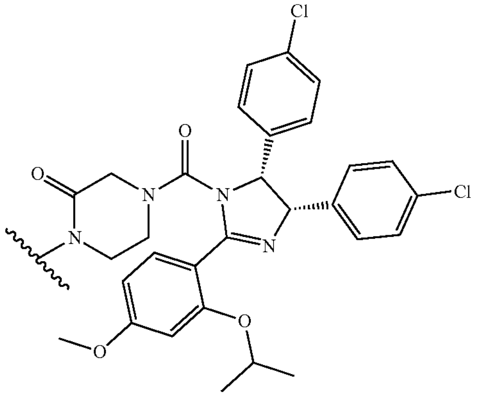

and

-continued (D4-b)

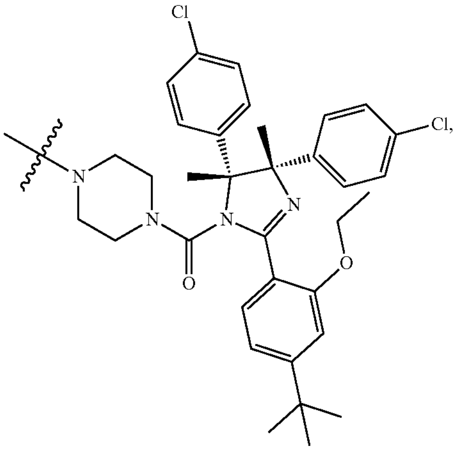

or a stereoisomer thereof.

Thus, in some embodiments, the bispecific compounds of the present invention are represented by any one of the following structures:

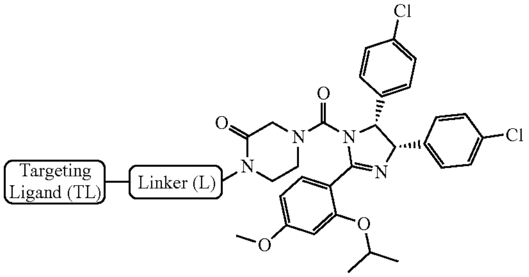

and

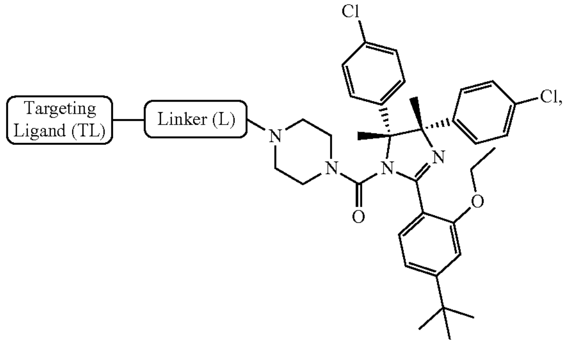

or a pharmaceutically acceptable salt or stereoisomer thereof.

In some embodiments, the bispecific compounds of the present invention are represented by any one of the following structures:

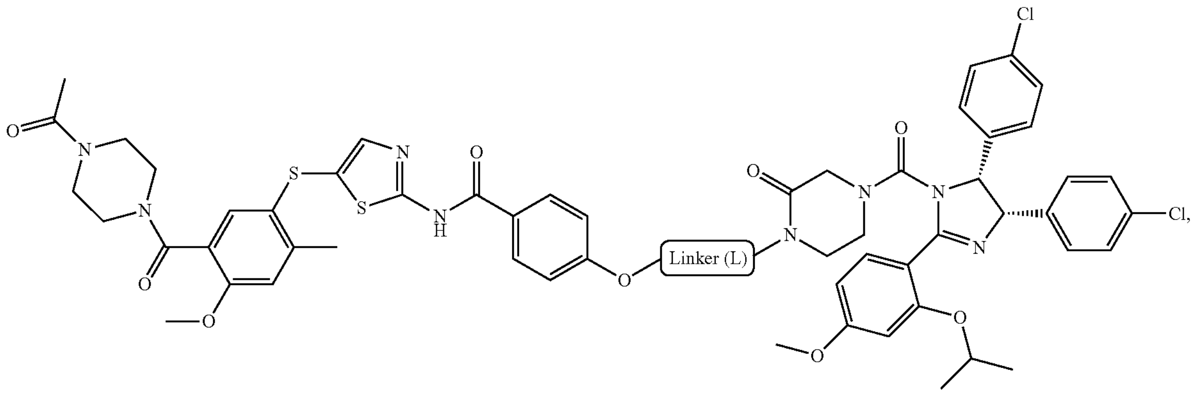

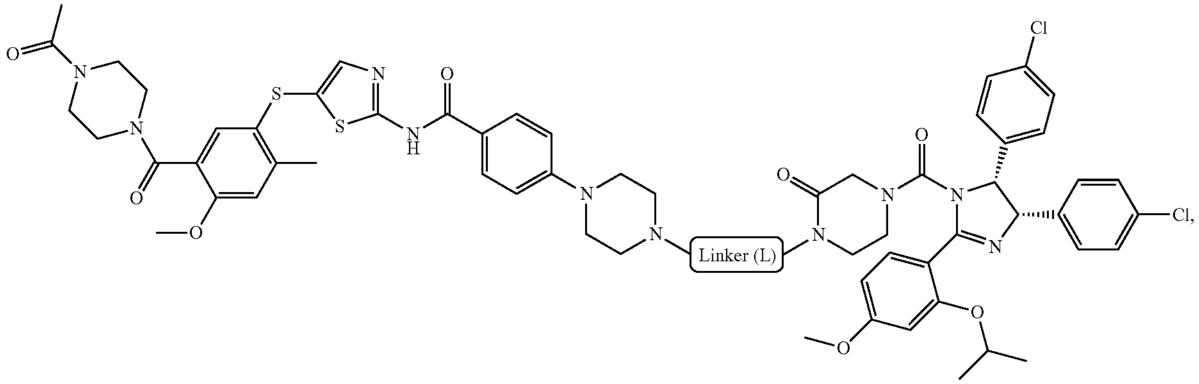

-continued
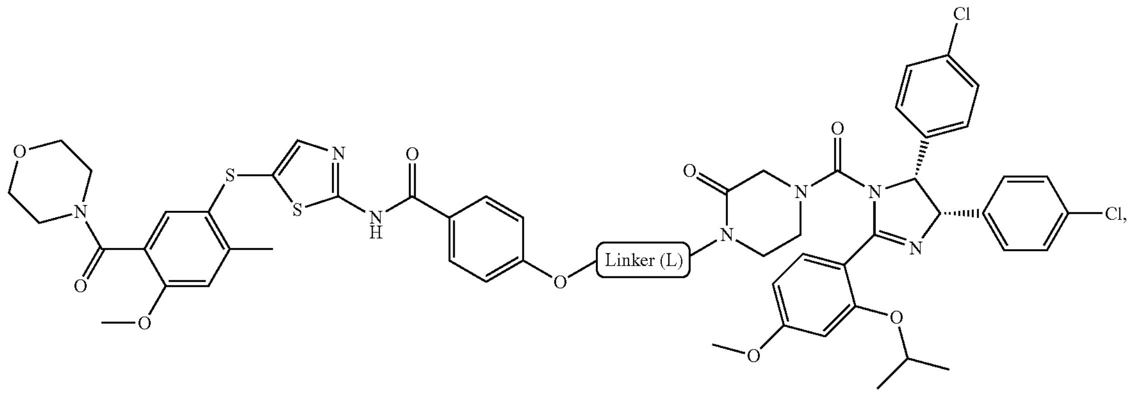
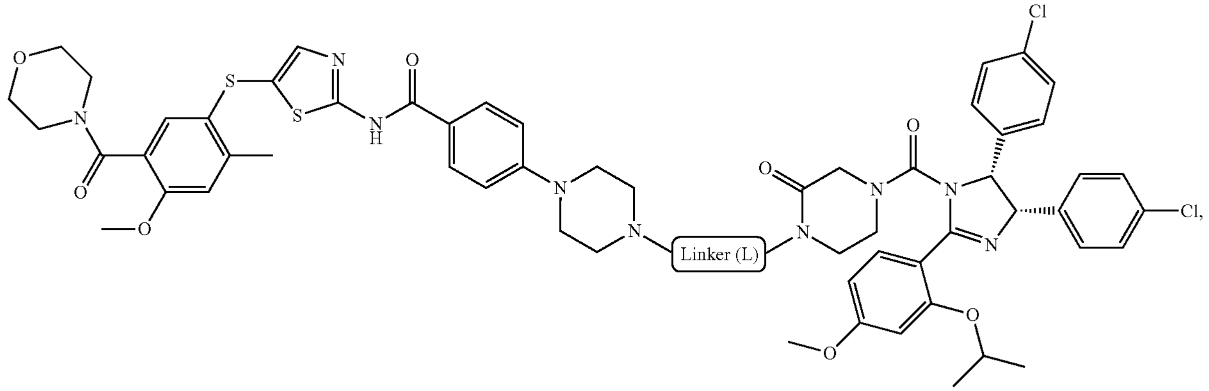
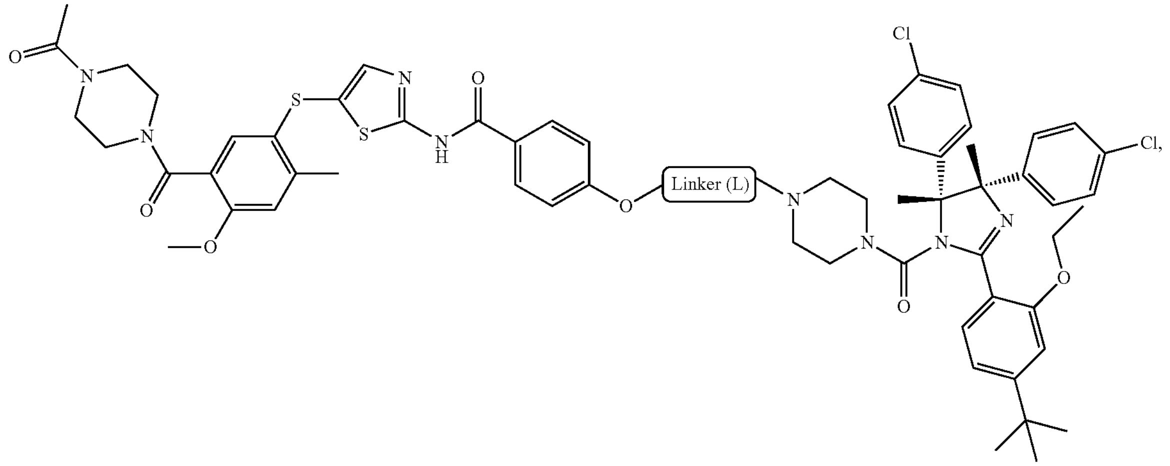

-continued

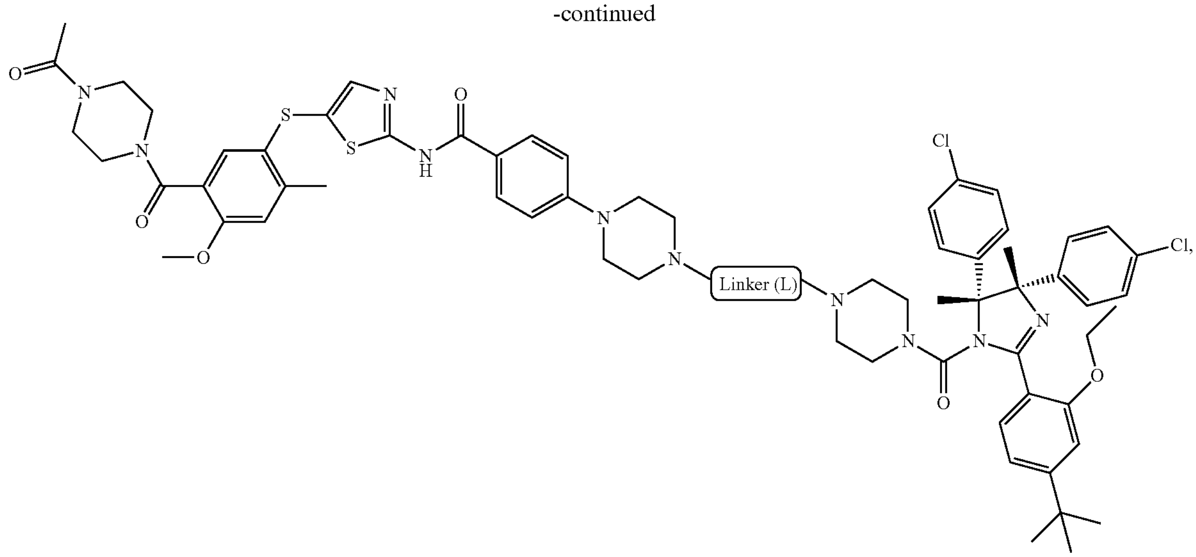

,

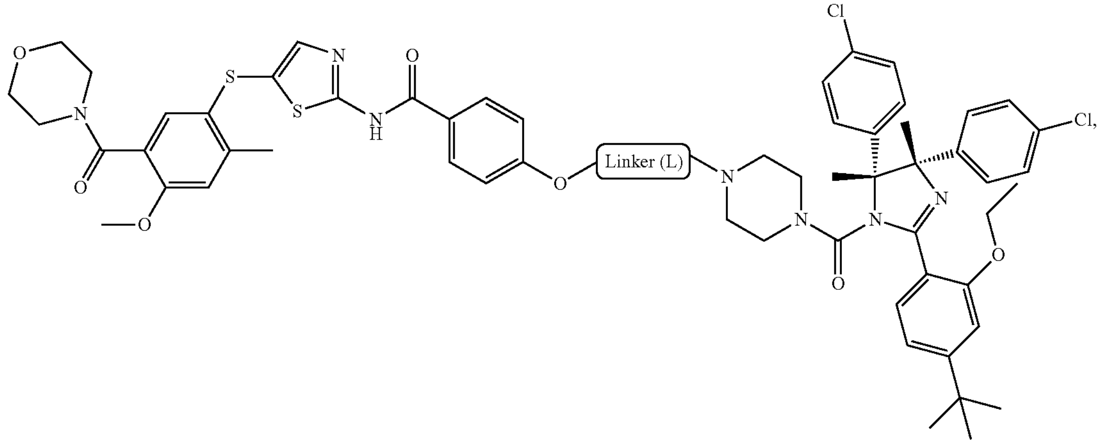

, and

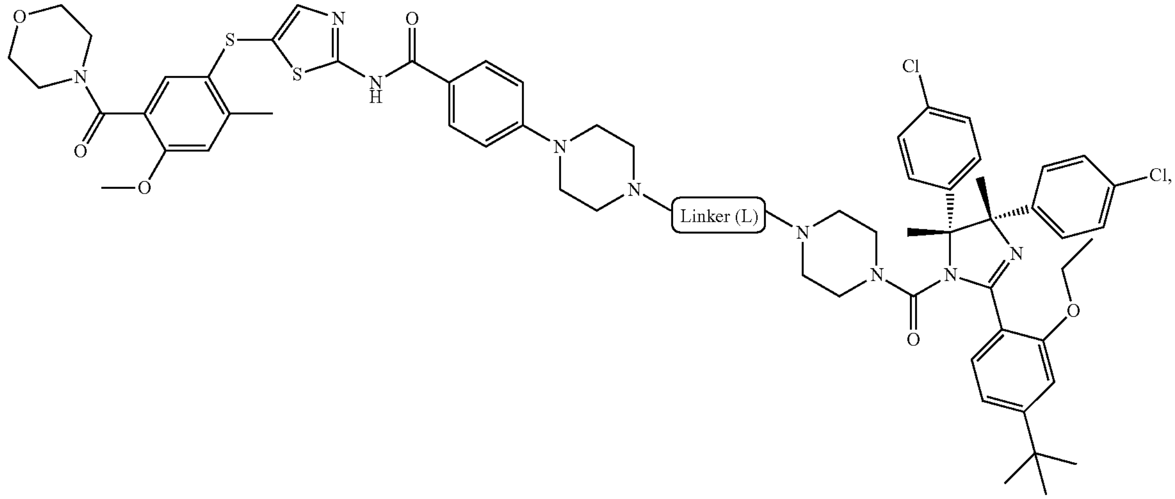

, or a pharmaceutically acceptable salt or stereoisomer thereof.

Yet other degrons that bind MDM2 and which may be suitable for use as degrons in the present invention are disclosed in U.S. Pat. No. 9,993,472 B2.

Thus, in some embodiments, the bispecific compounds of this invention may be represented by any structures generated by the combination of a TL1, any one of L1 to L11, and any one of D1 to D4, or a pharmaceutically acceptable salt or stereoisomer thereof.

In some embodiments, the bispecific compound of the present invention is represented by any one of the following structures:

(1)
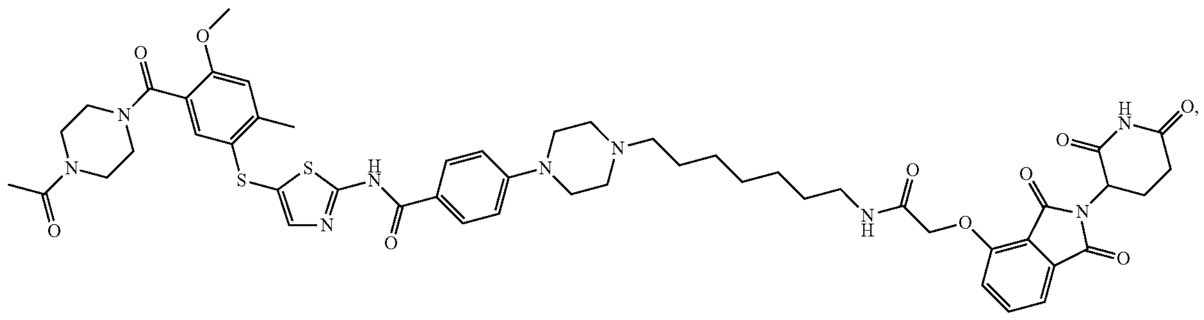
(2)
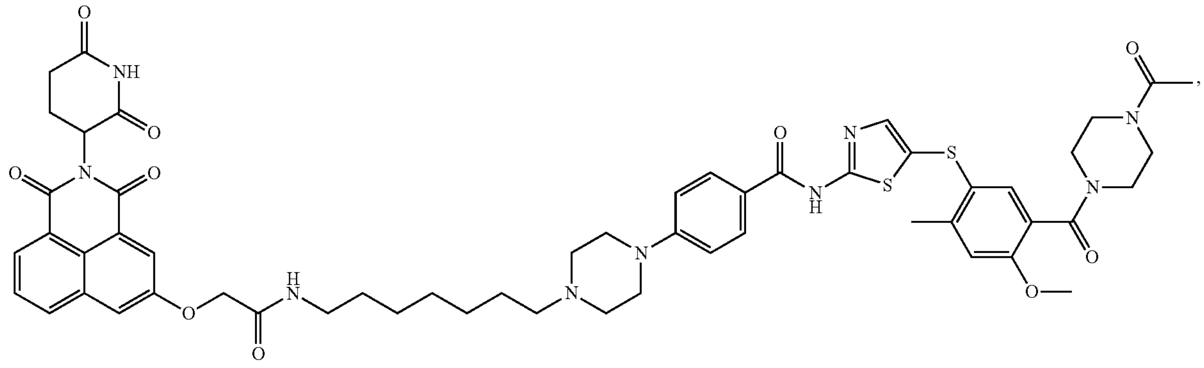
(3)
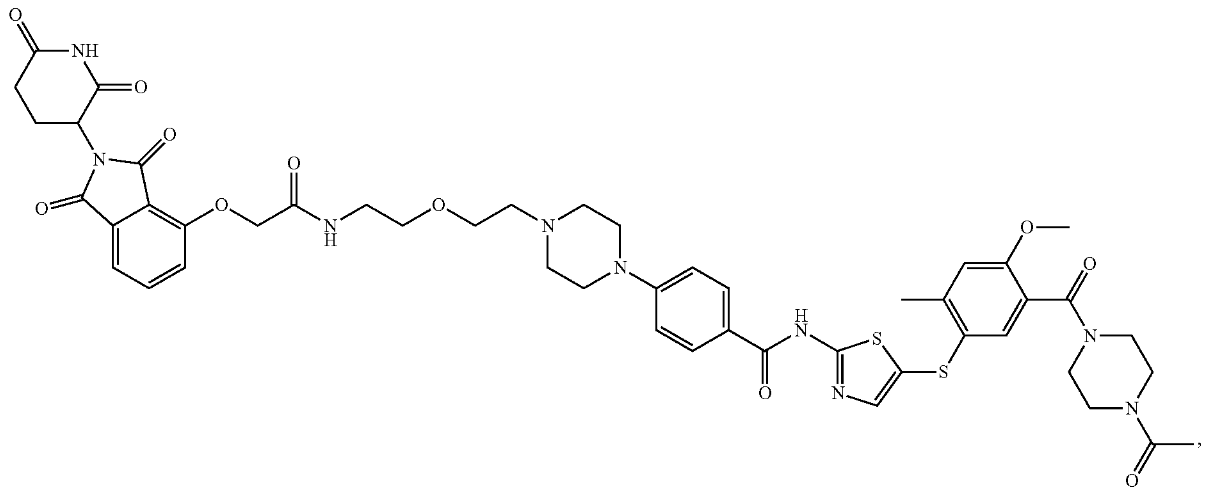
(4)
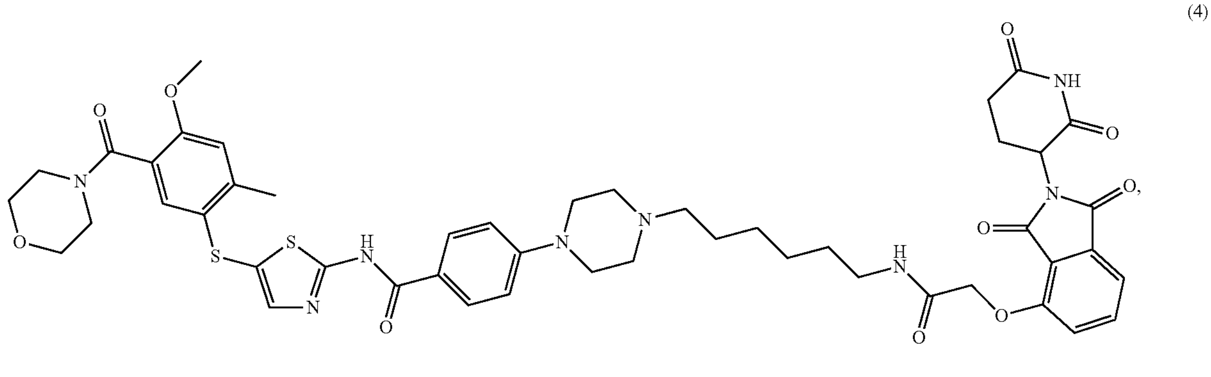

-continued (5)

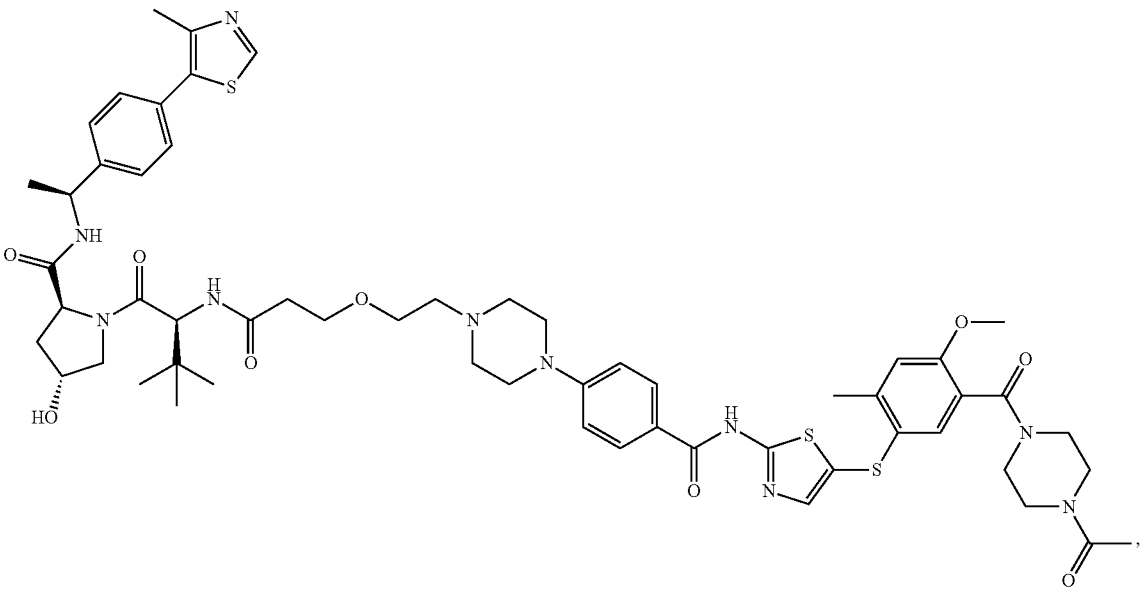

, and (6)

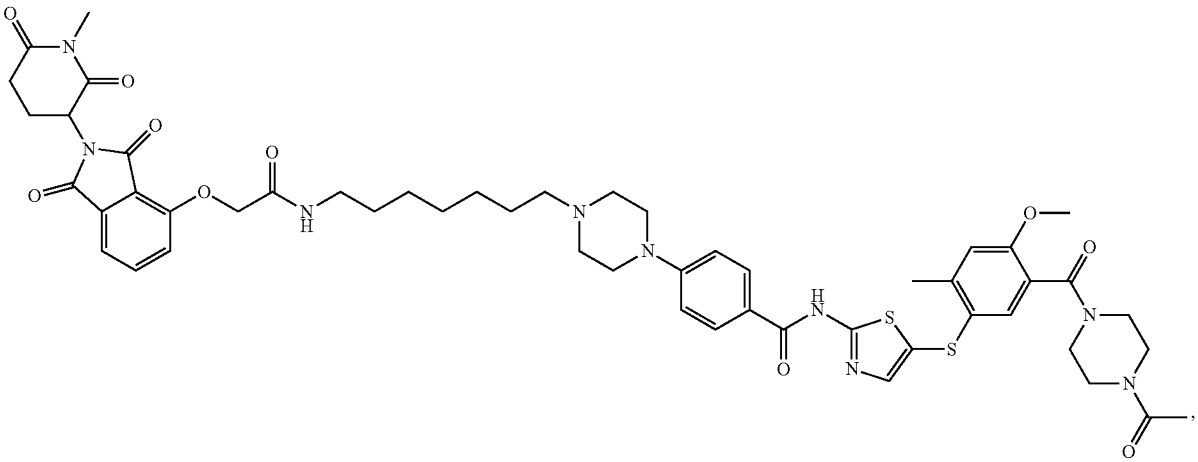

, or a pharmaceutically acceptable salt and stereoisomer thereof.

Bispecific compounds of formula (I) may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or abase. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

Bispecific compounds of formula (I) may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present invention may be made and used in the form of individual isomers and substantially free of other isomers, or in the form of a mixture of various isomers, e.g., racemic mixtures of stereoisomers.

The bispecific compounds of formula (I) embrace isotopic derivatives that have at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

In addition to isotopic derivatives, the term "bispecific compounds of formula (I)" embraces N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds.

Methods of Synthesis

In another aspect, the present invention is directed to a method for making a bispecific compound of formula (I), or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of a bispecific compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may also include one or more pharmaceutically acceptable excipients.

Broadly, bispecific compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the bispecific compound may be administered relatively quickly such as in the case of a single-dose treatment and/or an acute condition.

In some embodiments, the bispecific compounds are formulated for oral or intravenous administration (e.g., systemic intravenous injection).

Accordingly, bispecific compounds of formula (I) may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bispecific compounds of formula (I) may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bispecific compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compositions may be formulated for buccal or sublingual administration, examples of which include tablets, lozenges and gels.

The bispecific compounds of formula (I) may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bispecific compounds of formula (I) may be formulated for topical administration which as used herein, refers to administration intradermally by invention of the formulation to the epidermis. These types of compositions are typically in the form of ointments, pastes, creams, lotions, gels, solutions and sprays.

Representative examples of carriers useful in formulating bispecific compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bispecific compound of formula (I) or a pharmaceutically acceptable salt or a stereoisomer thereof that is effective in producing the desired therapeutic response in a particular patient suffering from a disease or disorder mediated by ITK and/or ZnF protein activity (i.e., aberrant ITK activity, aberrant ZnF activity, or both aberrant ITK activity and aberrant ZnF activity). The term "therapeutically effective amount" thus includes the amount of the bispecific compound or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of ITK and/or ZnF protein in diseased cells.

The total daily dosage of the bispecific compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the bispecific compound; and like factors well known in the medical arts (see, for example, *Goodman and Gilman's, The Pharmacological Basis of Therapeutics,* 10th Edition, A. Gilman, J. Hardman and L. Limbird, eds., McGraw-Hill Press, 155-173, 2001).

Bispecific compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, or in yet other embodiments from about 10 to about 30 mg per day. In some embodiments, the total daily dosage may range from 400 mg to 600 mg. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g., from 1 to 30 mg/kg per day in one or more dosages per day may be effective. By way of example, a suitable dose for oral administration may be in the range of 1-30 mg/kg of body weight per day, and a suitable dose for intravenous administration may be in the range of 1-10 mg/kg of body weight per day In some embodiments, a bispecific compound is administered in a dose between 100 mg per day and 250 mg per day. In other embodiments the bispecific compound is administered in a dose between 200 mg per day and 400 mg per day, e.g., 250-350 mg per day.

Methods of Use

In some aspects, the present invention is directed to treating diseases or disorders, cancerous and non-cancerous alike, characterized or mediated by ITK and/or ZnF protein, which entails administering a therapeutically effective amount of a bispecific compound of formula (I) or a pharmaceutically acceptable salt or stereoisomer thereof, to a subject in need thereof. A "disease" is generally regarded as a state of health of a subject wherein the subject cannot maintain homeostasis, and wherein if the disease is not ameliorated then the subject's health continues to deteriorate. In contrast, a "disorder" (or "condition") in a subject is a state of health in which the subject is able to maintain homeostasis, but in which the subject's state of health is less favorable than it would be in the absence of the disorder. Left untreated, a disorder may or may not cause a further decrease in the subject's state of health.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, the inventive bispecific compounds may be useful in the treatment of cell proliferative diseases and disorders (e.g., cancer or benign neoplasms). As used herein, the term "cell proliferative disease or disorder" refers to the conditions characterized by aberrant cell growth, or both, including noncancerous conditions such as neoplasms, precancerous conditions, benign tumors, and cancer.

Exemplary types of non-cancerous (e.g., cell proliferative) diseases or disorders that may be amenable to treatment with bispecific compounds of the present invention include inflammatory diseases and conditions, autoimmune diseases, neurodegenerative diseases, heart diseases, viral diseases, chronic and acute kidney diseases or injuries, metabolic diseases, allergic disorders, and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, pure red cell anemia and idiopathic thrombocytopenia), cholecystitis, rheumatoid spondylitis, osteoarthritis, gout, scleroderma, sepsis, septic shock, dacryoadenitis, cryopyrin associated periodic syndrome (CAPS), endotoxic shock, endometritis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniosis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcoidosis, bone resorption diseases, fibromyalgia, AIDS and other viral diseases such as Herpes Zoster, Herpes Simplex I or II, influenza virus, SARS-cov-2 and cytomegalovirus, diabetes Type I and II, obesity, insulin resistance and diabetic retinopathy, celiac disease, cystic fibrosis, Duchenne muscular dystrophy, acquired anti-drug antibodies, neurofibromatosis, phenylketonuria, Prader-Willi syndrome, sickle cell disease, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, varicosis, clonal hematopoiesis, and vaginitis.

In some embodiments, the bispecific compounds may be useful in the treatment of autoimmune diseases and disorders. As used herein, the term "autoimmune disease" refers to a disease or disorder wherein the immune system produces antibodies that attack normal body tissues. Representative examples of such diseases and disorders include rheumatoid arthritis, experimental autoimmune encephalomyelitis (EAE), multiple sclerosis, type 1 diabetes, lupus, inflammatory bowel disease (IBD), Guillain-Barre syndrome, chronic inflammatory demyelinating polyneuropathy, psoriasis, Graves' disease, Hashimoto's thyroiditis, myasthenia gravis, hemophagocytic lymphohistiocytosis, and vasculitis.

In some embodiments, the bispecific compounds may be useful in the treatment of graft-versus-host disease, e.g., graft-versus-host disease after stem cell transplantation or risk thereof.

In some embodiments, the bispecific compounds may be useful in the treatment of allograft rejection, e.g., allograft rejection after a solid organ transplant or risk thereof.

In some embodiments, the bispecific compounds may be useful in the treatment of cytokine release syndrome.

In some embodiments, the methods are directed to treating subjects having cancer. Broadly, the bispecific compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Both adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, skin, ovary, breast, skin and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include leukemia, multiple myeloma, and lymphoma (including T-cell lymphoma, Hodgkin's lymphoma, non-Hodgkin's lymphoma (NHL). Examples of NHL include diffuse large B-cell lymphoma (DLBCL), follicular lymphoma (FL), mantle cell lymphoma (MCL), cutaneous T-cell lymphoma (CTCL) (including mycosis fungoides and Sezary syndrome), peripheral T-cell lymphoma (PTCL) (including anaplastic large-cell lymphoma (ALCL), angioimmunoblastic T-cell lymphoma, hepatosplenic T-cell lymphoma, epithelial T-cell lymphoma, and gamma-delta T-cell lymphoma), germinal center B-cell-like diffuse large B-cell lymphoma, activated B-cell-like diffuse large B-cell lymphoma, Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, refractory NHL, relapsed NHL, childhood lymphomas, and small lymphocytic lymphoma. Examples of leukemia include childhood leukemia, hairy-cell leukemia, acute lymphocytic leukemia, acute myelocytic leukemia, acute myeloid leukemia (e.g., acute monocytic leukemia), chronic lymphocytic leukemia, chronic myelocytic leukemia, chronic myelogenous leukemia, mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchoalveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

Targeting ITK may be effective in treating any nonmalignant or malignant disease where T cells play a role in pathogenesis.

In some embodiments, the methods treat an ITK-mediated cancer, e.g., myofibroblastic tumor (IMT), breast cancer, colorectal cancer, esophageal squamous cell cancer (ESCC), renal cell cancer (RCC), colorectal cancer, melanoma, non-small cell lung cancer (NSCLC), cutaneous T-cell lymphoma, or peripheral T-cell lymphoma. In some embodiments, the methods treat an ITK-mediated cancer which is non-Hodgkin's lymphoma, including follicular lymphoma and small lymphocytic lymphoma/chronic lymphocytic leukemia. In some embodiments, the methods treat an ITK-mediated cancer which is T-cell lymphoma, including cutaneous T-cell lymphoma and subtypes of peripheral T-cell lymphoma.

Targeting of the ZnFs may be effective in treating any cancer where B cells, T cells, or myeloid cells play a role in pathogenesis.

In some embodiments, the methods treat a ZnF protein-mediated cancer e.g., multiple myeloma, myelodysplastic syndrome, acute myeloid leukemia, chronic myeloid leukemia, chronic lymphocytic leukemia, Hodgkin's lymphoma, Waldenstrom's macroglobulinemia, non-Hodgkin's lymphoma, e.g., mantle cell lymphoma, small lymphocytic lymphoma, diffuse large B-cell lymphoma, marginal zone lymphoma, lymphoplasmacytic lymphoma, follicular lymphoma, cutaneous T-cell lymphoma, T-cell prolymphocytic leukemia, T-cell large granular lymphocyte leukemia, or peripheral T-cell lymphoma. In some embodiments, the ZnF-mediated cancer is mediated by IKZF1, IKZF3, zinc finger protein 91 (ZFP91), ring finger protein 166 (RNF166), zinc finger protein 653 (ZNF653), or ZNF692.

In some embodiments, the ITK and ZnF protein-mediated cancer is multiple myeloma, myelodysplastic syndrome, acute myeloid leukemia, chronic myeloid leukemia, chronic lymphocytic leukemia, Hodgkin's lymphoma, Waldenstrom's macroglobulinemia, non-Hodgkin's lymphoma, e.g., mantle cell lymphoma, small lymphocytic lymphoma, diffuse large B-cell lymphoma, marginal zone lymphoma, lymphoplasmacytic lymphoma, follicular lymphoma, cutaneous T-cell lymphoma, T-cell prolymphocytic leukemia, T-cell large granular lymphocyte leukemia, or peripheral T-cell lymphoma.

The bispecific compounds of formula (I) and their pharmaceutically acceptable salts and stereoisomers may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been unsuccessful, or partially successful but who have become intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received prior therapy, such as chemotherapy, radioimmunotherapy, surgical therapy, immunotherapy, radiation therapy, targeted therapy or any combination thereof.

The methods of the present invention may entail administration of a bispecific compound of formula (I) or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days) followed by a 7-day "off" period. In other embodiments, the bispecific compound may be dosed twice a day (BID) over the course of two and a half days (for a total of 5 doses) or once a day (QD) over the course of two days (for a total of 2 doses). In other embodiments, the bispecific compound may be dosed once a day (QD) over the course of 5 days.

Combination Therapy

The bispecific compounds of formula (I) and their pharmaceutically acceptable salts and stereoisomers may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a bispecific compound of formula (I) in combination with one or more additional therapeutics known for use in treating a disease or condition (e.g., cancer). The dosage of the additional therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be suitable for use in combination with the inventive bispecific compounds are known in the art. See, e.g., U.S. Pat. No. 9,101,622 (Section 5.2 thereof) and U.S. Pat. No. 9,345,705 B2 (Columns 12-18 thereof). Representative examples of additional anti-cancer agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, a bispecific compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

When the active components of the combination are not administered in the same pharmaceutical composition, it is understood that they can be administered in any order to a subject in need thereof. For example, a bispecific compound of the present invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional therapeutic, to a subject in need thereof. In various aspects, the therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the (e.g., anticancer) therapeutics are administered within the same office visit. In another example, the combination anticancer therapeutics may be administered at 1 minute to 24 hours apart.

In some embodiments involving cancer treatment, a bispecific compound of formula (I) and the additional anticancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, the bispecific compound of the present invention may be used in combination with other anti-cancer agents, examples of which include Paclitaxel (e.g., ovarian cancer, breast cancer, lung cancer, Kaposi sarcoma, cervical cancer, and pancreatic cancer), Topotecan (e.g., ovarian cancer and lung cancer), Irinotecan (e.g., colon cancer, and small cell lung cancer), Etoposide (e.g., testicular cancer, lung cancer, lymphomas, and non-lymphocytic leukemia), Vincristine (e.g., leukemia), Leucovorin (e.g., colon cancer), Altretamine (e.g., ovarian cancer), Daunorubicin (e.g., acute myeloid leukemia (AML), acute lymphocytic leukemia (ALL), chronic myelogenous leukemia (CML), and Kaposi's sarcoma), Trastuzumab (e.g., breast cancer, stomach cancer, and esophageal cancer), Rituximab (e.g., non-Hodgkin's lymphoma), Cetuximab (e.g., colorectal cancer, metastatic non-small cell lung cancer and head and neck cancer), Pertuzumab (e.g., metastatic HER2-positive breast cancer), Alemtuzumab (e.g., chronic lymphocytic leukemia (CLL), cutaneous T-cell lymphoma (CTCL) and T-cell lymphoma), Panitumumab (e.g., colon and rectum cancer), Tamoxifen (e.g., breast cancer), Fulvestrant (e.g., breast cancer), Letrazole (e.g., breast cancer), Exemestane (e.g., breast cancer), Azacytidine (e.g., myelodysplastic syndromes), Mitomycin C (e.g., gastro-intestinal cancers, anal cancers, and breast cancers), Dactinomycin (e.g., Wilms tumor, rhabdomyosarcoma, Ewing's sarcoma, trophoblastic neoplasm, testicular cancer, and ovarian cancer), Erlotinib (e.g., non-small cell lung cancer and pancreatic cancer), Sorafenib (e.g., kidney cancer and liver cancer), Temsirolimus (e.g., kidney cancer), Bortezomib (e.g., multiple myeloma and mantle cell lymphoma), Pegaspargase (e.g., acute lymphoblastic leukemia), Cabometyx (e.g., hepatocellular carcinoma, medullary thyroid cancer, and renal cell carcinoma), Keytruda (e.g., cervical cancer, gastric cancer, hepatocellular carcinoma, Hodgkin lymphoma, melanoma, Merkel cell carcinoma, non-small cell lung cancer, urothelial carcinoma, and squamous cell carcinoma of the head and neck), Nivolumab (e.g., colorectal cancer, hepatocellular carcinoma, melanoma, non-small cell lung cancer, renal cell carcinoma, small cell lung cancer, and urothelial carcinoma), Regorafenib (e.g., colorectal cancer, gastrointestinal stromal tumor, and hepatocellular carcinoma), and dexamethasone (e.g., acute multiple myeloma).

In some embodiments, bispecific compounds of the present invention may be used in combination with an immune effector cell that expresses a chimeric antigen receptor (CAR T therapy). In some embodiments, bispecific compounds of the present invention may be used in combination with a vaccine that is designed to enhance an immune response, examples of which include talimogene laherparepvec, oncophage, Bacillus Calmette-Guerin, sipuleucel-T, dasiprotimut-T, multiepitope peptide, tecemotide, and rindopepimut.

Pharmaceutical Kits

The present bispecific compounds and/or compositions containing them may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a bispecific compound of formula (I) or a pharmaceutical composition thereof. The kits or pharmaceutical systems of the invention may also include printed instructions for using the bispecific compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Synthesis of N-(5-((5-(4-acetylpiperazine-1-carbonyl)-4-methoxy-2-methylphenyl)thio)thiazol-2-yl)-4-(4-(7-(2-((2-(2,6-dioxopiperidin-3-yl)-1,3-dioxoisoindolin-4-yl)oxy)acetamido)heptyl)piperazin-1-yl)benzamide (1)

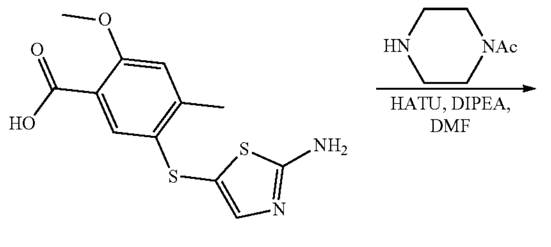

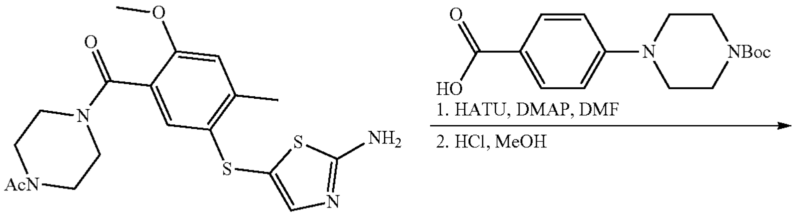

-continued

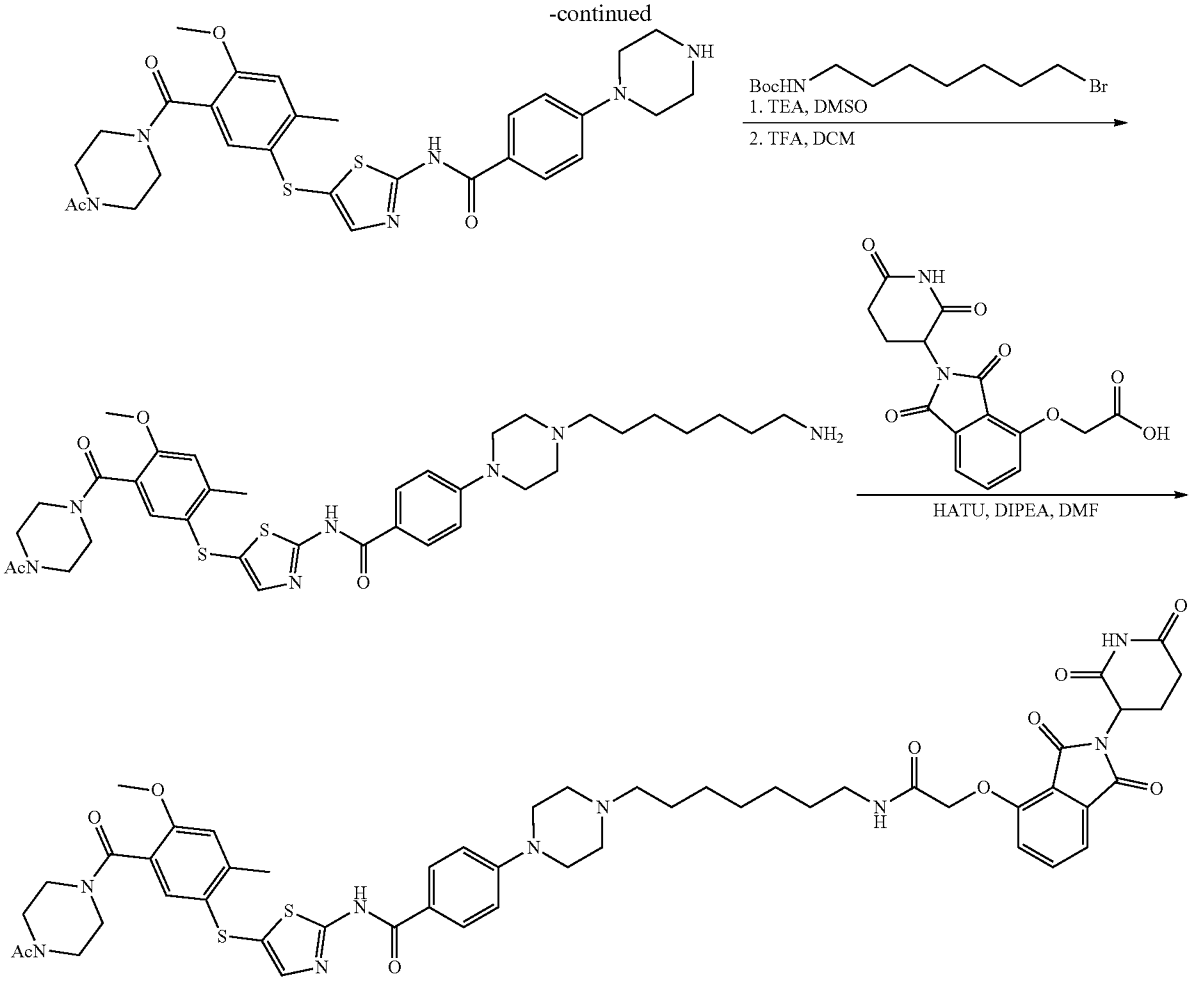

1

1-Acetylpiperazine (192 mg, 1.5 mmol), HATU (741 mg, 1.95 mmol) and DIPEA (388 mg, 3 mmol) were added to a solution of 5-((2-aminothiazol-5-yl)thio)-2-methoxy-4-methylbenzoic acid (444 mg, 1.5 mmol) in 5 mL of anhydrous DMF. The mixture was stirred for 30 minutes at room temperature and then the solvent was evaporated. The resulting residue was purified by flash chromatography to yield 1-(4-(5-((2-aminothiazol-5-yl)thio)-2-methoxy-4-methylbenzoyl)piperazin-1-yl)ethan-1-one as a light brown solid (548 mg, 90%). LC-MS: m/z 406.1 [M+1].

4-(4-(tert-butoxycarbonyl)piperazin-1-yl)benzoic acid (306 mg, 1 mmol), HATU (494 mg, 1.3 mmol) and DMAP (244 mg, 2 mmol) were added to a solution of 1-(4-(5-((2-aminothiazol-5-yl)thio)-2-methoxy-4-methylbenzoyl)piperazin-1-yl)ethan-1-one (406 mg, 1 mmol) in 5 mL of anhydrous DMF. The resulting mixture was warmed to 50° C. and stirred overnight. The reaction was cooled to room temperature and monitored by UPLC. After 1-(4-(5-((2-aminothiazol-5-yl)thio)-2-methoxy-4-methylbenzoyl)piperazin-1-yl)ethan-1-one was consumed (LC-MS: m/z 694.2 [M+1]), the solvent was evaporated to give a brown oil-like residue which was then dissolved in 3 mL of MeOH. This was followed by the addition of 3 mL of 4N HCl dioxane solution and stirred overnight at 40° C. The solvent was evaporated and the residue was purified by reverse phase HPLC (5-95% MeOH in $H_2O$) to yield N-(5-((5-(4-acetylpiperazine-1-carbonyl)-4-methoxy-2-methylphenyl)thio)thiazol-2-yl)-4-(piperazin-1-yl)benzamide (517 mg, 87%). LC-MS: m/z 594.2 [M+1].

Tert-butyl (7-bromoheptyl)carbamate (129 mg, 0.44 mmol) and DIPEA (0.115 mL, 0.66 mmol) were added to a solution of 1-(4-(5-((2-aminothiazol-5-yl)thio)-2-methoxy-4-methylbenzoyl)piperazin-1-yl)ethan-1-one (130.7 mg, 0.22 mmol) in DMSO (2 mL). The mixture was heated to 80° C. and stirred for 24 hours. The mixture was then cooled to room temperature, extracted, dried, filtered and concentrated to give a light brown residue which was then dissolved into 1 mL of DCM, followed by slow addition of 1 mL of TFA in an ice bath. The mixture was then warmed to room temperature and evaporated after 30 minutes. The residue was purified by reverse phase HPLC (5-95% MeOH in $H_2O$) to yield N-(5-((5-(4-acetylpiperazine-1-carbonyl)-4-methoxy-2-methylphenyl)thio)thiazol-2-yl)-4-(4-(7-aminoheptyl)piperazin-1-yl)benzamide (TFA salt) as a light grey solid (101 mg, 65% in two steps). LC-MS: m/z 707.3 [M+1].

2-((2-(2,6-dioxopiperidin-3-yl)-1,3-dioxoisoindolin-4-yl)oxy)acetic acid (14 mg, 0.0422 mmol), HATU (33 mg, 0.0844 mmol) and DIPEA (37 μL, 0.211 mmol) were added to a solution of N-(5-((5-(4-acetylpiperazine-1-carbonyl)-4-methoxy-2-methylphenyl)thio)thiazol-2-yl)-4-(4-(7-aminoheptyl)piperazin-1-yl)benzamide (29.8 mg, 0.0422 mmol) in 2 mL of DMF. The resulting mixture stirred for 30 minutes at room temperature. The solvent was evaporated and the residue was purified by reverse phase HPLC (5-95% MeOH in $H_2O$) to give the title compound (TFA salt) as an off-white solid (37.6 mg, 87%). $^1$H NMR (500 MHz, DMSO-$d_6$) δ 12.60 (s, 1H), 9.76 (s, 1H), 8.05-8.00 (m, 2H), 7.99-7.90 (m, 1H), 7.85-7.78 (m, 1H), 7.75 (d, J=2.9 Hz, 1H), 7.51 (d, J=7.1 Hz, 1H), 7.43-7.37 (m, 1H), 7.10 (d, J=8.8 Hz, 2H), 7.07-7.02 (m, 2H), 5.23-5.14 (m, 1H), 4.77 (d, J=3.8 Hz, 2H), 4.09 (d, J=11.4 Hz, 2H), 3.79 (s, 3H), 3.66-3.51 (m, 3H), 3.50-3.40 (m, 2H), 3.39-3.25 (m, 1H), 3.20-3.04 (m, 9H), 3.02 (s, 3H), 2.97-2.90 (m, 1H), 2.81-2.70 (m, 1H), 2.57-2.52 (m, 1H), 2.10-2.02 (m, 1H), 2.01 (s, 1H), 1.93 (s, 1H), 1.71-1.56 (br, 2H), 1.49-1.36 (m, 2H), 1.34-1.12 (m, 10H). $^{13}$C NMR (126 MHz, DMSO) δ 172.25, 170.12, 167.17, 167.12, 166.00, 155.58, 154.88, 152.81, 137.45, 133.50, 130.36, 130.00, 126.97, 124.58, 120.93, 117.28, 116.59, 114.52, 114.24, 68.16, 56.28, 55.91, 54.03, 50.89, 49.85, 46.93, 46.55, 45.80, 44.56, 42.28, 41.84, 40.94, 38.72, 31.56, 29.36, 28.54, 27.09, 26.47, 26.37, 23.56, 21.68, 20.73, 18.54, 17.20. LC-MS: m/z 1023.2 [M+1].

Example 2: Synthesis of N-(5-((5-(4-acetylpiperazine-1-carbonyl)-4-methoxy-2-methylphenyl)thio)thiazol-2-yl)-4-(4-(7-(2-((2-(2,6-dioxopiperidin-3-yl)-1,3-dioxo-2,3-dihydro-1H-benzo[de]isoquinolin-5-yl)oxy)acetamido)heptyl)piperazin-1-yl)benzamide (2)

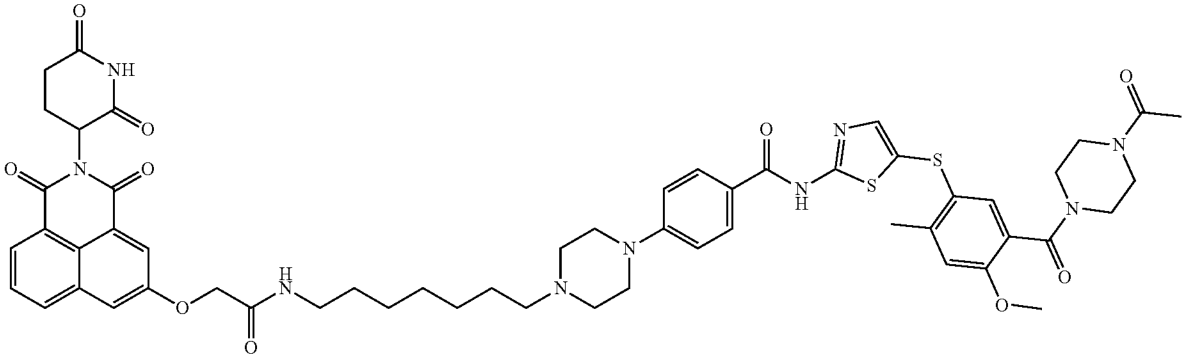 [SMILES: COc1cc(C)c(Sc2cnc(NC(=O)c3ccc(N4CCN(CCCCCCCNC(=O)COc5cc6c7c(cccc7c5)C(=O)N(C5CCC(=O)NC5=O)C6=O)CC4)cc3)s2)cc1C(=O)N1CCN(C(C)=O)CC1]

Compound 2 was prepared according to similar procedures as compound 1 from N-(5-((5-(4-acetylpiperazine-1-carbonyl)-4-methoxy-2-methylphenyl)thio)thiazol-2-yl)-4-(4-(7-aminoheptyl)piperazin-1-yl)benzamide (29.8 mg, 0.0422 mmol) and 2-((2-(2,6-dioxopiperidin-3-yl)-1,3-dioxo-2,3-dihydro-1H-benzo[de]isoquinolin-5-yl)oxy)acetic acid (16.1 mg, 0.0422 mmol). The title compound (TFA salt) was obtained as a light grey solid (25.3 mg, 56%). $^1$H NMR (500 MHz, DMSO-$d_6$) δ 12.59 (s, 1H), 11.02 (s, 1H), 9.75 (s, 1H), 8.46-8.15 (m, 4H), 8.03 (s, 1H), 8.01 (s, 1H), 7.98-7.92 (m, 1H), 7.90-7.81 (m, 1H), 7.75 (d, J=2.9 Hz, 1H), 7.14-7.01 (m, 4H), 5.91-5.77 (m, 1H), 4.74 (d, J=3.8 Hz, 2H), 4.08 (d, J=11.1 Hz, 2H), 3.79 (s, 3H), 3.48-3.26 (m, 6H), 3.21-3.02 (m, 12H), 2.99-2.87 (m, 1H), 2.64-2.55 (m, 1H), 2.47 (s, 3H), 2.10-2.02 (m, 1H), 2.01 (s, 1H), 1.93 (s, 1H), 1.69-1.55 (br, 2H), 1.51-1.38 (br, 2H), 1.31-1.12 (dd, J=13.8, 8.0 Hz, 10H). LC-MS: m/z 1073.3 [M+1].

Example 3: Synthesis of N-(5-((5-(4-acetylpiperazine-1-carbonyl)-4-methoxy-2-methylphenyl)thio)thiazol-2-yl)-4-(4-(2-(2-(2-((2-(2,6-dioxopiperidin-3-yl)-1,3-dioxoisoindolin-4-yl)oxy)acetamido)ethoxy)ethyl)piperazin-1-yl)benzamide (3)

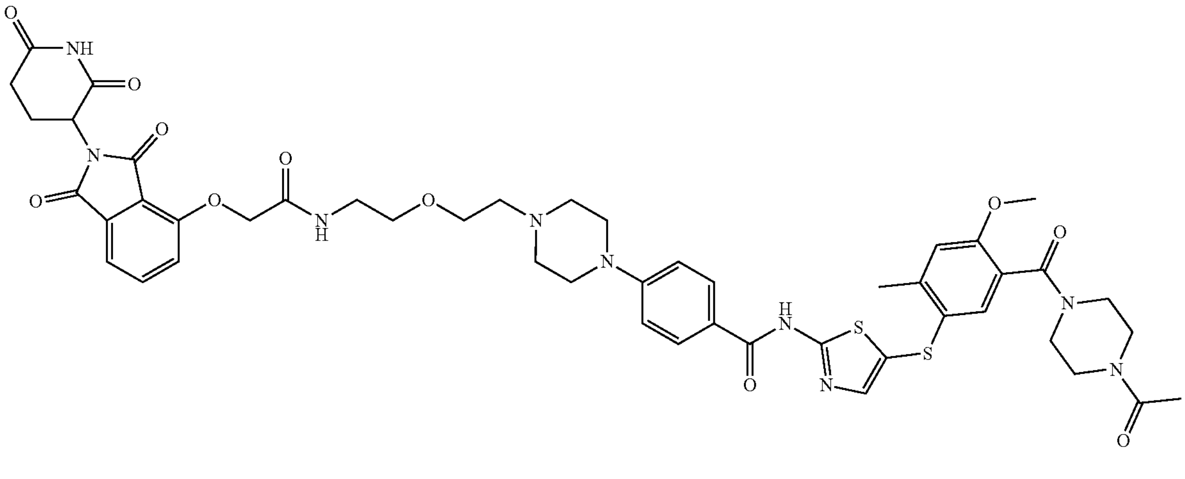 [SMILES: COc1cc(C)c(Sc2cnc(NC(=O)c3ccc(N4CCN(CCOCCNC(=O)COc5cccc6c5C(=O)N(C5CCC(=O)NC5=O)C6=O)CC4)cc3)s2)cc1C(=O)N1CCN(C(C)=O)CC1]

Compound 3 was prepared according to similar procedures as compound 1 from N-(5-((5-(4-acetylpiperazine-1-carbonyl)-4-methoxy-2-methylphenyl)thio)thiazol-2-yl)-4-(4-(7-aminoheptyl)piperazin-1-yl)benzamide (29.8 mg, 0.0422 mmol), tert-butyl (2-(2-bromoethoxy)ethyl)carbamate (22.5 mg, 0.0844 mmol) and 2-((2-(2,6-dioxopiperidin-3-yl)-1,3-dioxoisoindolin-4-yl)oxy)acetic acid (14 mg, 0.0422 mmol). The title compound (TFA salt) was obtained as a light grey solid (25.3 mg, 56%). LC-MS: m/z 995.3 [M+1].

Example 4: Synthesis of 4-(4-(6-(2-((2-(2,6-dioxopiperidin-3-yl)-1,3-dioxoisoindolin-4-yl)oxy)acetamido)hexyl)piperazin-1-yl)-N-(5-((4-methoxy-2-methyl-5-(morpholine-4-carbonyl)phenyl)thio)thiazol-2-yl)benzamide (4)

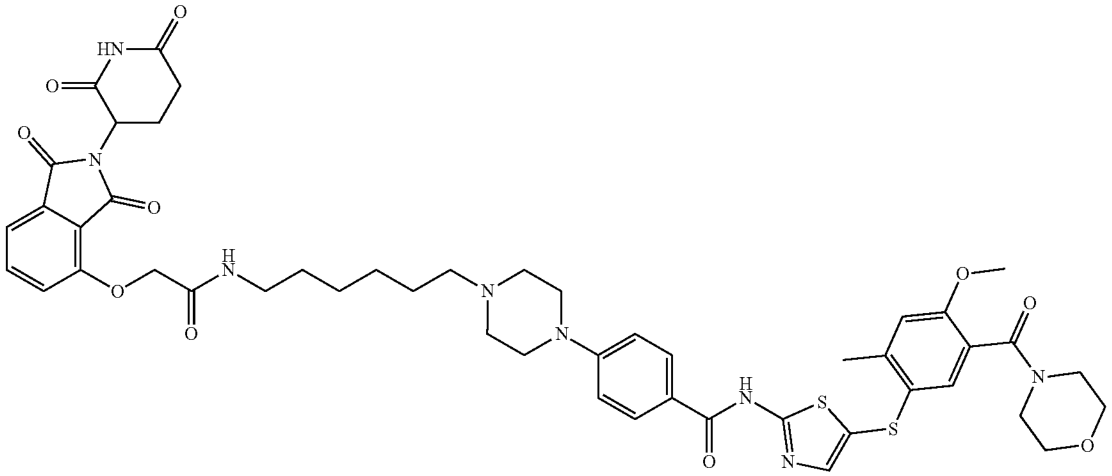 [SMILES: COc1cc(C)c(Sc2cnc(NC(=O)c3ccc(N4CCN(CCCCCCNC(=O)COc5cccc6c5C(=O)N(C5CCC(=O)NC5=O)C6=O)CC4)cc3)s2)cc1C(=O)N1CCOCC1]

Compound 4 was prepared according to similar procedures as compound 1 from 5-((2-aminothiazol-5-yl)thio)-2-methoxy-4-methylbenzoic acid (17.5 mg, 0.059 mmol), morpholine (6 mg, 0.69 mmol) and 2-((2-(2,6-dioxopiperidin-3-yl)-1,3-dioxoisoindolin-4-yl)oxy)acetic acid (14 mg, 0.0422 mmol). The title compound (TFA salt) was obtained as a light grey solid (20.3 mg, 36% in 6 steps). LC-MS: m/z 966.3 [M+1].

Example 5: Synthesis of (2S,4R)-1-((S)-2-(3-(2-(4-(4-((5-((5-(4-acetylpiperazine-1-carbonyl)-4-methoxy-2-methylphenyl)thio)thiazol-2-yl)carbamoyl)phenyl)piperazin-1-yl)ethoxy)propanamido)-3,3-dimethylbutanoyl)-4-hydroxy-N—((S)-1-(4-(4-methylthiazol-5-yl)phenyl)ethyl)pyrrolidine-2-carboxamide (5)

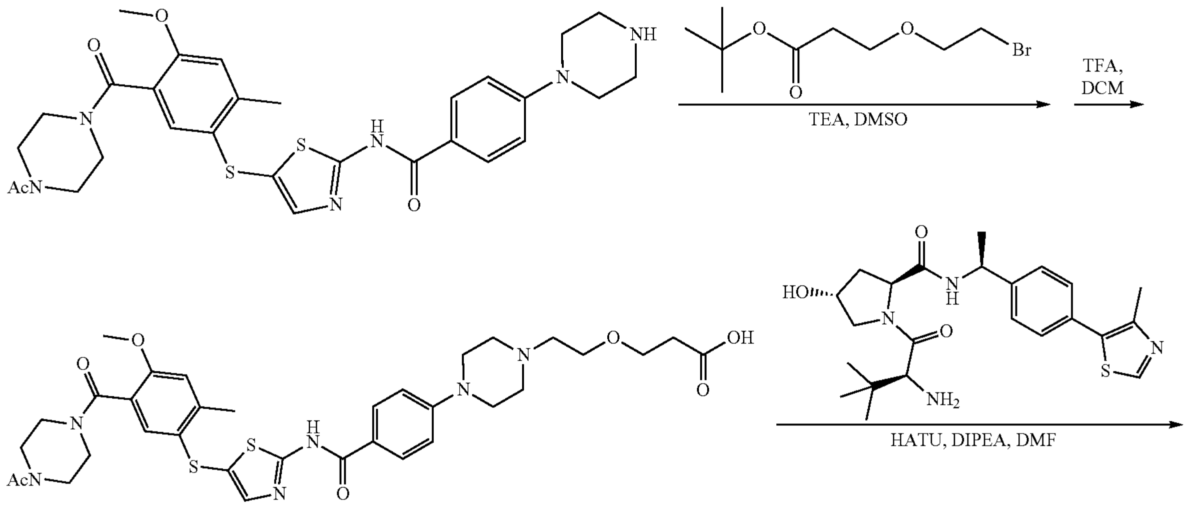

-continued

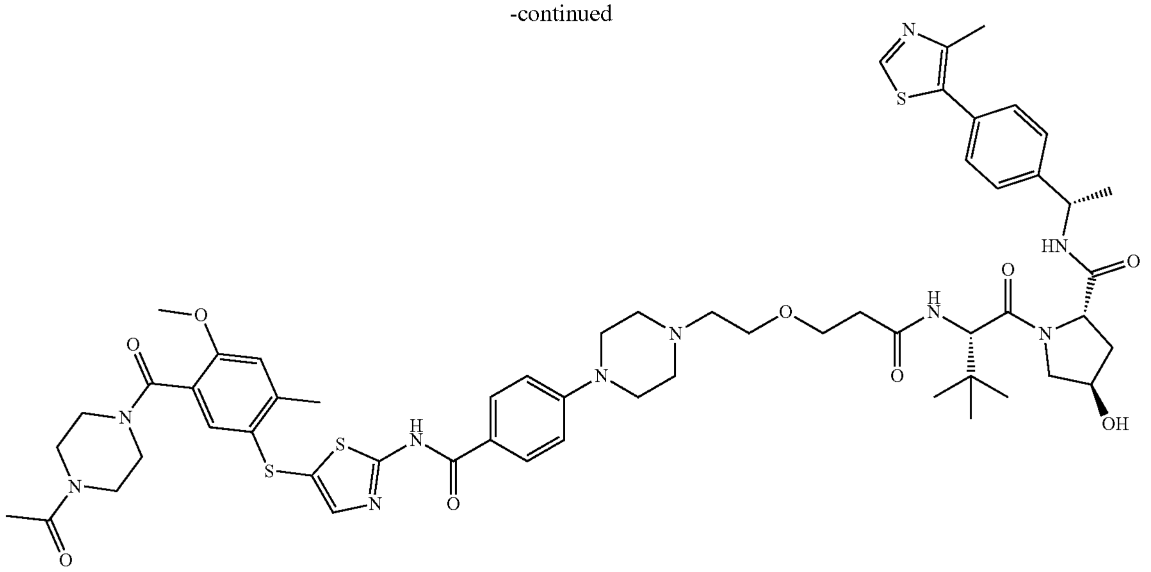

5 tert-Butyl 3-(2-bromoethoxy)propanoate (111 mg, 0.44 mmol) and DIPEA (0.115 mL, 0.66 mmol) were added to a solution of N-(5-((5-(4-acetylpiperazine-1-carbonyl)-4-methoxy-2-methylphenyl)thio)thiazol-2-yl)-4-(piperazin-1-yl)benzamide (130.7 mg, 0.22 mmol) in DMSO (2 mL). The mixture was heated to 80° C. and stirred for 24 hours. The mixture was then cooled to room temperature, extracted, dried, filtered and concentrated to give a light brown residue which was then dissolved into 1 mL of DCM, followed by slow addition of 1 mL of TFA in an ice bath. The mixture was then warmed to room temperature and evaporated after 8 hours. The residue was purified by reverse phase HPLC (5-95% MeOH in $H_2O$) to yield 3-(2-(4-(4-((5-((5-(4-acetylpiperazine-1-carbonyl)-4-methoxy-2-methylphenyl)thio)thiazol-2-yl)carbamoyl)phenyl)piperazin-1-yl)ethoxy)propanoic acid (TFA salt) as a light grey solid (86 mg, 55% in two steps). LC-MS: m/z 710.3 [M+1].

(2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (18.7 mg, 0.0422 mmol), HATU (33 mg, 0.0844 mmol) and DIPEA (37 μL, 0.211 mmol) were added to a solution of 3-(2-(4-(4-((5-((5-(4-acetylpiperazine-1-carbonyl)-4-methoxy-2-methylphenyl)thio)thiazol-2-yl)carbamoyl)phenyl)piperazin-1-yl)ethoxy)propanoic acid (30 mg, 0.0422 mmol) in 2 mL of DMF. The resulting mixture stirred for 30 minutes at room temperature. The solvent was concentrated in vacuo and purified by reverse phase HPLC (5-95% MeOH in $H_2O$) to yield the title compound (TFA salt) as an off-white solid (39 mg, 82%). LC-MS: m/z 1136.5 [M+1].

Example 6: Synthesis of N-(5-((5-(4-acetylpiperazine-1-carbonyl)-4-methoxy-2-methylphenyl)thio)thiazol-2-yl)-4-(4-(2-(2-(2-((2-(2,6-dioxopiperidin-3-yl)-1,3-dioxoisoindolin-4-yl)oxy)acetamido)ethoxy)ethyl)piperazin-1-yl)benzamide (6)

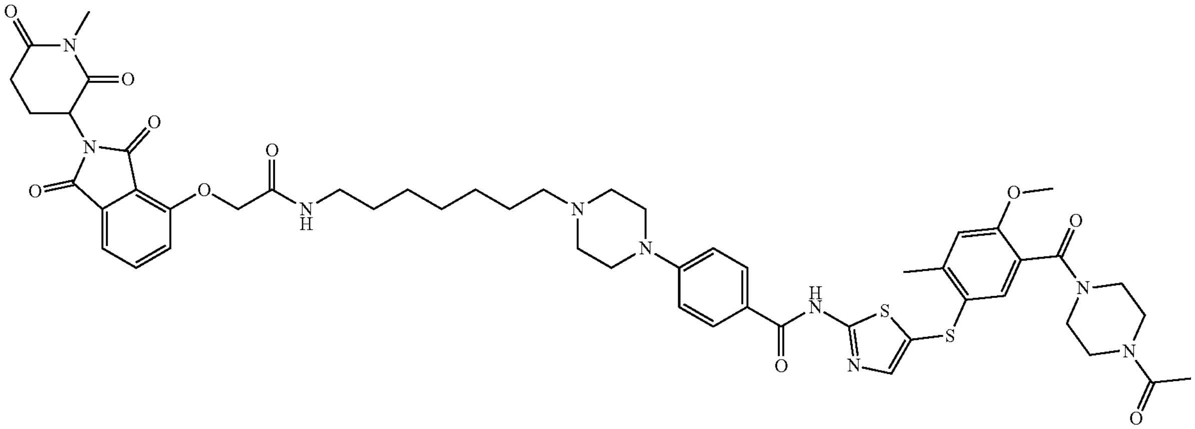 [SMILES: COc1cc(C)c(Sc2cnc(NC(=O)c3ccc(N4CCN(CCCCCCCNC(=O)COc5cccc6c5C(=O)N(C5CCC(=O)N(C)C5=O)C6=O)CC4)cc3)s2)cc1C(=O)N1CCN(C(C)=O)CC1]

Compound 6 was prepared according to similar procedures as compound 1 from N-(5-((5-(4-acetylpiperazine-1-carbonyl)-4-methoxy-2-methylphenyl)thio)thiazol-2-yl)-4-(4-(7-aminoheptyl)piperazin-1-yl)benzamide (29.8 mg, 0.0422 mmol) and 2-((2-(1-methyl-2,6-dioxopiperidin-3-yl)-1,3-dioxoisoindolin-4-yl)oxy)acetic acid (14.6 mg, 0.0422 mmol). The title compound (TFA salt) was obtained as alight grey solid (35 mg, 80%). LC-MS: m/z 1035.4 [M+1].

Example 7: ITK Degradation

Figure 1B:
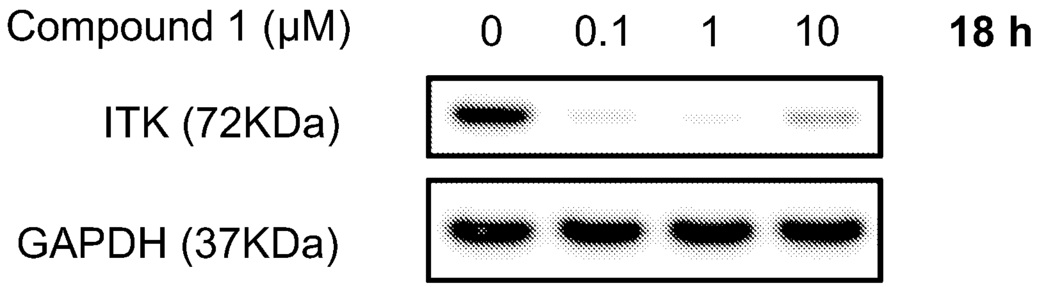

DERL-2 cells (hepatosplenic T-cell lymphoma) were treated with compound 1 for either 4 hours (FIG. 1A) or 18 hours (FIG. 1B) at the indicated doses. After treatment, DERL-2 cells were lysed in Cell Lysis Buffer (Cell Signaling Technology®) on ice for 30 minutes and lysates were clarified by centrifugation. Immunoblotting for ITK was performed to evaluate changes in protein levels upon ITK degrader treatment. All samples were run with equal total protein content and immunoblotting was performed using antibodies that detect total ITK protein as well as GAPDH as a loading control followed by washing and binding of horseradish peroxidase (HRP)-conjugated secondary antibodies. Blots were developed using SuperSignal™ Pico chemiluminescent substrate (Thermo Scientific). Treatment of DERL-2 cells with compound 1 led to rapid and pronounced degradation of ITK protein (FIG. 1A and FIG. 1B).

Example 8: ITK Degradation

DERL-2 cells were treated with compound 1, compound 2 or ITK inhibitor (BMS509744) for 18 hours (FIG. 2) at the indicated doses. After 18 hours, DERL-2 cells were lysed in Cell Lysis Buffer (Cell Signaling Technology®) on ice for 30 minutes and lysates were clarified by centrifugation. Immunoblotting for ITK was performed to evaluate changes in protein levels upon ITK degrader treatment. All samples were run with equal total protein content and immunoblotting was performed using antibodies that detect total ITK protein as well as GAPDH as a loading control followed by washing and binding of horseradish peroxidase (HRP)-conjugated secondary antibodies. Blots were developed using SuperSignal™ Pico chemiluminescent substrate (Thermo Scientific).

Figure 2:
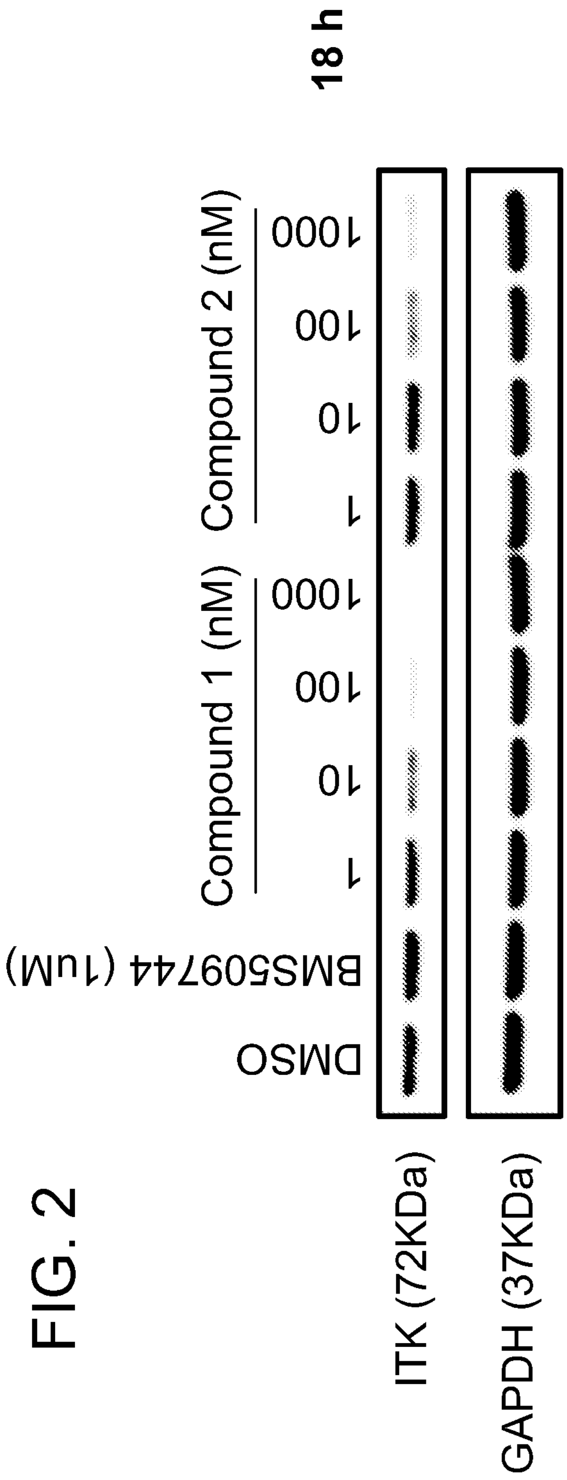
FIG. 2 is an immunoblot that shows ITK degradation in DERL-2 cells after the treatment of DMSO, BMS509744, compound 1, and inventive compound 2 after 18 h.

Treatment of DERL-2 cells with compound 1 or compound 2 led to rapid and pronounced degradation of ITK protein (FIG. 2). Treatment with compound 1 led to the most pronounced degradation of ITK protein, with degradation evident at 1 nM and maximal degradation at 1000 nM. Treatment with compound 2 led to degradation of ITK protein at 100 nM and maximal degradation at 1000 nM. These results indicate that ITK is a degradable kinase and compound 1 is a highly potent degrader of ITK protein.

Example 9: Activated E3 Ligase in ITK Degradation

DERL-2 cells were treated with compound 1, the NEDD8-activating enzyme (NAE) inhibitor MLN4924, or in combination for 18 hours (FIG. 3) at 1p M. After 18 hours, DERL-2 cells were lysed in Cell Lysis Buffer (Cell Signaling Technology®) on ice for 30 minutes and lysates were clarified by centrifugation. Western blot was performed as described in Example 7.

Figure 3:
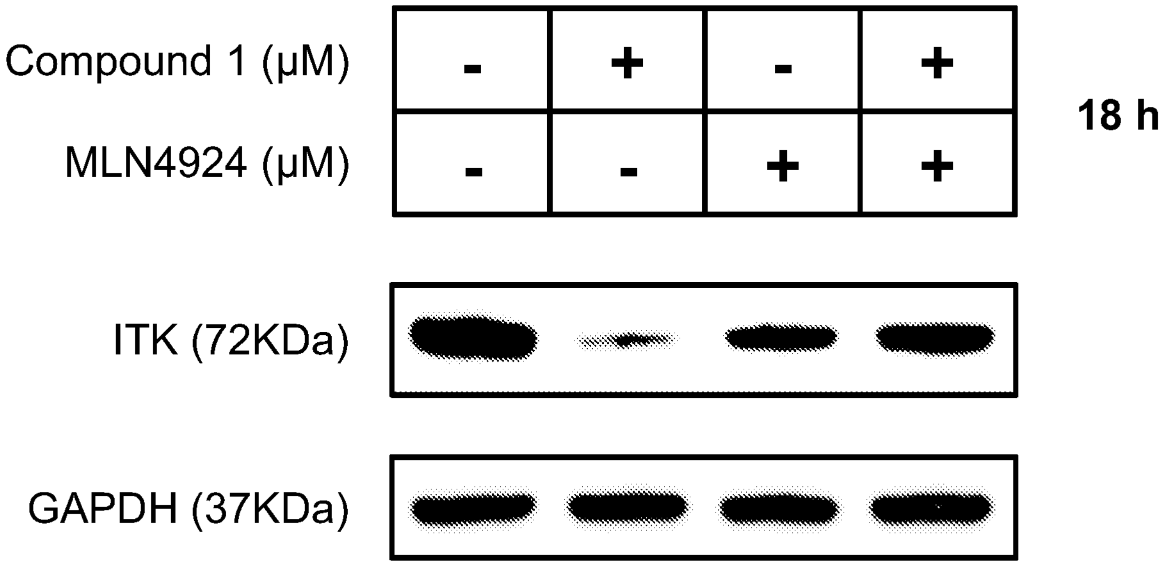
FIG. 3 is an immunoblot that shows ITK degradation is dependent on neddylation as degradation is blocked by MLN4924.

Treatment of DERL-2 cells with MLN4924 rescued the degradation induced by compound 1 (FIG. 3). Because NAE is essential for the activity of many E3 ubiquitin ligases, these results strongly suggest that E3 ligase activity is required for degradation induced by compound 1.

Example 10: DERL-2 Cells Supplemented with IL-2

DERL-2 cells supplemented in culture with IL-2 (FIG. 4A) or without IL-2 (FIG. 4B and FIG. 4C) were treated with compound 1 at the indicated doses. Cells were split at 1:5 ratio with fixed concentration of compound 1 every two days. Cell numbers and cell death were quantified by flow cytometry. Propidium iodide (PI) solution, a marker of cell death, was added to cells 5 minutes before flow cytometry detection. Percent PI-positive is used to quantify cell death.

Figure 4A:
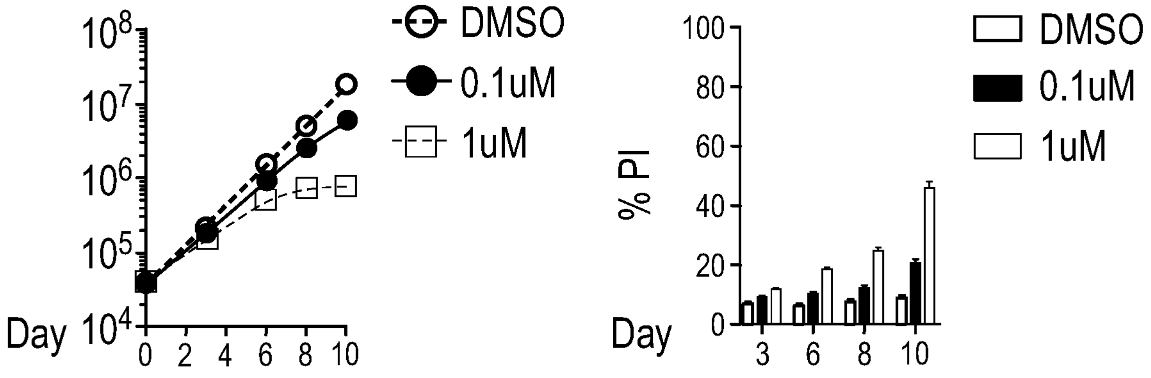
FIG. 4A-FIG. 4C are a series of graphs that show that compound 1 (μM) inhibits proliferation and induces cell death of T-cell lymphoma (TCL) cells.
Figure 4B:
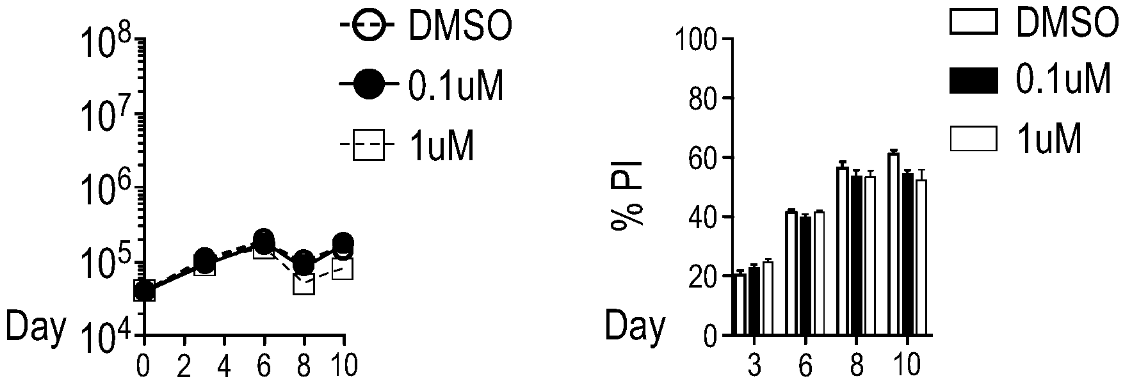
Figure 4C:
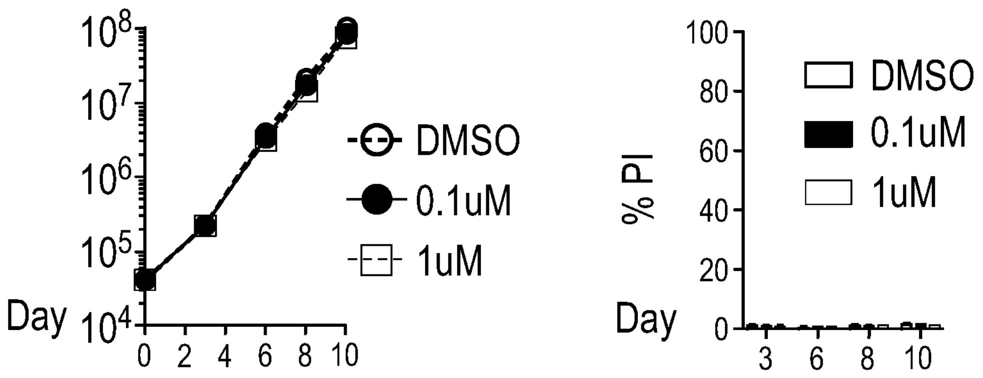

Treatment of DERL-2 cells with compound 1 inhibited cell proliferation >10-fold and induced cell death compared with DMSO treatment (FIG. 4A). Without IL-2 supplementation, DERL-2 cells did not proliferate and had a high percentage of cell death, confirming their dependence on IL-2 (FIG. 4B). In contrast, Hut78 cells, a cell line known to be independent of IL-2, were treated with compound 1 or DMSO as a negative control. Compound 1 did not inhibit cell growth or induce cell death of Hut78 cells (FIG. 4C). **p<0.01.

Example 11: Compound 1 Induced Cell Death of T-Cell Lymphoma Cells

DERL-2 cells in culture with IL-2 were treated with either 1 μM of compound 1, 1 μM BMS509744 or DMSO. Cells were split at 1:5 ratio and fresh compounds were added every two days. Cell numbers and cell death were quantified by flow cytometry. PI solution was added to cells 5 minutes before flow cytometry detection to indicate cell death.

Figure 5:
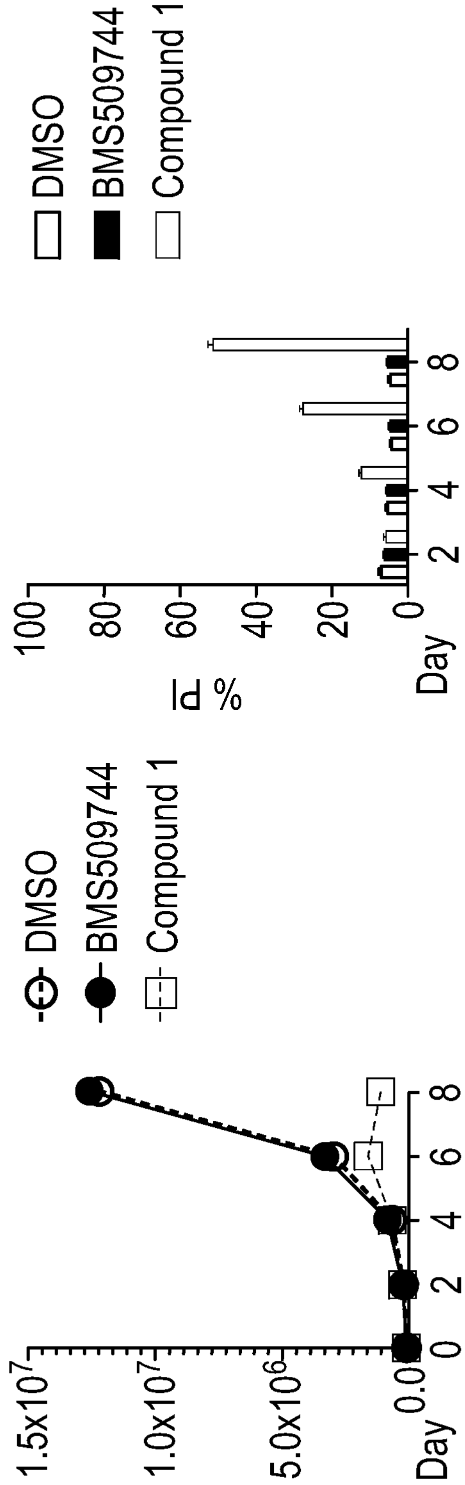
FIG. 5 is a series of graphs that show that compound 1, but not the parental inhibitor (BMS509744), blocks cell proliferation and induces cell death of TCL cells. DERL-2 in culture with IL-2 were treated with either 1 μM compound 1, 1 μM BMS509744, or DMSO.

FIG. 5 shows that compound 1, but not the parental inhibitor (BMS509744), blocked cell proliferation and induced cell death of TCL cells. **p<0.01.

Example 12: ITK Degradation Induced by Compound 1

DERL-2 cells were pre-treated with or without 10 μM BMS509744 for 4 hours. After 4 hours, 100 nM compound 1 was added and cells were cultured for another 4 hours. After treatment, DERL-2 cells were lysed in Cell Lysis Buffer (Cell Signaling Technology®) on ice for 30 minutes and lysates were clarified by centrifugation. Western blot was performed as described in Example 7 to detect protein expression levels of ITK, IKZF1, IKZF3, and GAPDH.

Figure 6:
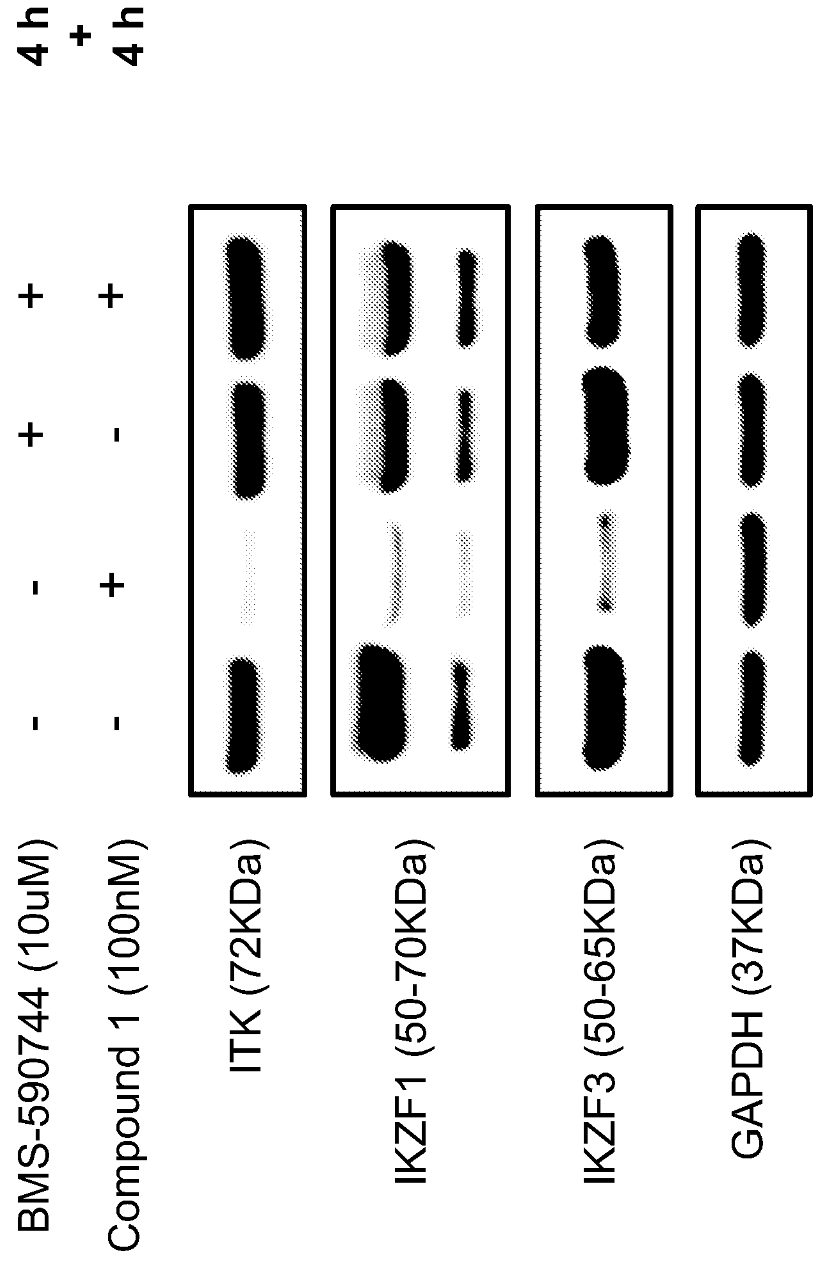
FIG. 6 is an immunoblot that shows ITK degradation in DERL-2 cells after being treated with compound 1 that is rescued by co-treatment with 10-fold excess BMS509744.

Pre-treatment of DERL-2 cells with excessive amount of BMS509744 rescued the degradation induced by compound 1 (FIG. 6). These results indicate that binding to ITK is required for degradation induced by compound 1.

Example 13: ITK Degradation in Hut78 Cells

Hut78 cells (mycosis fungoides and Sezary syndrome) were treated with or without 1 μM of compound 1 for 18 hours. After treatment, Hut78 cells were lysed in Cell Lysis Buffer (Cell Signaling Technology®) on ice for 30 minutes and lysates were clarified by centrifugation. Immunoblotting for ITK was performed as described in Example 7 to evaluate changes in protein levels upon ITK degrader treatment.

Figure 7:
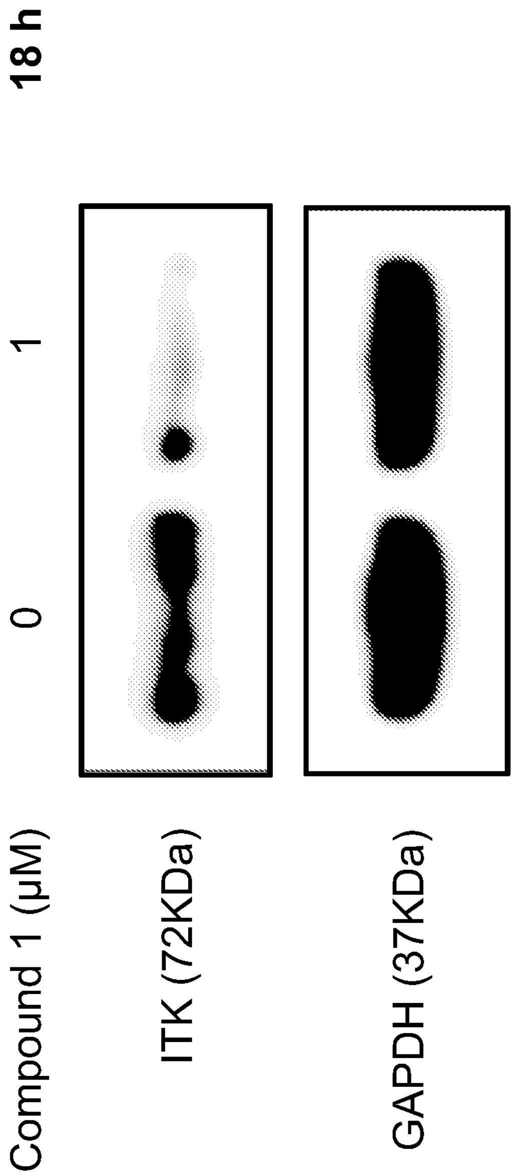
FIG. 7 is an immunoblot that shows in vitro ITK degradation in Hut78 cells 18 h after treatment of xenografted mice with compound 1.

As shown in FIG. 7, treatment of Hut78 cells with compound 1 led to pronounced degradation of ITK protein.

Example 14: Proteome-Wide Profiling of Representative Degrader Compounds

Proteome-wide profiling experiments were performed according to the reported protocol (B. Jiang et al., Angew. Chem. Int. Ed. Engl. 58:6321-6326 (2019)). Molt4 cells were treated with DMSO vehicle, 100 nM of compound 1 or 100 nM of compound 2 for 5 hours. Protein abundance measurements were made using TMT quantitative mass spectrometry and significant changes were assessed by moderated t-test as implemented in the limma package. The $\log_2$ fold change ($\log_2$ FC) is shown on the y-axis and negative $\log_{10}$ p value ($-\log_{10}$ p value) on the x-axis for three independent biological replicates of each treatment.

Figure 8A:
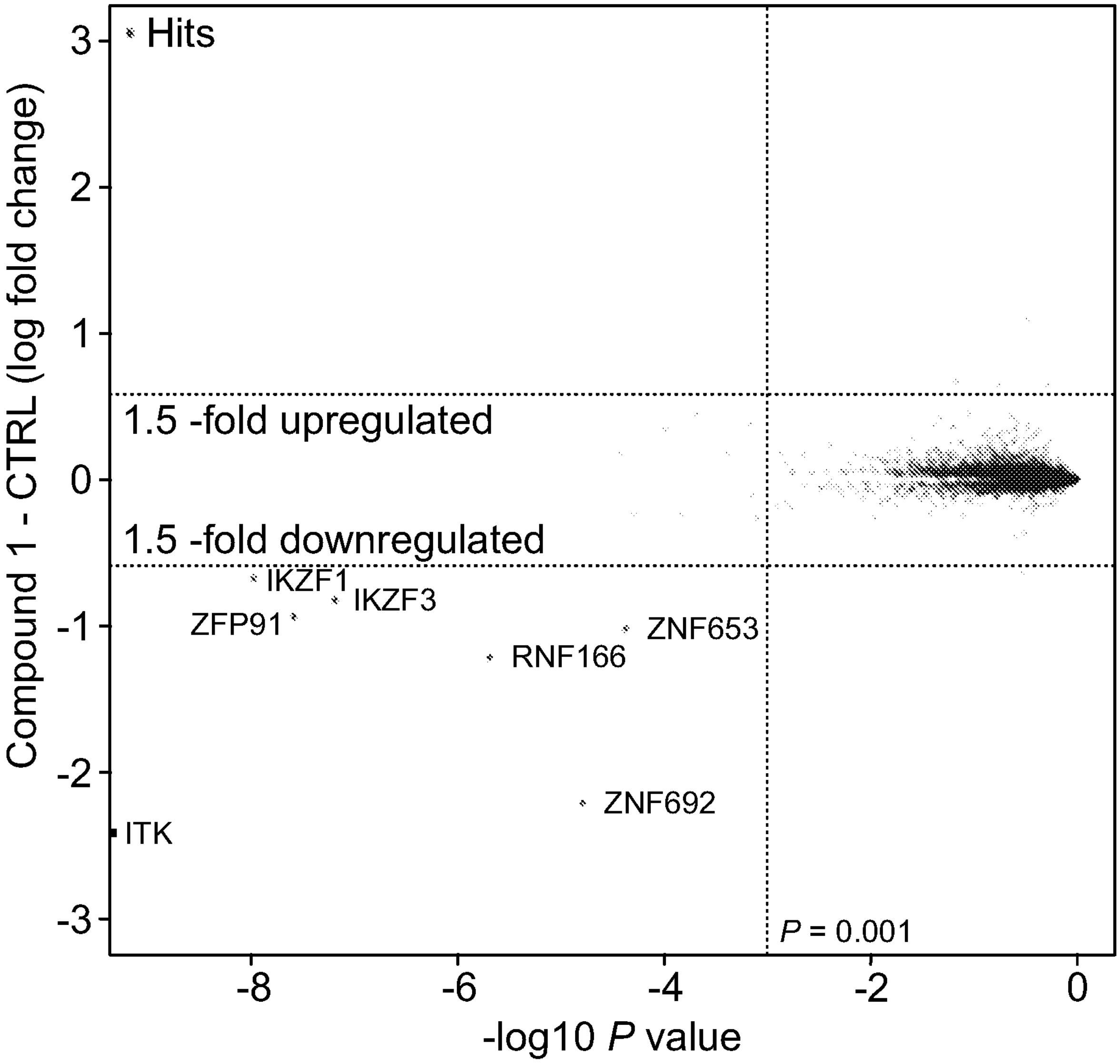
FIG. 8A and FIG. 8B are scatterplots depicting the change in relative protein abundance in MOLT4 cells after treatment of compound 1 and compound 2, respectively, (100 nM, 5 hour) compared to DMSO vehicle control treated cells.
Figure 8B:
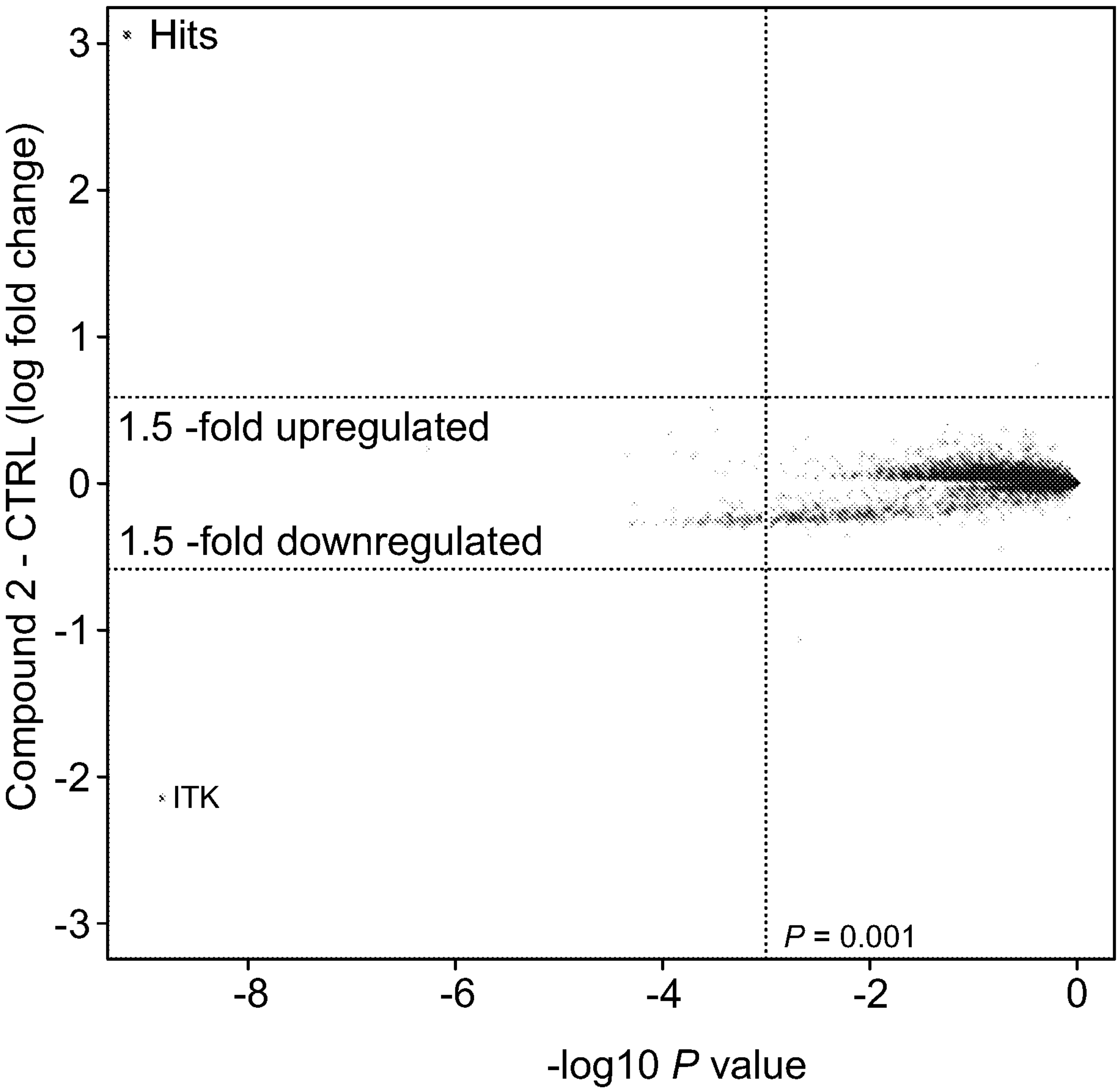

As shown in FIG. 8A, compound 1 downregulated ITK, IKZF1, IKZF3, ZFP91, RNF166, ZNF653 and ZNF692. As shown in FIG. 8B, compound 2 selectively downregulated ITK.

Example 15: Mouse Pharmacokinetic (PK) Studies

Standard PK studies were conducted using male C57Bl/6 mice obtained from Scripps Fla. A single 2 mg/kg intravenous (IV) injection of compound 1 solution in 5/90 DMSO/10% Captisol® was evaluated. Plasma concentrations of compound 1 reported at each of the 8 time points (5 min, 15 min, 30 min, 1 h, 2 h, 4 h, 6 h and 8 h post dosing) are the average values from 3 test animals. Results are shown in Table 1.

tumors. Tumor tissues were cut into small pieces and dissociated into single cell suspension following the instruction of Tumor Dissociation Kit (Miltenyi Biotec, #130-095-929). Suspension cells were then depleted of mouse cells (Catalog #19849, STEMCELL technology). Purified tumor cells were lysed in Cell Lysis Buffer (Cell Signaling Technology®) on ice for 30 minutes and lysates were clarified by centrifugation. Immunoblotting for ITK was performed as described in Example 7 to evaluate protein level changes.

Figure 9:
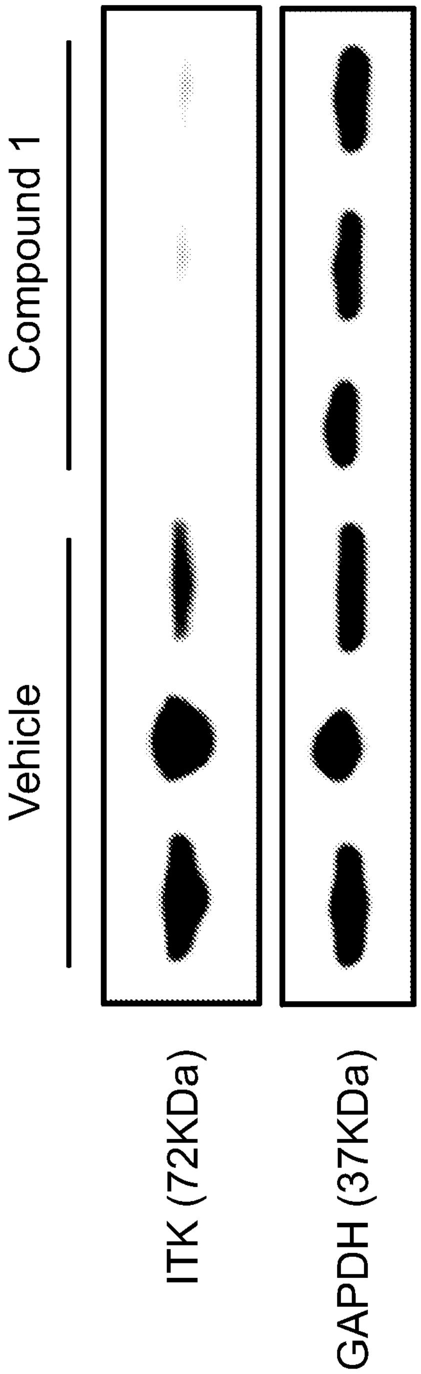
FIG. 9 is an immunoblot that shows in vivo ITK degradation in Hut78 cells after the treatment of compound 1 at 50 mg/kg for 3 dose in 24 h.

As shown in FIG. 9, treatment of engrafted Hut78 cells with compound 1 led to significant degradation of ITK protein in vivo.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be

TABLE 1

Result from mouse PK study

| $T_{1/2}$ hr | $T_{max}$ hr | $C_{max}$ ng/mL | $C_{max}$ µM | $AUC_{last}$ min*ng/mL | $AUC_{last}$ µM · hr | $AUC_{INF\_obs}$ min · ng/mL | AUC % Extrap | $Cl_{\_obs}$ mL/min/kg | $MRT_{INF\_obs}$ hr | $V_{SS\_obs}$ L/kg |
|---|---|---|---|---|---|---|---|---|---|---|
| 2.18 | 0.08 | 1707 | 1.67 | 82031 | 1.34 | 86524 | 5.14 | 25.20 | 1.96 | 2.94 |

The results indicate that the compound 1 disclosed herein has a good in vivo metabolic stability, exposure and clearance rate, which has obvious advantages than the reported selective ITK inhibitor BMS-509744 for in vivo use (Das et al., Bioorg. Med. Chem. Lett. 16:3706-3712 (2006)).

Example 16: In Vivo Degradation Studies

In vivo degradation studies were conducted using female NSG mice. 6 eight-week-old NSG mice were injected subcutaneously with $1*10^7$ of Hut78 cells. The injected mice were monitored for tumor formation twice a week until tumor growth reaches an average of 500 $mm^3$. Mice were then randomized into 3 mice per group, and treated with either vehicle (7.5% DMSO, 20% (2-hydroxypropyl)-β-cyclodextrin [HP-β-CD]) or compound 1 at 50 mg/kg via intraperitoneal injection for 3 doses (every 8 hours×3). Four hours after the last doing, mice were sacrificed to harvest made to the illustrative embodiments and that other arrangements may be devised without departing from the spirit and scope of the present invention as defined by the appended claims.

What is claimed is:

1. A compound of formula (I), (I)

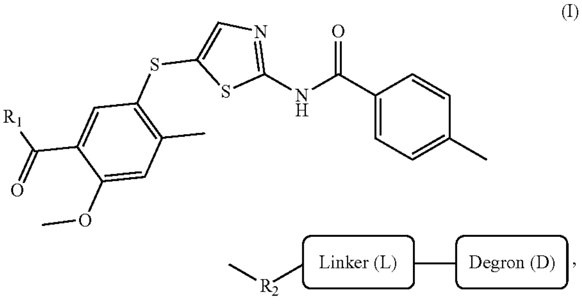

wherein
$R^1$ represents
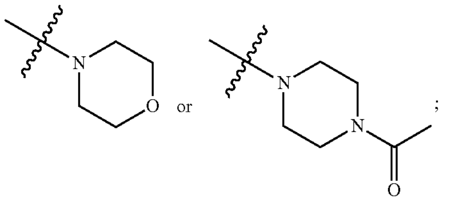
and
$R^2$ represents O or
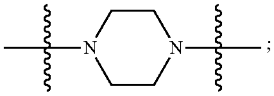 [SMILES: *N1CCN(*)CC1]
wherein the degron has a structure represented by any one of formulas D1a-j:
(D1-a)
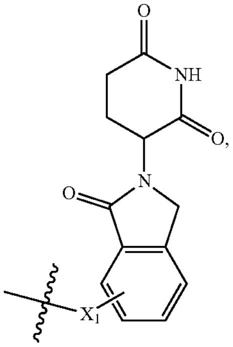
(D1-b)
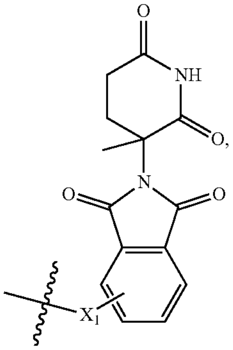
(D1-c)
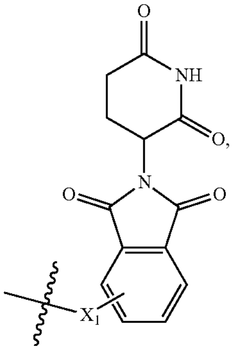
-continued
(D1-d)
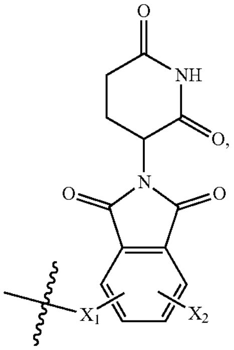
(D1-e)
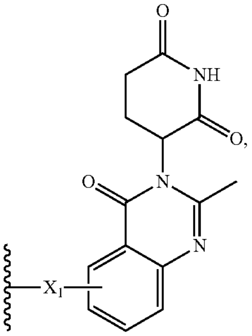
(D1-f)
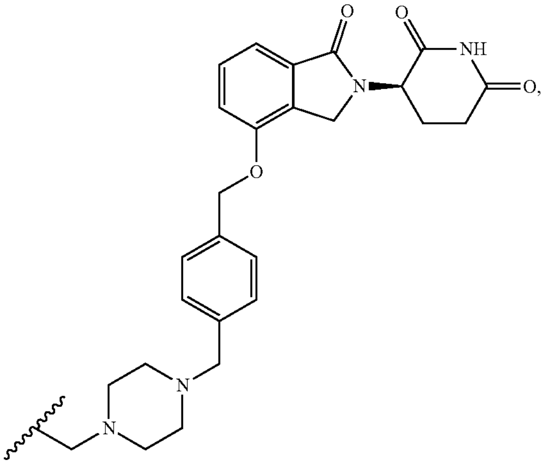
(D1-g)
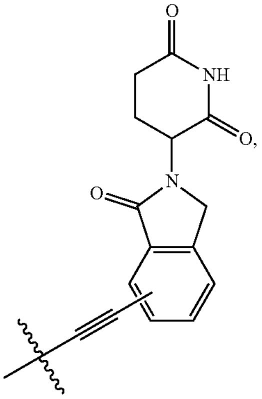

-continued
(D1-h)
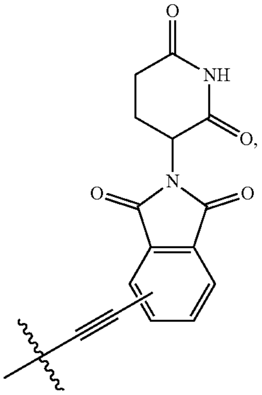
(D1-i)
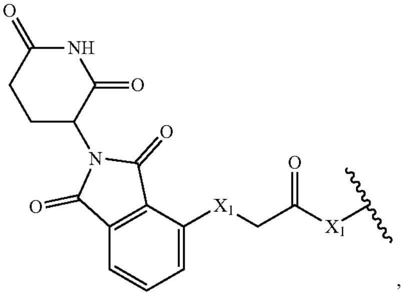
,
(D1-j)
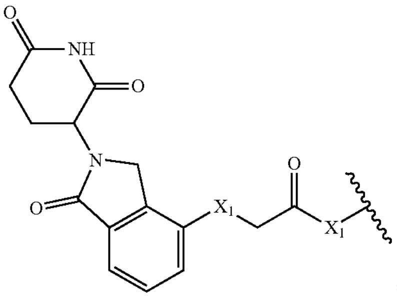
, and
(D1-k)
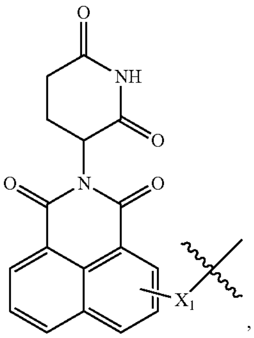
,
wherein $X_1$ is independently absent, $CH_2$, NH, or O; and $X_2$ is alkyl, halo, CN, $CF_3$, $OCHF_2$ or $OCF_3$, or has a structure represented by any one of formulas D2-a-f:
(D2-a)
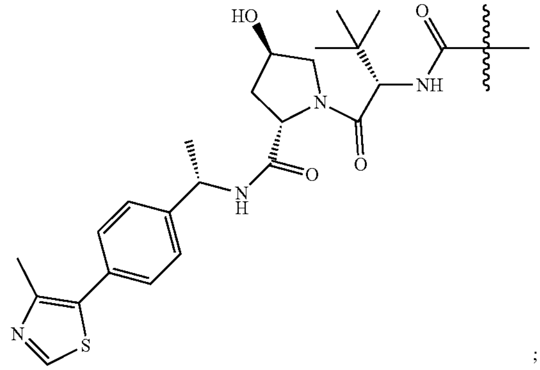
;
(D2-b)
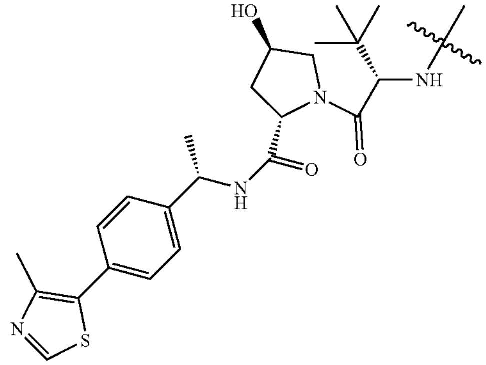
;
(D2-c)
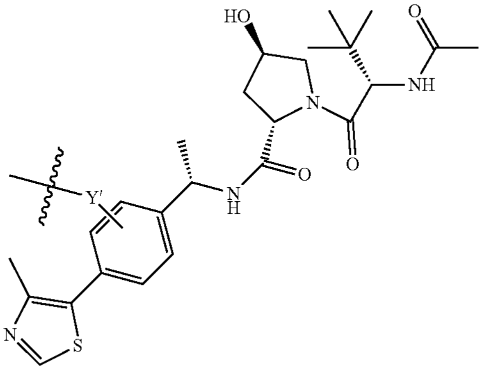
,
wherein Y' is a bond, NH, O or $CH_2$;

(D2-d)
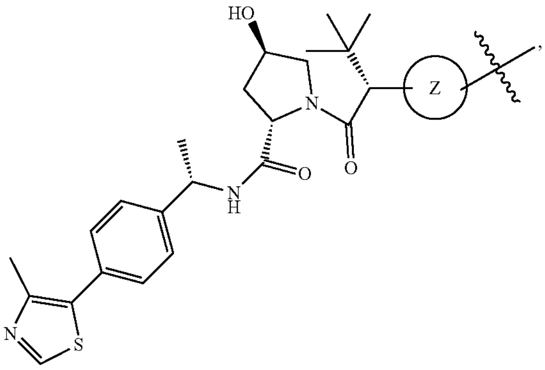
,
wherein Z is a $C_5$-$C_6$ carbocyclic or a 5-6 membered heterocyclic group;
(D2-e)
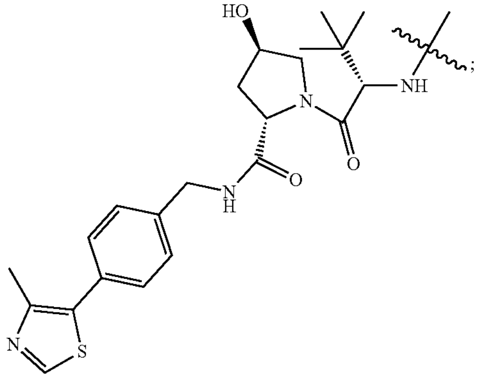
; and
(D2-f)
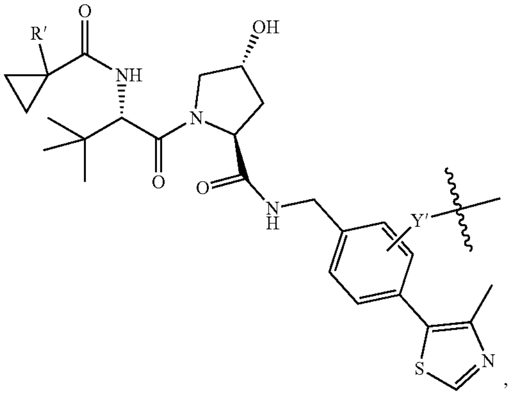
,
wherein R' is H, F or CN, and Y' is a bond, NH, O or $CH_2$, or a stereoisomer thereof, or
has a structure represented by any one of formulas D3-a-c:
(D3-a)
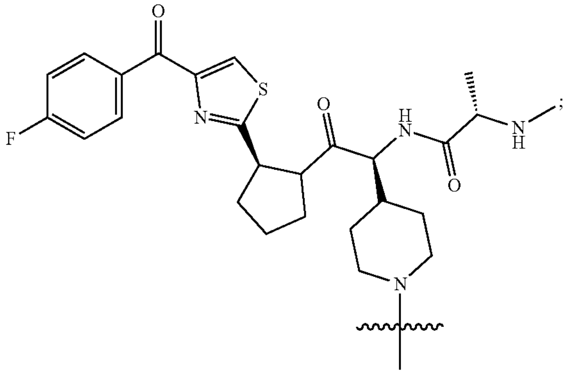
;
(D3-b)
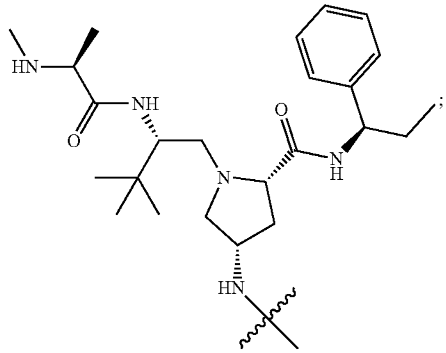
; and
(D3-c)
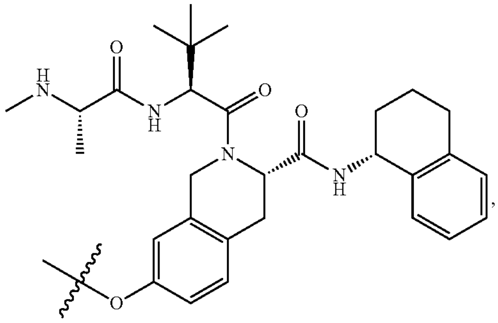
, or a stereoisomer thereof, or has a structure represented by any one of formulas D4-a-b:

(D4-a)

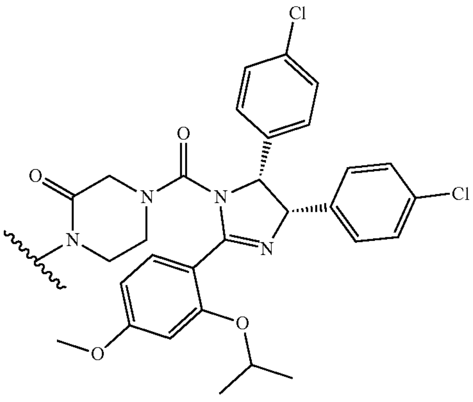

and (D4-b)

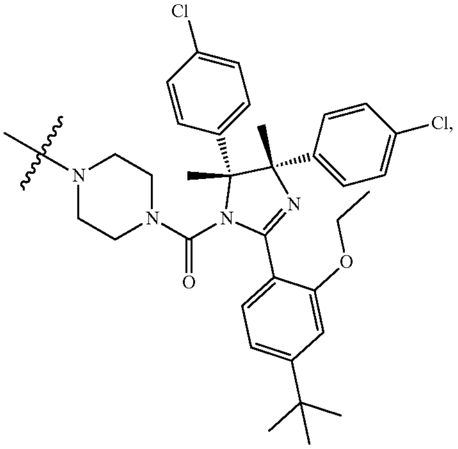

and the linker comprises an alkylene chain or a polyethylene glycol chain, either of which may be interrupted by and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, $—S(O)_2—$, —OS(O)—, —S(O)O—, —S(O)—, $—OS(O)_2—$, $—S(O)_2O—$, $—N(R')S(O)_2—$, $—S(O)_2N(R')—$, —N(R')S(O)—, —S(O)N(R')—, $—N(R')S(O)_2N(R')—$, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different, or a pharmaceutically acceptable salt or stereoisomer thereof.

2. The compound of claim 1, wherein $R_1$ represents

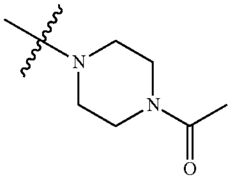 [SMILES: *N1CCN(C(C)=O)CC1]

and the compound is represented by formula Ia:

(Ia)

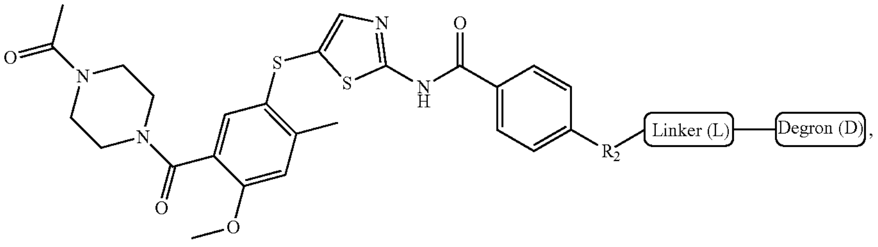

or a pharmaceutically acceptable salt or stereoisomer thereof.

3. The compound of claim 2, wherein $R_2$ represents O and the compound is represented by formula Ia1:

(Ia1)

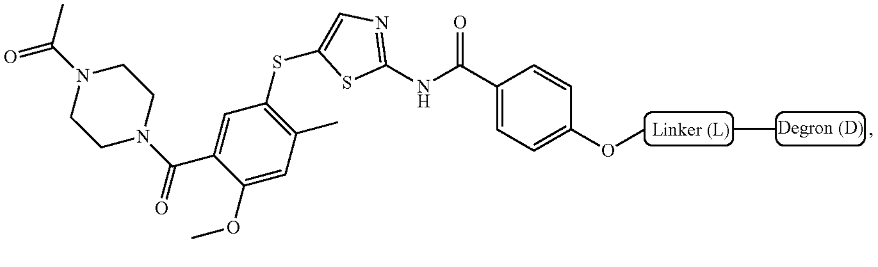

or a pharmaceutically acceptable salt or stereoisomer thereof, or wherein $R_2$ represents

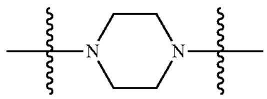 [SMILES: *N1CCN(*)CC1]

and the compound is represented by formula Ia2:

(Ia2)

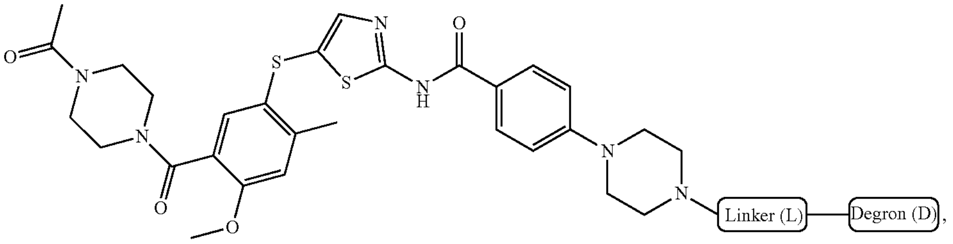

or a pharmaceutically acceptable salt or stereoisomer thereof.

4. The compound of claim 1, wherein $R_1$ represents

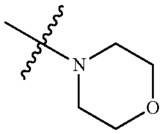 [SMILES: *N1CCOCC1]

and the compound is represented by formula Ib:

(Ib)

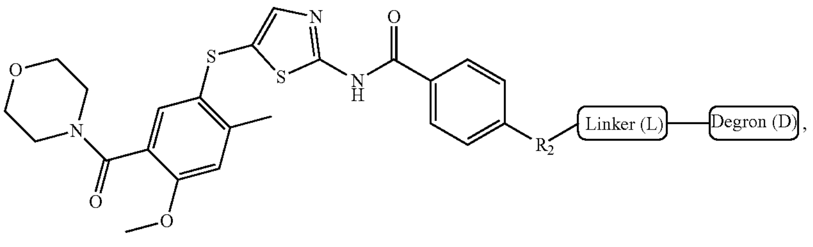

or a pharmaceutically acceptable salt or stereoisomer thereof.

5. The compound of claim 4, wherein $R_2$ represents O and the compound is represented by formula Ib1:

(Ib1)

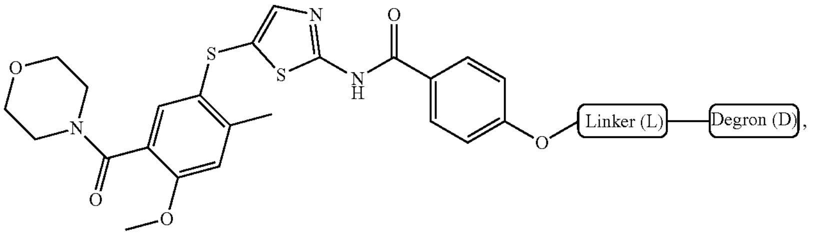

or a pharmaceutically acceptable salt or stereoisomer thereof, or wherein $R_2$ represents

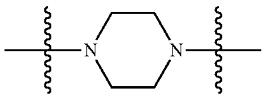 [SMILES: *N1CCN(*)CC1]

and the compound is represented by formula Ib2:

(Ib2)

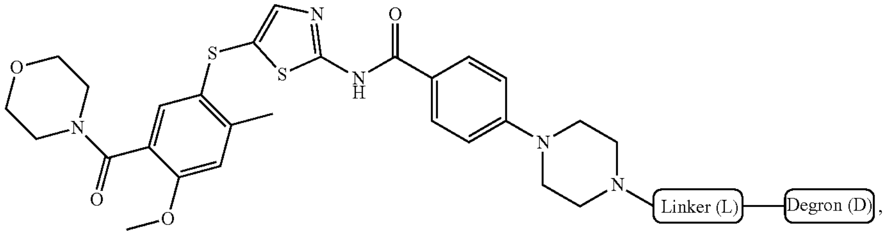

or a pharmaceutically acceptable salt or stereoisomer thereof.

6. The compound of claim 1, wherein the linker comprises an alkylene chain which may be interrupted by and/or terminate at either or both termini in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

7. The compound of claim 1, wherein the linker comprises a polyethylene glycol chain which may terminate at either or both termini in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —S—CR')N(R')—, —N(R')C(NR')N(R')—, —OB(Me)O—, —$S(O)_2$—, —OS(O)—, —S(O)O—, —S(O)—, —$OS(O)_2$—, —$S(O)_2O$—, —$N(R')S(O)_2$—, —$S(O)_2N(R')$—, —N(R')S(O)—, —S(O)N(R')—, —$N(R')S(O)_2N(R')$—, —N(R')S(O)N(R')—, $C_{3-12}$ carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

8. The compound of claim 1, wherein the linker is represented by any one of the following structures:

(L10-a)

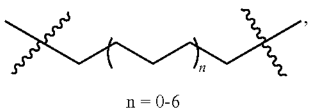

n = 0-6

-continued (L10-b)

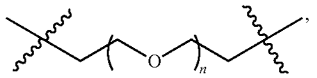

n = 1-6

-continued (L10-c)

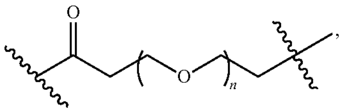

n = 1-6

(L10-d)

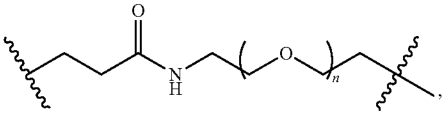

n = 1-6

(L10-e)

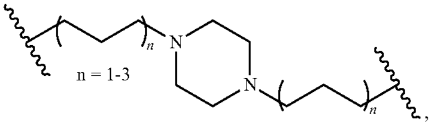

n = 1-3 n = 1-3

(L11-a)

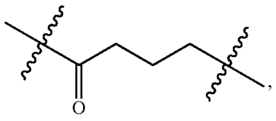

(L11-b)

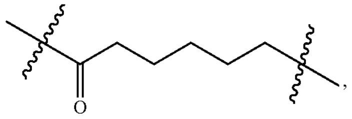

(L11-c)

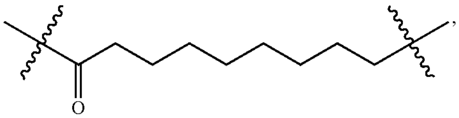

-continued
(L11-d)
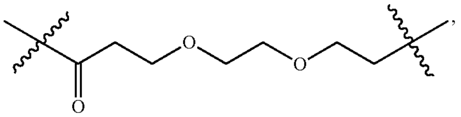
(L11-e)
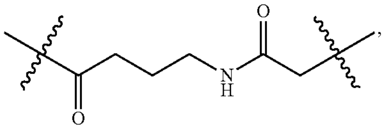
(L11-f)
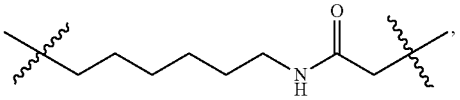
(L11-g)
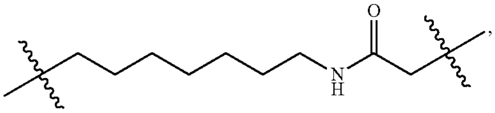
(L11-h)
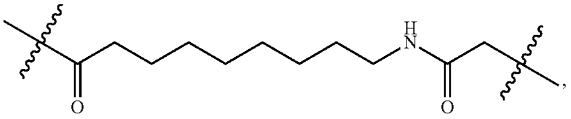
(L11-i)
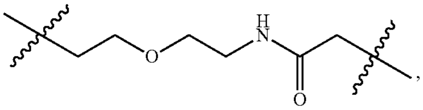
(L11-j)
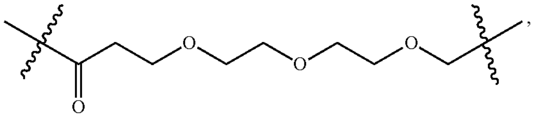
(L11-k)
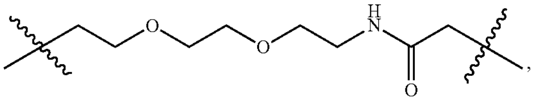
(L11-l)
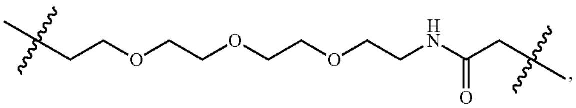
(L11-m)
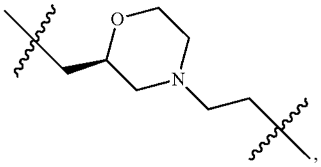
-continued
(L11-n)
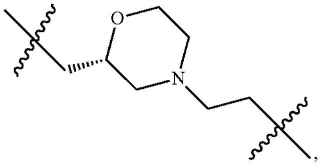
(L11-o)
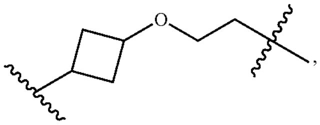
(L11-p)
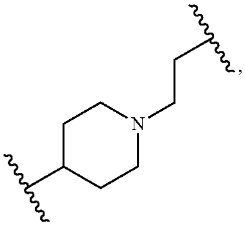
(L11-q)
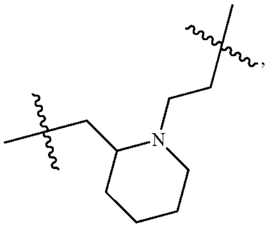
(L11-r)
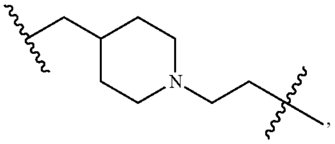
(L11-s)
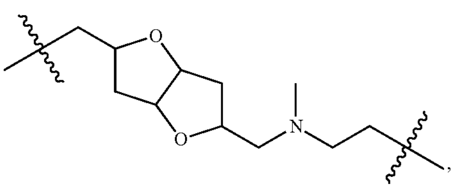
and
(L11-t)
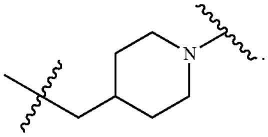
9. The compound of claim 1, which is represented by any one of the following structures:

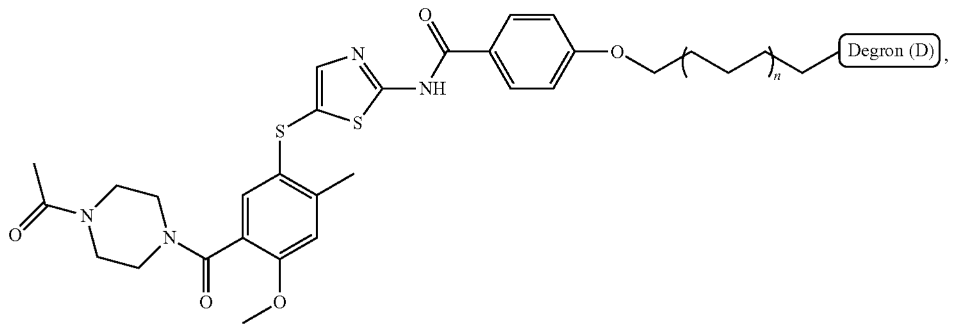
n = 0-6
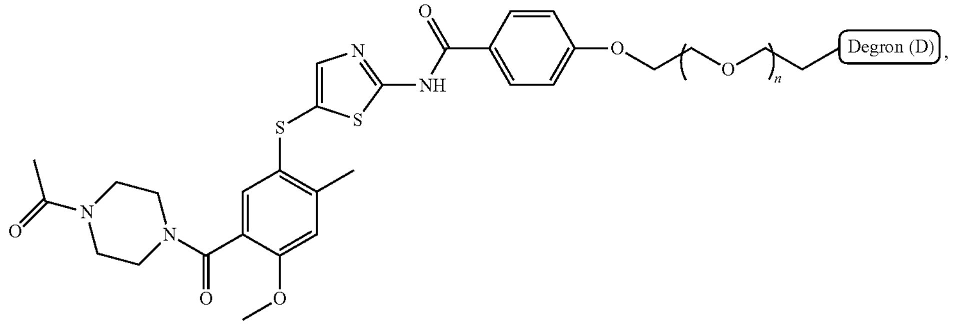
n = 1-6
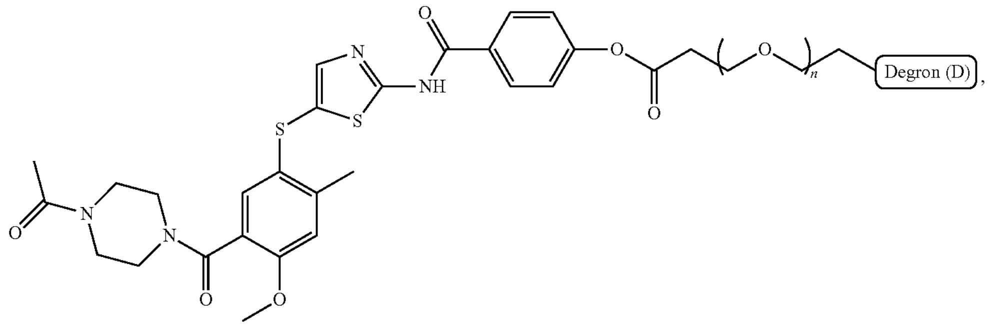
n = 1-6
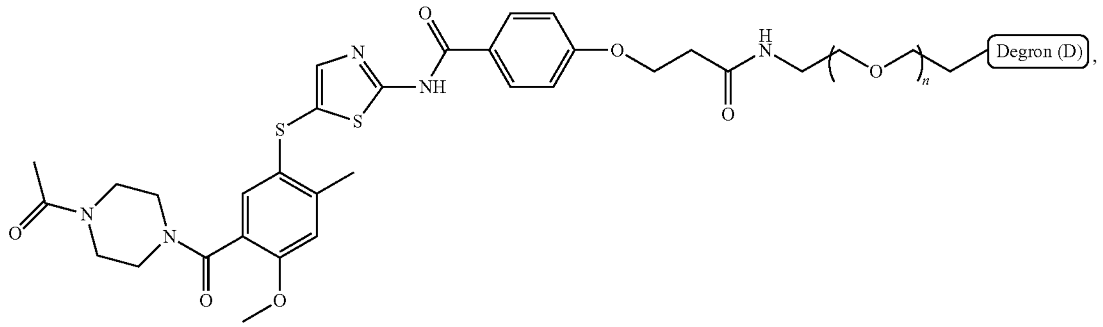
n = 1-6

-continued
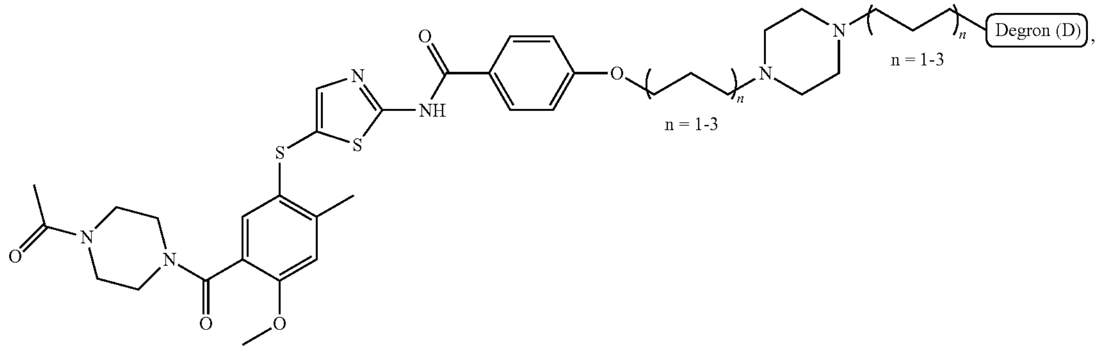
n = 1-3 n = 1-3
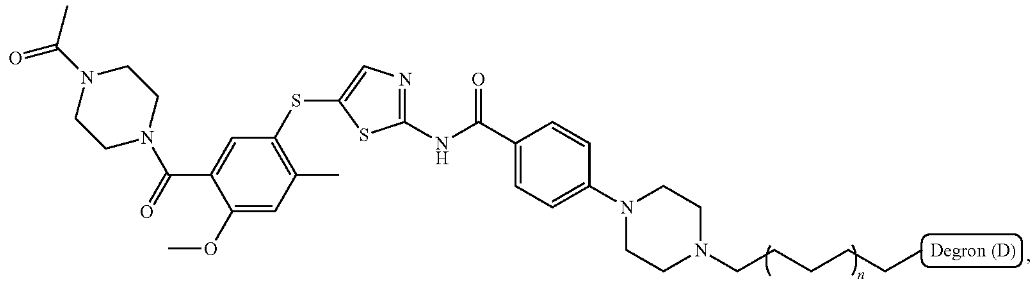
n = 0-6
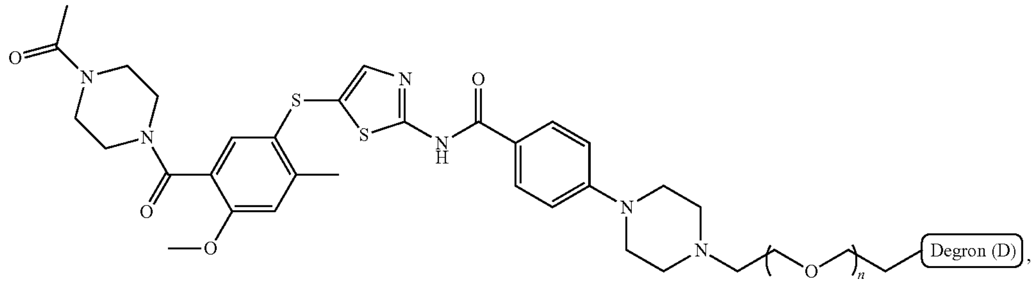
n = 1-6
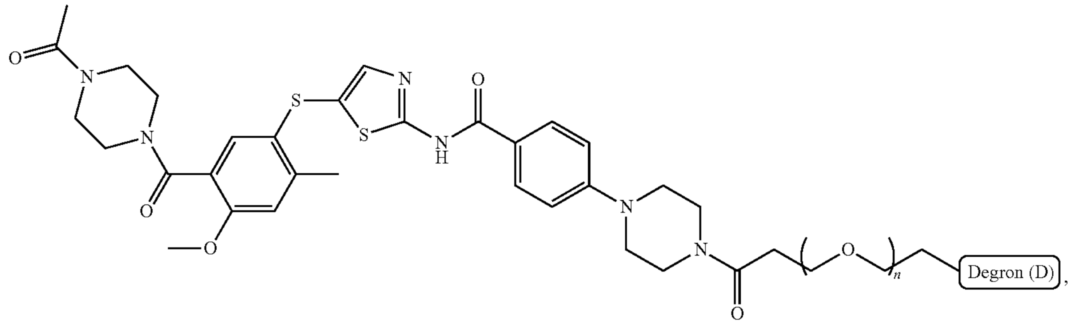
n = 1-6
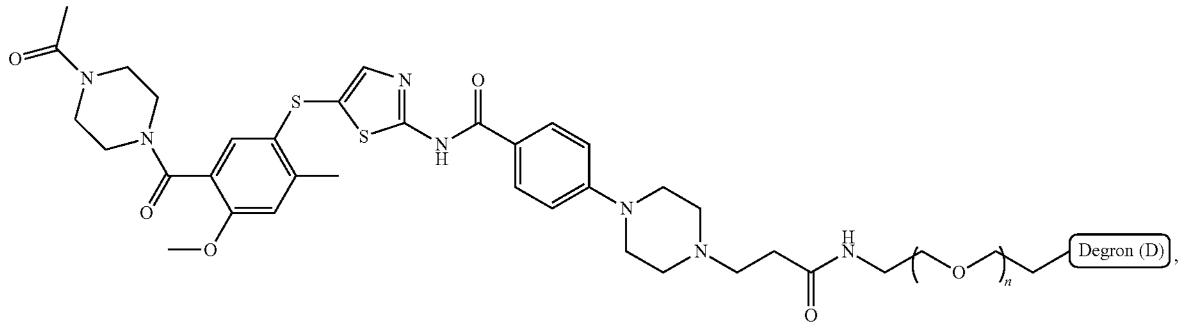
n = 1-6

-continued
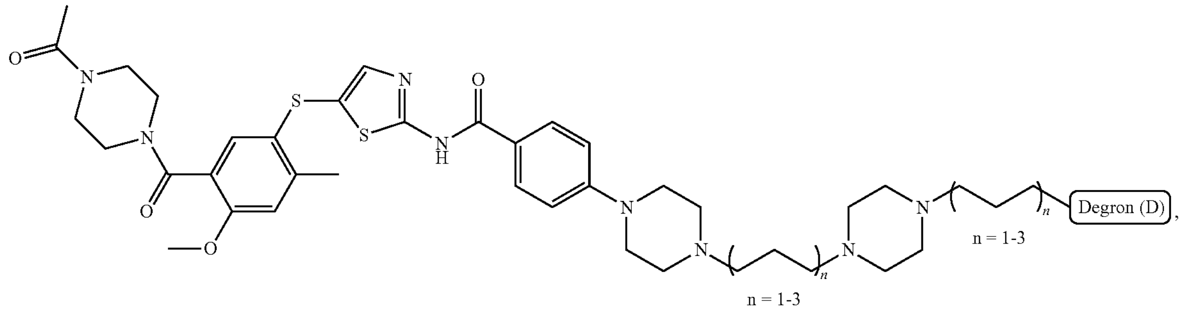
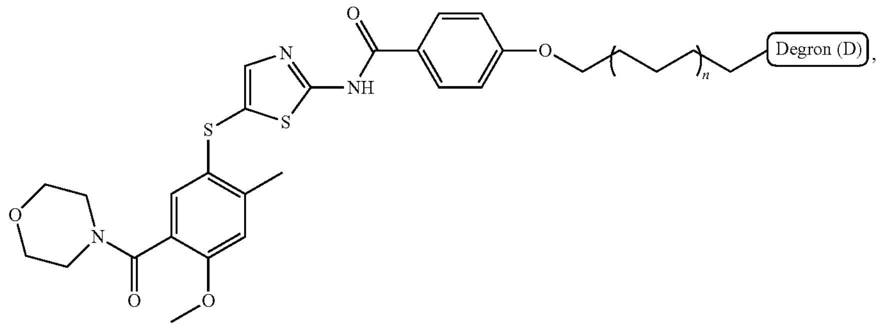
n = 0-6
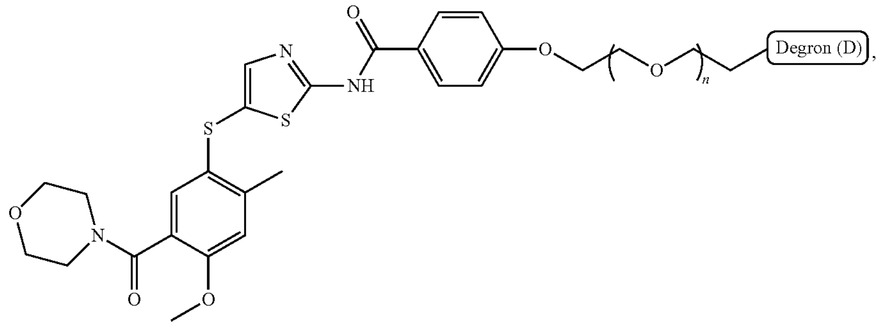
n = 1-6
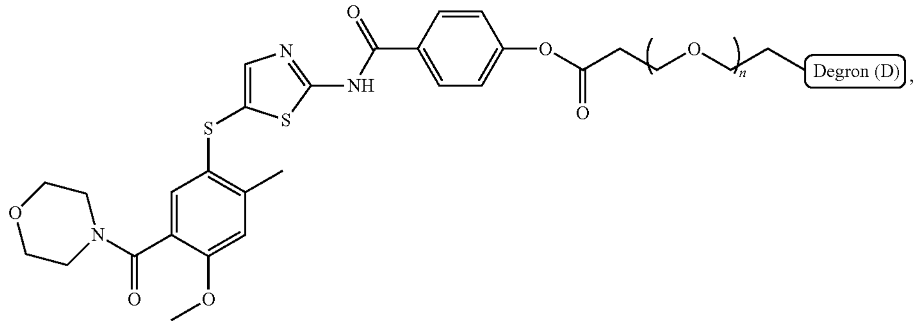
n = 1-6

-continued
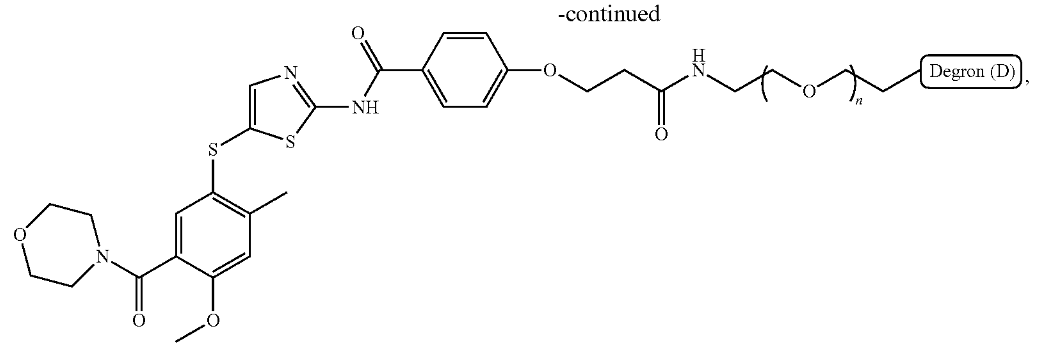
n = 1-6
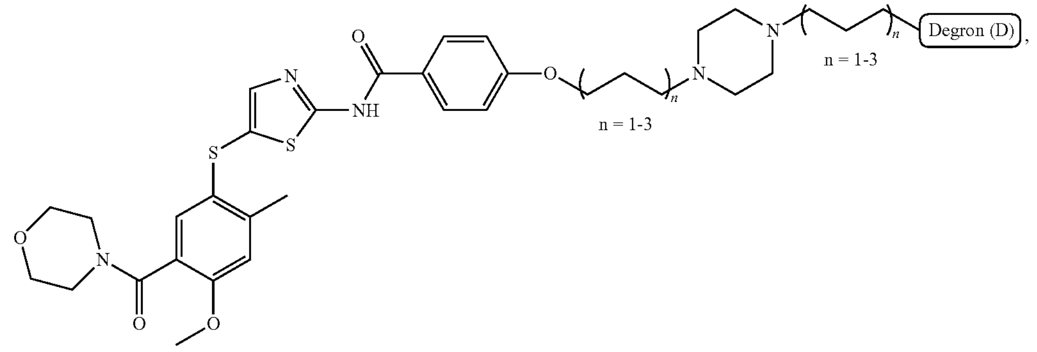
n = 1-3
n = 1-3
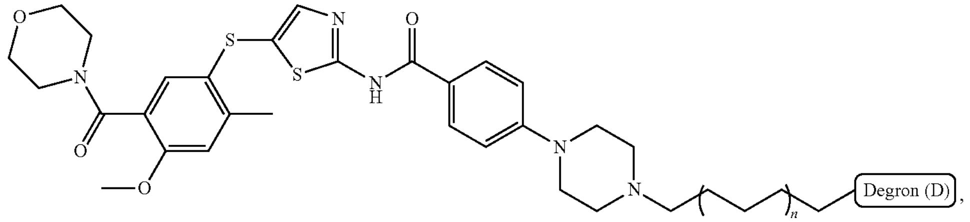
n = 0-6
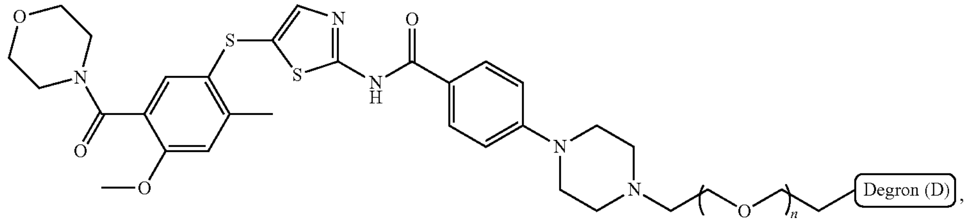
n = 1-6
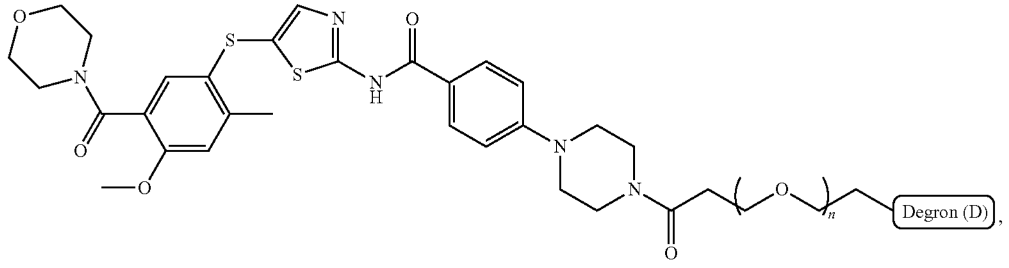
n = 1-6

-continued
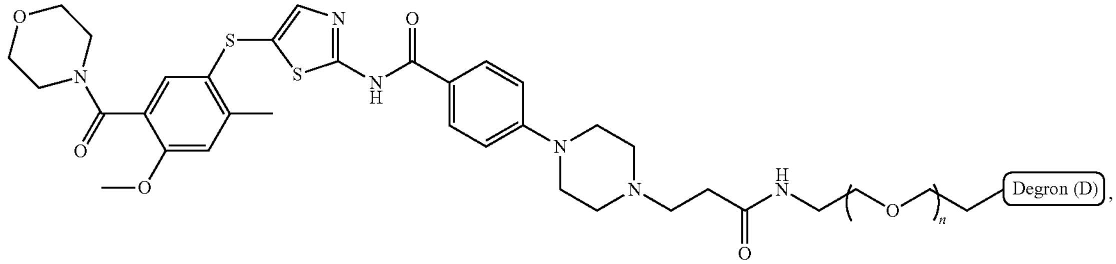,
n = 1-6
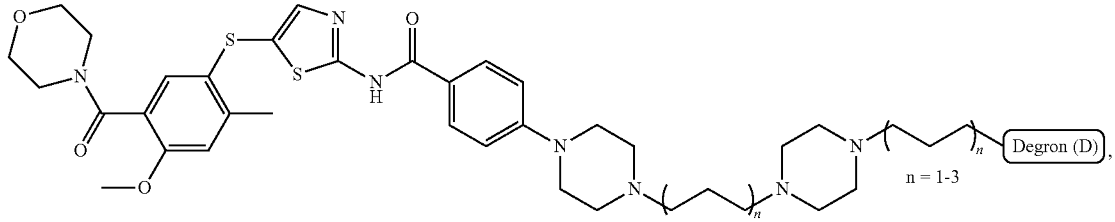,
n = 1-3
n = 1-3
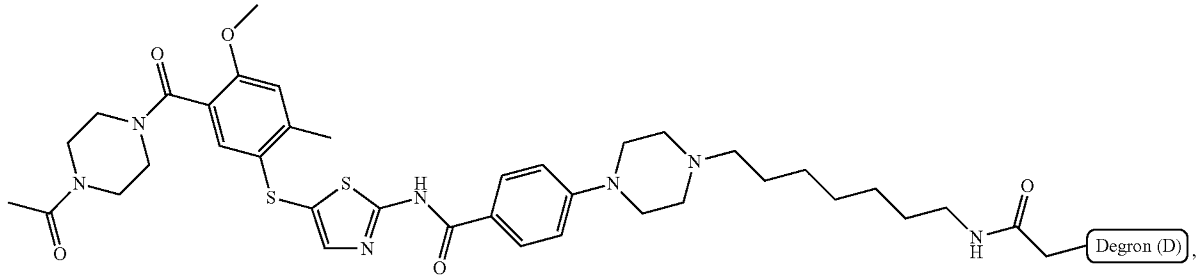,
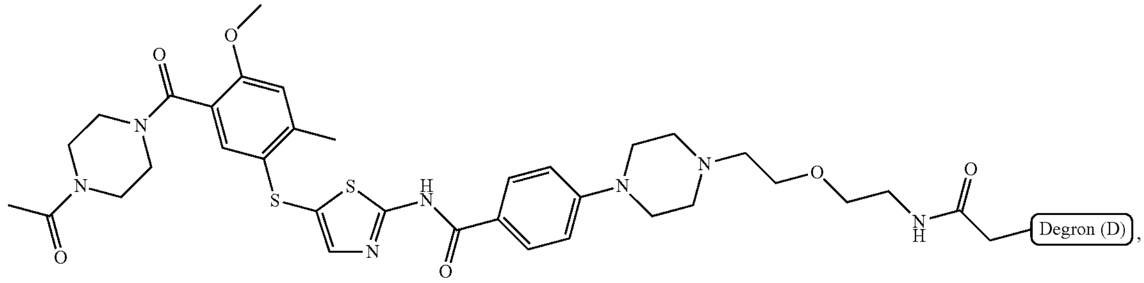,
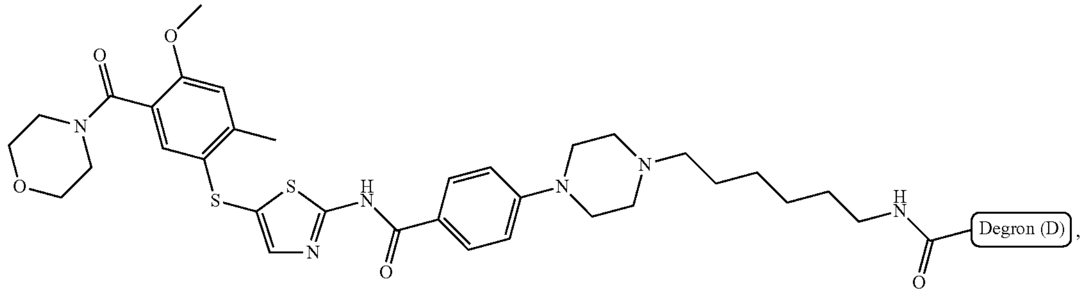, and
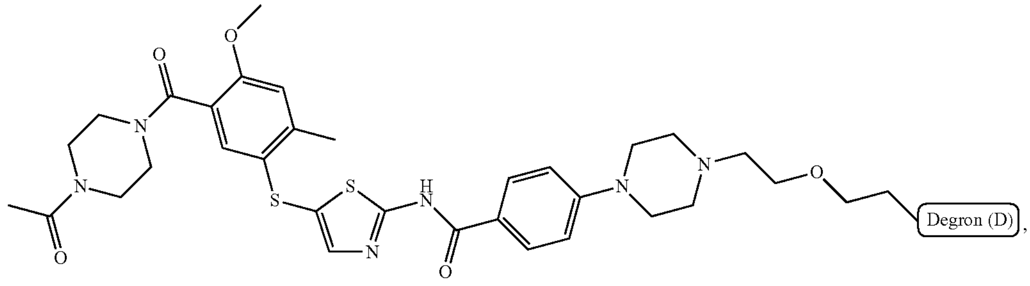 [SMILES: CCCOCCN1CCN(c2ccc(C(=O)Nc3ncc(Sc4cc(C(=O)N5CCN(C(C)=O)CC5)c(OC)cc4C)s3)cc2)CC1], or a pharmaceutically acceptable salt or stereoisomer thereof, wherein each "n" may be the same or different.
10. The compound of claim 1, wherein the degron has a structure represented by any one of formulas D1a-j:
(D1-a)
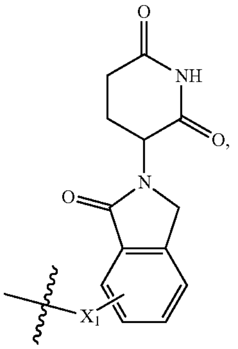
(D1-b)
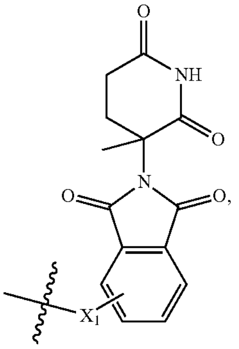
(D1-c)
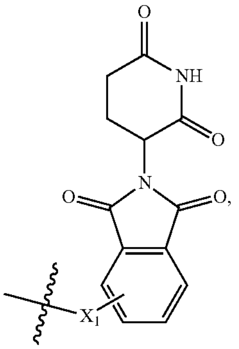
(D1-d)
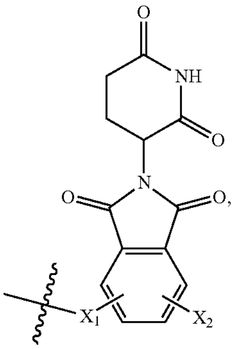
-continued
(D1-e)
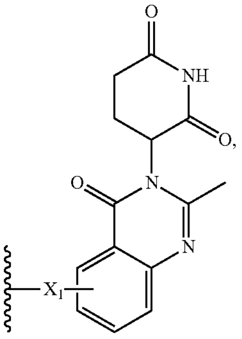
(D1-f)
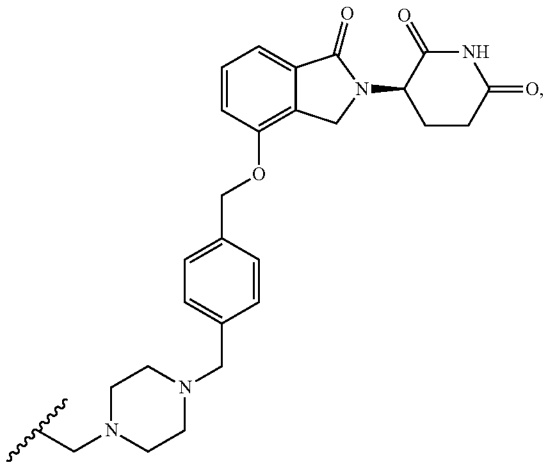
(D1-g)
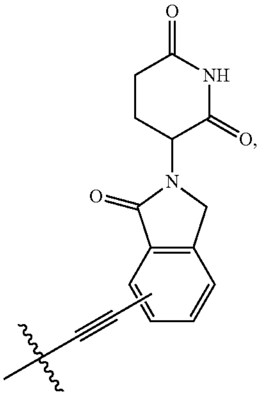
(D1-h)
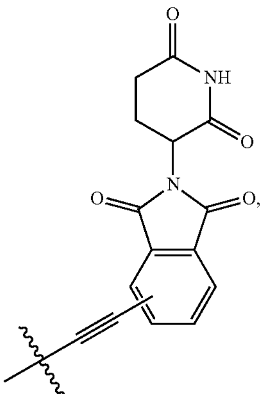

-continued
(D1-i)
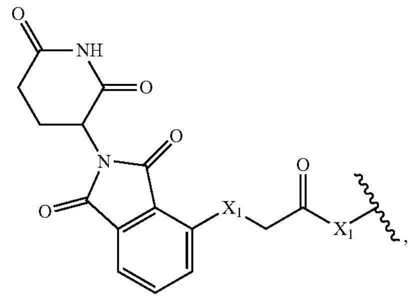
(D1-j)
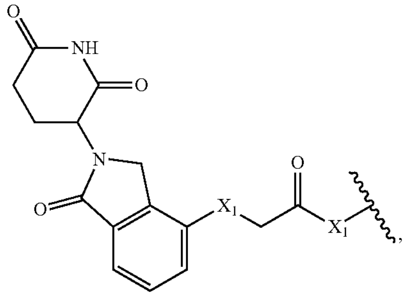
, and
-continued
(D1-k)
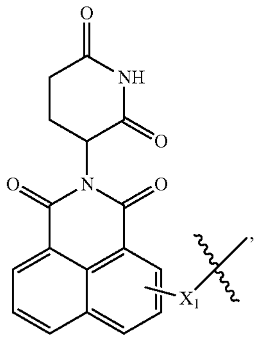
wherein $X_1$ is independently absent, $CH_2$, NH, or O; and $X_2$ is alkyl, halo, CN, $CF_3$, $OCHF_2$ or $OCF_3$.
11. The compound of claim 10, which is represented by any one of the following structures:
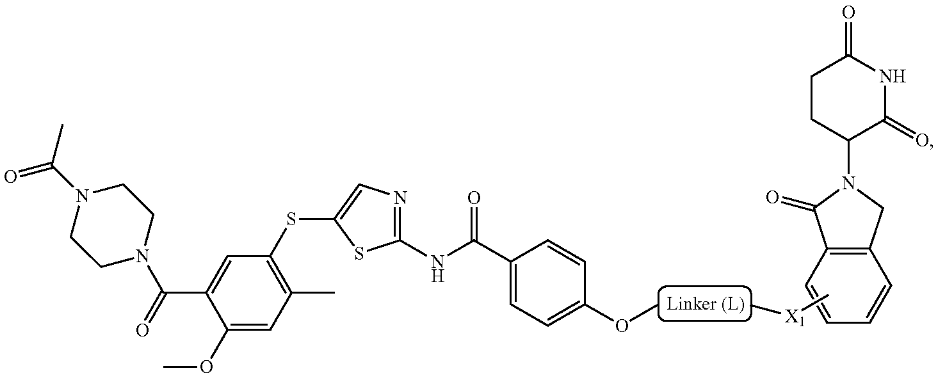
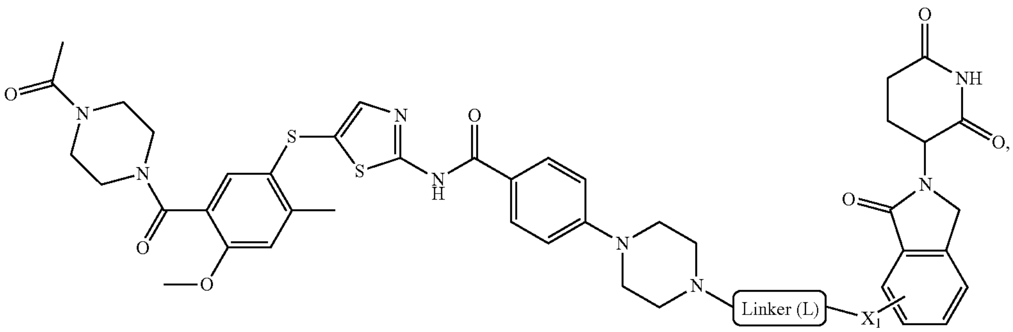

-continued
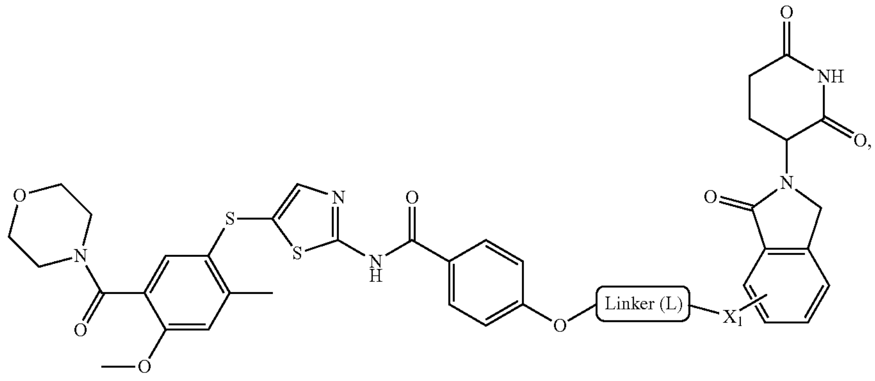
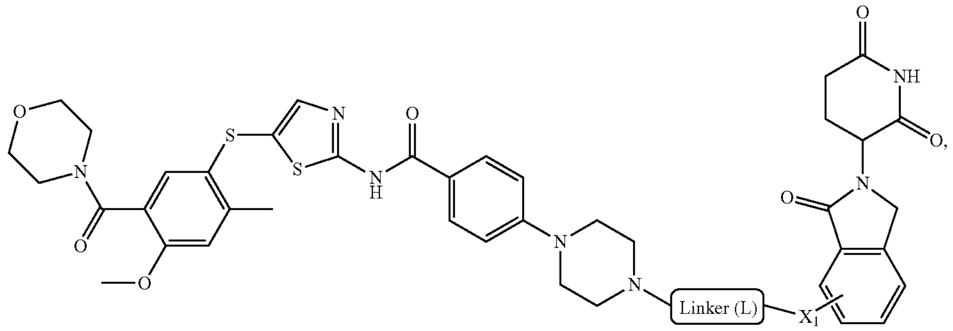
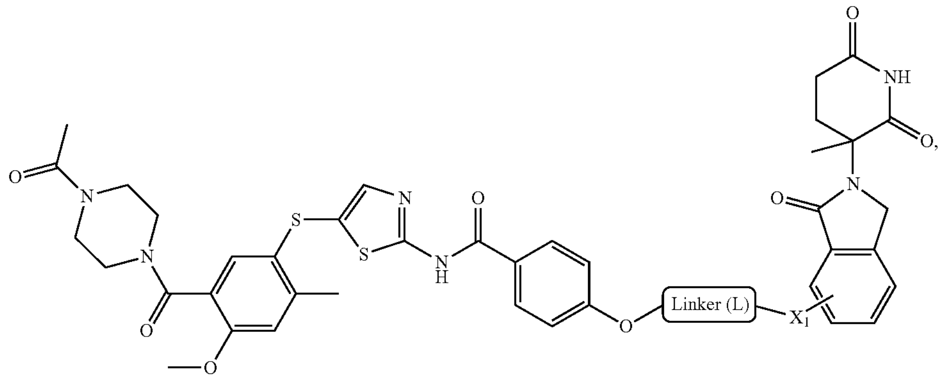
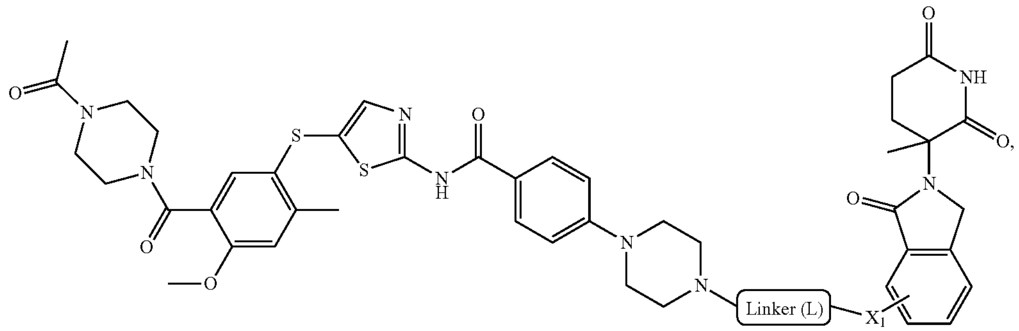

-continued
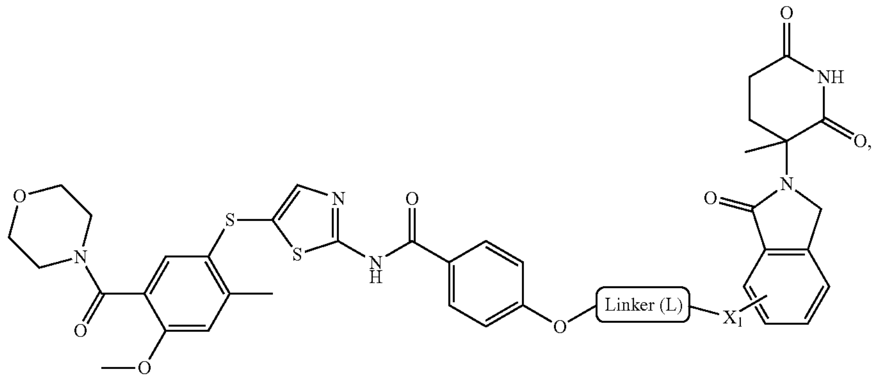
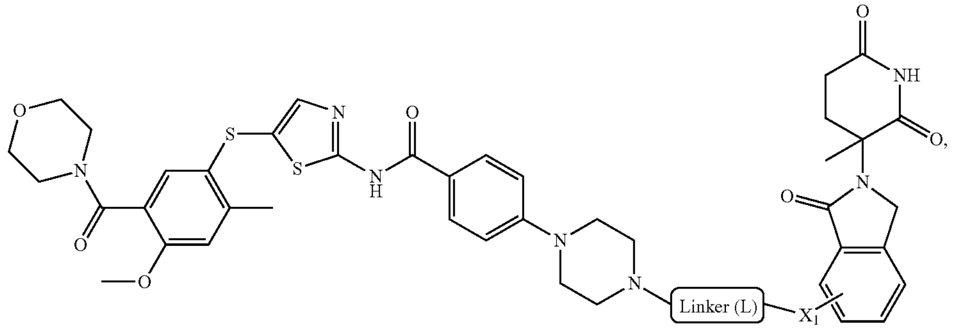
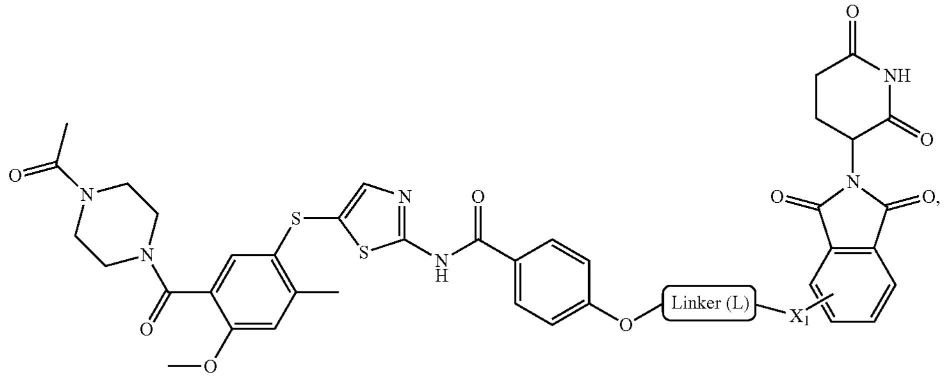
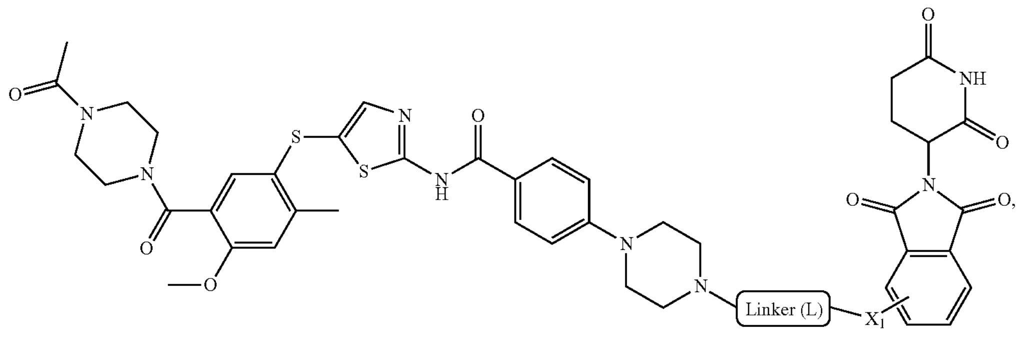

-continued
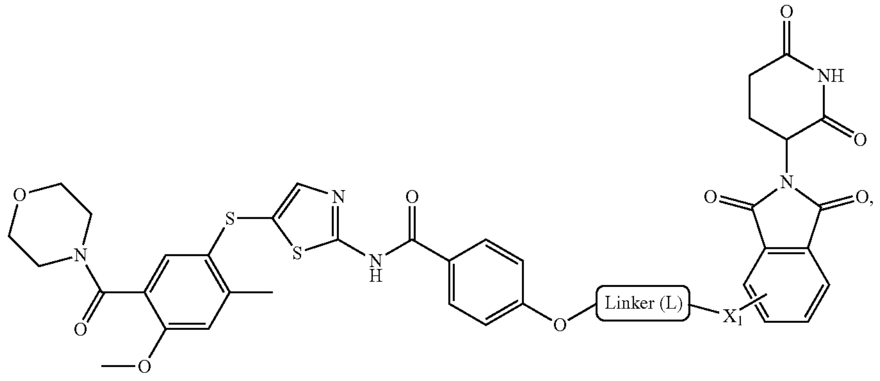
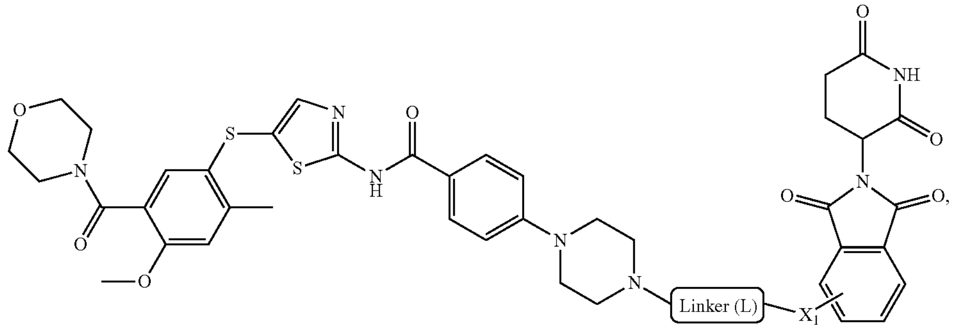
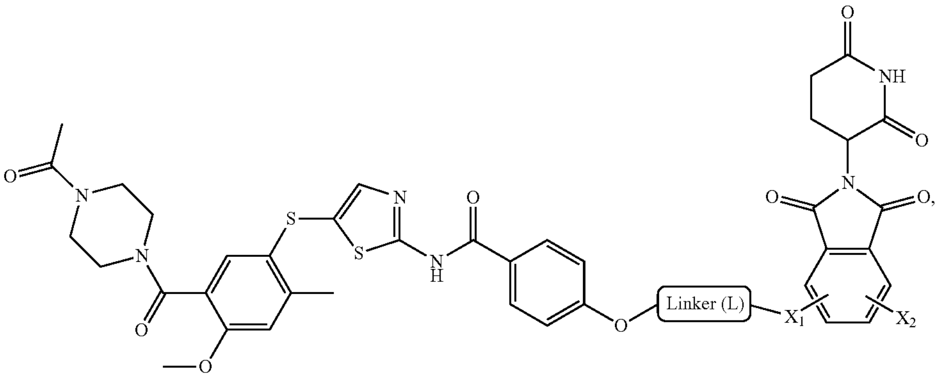
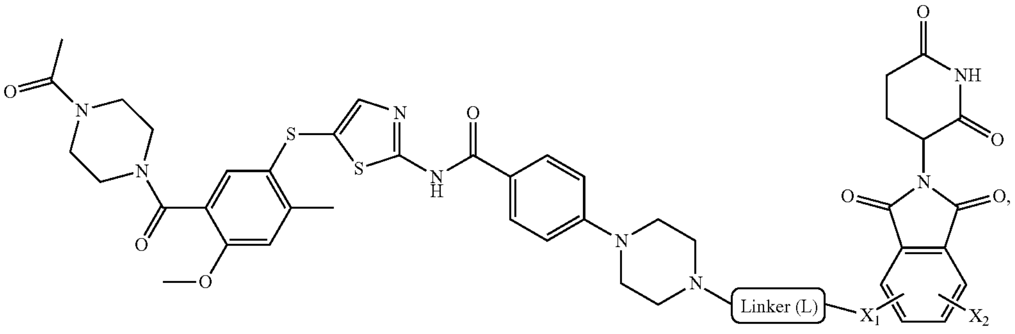

-continued
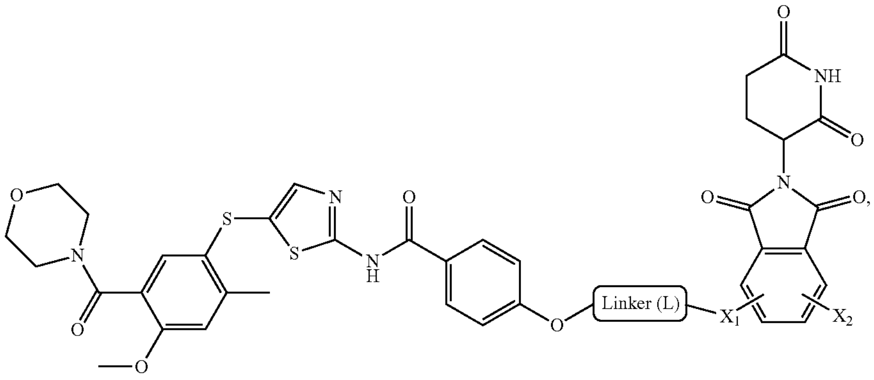
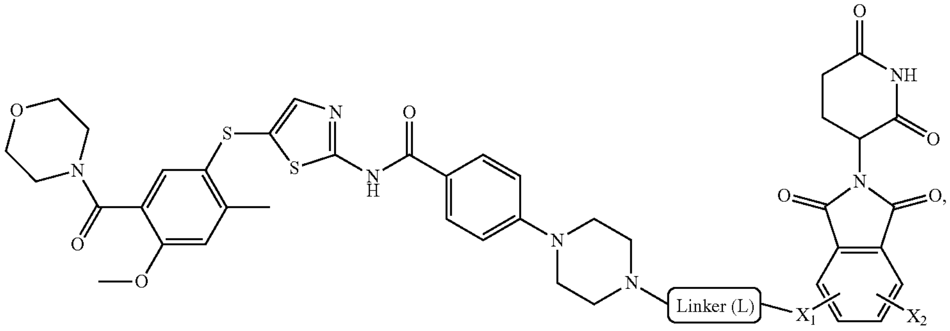
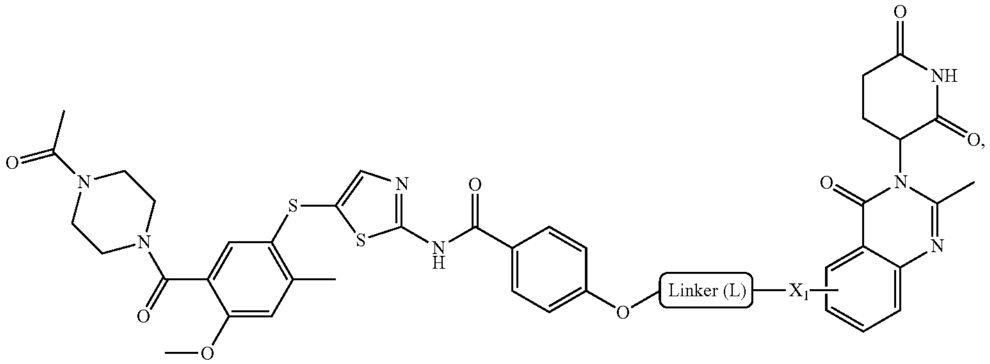
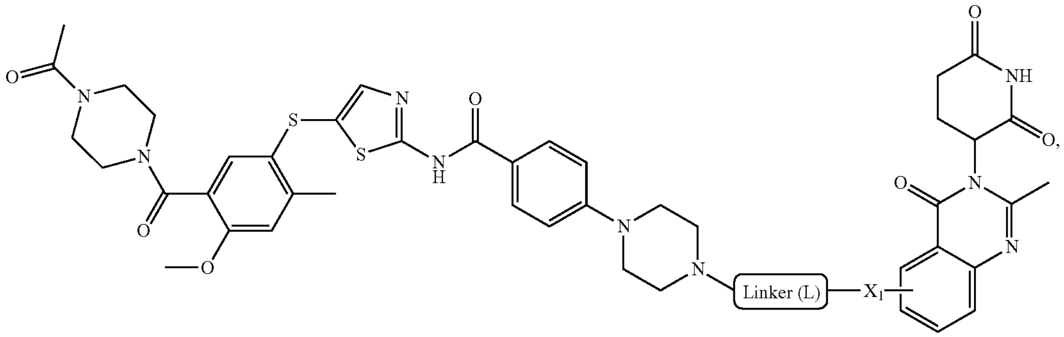

-continued
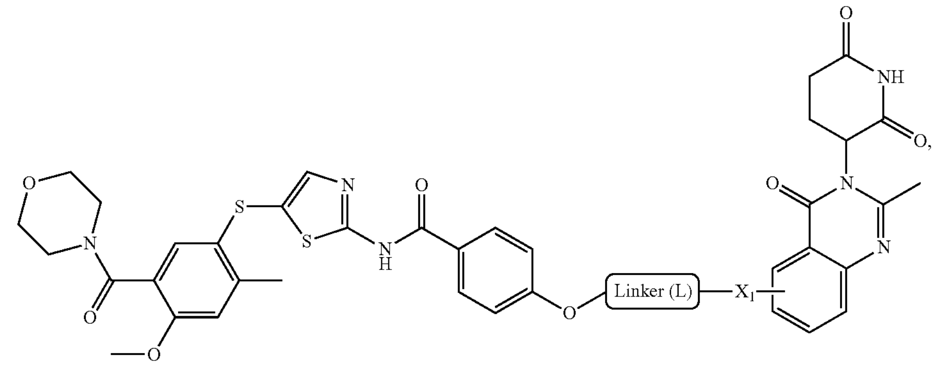
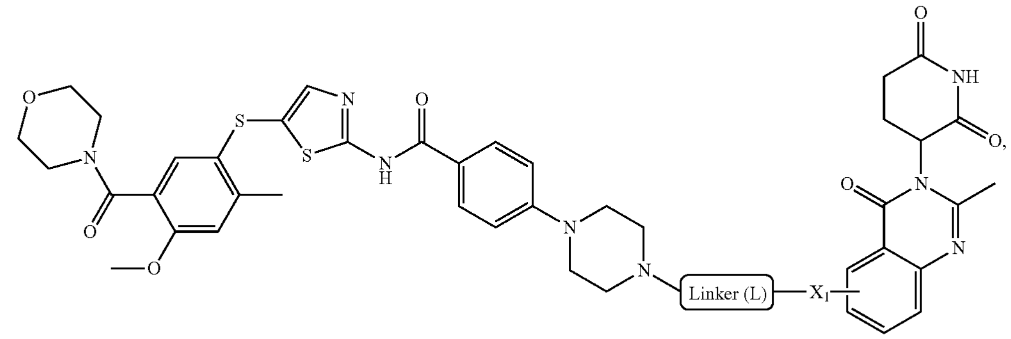
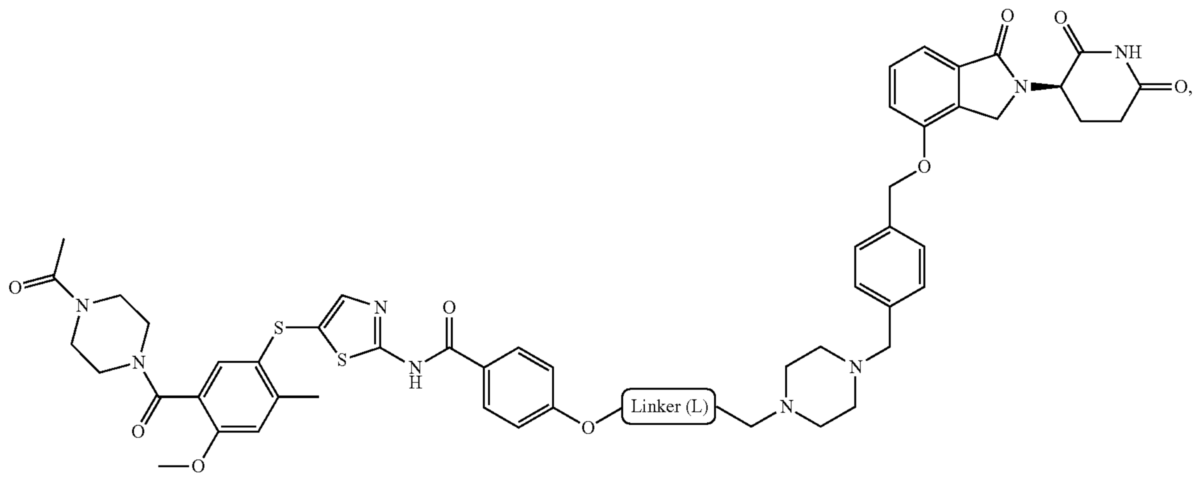
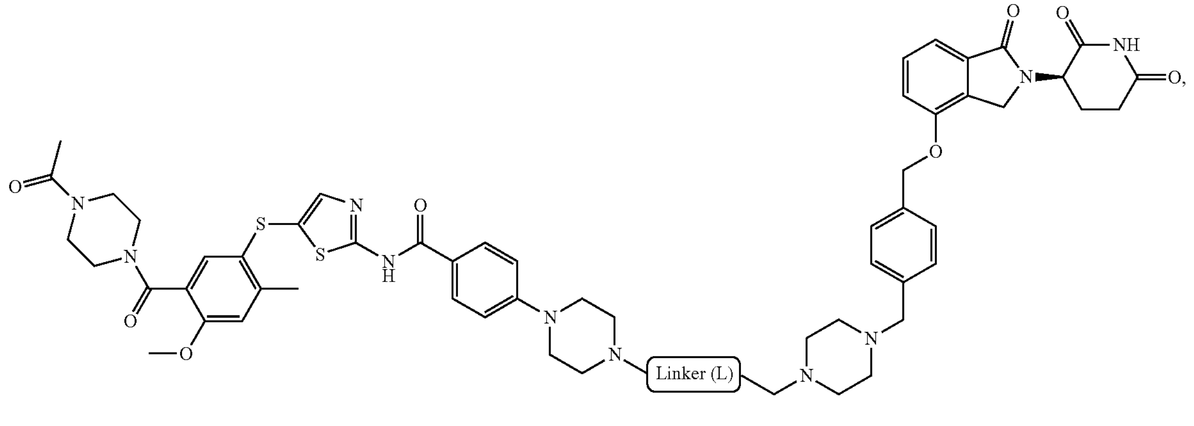

-continued
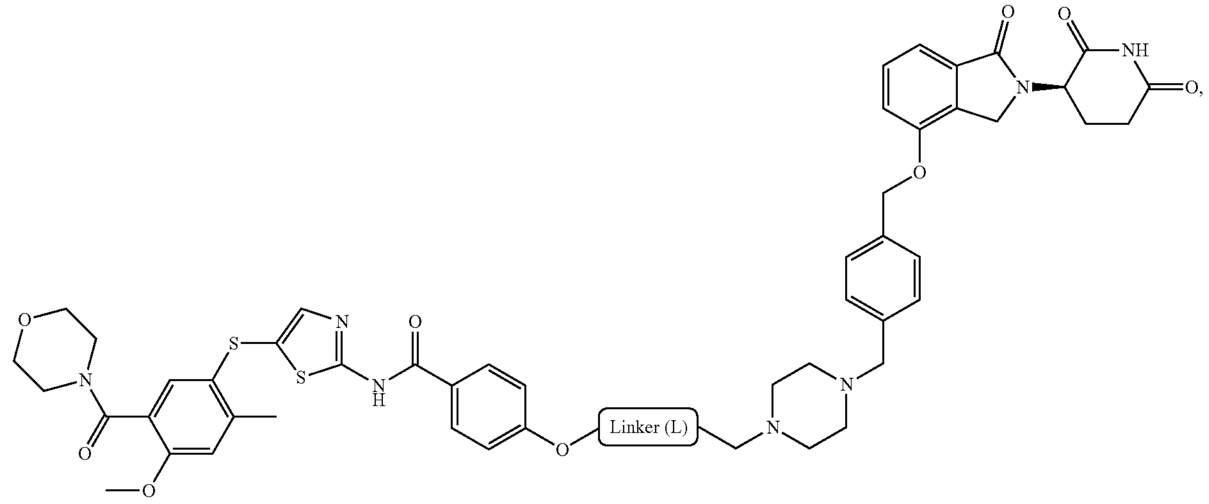
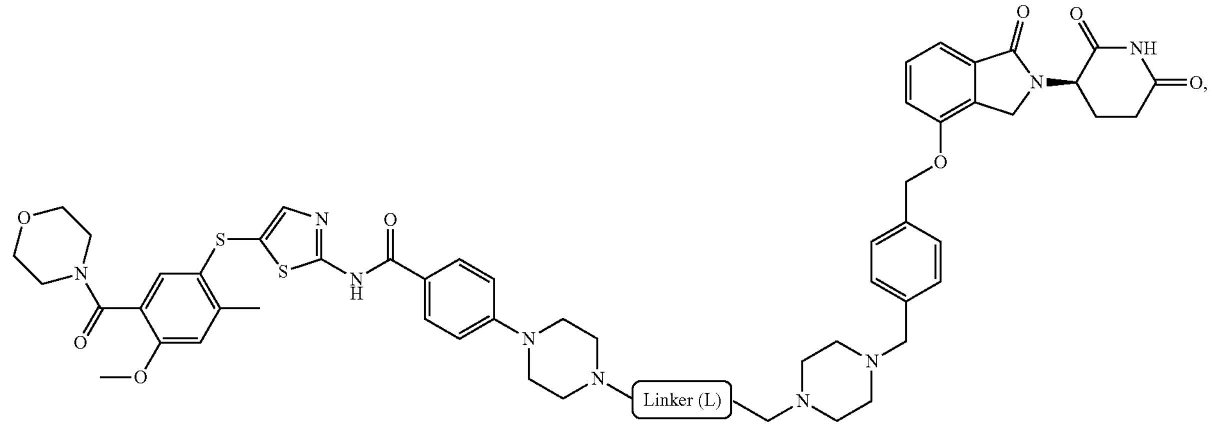
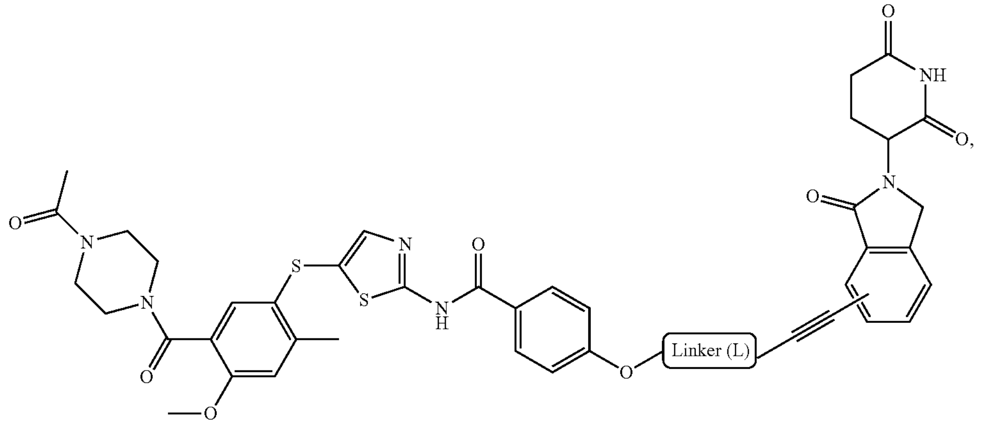
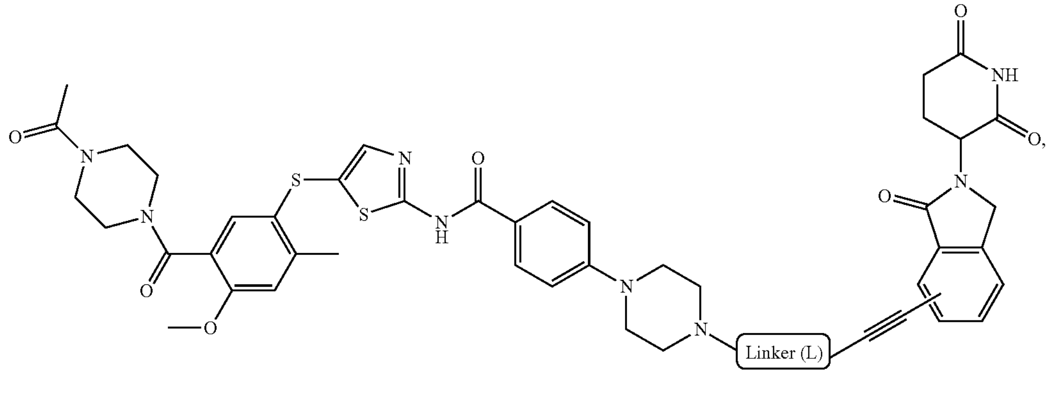

-continued
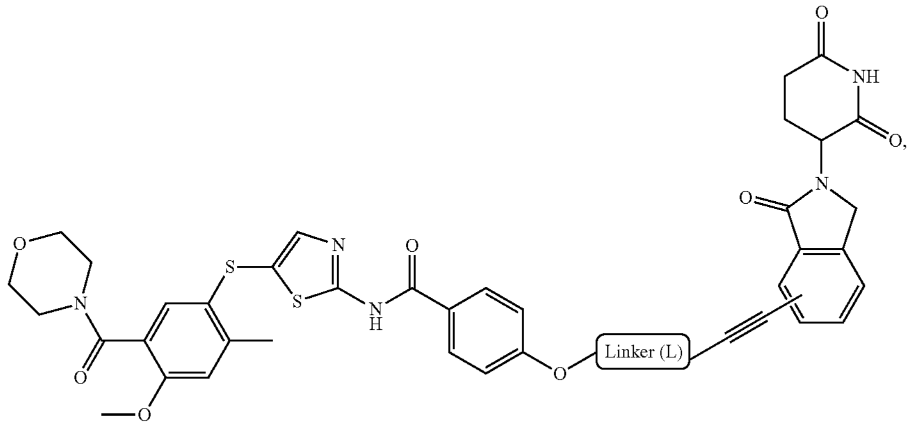
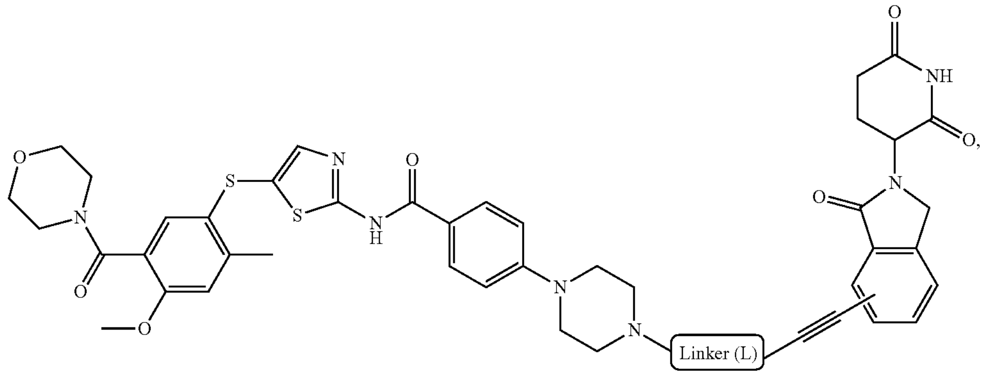
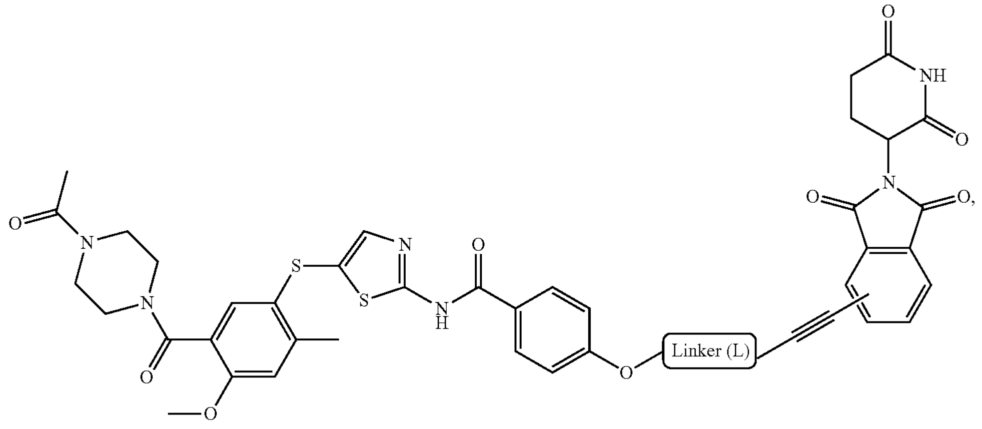
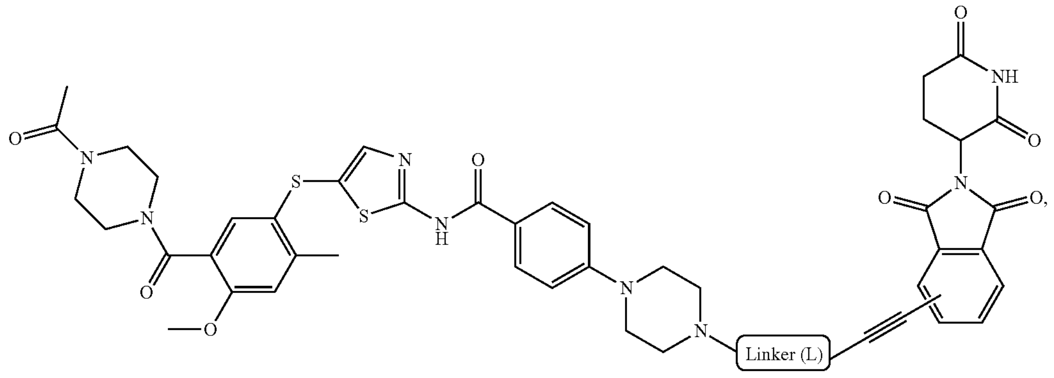

-continued
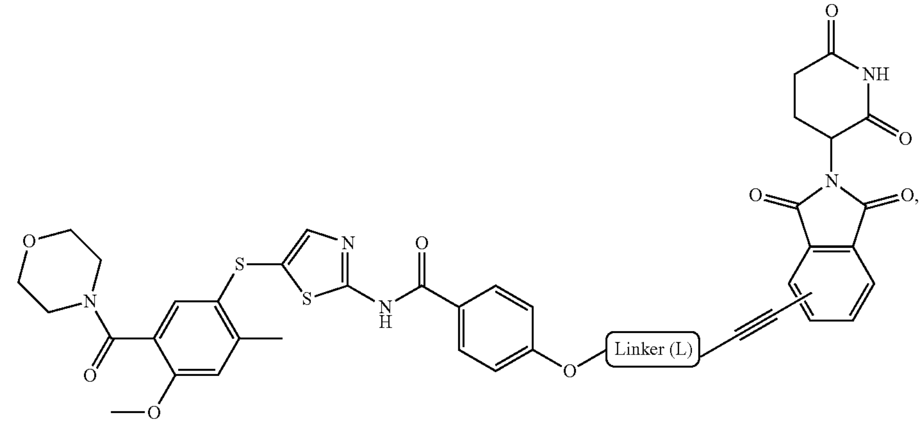
,
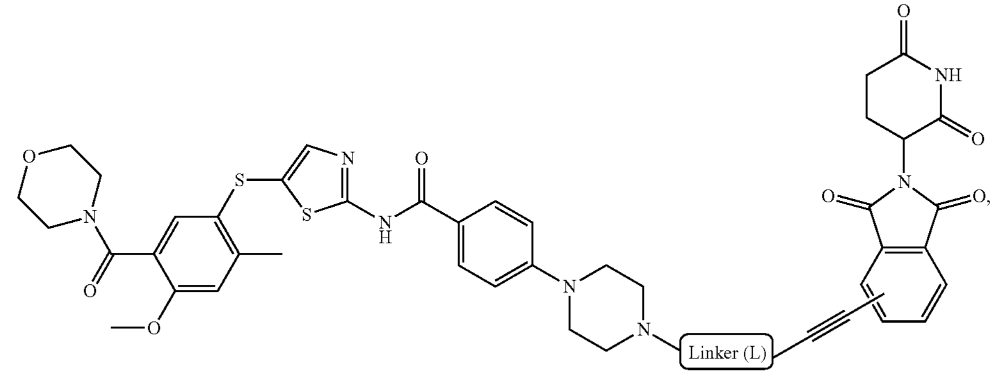
,
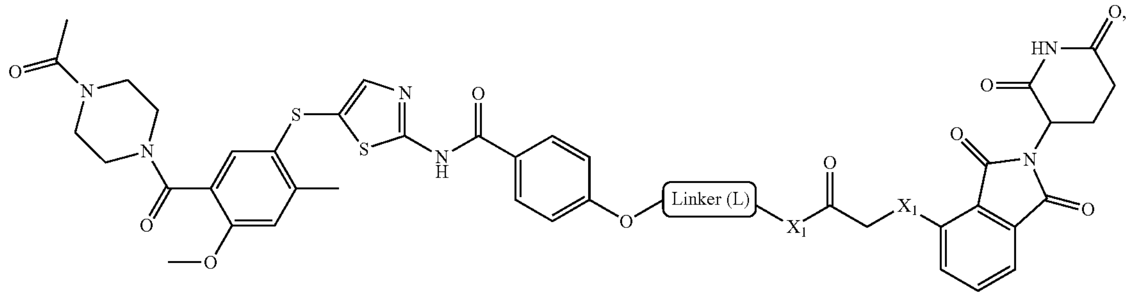
,
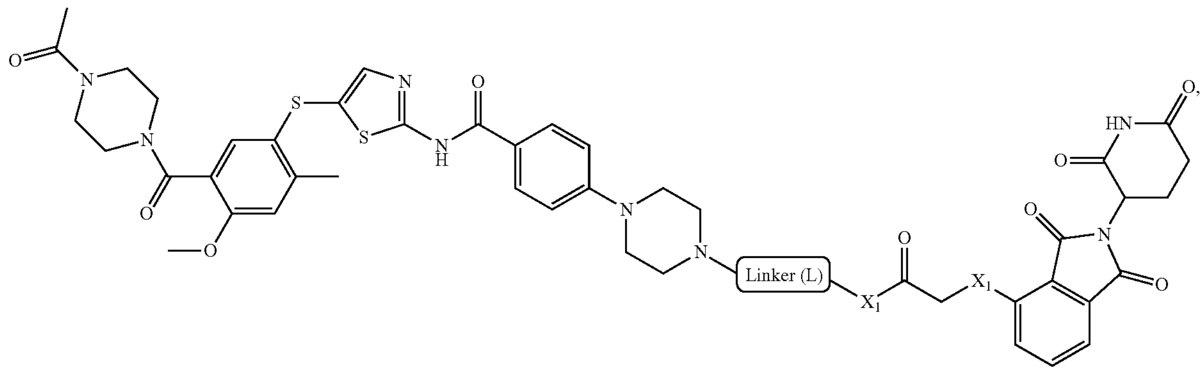
,

-continued
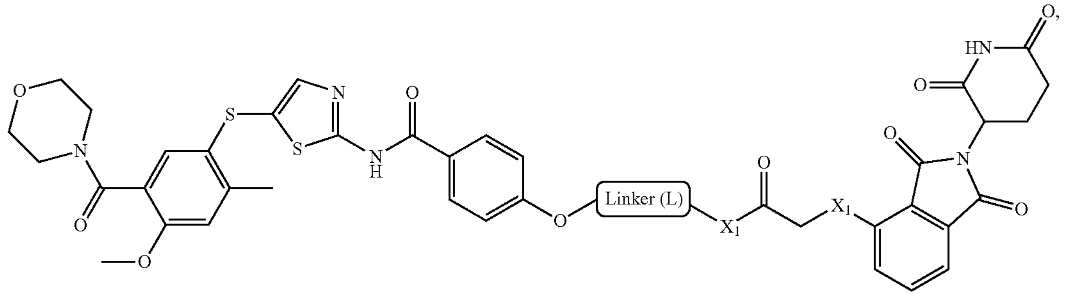
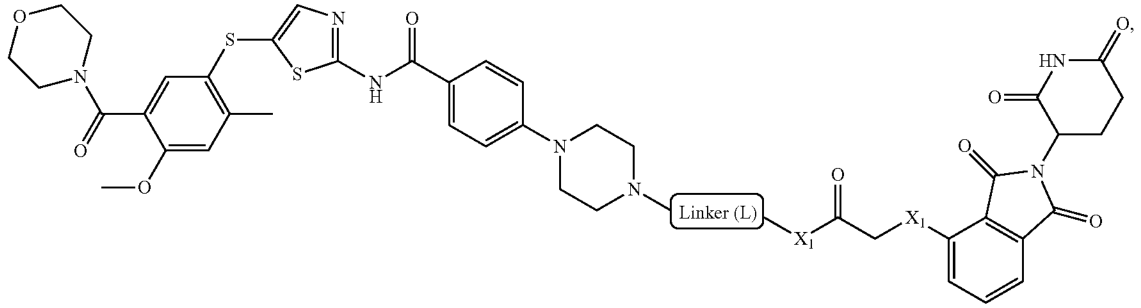
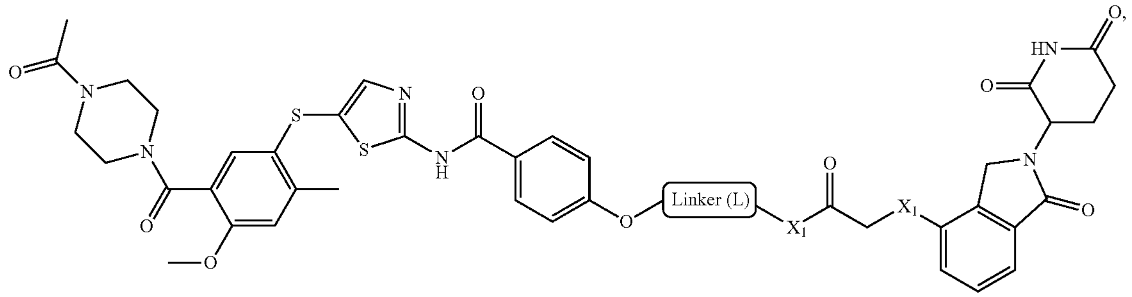
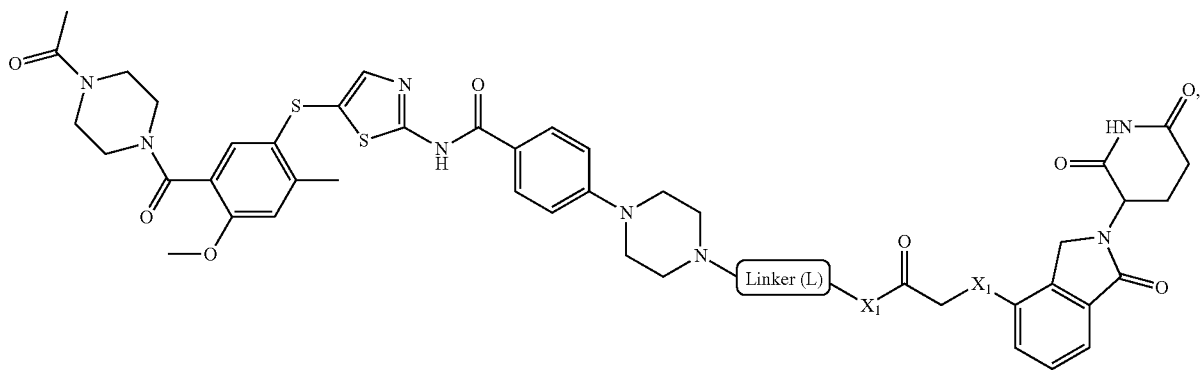
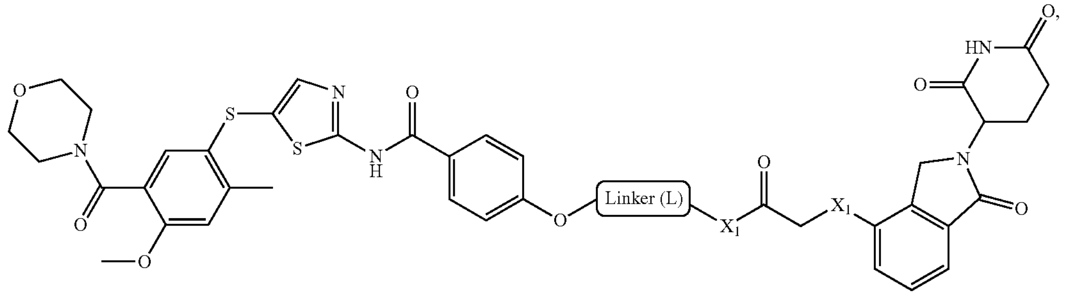

-continued
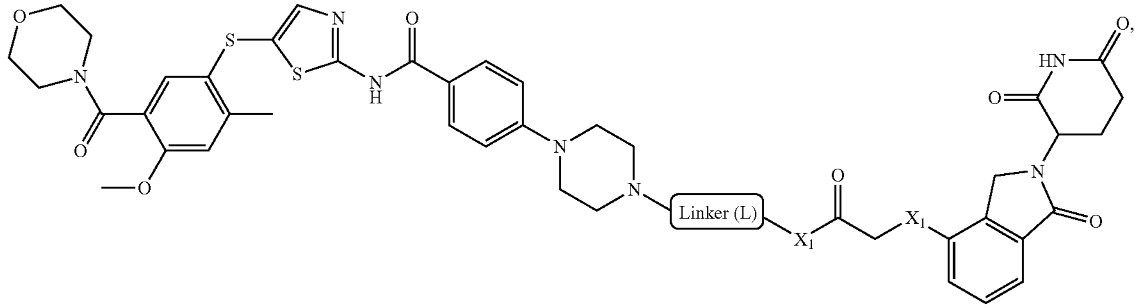
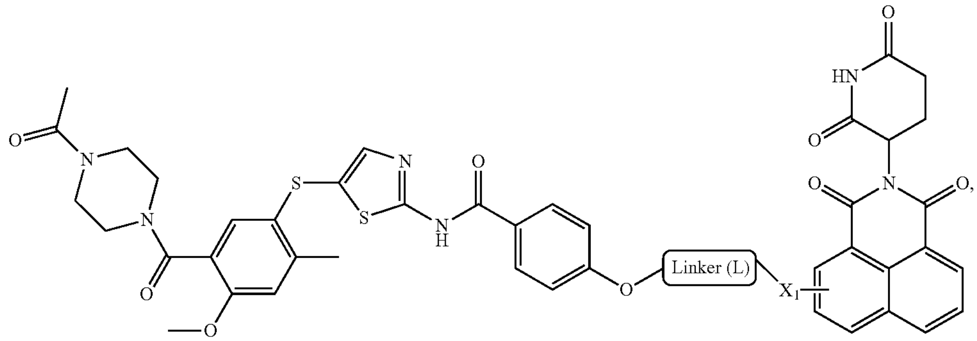
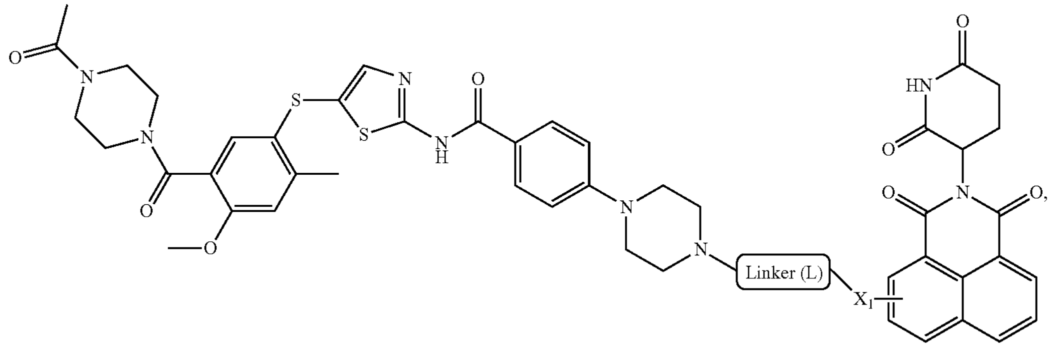
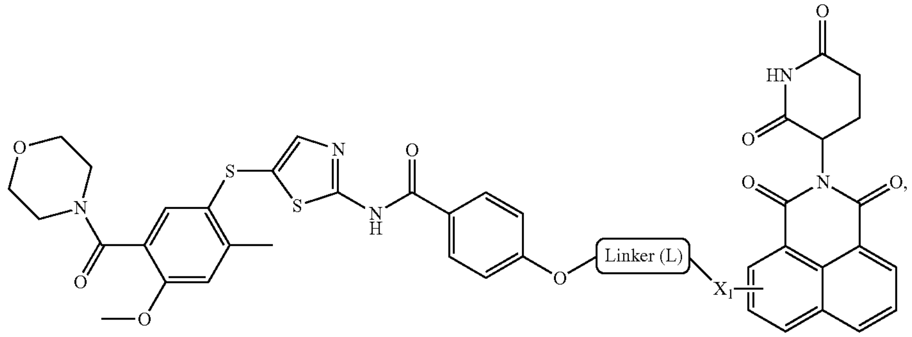
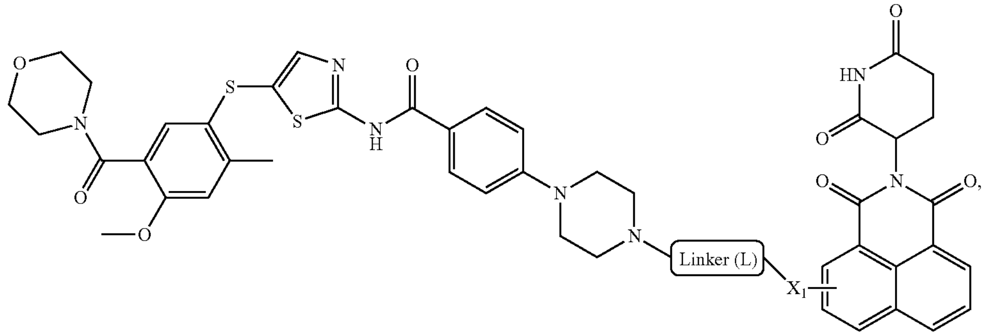
and

-continued
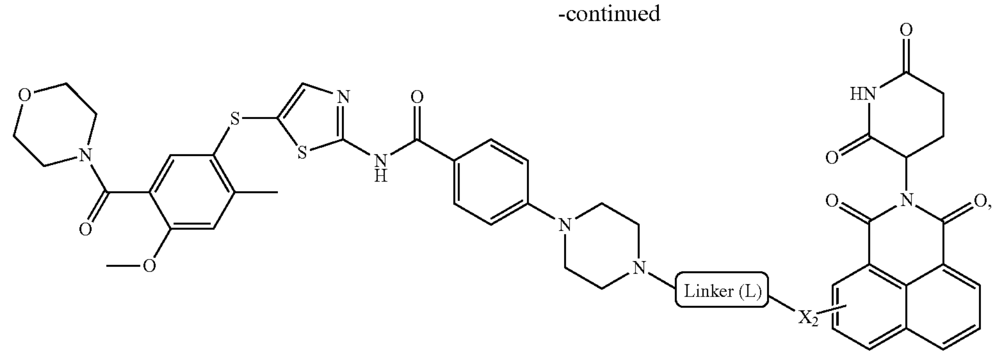
or a pharmaceutically acceptable salt or stereoisomer thereof.
12. The compound of claim 1, wherein the degron has a structure represented by any one of formulas D2-a-f:
(D2-a)
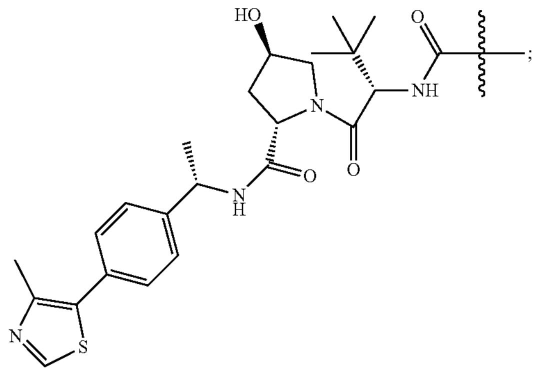
(D2-b)
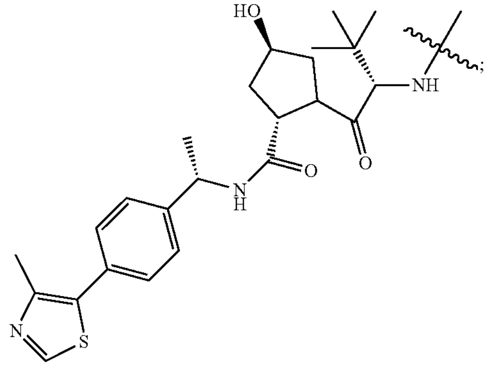
-continued
(D2-c)
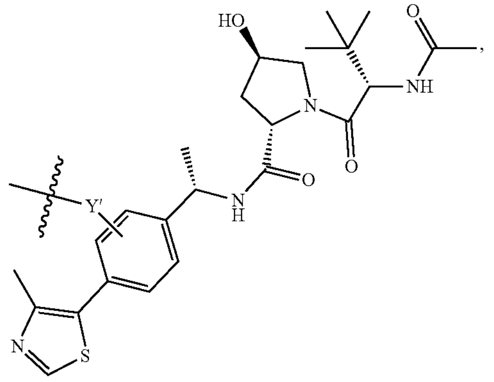
wherein Y' is a bond, NH, O or $CH_2$;
(D2-d)
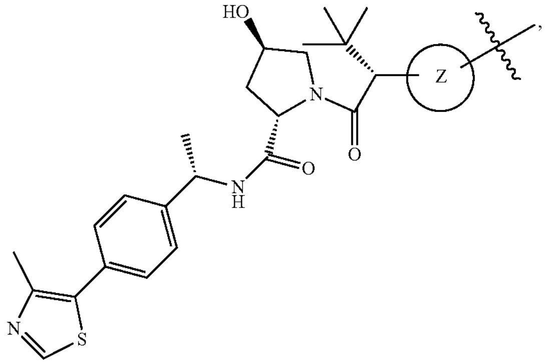
wherein Z is a $C_5$-$C_6$ carbocyclic or a 5-6 membered heterocyclic group;

-continued
(D2-e)
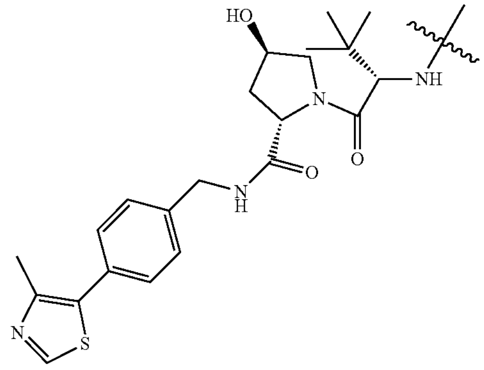
; and
(D2-f)
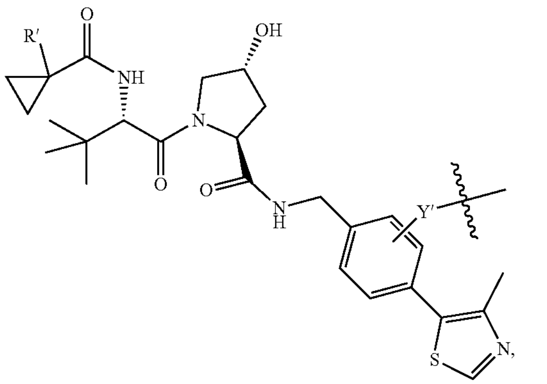
wherein R' is H, F or CN, and Y' is a bond, NH, O or $CH_2$, or a stereoisomer thereof.
13. The compound of claim 12, which is represented by any one of the following structures:
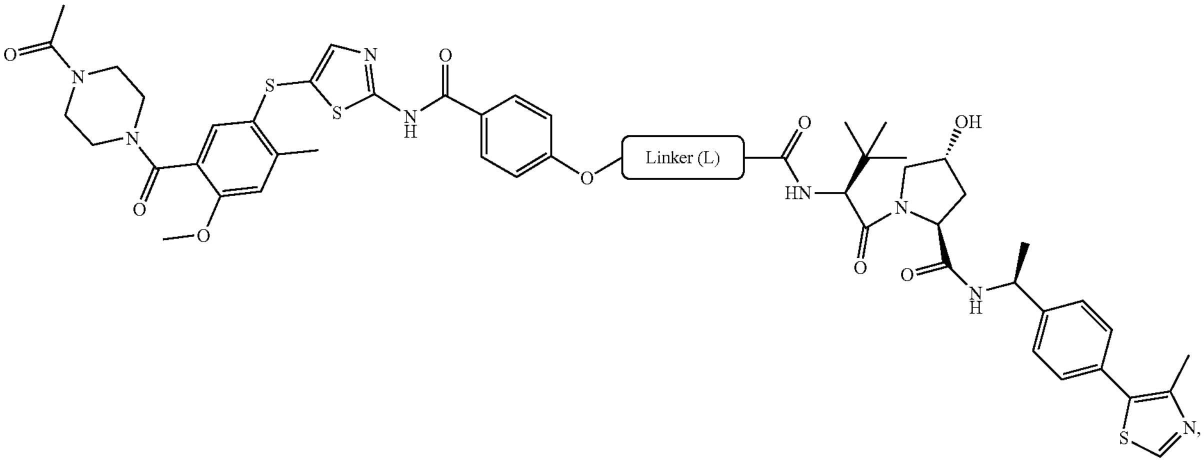
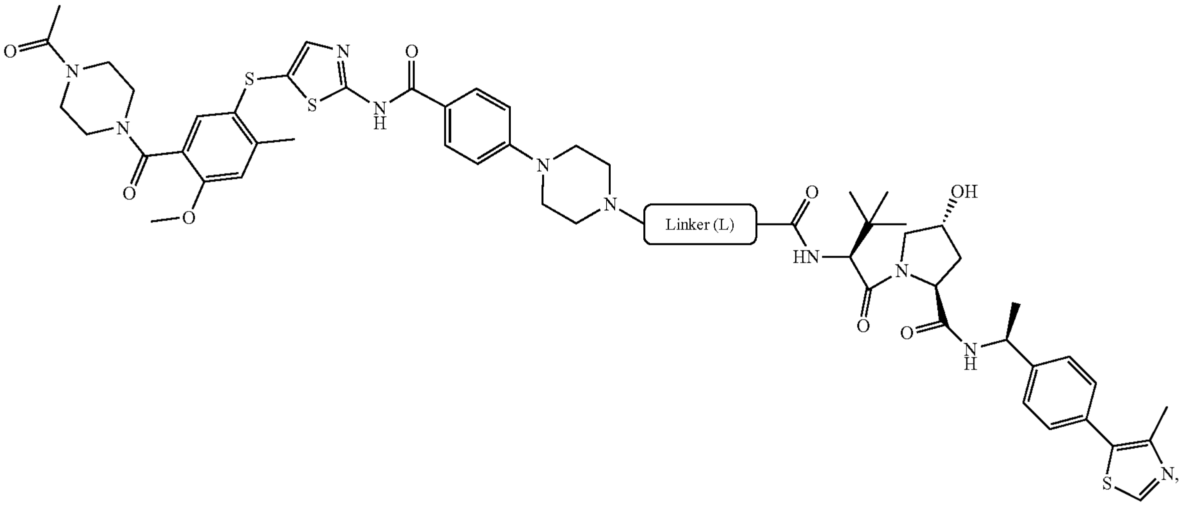

-continued
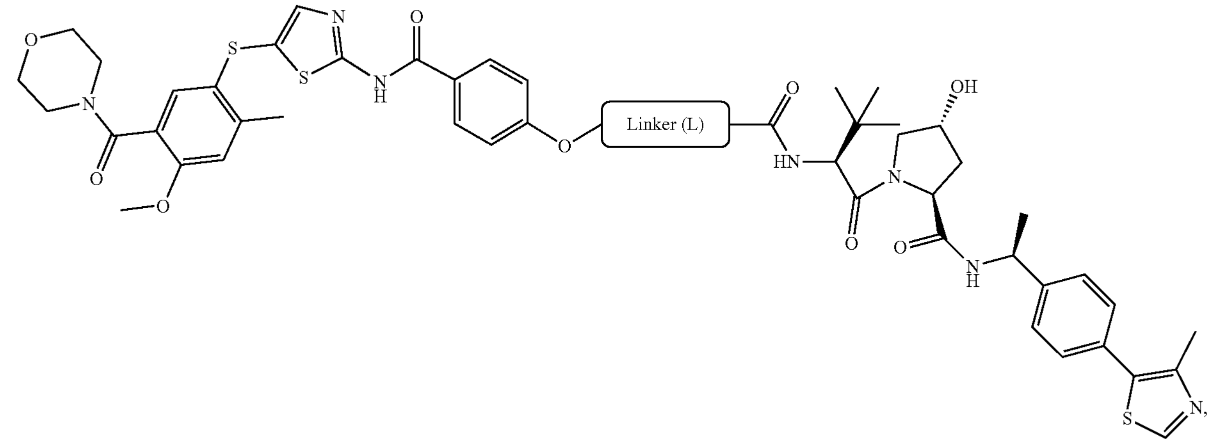
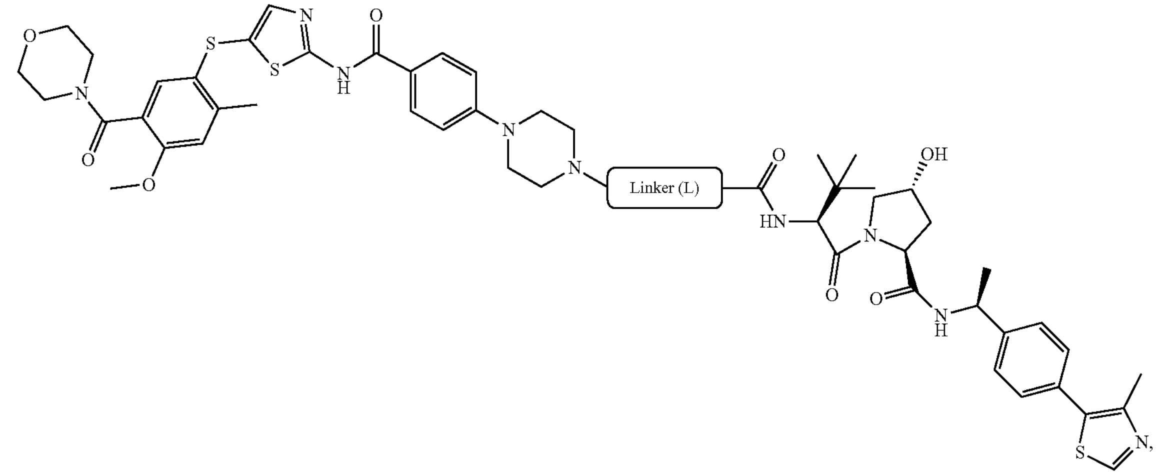
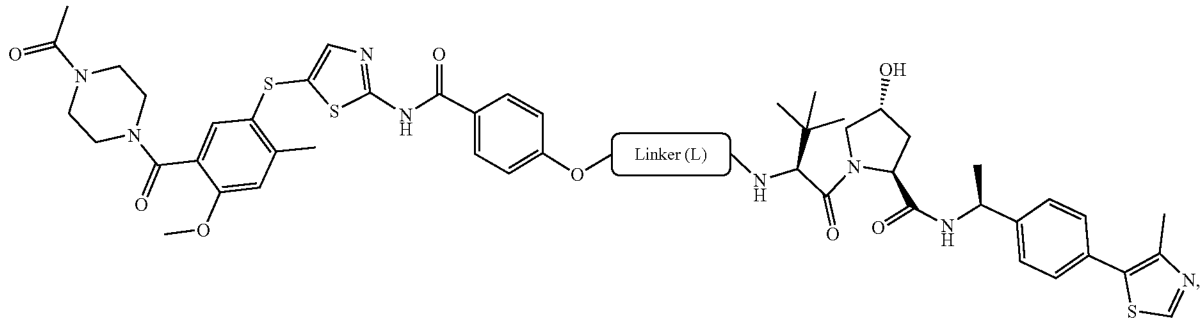
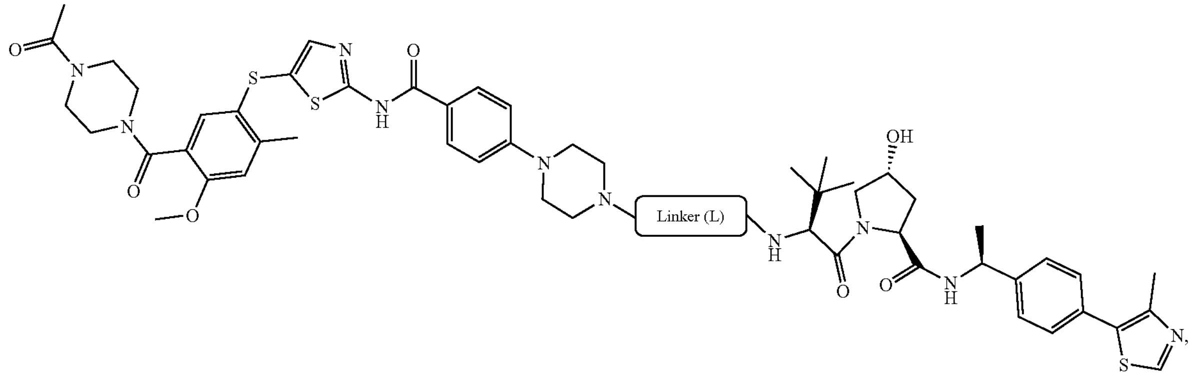

-continued
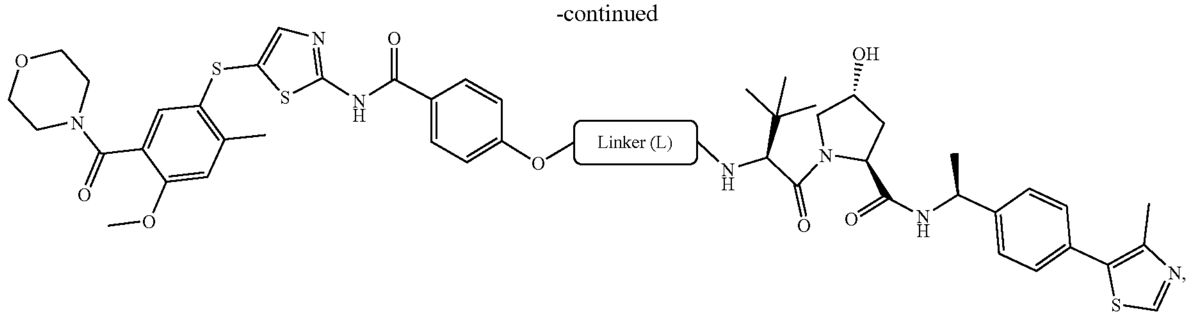
,
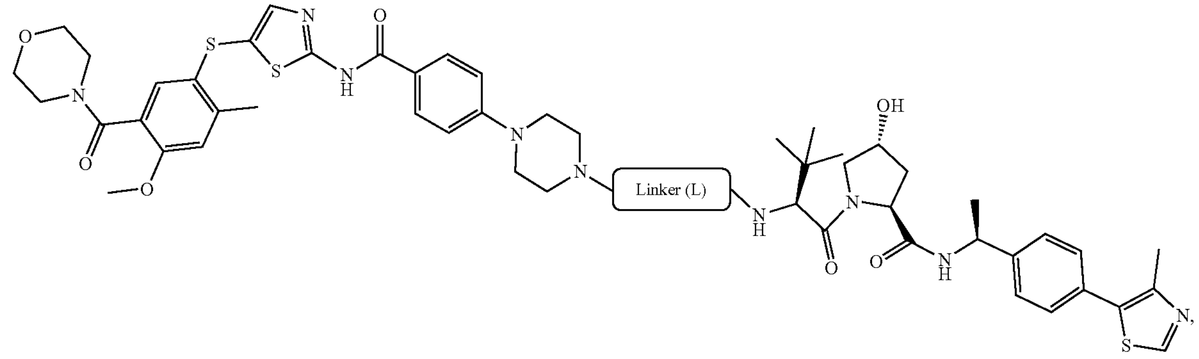
,
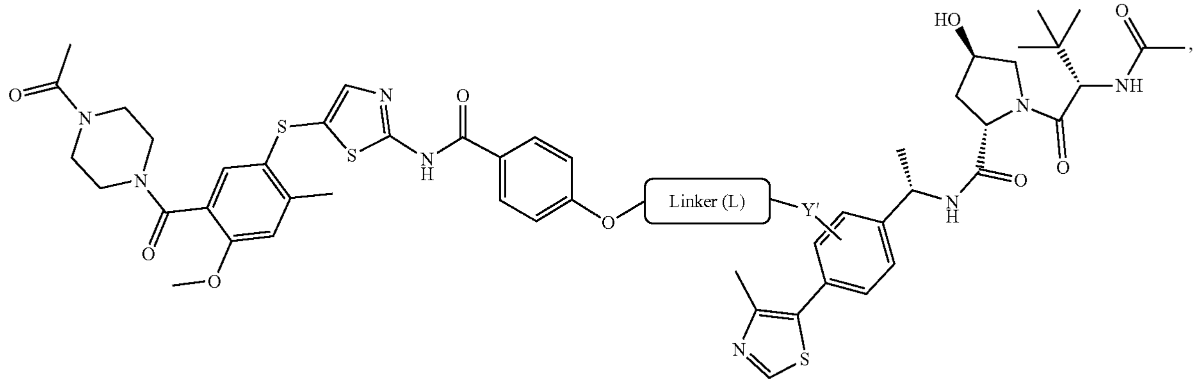
,
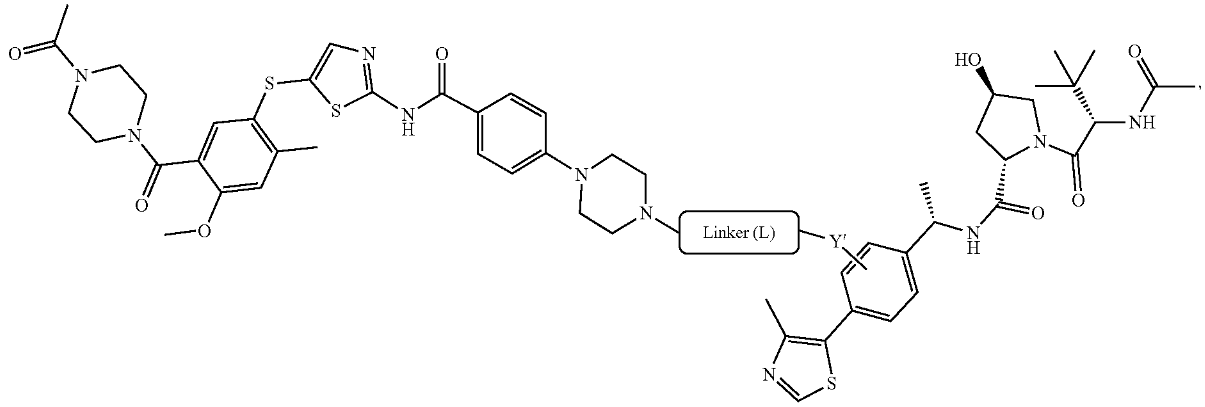
,

-continued
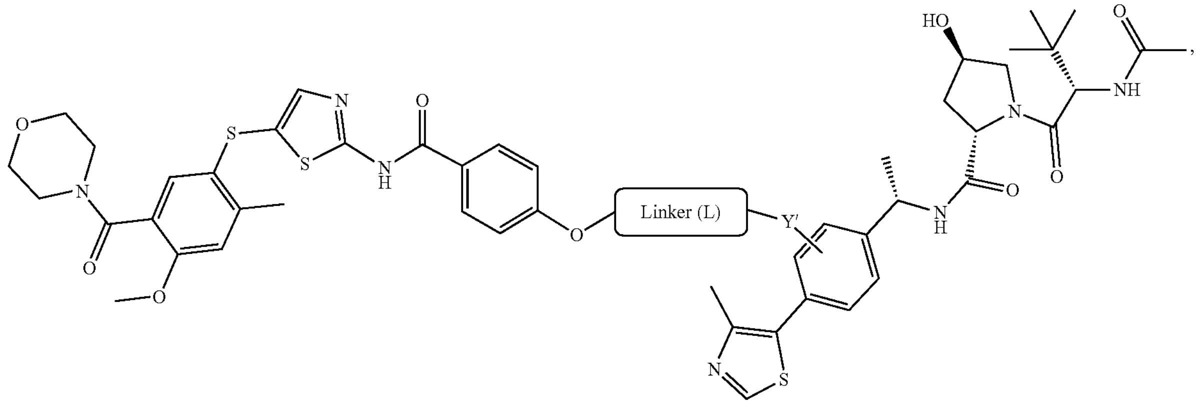
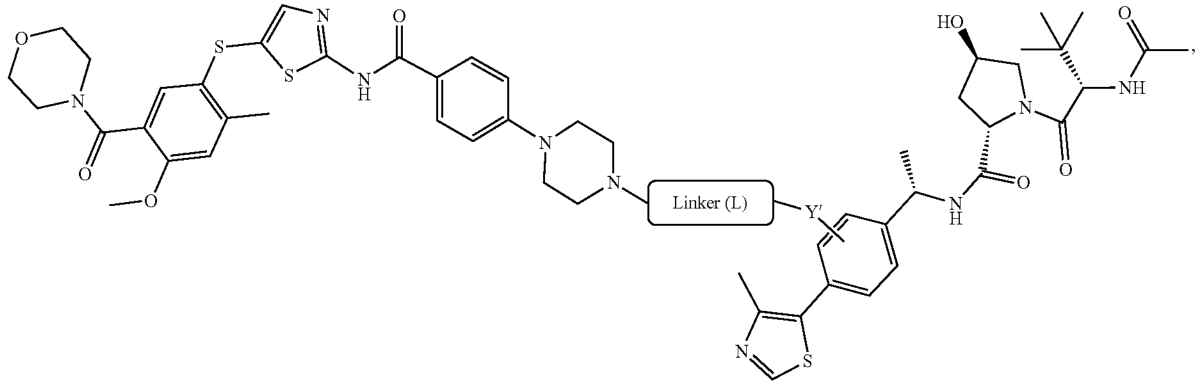
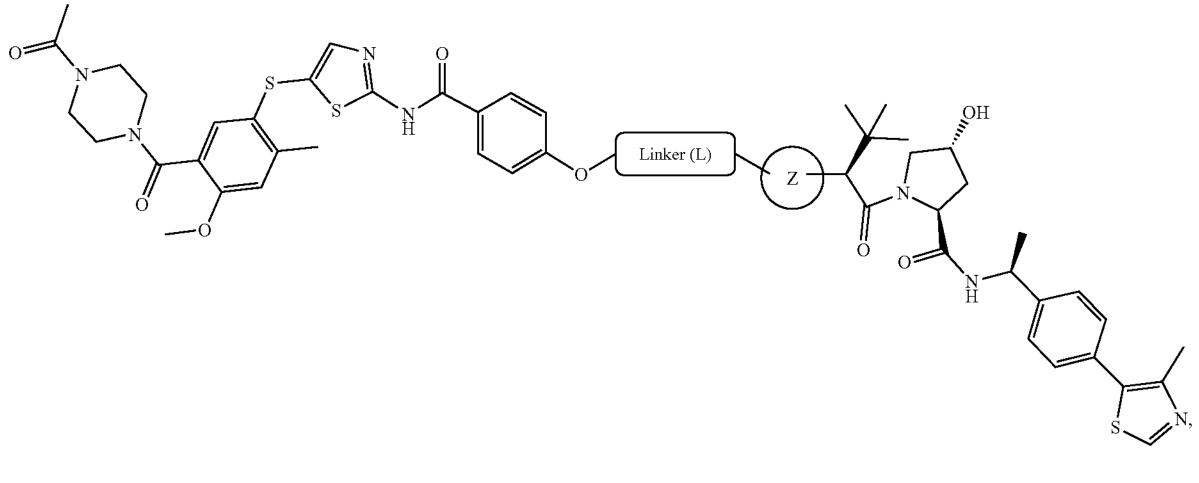

-continued
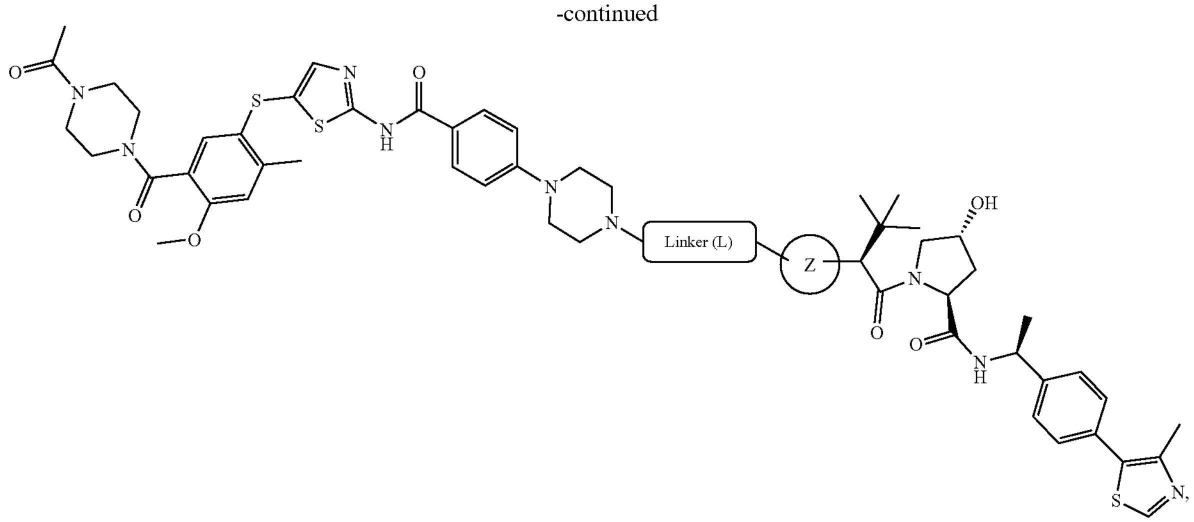
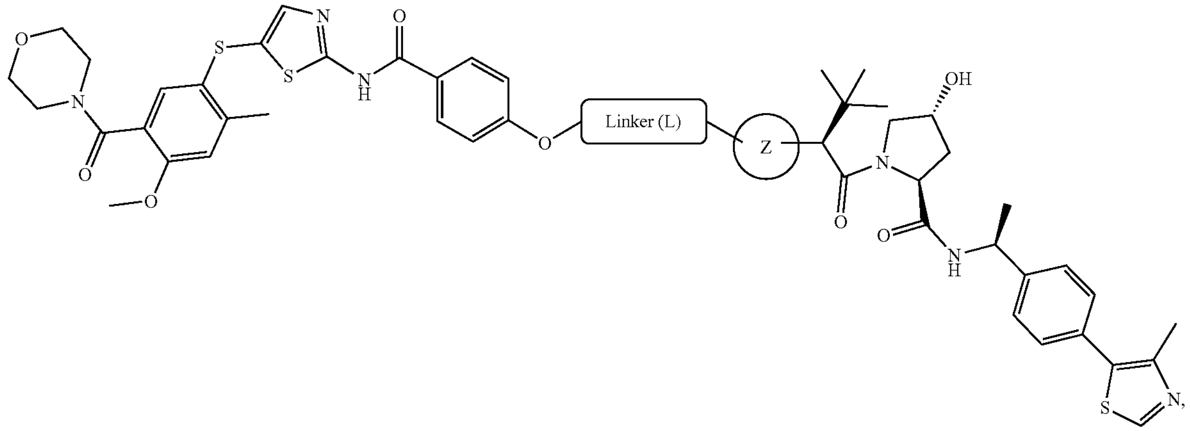
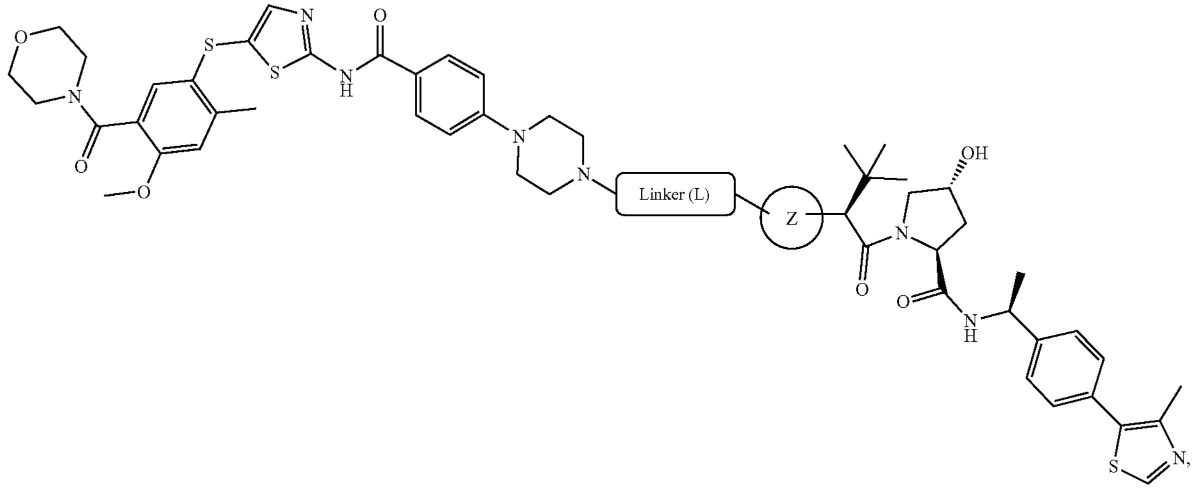
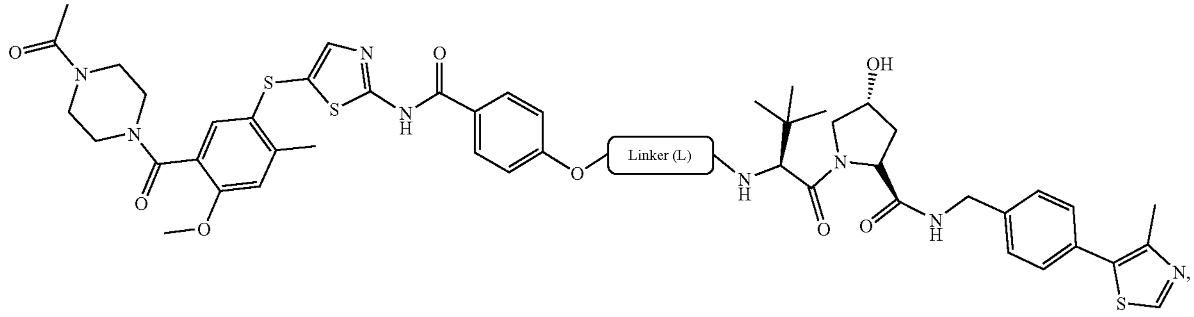

-continued
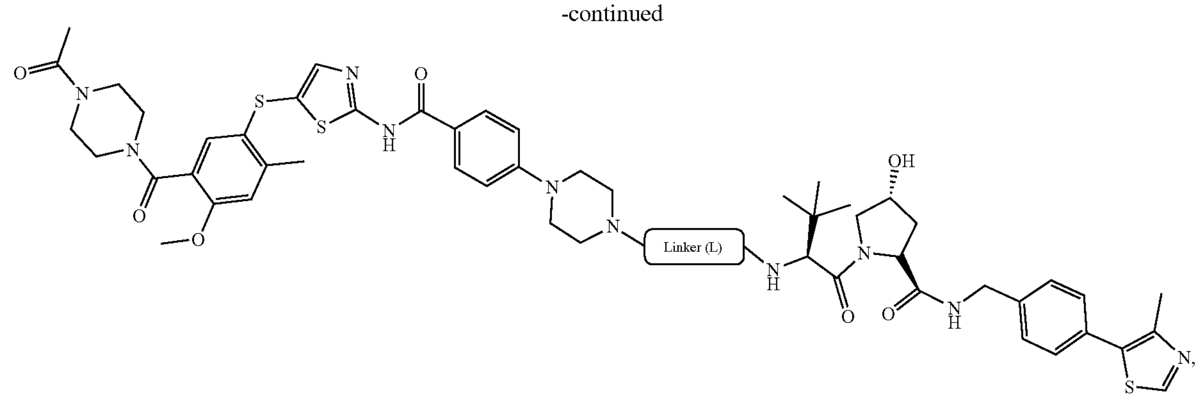
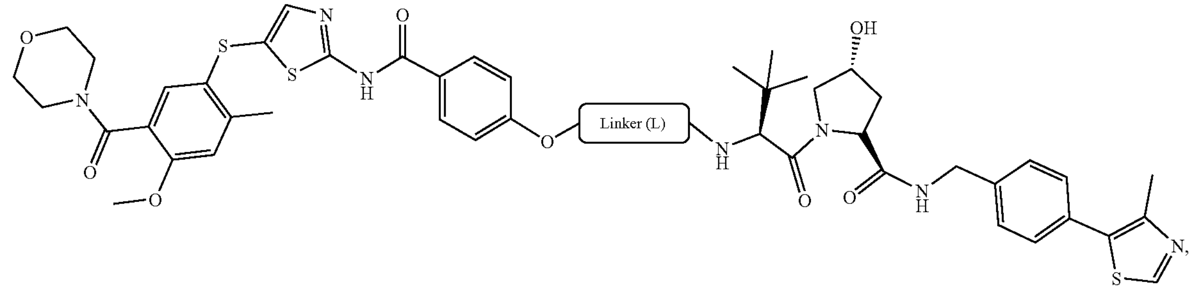
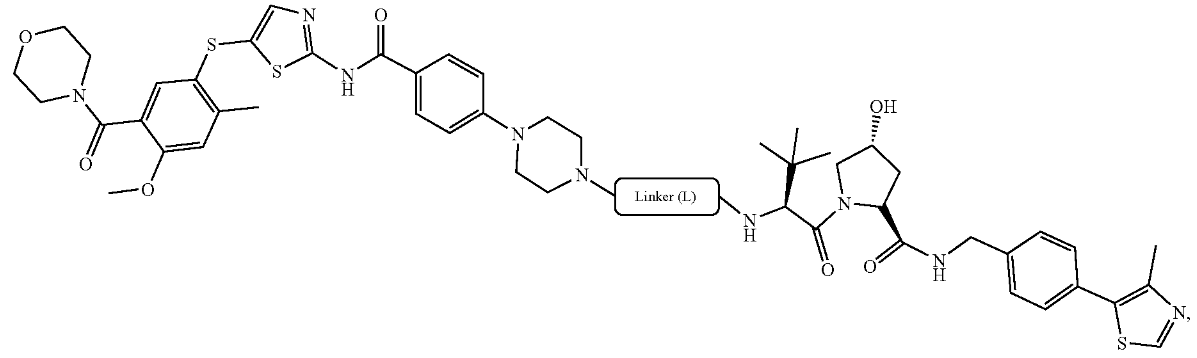
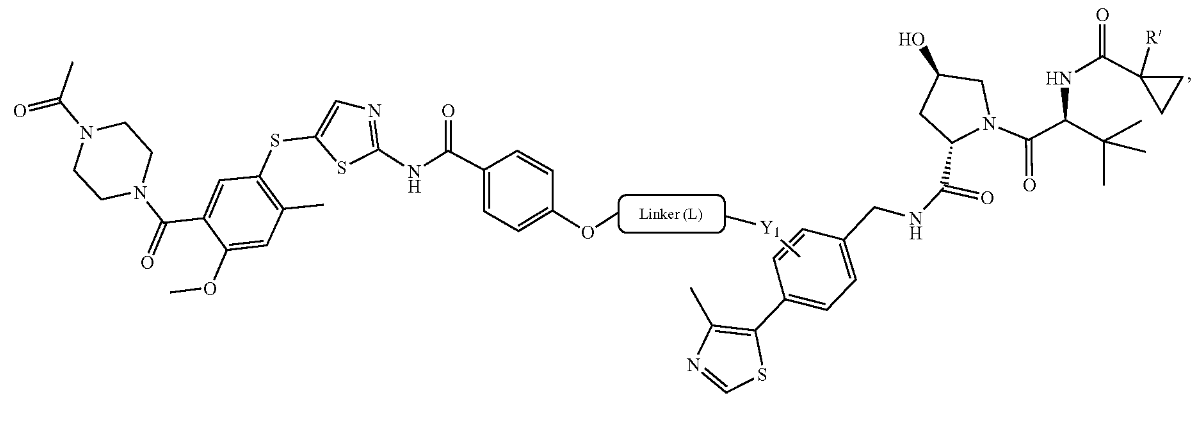

-continued
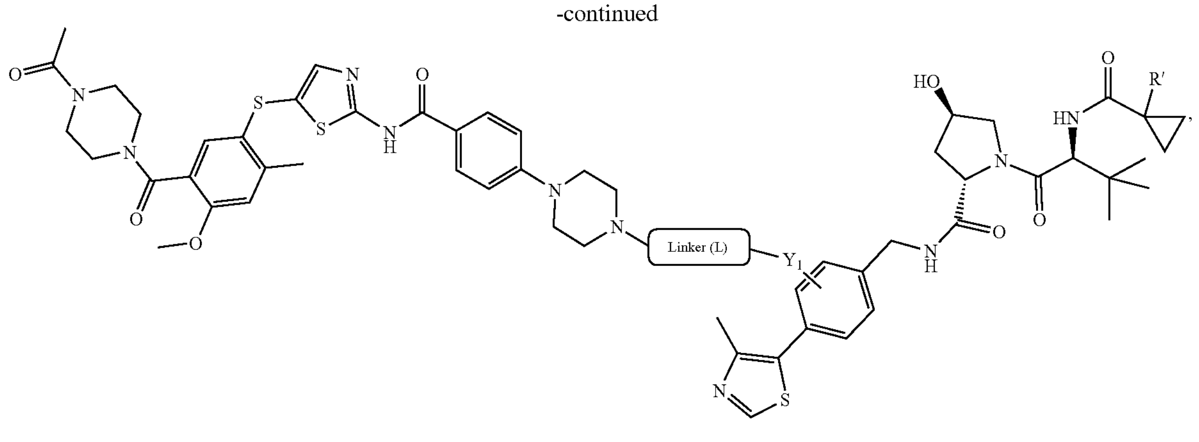
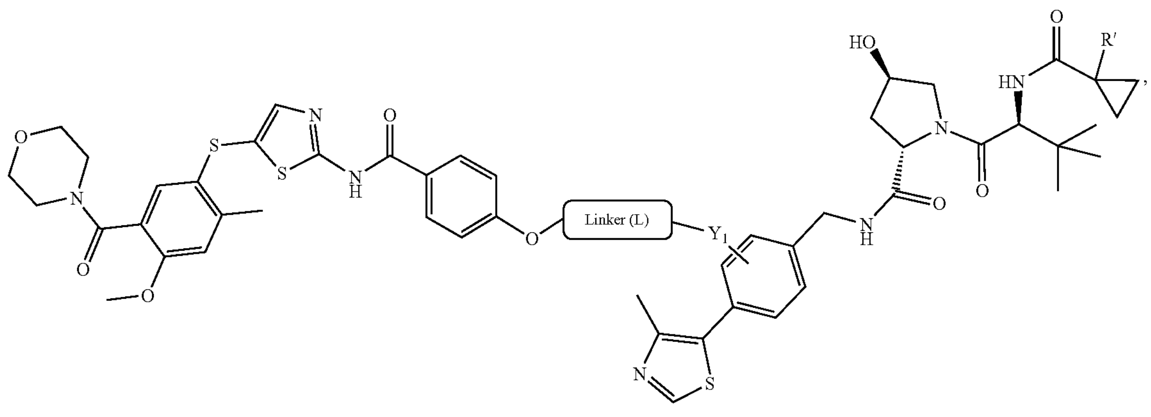
, and
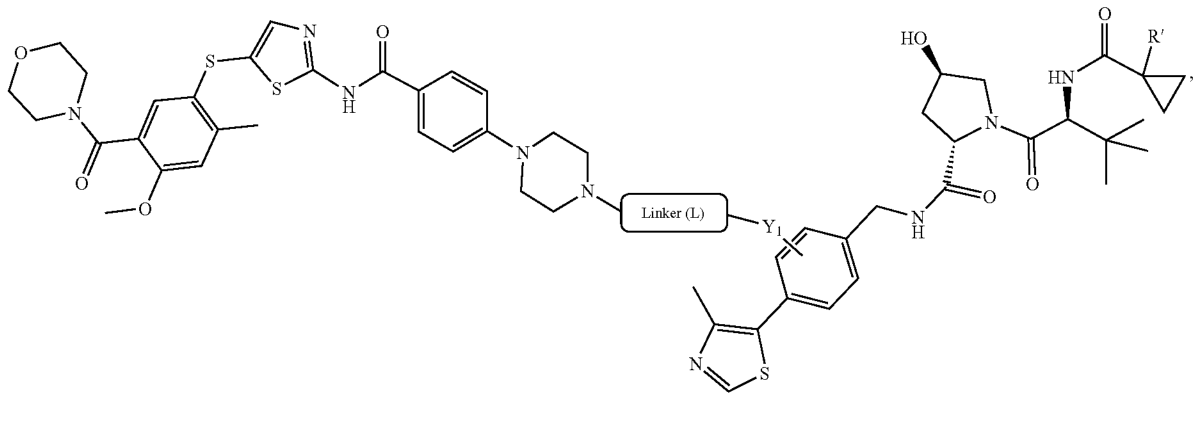
or a pharmaceutically acceptable salt or stereoisomer thereof.
14. The compound of claim 1, wherein the degron has a structure represented by any one of formulas D3-a-c:

-continued
(D3-a)
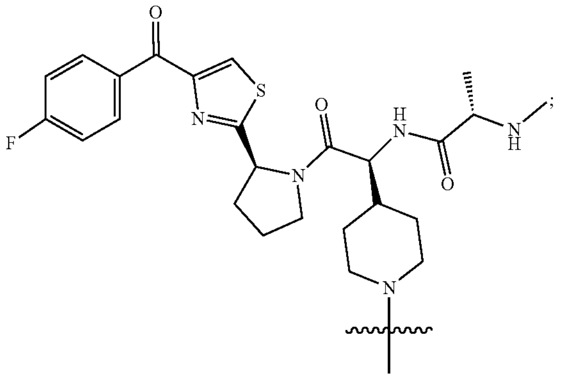
(D3-b)
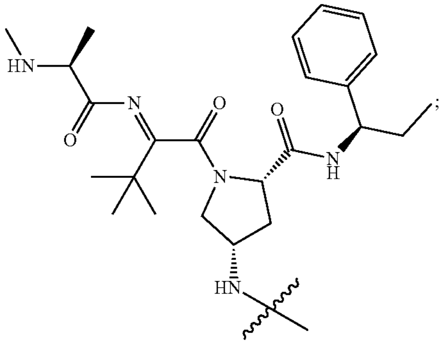
; and
(D3-c)
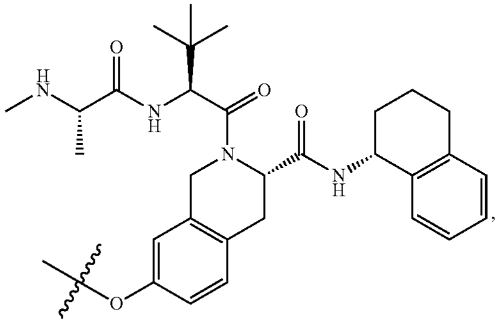
,
or a stereoisomer thereof.
15. The compound of claim 14, which is:
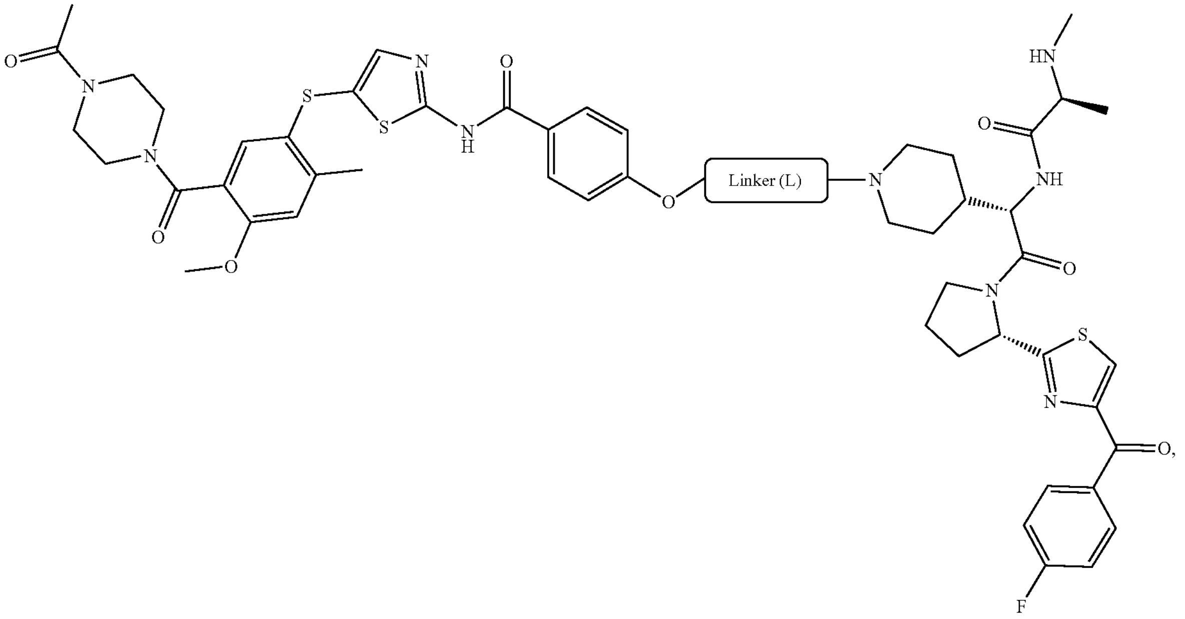
, -continued
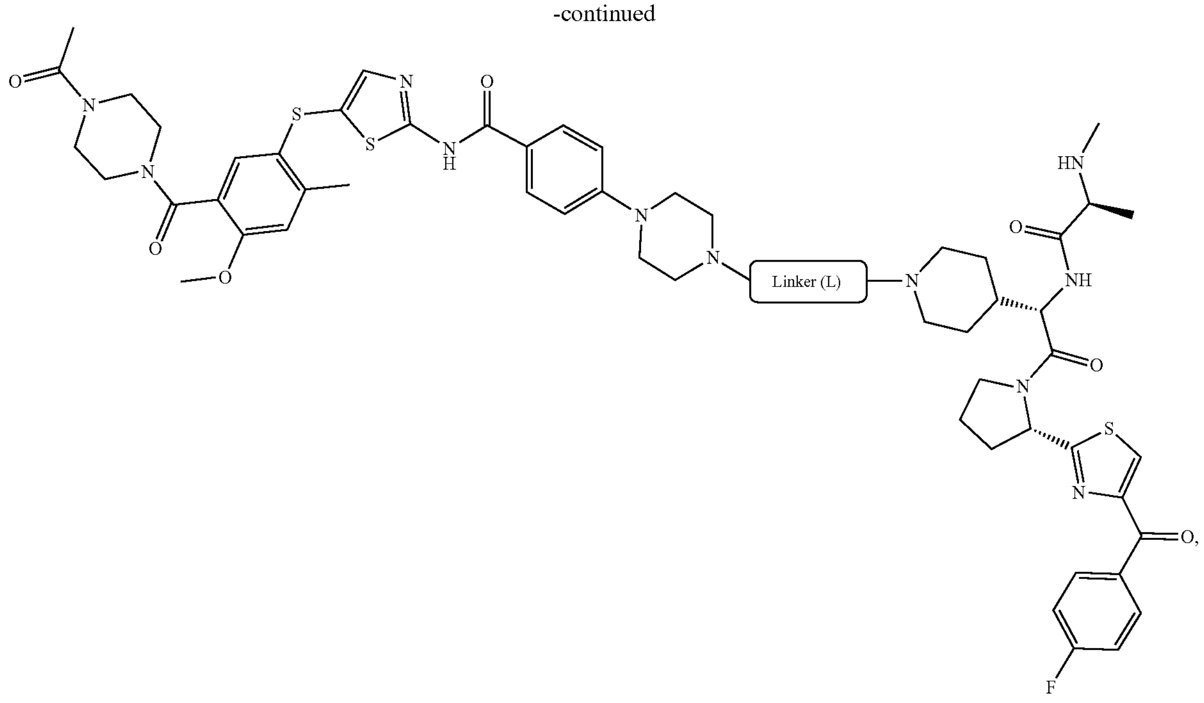
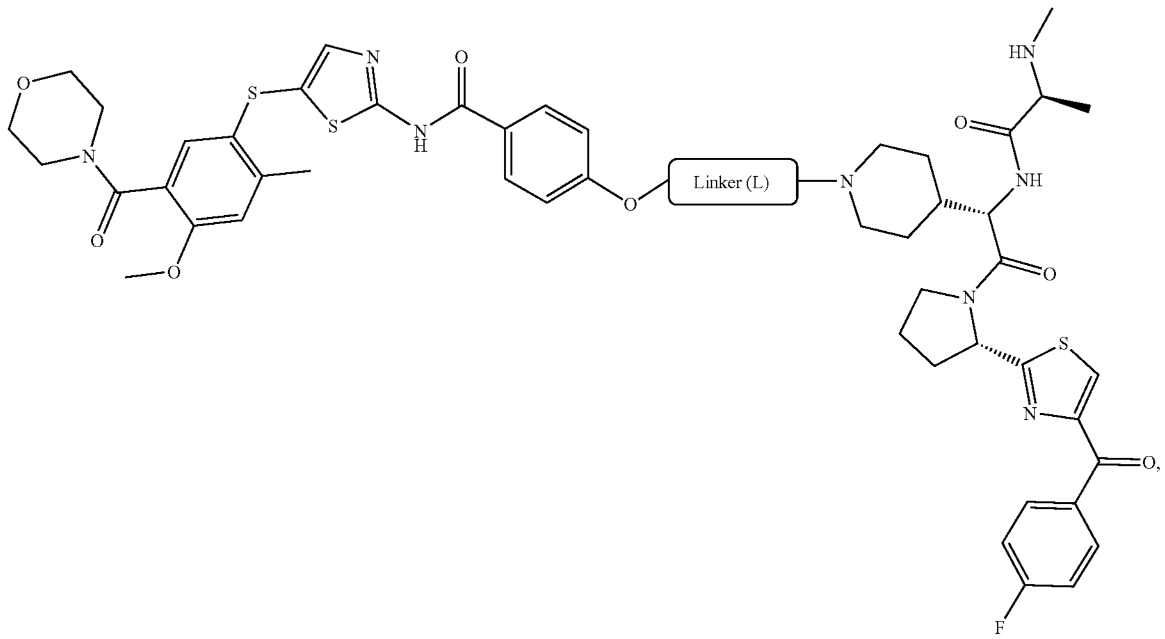

-continued
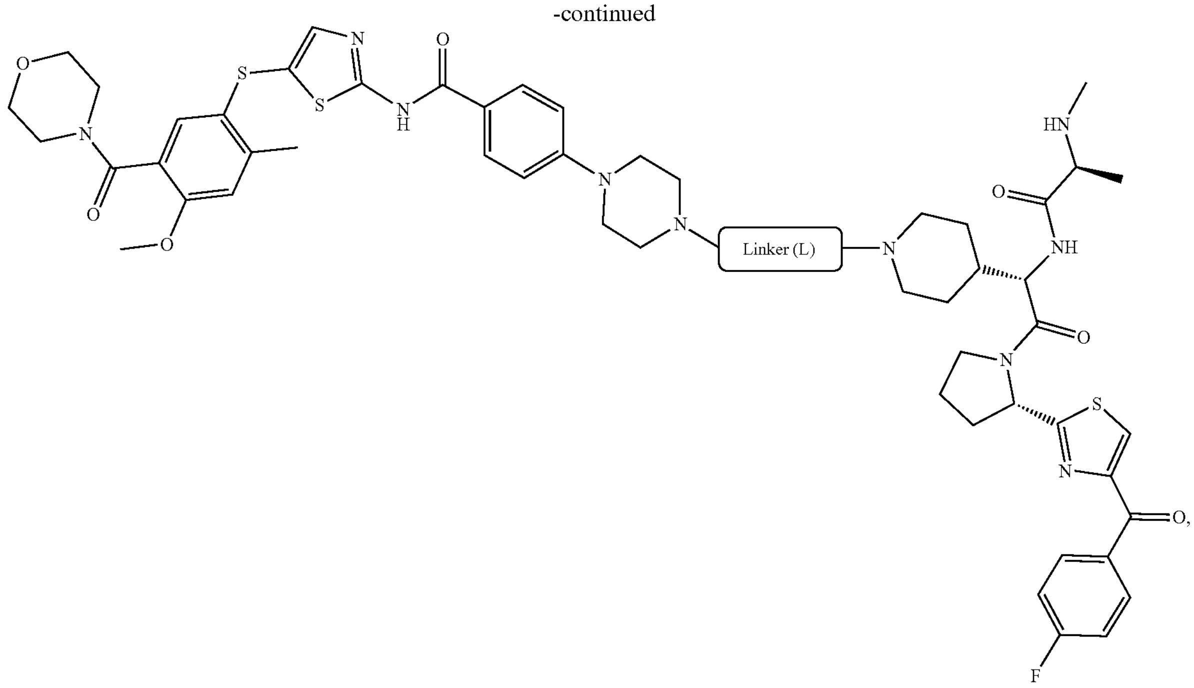
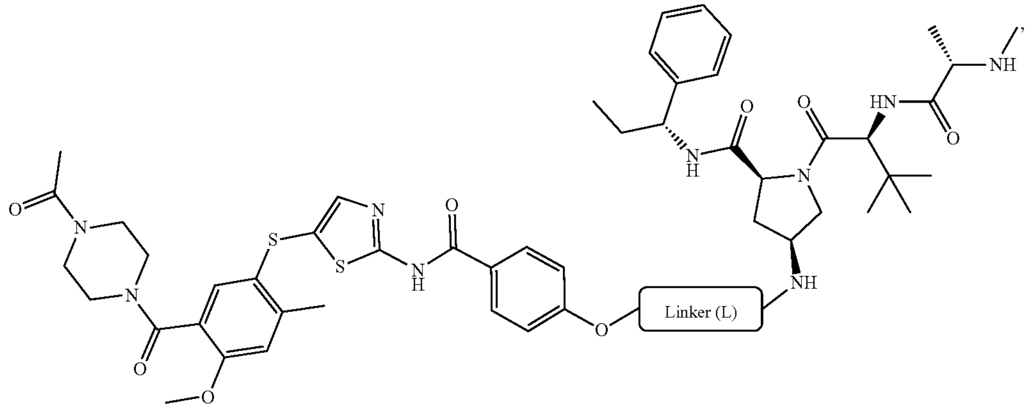
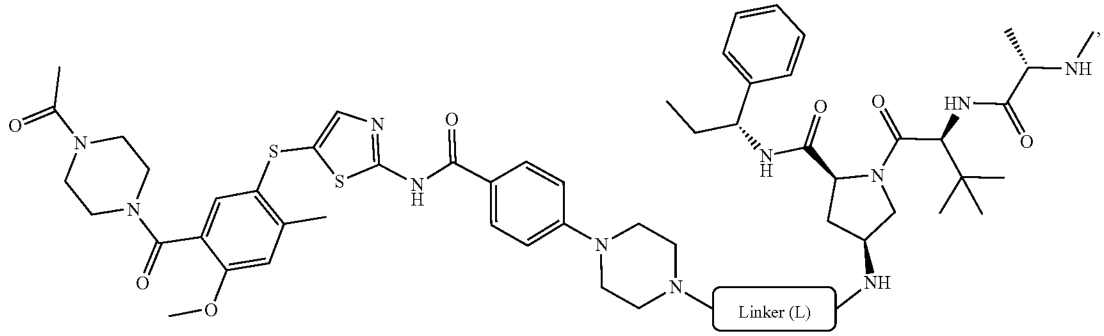

-continued
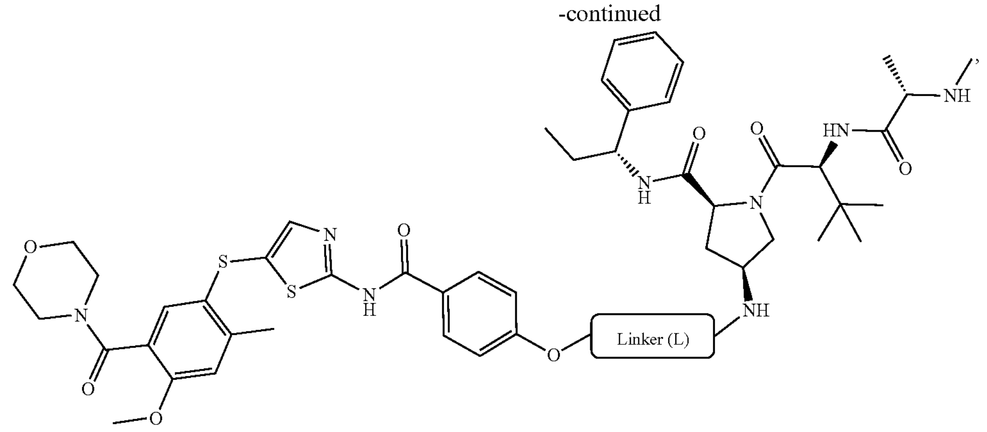
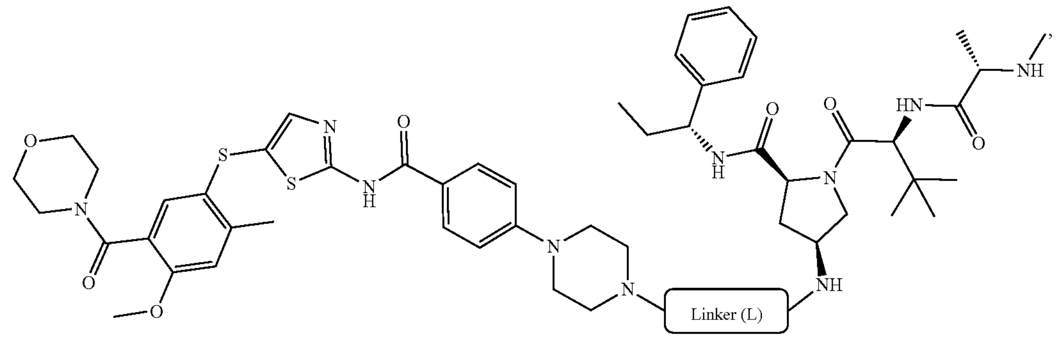
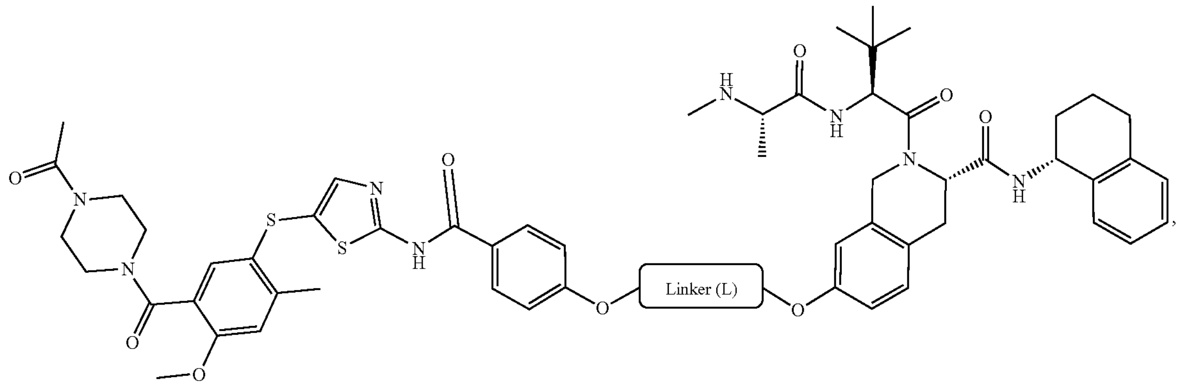
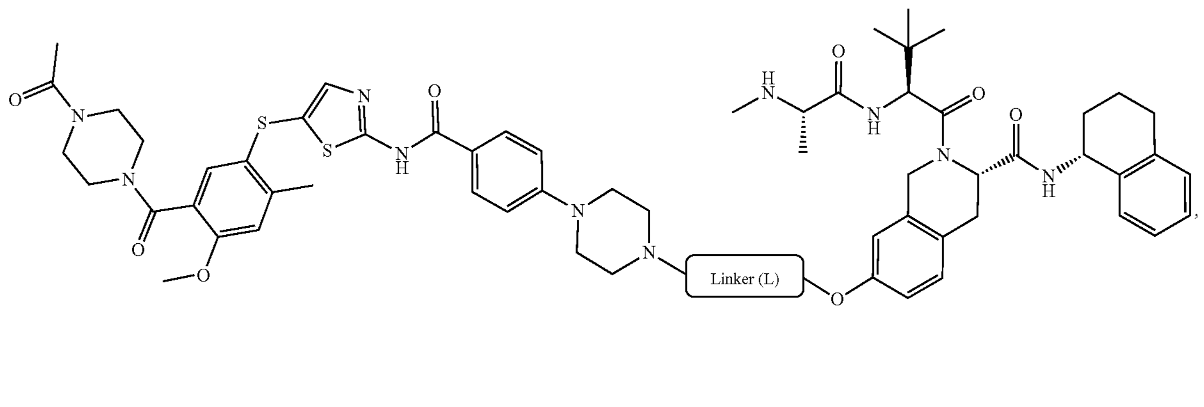

-continued
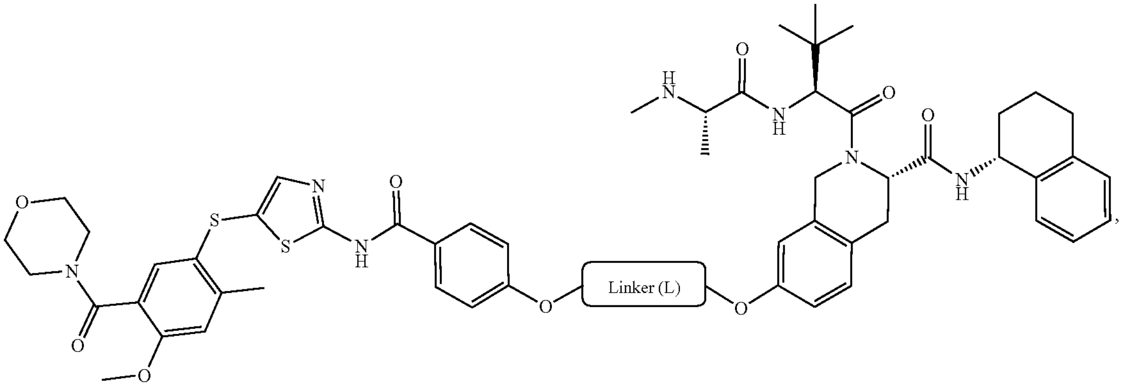
, and
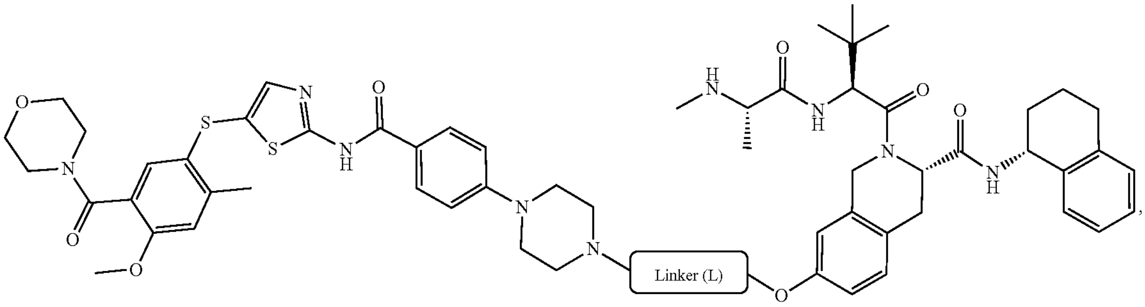
,
or a pharmaceutically acceptable salt or stereoisomer thereof.
16. The compound of claim 1, wherein the degron has a structure represented by any one of formulas D4-a-b:
(D4-a)
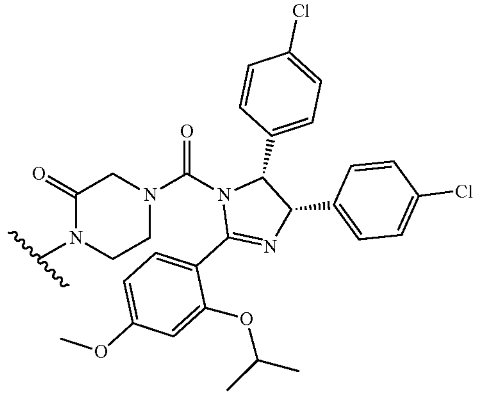
and
-continued
(D4-b)
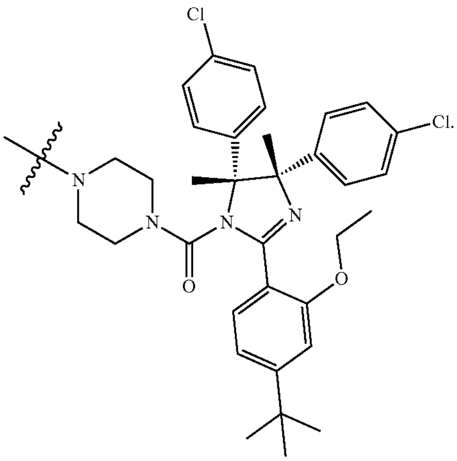

17. The compound of claim 16, which is:
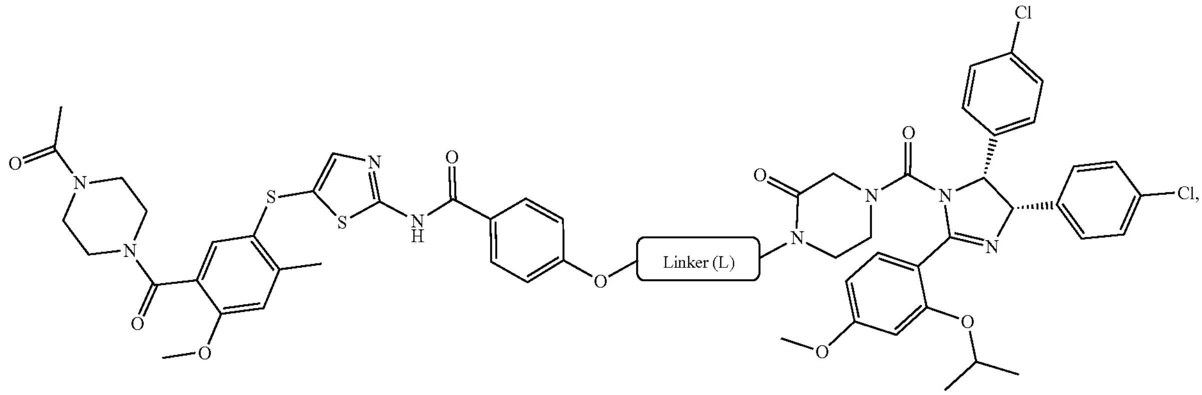
,
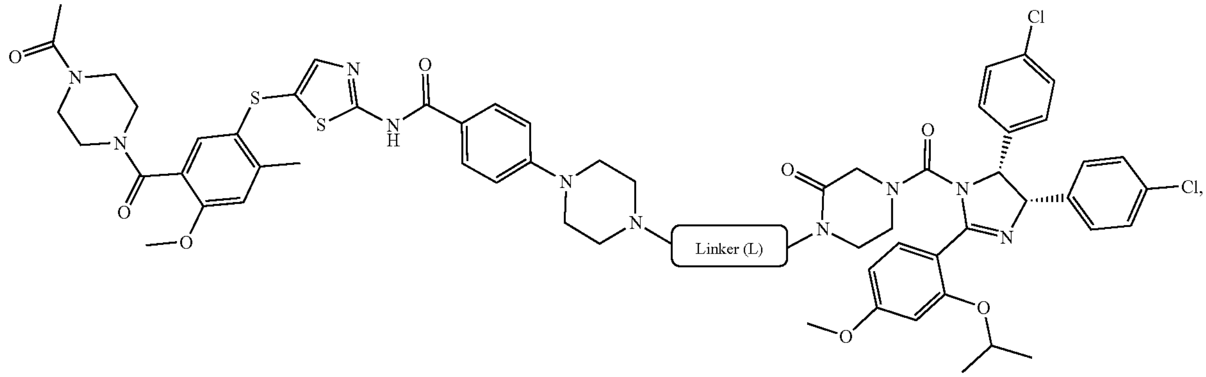
,
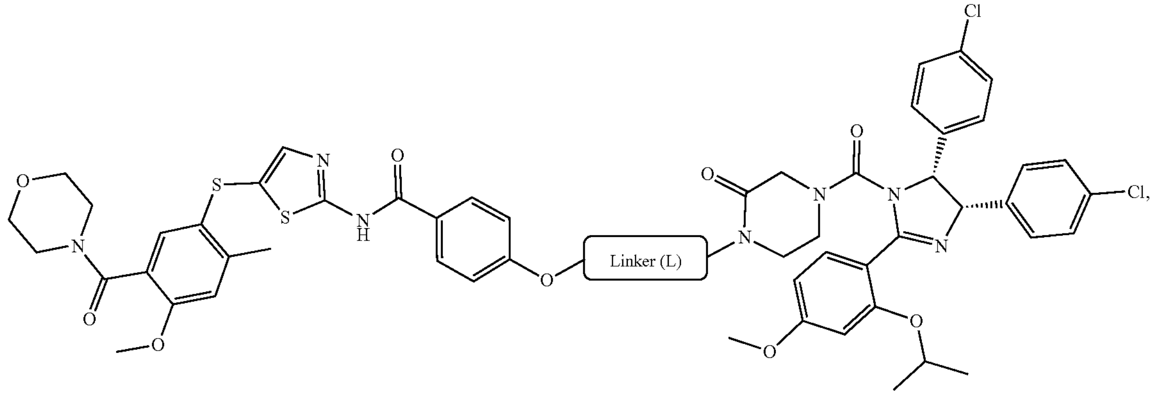
,
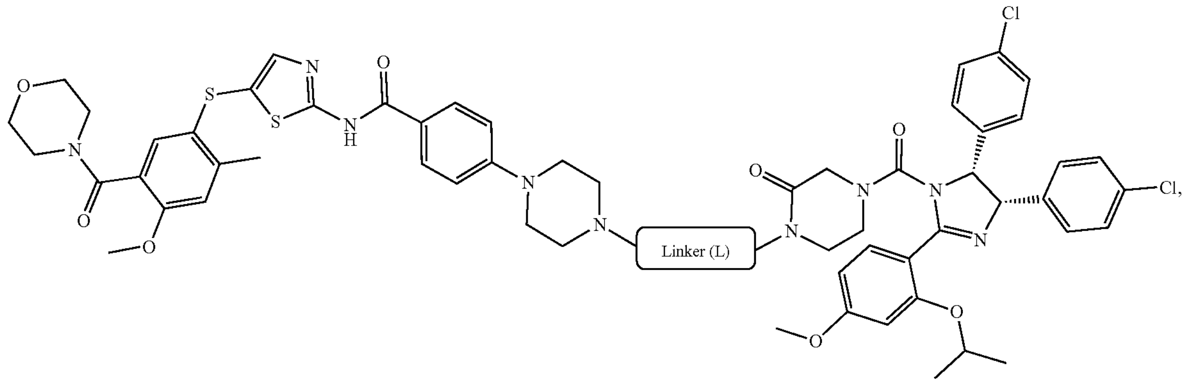
, -continued
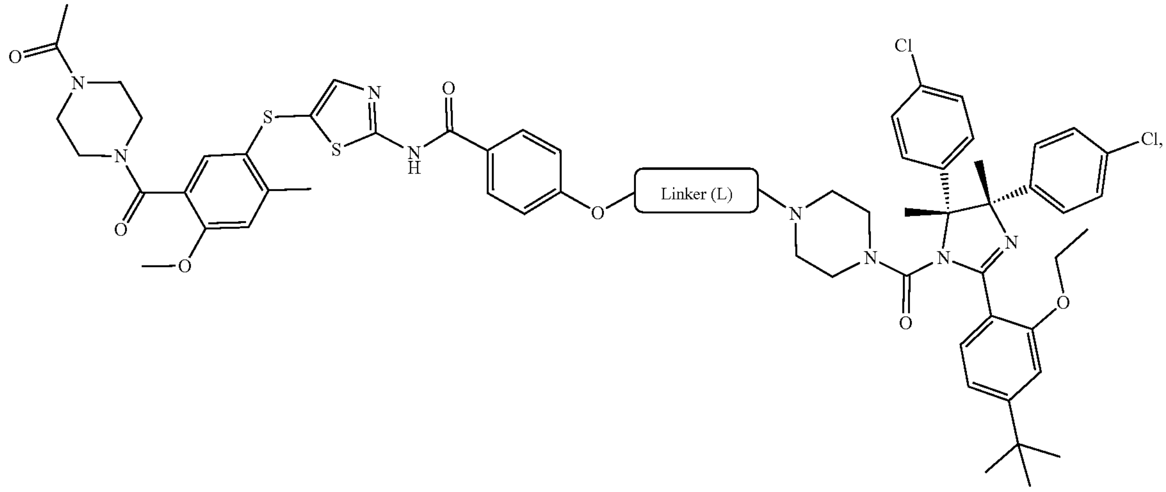
,
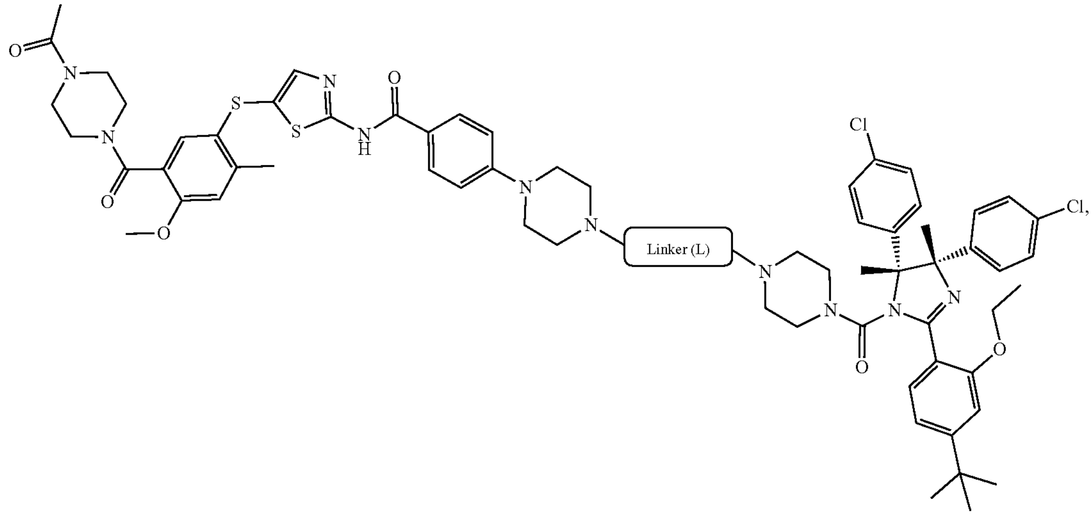
,
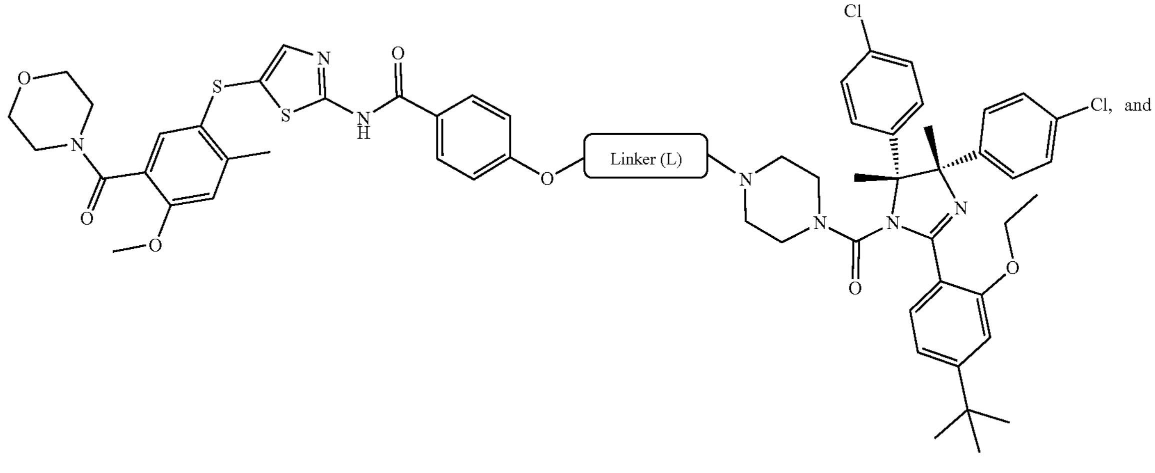
, and -continued
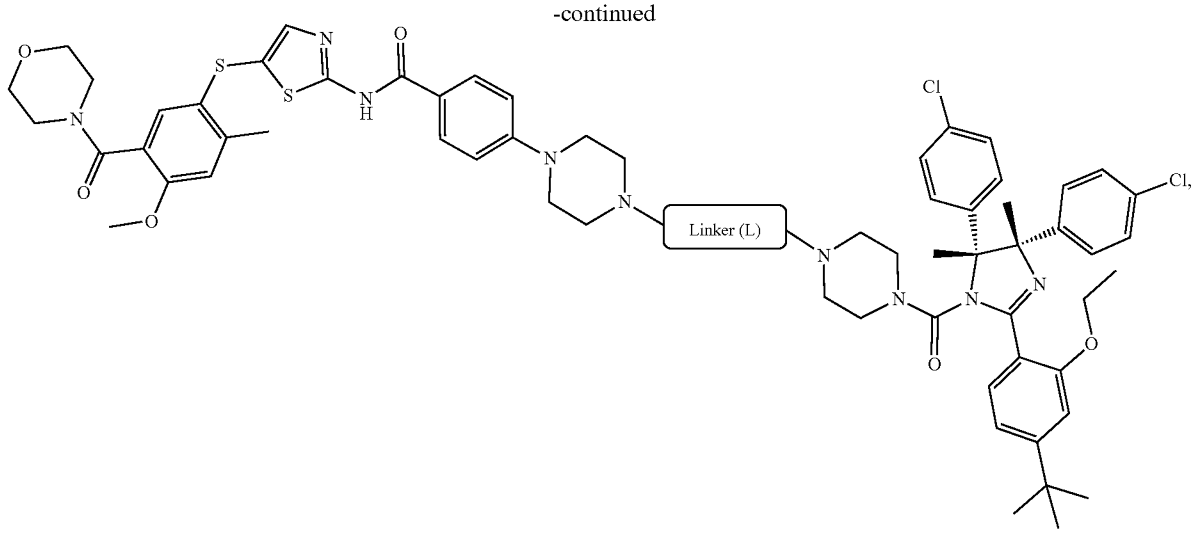
or a pharmaceutically acceptable salt or stereoisomer thereof.
18. The compound of claim 1, which is represented by any one of the following structures:
(1)
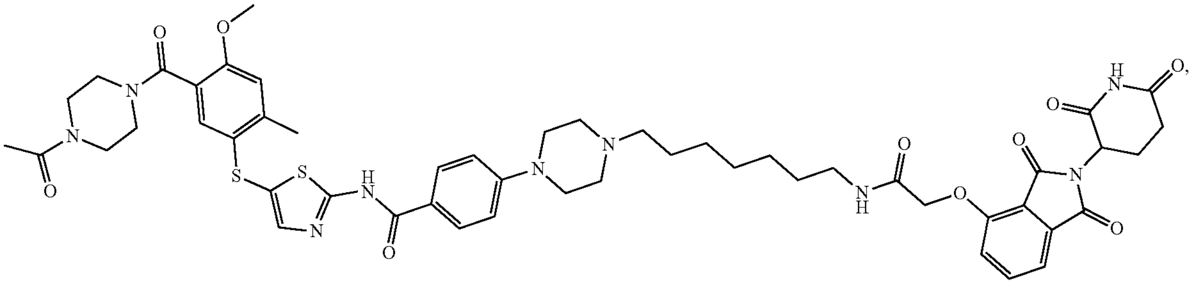
(2)
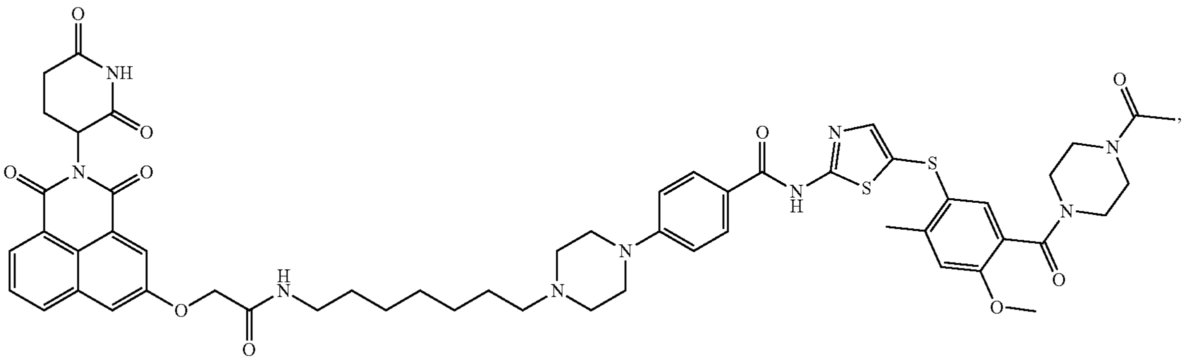

-continued
(3)
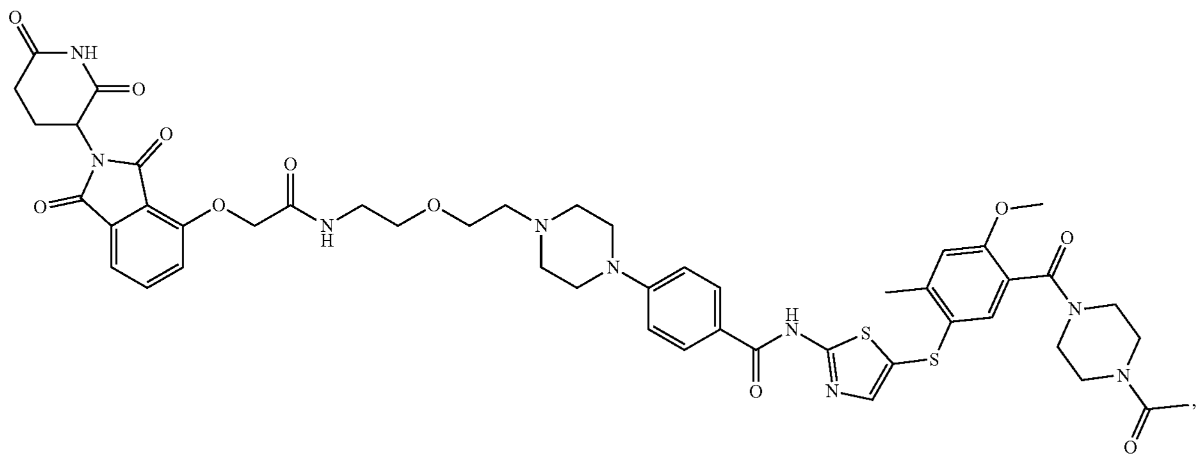
(4)
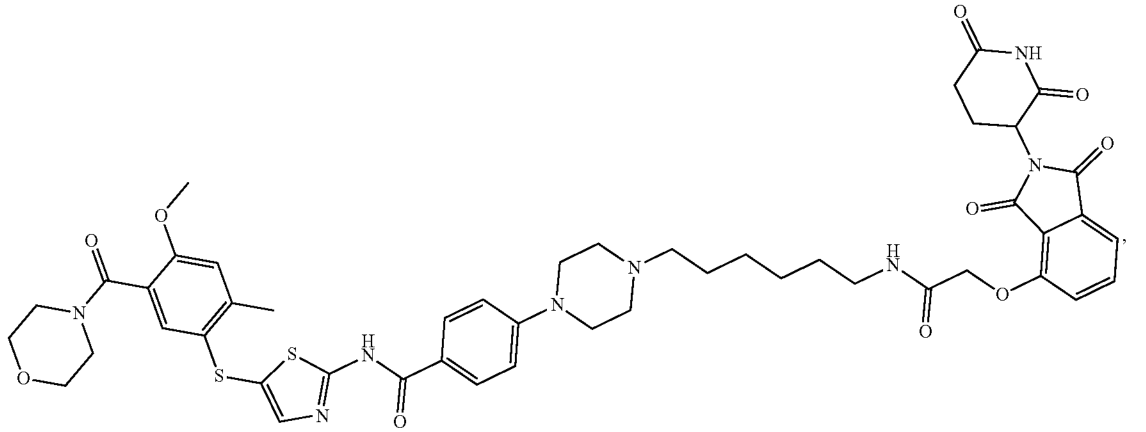
(5)
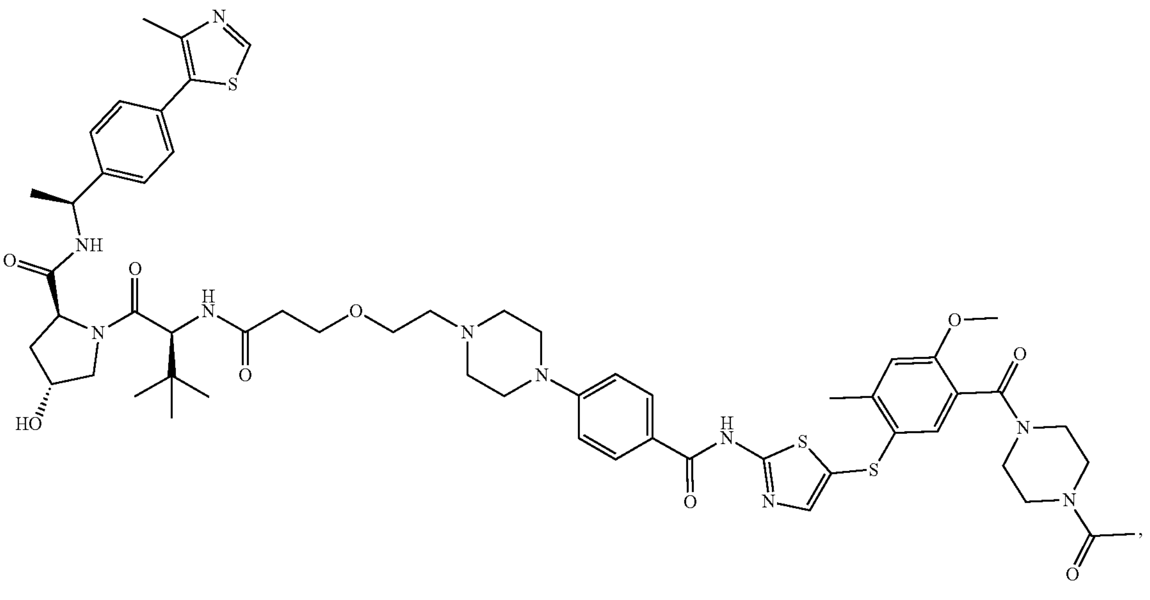

-continued (6)

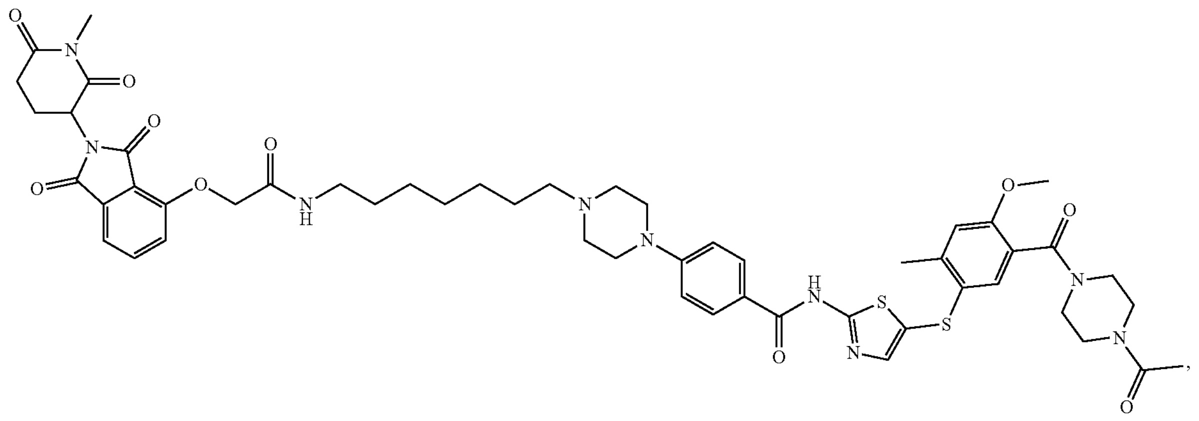

or a pharmaceutically acceptable salt or stereoisomer thereof.

19. The compound of claim 18, which is:

(1)

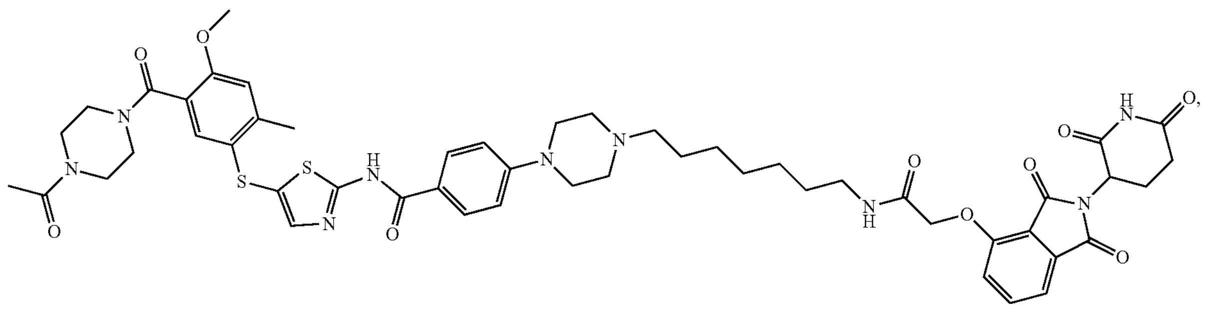

or a pharmaceutically acceptable salt thereof.

20. A pharmaceutical composition, comprising a therapeutically effective amount of the compound or pharmaceutically acceptable salt or stereoisomer of claim 1, and a pharmaceutically acceptable carrier.

21. The pharmaceutical composition of claim 20, which is in the form of a tablet, a capsule, or a liquid suitable for oral or parenteral administration.

22. A method of treating a disease or disorder, comprising administering a therapeutically effective amount of the compound or pharmaceutically acceptable salt or stereoisomer of claim 1 to a subject in need thereof, wherein the disease or disorder is inflammatory myofibroblastic tumor (IMT), breast cancer, colorectal cancer, esophageal squamous cell cancer (ESCC), renal cell cancer (RCC), colorectal cancer, melanoma, non-small cell lung cancer (NSCLC), cutaneous T-cell lymphoma, peripheral T-cell lymphoma, multiple myeloma, myelodysplastic syndrome, acute myeloid leukemia, chronic myeloid leukemia, chronic lymphocytic leukemia, Hodgkin's lymphoma, Waldenstrom's macroglobulinemia, non-Hodgkin's lymphoma, mantle cell lymphoma, small lymphocytic lymphoma, diffuse large B-cell lymphoma, marginal zone lymphoma, lymphoplasmacytic lymphoma, follicular lymphoma, T-cell prolymphocytic leukemia, or T-cell large granular lymphocyte leukemia.

23. The method of claim 22, wherein the disease or disorder is inflammatory myofibroblastic tumor (IMT), breast cancer, colorectal cancer, esophageal squamous cell cancer (ESCC), renal cell cancer (RCC), colorectal cancer, melanoma, non-small cell lung cancer (NSCLC), cutaneous T-cell lymphoma, or peripheral T-cell lymphoma.

24. The method of claim 22, wherein the disease or disorder is multiple myeloma, myelodysplastic syndrome, acute myeloid leukemia, chronic myeloid leukemia, chronic lymphocytic leukemia, Hodgkin's lymphoma, Waldenstrom's macroglobulinemia, non-Hodgkin's lymphoma, mantle cell lymphoma, small lymphocytic lymphoma, diffuse large B-cell lymphoma, marginal zone lymphoma, lymphoplasmacytic lymphoma, follicular lymphoma, cutaneous T-cell lymphoma, T-cell prolymphocytic leukemia, T-cell large granular lymphocyte leukemia, or peripheral T-cell lymphoma.

25. The method of claim 22, wherein the subject is administered an additional therapeutic agent.

26. The method of claim 25, wherein the additional therapeutic agent is an immune effector cell that expresses a chimeric antigen receptor.

27. The method of claim 22, wherein the disease or disorder is cutaneous T-cell lymphoma, peripheral T-cell lymphoma, multiple myeloma, acute myeloid leukemia, chronic myeloid leukemia, chronic lymphocytic leukemia, Hodgkin's lymphoma, non-Hodgkin's lymphoma, mantle cell lymphoma, small lymphocytic lymphoma, diffuse large B-cell lymphoma, marginal zone lymphoma, lymphoplasmacytic lymphoma, follicular lymphoma, T-cell prolymphocytic leukemia, or T-cell large granular lymphocyte leukemia.

* * * * *